United States Patent [19]
Katz et al.

[11] Patent Number: 6,004,787
[45] Date of Patent: Dec. 21, 1999

[54] METHOD OF DIRECTING BIOSYNTHESIS OF SPECIFIC POLYKETIDES

[75] Inventors: Leonard Katz, Waukegan; Stefano Donadio; James B. McAlpine, both of Libertyville, all of Ill.

[73] Assignee: Abbott Laboratories, Abbott Park, Ill.

[21] Appl. No.: 08/439,009

[22] Filed: May 11, 1995

Related U.S. Application Data

[62] Division of application No. 07/642,734, Jan. 17, 1991, Pat. No. 5,824,513.

[51] Int. Cl.[6] .......................... C12N 9/00; C12N 15/520; C12N 15/76; C12N 15/00

[52] U.S. Cl. ................. 435/183; 435/252.3; 435/252.35; 435/320.1; 435/471; 536/23.2; 935/14; 935/29; 935/75

[58] Field of Search .......................... 514/29; 435/697.1, 435/76, 172.3, 252.3, 252.35, 320.1, 183, 471; 530/350; 536/23.2, 23.7

[56] References Cited

U.S. PATENT DOCUMENTS

| | | | |
|---|---|---|---|
| 4,874,748 | 10/1989 | Katz et al. | 514/29 |
| 4,935,340 | 6/1990 | Baltz et al. | 435/6 |
| 5,081,023 | 1/1992 | Yaginuma et al. | 435/76 |
| 5,087,563 | 2/1992 | Beremand et al. | 435/69.7 |
| 5,110,728 | 5/1992 | Kridl et al. | 435/69.1 |
| 5,141,926 | 8/1992 | Weber et al. | 514/29 |
| 5,252,474 | 10/1993 | Gewain et al. | 435/172.3 |

FOREIGN PATENT DOCUMENTS 238 323  3/1987  European Pat. Off. .

OTHER PUBLICATIONS

Baltz, R. H., et al., Annual Review of Microbiology, vol. 42, "Genetics of Streptomyces fradiae and tylosin biosynthesis", pp. 547 and 558–574, 1988.

E. L. V. Harris and S. Angal, Eds., Protein Purification Methods: A Practical Approach, "Initial planning", pp. 57–67, IRL Press, New York, New York, 1989.

Ashworth, D. M., et al., Journal of the Chemical Society, Perkin Transactions, vol. 1, "On the biosynthetic origins of the hydrogen atoms in the macrotetrolide antibiotics and their mode of assembly catalysed by a nonactin polyketide synthase", p. 1461, 1989.

Otten, S. L., et al., Journal of Bacteriology, vol. 172, "Cloning and expression of daunorubicin biosynthesis genes from *Streptomyces peucitius* and *S. peucetius* subsp. *caesius*", pp. 3427–3434, 1990.

Richardson, M. A., et al., Journal of Bacteriology, vol. 172, "Cloning of spiramycin biosynthetic genes and their use in constructing *Streptomyces ambofaciens* mutants defective in spiramycin biosynthesis", pp. 3790–3798, 1990.

(List continued on next page.)

*Primary Examiner*—Robert A. Wax
*Assistant Examiner*—William W. Moore
*Attorney, Agent, or Firm*—Dianne Casuto

[57] ABSTRACT

A method to produce novel polyketide structures by designing and introducing specified changes in the DNA governing the synthesis of the polyketide is disclosed. The biosynthesis of specific polyketide analogs is accomplished by genetic manipulation of a polyketide-producing microorganism by isolating a polyketide biosynthetic gene-containing DNA sequence, identifying enzymatic activities associated within the DNA sequence, introducing one or more specified changes into the DNA sequence which codes for one of the enzymatic activities which results in an altered DNA sequence, introducing the altered DNA sequence into the polyketide-producing microorganism to replace the original sequence, growing a culture of the altered microorganism under conditions suitable for the formation of the specific polyketide analog, and isolating the specific polyketide analog from the culture. The method is most useful when the segment of the chromosome modified is involved in an enzymatic activity associated with polyketide biosynthesis, particularly for manipulating polyketide synthase genes from Saccarharopolyspora or Streptomyces.

39 Claims, 93 Drawing Sheets

OTHER PUBLICATIONS

Hopwood, D. A., et al., in GIM 90: Proceedings of the 6th International Symposium on Genetics of Industrial Microorganisms, H. Heslot et al., Eds., vol. 1, "Hybrid pathways for the production of secondary metabolites", pp. 259–270, Societe Francaise de, 1990.

Salas, J.A., et al., BIOTEC–90, "Genetic manipulation of antibiotic biosynthesis by actinomycetes", pp. 47–52, 1990.

Li, T., et al., Chinese Journal of Biotechnology, vol. 7, "Cloning and expression of spiramycin polyketide synthase genes and resistance genes from *S. spiramyceticus* U–1941", pp. 33–42, 1991.

Kakinuma, S., et al., Tetrahedron, vol. 47, "Genetic studies of the biosynthesis of kalafungin, a benzoisochromanequinone antibiotic", pp. 6059–6068, 1991.

Robinson, J. A., Philosophical Transactions of the Royal Society of London, Series B: Biological Sciences, vol. 332, "Polyketide synthase complexes: their structure and function in antibiotic biosynthesis", pp. 107–114, 1991.

D.A. Hopwood, et al., "Production of 'Hybrid' Antibiotics by Genetic Engineering", *Nature*, vol. 314, issued Apr. 18, 1985, pp. 642–644.

F. Malpartide, et al., "Homology Between Streptomyces Genes Coding for Synthesi of Different Polyketides Used to Clone Antibiotic Biosynthetic Genes", *Nature* vol. 325, issued Jan. 26, 1987, pp. 818–821.

J. Mark Weber, et al., "Genetic Analysis of Erythromycin Production in Streptomyce Erythreus", *Journal of Bacteriology*, vol. 164, No. 1, issued Oct. 1985, pp. 425–433.

J. Mark Weber, et al., "Organization of a Cluster of Erythromycin Genes in *Saccharopolyspora Erythraea*", *Journal of Bacteriology*, vol. 172, No. 5, issued May 1990, pp. 2372–2383.

Cortes, et al., "An Unusually Large Multifunctional Polypeptide in the Erythromycin producing Polyketide Synthase of *Saccharopolyspora Erythraea*", *Nature*, vol. 348(8), pp. 176–178 (1990).

Tuan, et al., "Cloning of Genes Involved in Erythromycin Biosynthesis from *Saccharopolyspora Erythraea* Using a Novel *Actinomycete–Escherichia Coli* Cosmid", *Gene*, vol. 90 pp. 21–29 (1990).

Huber, et al., "Branched–Chain Fatty Acids Produced by Mutants of *Streptomyces Fradiase*, Putative Precursors of the Lactone Ring of Tylosin", *Antimicrobial Agents and Chemotherapy*, vol. 34(8), pp. 1535–1541 (1990).

Hopwood, et al., "Molecular Genetics of Polyketides and Its Comparison to Fatty Acid Biosynthesis", *Annual Rev. Genetics*, 1990, pp. 37–66.

Bibb, et al., "Analysis of the Nucleotide Sequence of the *Streptomyces Glaucescens* tcml Genes Provides Key Information About the Enzymology of Polyketide Antibiotic Biosynthesis", *The EMBO Journal*, vol. 8(9), pp. 2727–2736 (1989).

Vara, et al., "Cloning of Genes Governing the Deoxysugar Portion of the Erythromycin Biosynthesis Pathway in *Saccharopolyspora Erythraea*", *Journal of Bacteriology*, vol. 171(11), pp. 5872–5881 (1989).

Dhillon, et al., "Molecular Characterization of a Gene From *Saccharopolyspora–Erythraea* (*Streptomyces–Erythraeus*) Which is Involved in Erythromycin Biosynthesis", *Molecular Microbiology*, vol. 3(10), pp. 1405–1414 (1989).

Sherman, et al., "Structure and Deduced Function of the Granaticin–Producing Polyketide Synthase Gene Cluster of *Streptomyces Violaceoruber* TU22", *The EMBO Journal*, vol. 8(9), pp. 2717–2725 (1989).

Kirst, et al., "New Directions for Macrolide Antibiotics: Structural Modifications and In Vitro Activity", *Antimicrobial Agents and Chemotherapy*, vol. 33(9), pp. 1413–1418 (1989).

Donadio, et al., "Genetic Studies on Erythromycin Biosynthesis in *Saccharopolyspora Erythraea*", *Genetics and Molecular Biology of Industrial Microorganism*, pp. 53–59 (1989).

Kinoshita, et al., "Isolation of Proposed Intermediates in he Biosynthesis of Mycinamicins", *J. Chem. Soc. Chem. Commun.*, pp. 943–945 (1988).

Tomich, P.K., "Streptomyces Cloning: Possible Construction of Novel Compounds and Regulation of Antibiotic Biosynthetic Genes", *Antimicrobial Agents and Chemotherapy*, vol. 32(10), pp. 1472–1476 (1988).

Stanzak, et al., "Cloning and Expression in *Streptomyces Lividans* of Clustered Erythromycin Biosynthesis Genes From *Streptomyces Erythreus*", *Bio/Technology*, vol. 4, pp. 229–232 (1986).

FIG. 2-1

```
  1 GTCGACCTGCGGGCGATCGTGCAGCGCCCGACGAGGTCGTGCATCAGGCCGACGTTGACC  60
 61 CGCTCGGCTTCCGGGTCGGAGGTGGCGCTGCCCAGGTGGAACCGCCCTGCGTGCGCC    120
121 ACCAGGTGCACGATCACGTCGGCGTCCTCGATCGCGGGCCCGGTTCCAGC             180
181 AGGTCGGCGCGCAGGTCCTCGACCTCCGCGGGGAACCGGGGCGCTCCGCCG            240
241 CGGGACACCGCGCGCAGCCGGACCGGGTCGCGCAGCTCGCGCAGAACCGCGCTCCCG      300
301 ACGAAGCCGGAAGCGCCCAGAAGGGTGATCAATTGACGCGGAATCACTGATCCCATTC     360
361 ACCGGAGCATTTGCTCGCTTTCCAGGTCGGTGCTACGGGCGAAATTCAAAGAATCTCCC    420
421 AGCGCGATGTGCGGCAACCCGTCACTGGCCACCACAGTAGTCGCCGTTGATCTTG        480
481 TCAACATGCAGATGTTCACAGGTTCGTTGGCTTCGACGAGGCGATGTCAACCTCTTGATCC  540
541 TTCCTATATTGTTCGCCCATTGCTGTCGTCGAGTAGGGGACGCGTGGCGGACCTGTC      600
```

```
601 AAAGCTCTCCGACAGTCGGACTGCACAACCTGGGAGGATCGTTCGTCCGTGGCCCTGTC 660
    -------+---------+---------+---------+---------+---------+

661 GGGGTGCAATGAATCCGCCTTGCGGGCCCGTGCGCGCCAATTGCGTGCACATCTCGATCG 720
    -------+---------+---------+---------+---------+---------+

721 ATTTCCCGATGCCGGTGTGTCGAAGGTGTCGGGGCCGCTCGGCCGCACGAGCAGGCGGA  780
    -------+---------+---------+---------+---------+---------+
               V  S  G  P  R  S  R  T  T  S  R  R  T

781 CGCCGGTCCGCATCGGGCGGTCGTCGTCGCCTCCTCGACCTCCGAGCTGCTCGACGGCC  840
    -------+---------+---------+---------+---------+---------+
     P  V  R  I  G  A  V  V  V  A  S  S  T  S  E  L  L  D  G  L

841 TGGCCGCCGTCGCCGACGGCCGGCCGCACGCCTCGGTGGTCCGCGGTGTCGCGGGCCGT  900
    -------+---------+---------+---------+---------+---------+
     A  A  V  A  D  G  R  P  H  A  S  V  V  R  G  V  A  R  P  S

901 CCGGCGGCCGGTGGTGTTCGTTCCCGGGCGCGGCCAGGGCGCAATGGGCCGGATGGCGGGGCG 960
    -------+---------+---------+---------+---------+---------+
     A  P  V  V  F  V  P  G  Q  G  A  Q  W  A  G  M  A  G  E

961 AACTCCCTCGGGCGAGTCAAGGGTTTTCGCCGCCGATGGACGCGTGCGCGGGGCGTTCG 1020
    -------+---------+---------+---------+---------+---------+
```

```
        L  L  G  E  S  R  V  F  A  A  A  M  D  A  C  A  R  A  F  E   -
      AGCCCGTGACCGACTGGACGCGCTGGCGCAGGTCCTGGACTCTCCCGAGCAGTCGCGCCGCG
1021  ------+---------+---------+---------+---------+---------+ 1080
        P  V  T  D  W  T  L  A  Q  V  L  D  S  P  E  Q  S  R  R  V   -
      TCGAGGTCGTCCAGCCCGCCCTGTTCGCGGTGCAGACGTCGCTGGCCGCGCTCTGGCGCT
1081  ------+---------+---------+---------+---------+---------+ 1140
        E  V  V  Q  P  A  L  F  A  V  Q  T  S  L  A  A  L  W  R  S   -
      CCTTCGGCGTGACCCCCGACGCCGTGGTGGGCCACAGCATCGGCGAGCTGGCCGCCGCGC
1141  ------+---------+---------+---------+---------+---------+ 1200
        F  G  V  T  P  D  A  V  V  G  H  S  I  G  E  L  A  A  A  H   -
      ACGTGTGCGGGTGCCGCCGACGCCGCGCGCGCCGCGCTGTGGAGCCCGG
1201  ------+---------+---------+---------+---------+---------+ 1260
        V  C  G  A  A  G  A  A  D  A  A  R  A  A  A  L  W  S  R  E   -
      AGATGATTCCGTTGGTGGGCAACGGCGACATGGCAGCCGTCGCTCTCCGCCGACGAGA
1261  ------+---------+---------+---------+---------+---------+ 1320
        M  I  P  L  V  G  N  G  D  M  A  A  V  A  L  S  A  D  E  I   -
      TCGAGCCGGCATCGCCCGGTGTGGGACGACGTGCTGCGGGGTCAACGGTCCGC
1321  ------+---------+---------+---------+---------+---------+ 1380
```

FIG. 2-4

```
       E   P   R   I   A   R   W   D   D   D   V   V   L   A   G   V   N   G   P   R   -
      GCTCGGTTCTGCTGACCGGGTCGCGGAACCGGTCGCGCGGGTCGCGCGGGTCCAGGAGCTCTCGG
1381  ---------+---------+---------+---------+---------+---------+  1440
       S   V   L   L   T   G   S   P   E   P   V   A   R   R   V   Q   E   L   S   A   -
      CCGAGGGGGTCCGCGCACAGGTCATCAATGTGTCGATGGCGGCACTCGGCGCAGTCG
1441  ---------+---------+---------+---------+---------+---------+  1500
       E   G   V   R   A   Q   V   I   N   V   S   M   A   A   H   S   A   Q   V   D   -
      ACGACATCGCCGAGGGGATGCGCTCGGCCCTGGCCGTGGTTCGCGCCCGGTGGCTCGGAGG
1501  ---------+---------+---------+---------+---------+---------+  1560
       D   I   A   E   G   M   R   S   A   L   A   W   F   A   P   G   G   S   E   V   -
      TGCCCTTCTACGCCAGCCTCACCGGAGGTGCGGTCGACACGGGGAGCTGGTGGCCGACT
1561  ---------+---------+---------+---------+---------+---------+  1620
       P   F   Y   A   S   L   T   G   G   A   V   D   T   R   E   L   V   A   D   Y   -
      ACTGGCGCCGCAGCTTCCGGCTGCCGGTGCGCTTCGACGAGGCGATCCGGTCCGCCCTGG
1621  ---------+---------+---------+---------+---------+---------+  1680
       W   R   S   F   R   L   P   V   R   F   D   E   A   I   R   S   A   L   E   -
```

FIG.2-5

```
1681  AGGTCGGTCCCGGCACGTTCGTCGAAGCGAGCCCGGTGCTGGCCGCCGCTCC  1740
         V  G  P  G  T  F  V  E  A  S  P  H  P  V  L  A  A  A  L  Q

1741  AGCAGACGCTCGACGCCGAGGGCTCCTCGGCCGCGGTGGTCCCGACGCTGCAACGCGGGC  1800
         Q  T  L  D  A  E  G  S  S  A  A  V  V  P  T  L  Q  R  G  Q

1801  AGGGCGGCATGCGGCGGTTCCTGCTGGCCGCGGCCCAGGCGTTCACCGGCGGGCGTGGCCG  1860
         G  G  M  R  R  F  L  L  A  A  A  Q  A  F  T  G  G  A  V

1861  TCGACTGGACCGCCGCCTACGACGACGTGGGGCCGAACCCGGCTCTCTGCCGGAGTTCGC  1920
         D  W  T  A  A  Y  D  D  V  G  P  N  P  A  L  C  R  S  S  R

1921  GCCGGGCCGAGGAGGAAGACGAGCCGGTCGACTGGAACGCGCCACCGCA  1980
         R  P  R  K  T  S  R  P  S  P  A  S  T  G  T  R  H  R  T

1981  CGTGCTGCGAGCGGCTGCTCGCGGTCGTCAACGGCGAGACCGCGTTGGGCGGCCGCG  2040
         C  C  E  R  L  L  A  V  V  N  G  E  T  A  A  L  A  G  R  E
```

FIG. 2-6

```
2041 AAGCCGACGCCGAGGCCACGTTCCGCGAGCTGGGGCTGGACTCGGTGCTGGCCGCGCAGC 2100
          A  D  A  E  A  T  F  R  E  L  G  L  D  S  V  L  A  A  Q  L

2101 TGCGCGCCAAGGTGAGCGCCGCGATCGGCCGAGGTCAACATCGCCCTGCTCTACGACC 2160
          R  A  K  V  S  A  A  I  G  R  E  V  N  I  A  L  L  Y  D  H

2161 ACCCGACTCCGCGTGCCTCGCGGAAGCACTCGCGGGAACCGAGGTCGCACAACGGG 2220
          P  T  P  R  A  L  A  E  A  L  A  A  G  T  E  V  A  Q  R  E

2221 AAACCCGGCGCGGGACCAACGAAGCGGCCCCGGGCGAACCGGTCGCGGTCGTCGCGATGG 2280
          T  R  A  R  T  N  E  A  A  P  G  E  P  V  A  V  V  A  M  A

2281 CCTGCCCGGCTGCCCGGGGTGTGAGCACCCCGGAGGAGTTCTGGGAGCTGCTGTCGGAGG 2340
          C  R  L  P  G  G  V  S  T  P  E  E  F  W  E  L  L  S  E  G

2341 GCCGCGACGCGGTCGCCGACTGCGGACCGACGAGCCTGGGACTCGCTGTTCC 2400
```

FIG. 2-7

```
        R  D  A  V  A  G  L  P  T  D  R  G  W  D  L  D  S  L  F  H  -
     ACCCCGACCCCACGCGCTCGGGCTGCCAACCGGCACCAGCGCGGGGCGGGTTTCCTGACCGAGG
2401 ----------+---------+---------+---------+---------+---------+ 2460

P  D  P  T  R  S  G  T  A  H  Q  R  G  G  G  F  L  T  E  A  -
     CGACCGCGTTCGACCCGGCCTTCTTCGGCATGTCCCCGCGAGGCGCTGGCCGTCGACC
2461 ----------+---------+---------+---------+---------+---------+ 2520

T  A  F  D  P  A  F  F  G  M  S  P  R  E  A  L  A  V  D  P  -
     CGCAGCAGCGGGCTCATGCTCGAGCTCTCCTGGGAAGTGCTGGAACGGGCGGGAATCCCGC
2521 ----------+---------+---------+---------+---------+---------+ 2580

Q  Q  R  L  M  L  E  L  S  W  E  V  L  E  R  A  G  I  P  P  -
     CGACCTCGTTGCAGGCCCTCGCCCACTGGGCCTGTGTTCGTTCGGCCTGATCCCGCAGGAGTACG
2581 ----------+---------+---------+---------+---------+---------+ 2640

T  S  L  Q  A  S  P  T  G  V  F  V  G  L  I  P  Q  E  Y  G  -
     GCCCGGCGGCTGGCCGAGGGCGAGGCGTCGAGGCTACCTGATGACCGGTACGACCA
2641 ----------+---------+---------+---------+---------+---------+ 2700

P  R  L  A  E  G  G  E  G  V  E  G  Y  L  M  T  G  T  T  T  -
     CGAGGCGTCGCCCTCCGGCCATCGCGCCTACACGCTCGGCCTGGAGGGCCCGGATCAGCG
2701 ----------+---------+---------+---------+---------+---------+ 2760
```

FIG. 2-8

```
         S   V   A   S   G   R   I   A   Y   T   L   G   L   E   G   P   A   I   S   V
      TGGACACCGGCGTGCTCGTCCTCGCTGGTCGCTGGTGCACCTGGCGGTGCCAGTCGCTGCGGC
2761  ------+---------+---------+---------+---------+---------+  2820

D   T   A   C   S   S   L   V   A   V   H   L   A   C   Q   S   L   R   R
      GCGGGCGAGTGTCGTCGCTGGGCGATGGCAGGCGGTGTCACGGTGATGCCGACGCCCGGCATGC
2821  ------+---------+---------+---------+---------+---------+  2880

G   E   S   S   L   A   M   A   G   G   V   T   V   M   P   T   P   G   M   L
      TGGTGGACTTCAGCCGGATGAACTCGCTGGCCCCGGACGGCCGGTGCAAGGCTTTCTCCG
2881  ------+---------+---------+---------+---------+---------+  2940

V   D   F   S   R   M   N   S   L   A   P   D   G   R   C   K   A   F   S   A
      CCGGCGCCAACGGTTTCGGCATGGCCGAGGGCGCCGGGATGCTCCTGCTGGAGCGGCTTT
2941  ------+---------+---------+---------+---------+---------+  3000

G   A   N   G   F   G   M   A   E   G   A   G   M   L   L   E   R   L   S
      CGGACGCCCGCCGCAACGGCCACCCGGTGCTCGCCGTGCTCAGGGGACGGCGGTCAACT
3001  ------+---------+---------+---------+---------+---------+  3060

D   A   R   R   N   G   H   P   V   L   A   V   L   R   G   T   A   V   N   S
      CCGACGGCCGAGCAACGGGCTGTCGGCCCAACGGGCCCAAGGGGCCAGGTGCGGGTCATCC
```

FIG. 2-9

```
3061 AGCAGGGCGCTGGCAGAGTCCGGTCTCGGGCCCGCCGACATCGACGCCGTCGAGGCGCACG 3120
        D  G  A  S  N  G  L  S  A  P  N  G  R  A  Q  V  R  V  I  Q

3121 GCACCGGTACCCGACTCGGGCGACCCGATCGAGGCGCGGGCGCTGTTCGAGGCGTACGGGC 3180
        Q  A  L  A  E  S  G  L  G  P  A  D  I  D  A  V  E  A  H  G

3181 GCGACCGCGAGCAGCCGCTGCACCTGGGCTCGGTCAAGTCCAACCTCGGCCACACCCAGG 3240
        T  G  T  R  L  G  D  P  I  E  A  R  A  L  F  E  A  Y  G  R

3241 CGGCCGCCGGTGTTGCCGGGGTGATCAAGATGGTGCTGGCGATGCGCGGCACCCTTC 3300
        D  R  E  Q  P  L  H  L  G  S  V  K  S  N  L  G  H  T  Q  A

3301 CCCGCACTCTGCACGCATCGAGCGGTCGAAGGAGATCGACTGGTCATCCGGTGCGATCA 3360
        A  A  G  V  A  G  V  I  K  M  V  L  A  M  R  A  G  T  L  P 3361                                                              3420
        R  T  L  H  A  S  E  R  S  K  E  I  D  W  S  S  G  A  I  S
```

```
3421  GCCTGCTCGACGAGCCGGAGCCGTGGCCCGGCGCGGGCGACCGCGGGCCGGGGGGTCT  3480
          L  L  D  E  P  E  P  W  P  A  G  A  R  P  R  R  A  G  V  S  -

3481  CGTCGTTCGGCATCAGCGGCACCAACGCGCACGCCATCATCGAGGAAGCTCCGCAGGTCG  3540
          S  F  G  I  S  G  T  N  A  H  A  I  I  E  E  A  P  Q  V  V  -

3541  TCGAAGGCGAGCGGGTCGAGGCCGGGGACGTCGTGGCCCCTGGGTGCTTTCGGCGAGCA  3600
          E  G  E  R  V  E  A  G  D  V  V  A  P  W  V  L  S  A  S  S  -

3601  GCGCGGAAGGTCTGCGCGCCCAGGCGGCGGCCCGCCTGCGCGCACCTGCGCGAGCACCCCG  3660
          A  E  G  L  R  A  Q  A  A  A  R  L  A  A  H  L  R  E  H  P  G  -

3661  GTCAGGACCCGCGCGACATCGCTTACTCGCTCGCGACGGGCCGCGCTGCCCCACC  3720
          Q  D  P  R  D  I  A  Y  S  L  A  T  G  R  A  A  L  P  H  R  -

3721  GCGCCCGCCTTCGCCCCCGTCGACGAGTCCGCGGTGCTCGACGGTCTCGCGGA  3780
          A  A  F  A  P  V  D  E  S  A  A  L  R  V  L  D  G  L  A  T  -
```

FIG. 2-10

```
3781  CGGGAAACGCCGACGGTGCCGCCGTTGGAACGAGCCGGCGCAGCGCGCCGTCTTCG
      ----------+---------+---------+---------+---------+---------+  3840
        G  N  A  D  G  A  A  V  G  T  S  R  A  Q  Q  R  A  V  F  V  -

3841  TCTTCCCCGGGCAGGGTTGGCAGTGGGCGCATGGCCGTCGACCTGCTCGACACCTCCC
      ----------+---------+---------+---------+---------+---------+  3900
        F  P  G  Q  G  W  Q  W  A  G  M  A  V  D  L  L  D  T  S  P  -

3901  CGGTTTTCGCAGCCGCGTTGCGCGAGTGCGCCGACGCGCTCGAACCGCATCTGGACTTCG
      ----------+---------+---------+---------+---------+---------+  3960
        V  F  A  A  A  L  R  E  C  A  D  A  L  E  P  H  L  D  F  E  -

3961  AGGTGATCCCGGTTCCTGCGCGGGAAGCCGCGAGGCGGGAGCAGGACGCGGCGCTGTCGA
      ----------+---------+---------+---------+---------+---------+  4020
        V  I  P  F  L  R  A  E  A  A  R  R  E  Q  D  A  A  L  S  T  -

4021  CCGAGCGCGGTGGACGTGGTGCAGCCCGTGATGTTCGCGGTCATGGTCTCGCTGGCGTCGA
      ----------+---------+---------+---------+---------+---------+  4080
        E  R  V  D  V  V  Q  P  V  M  F  A  V  M  V  S  L  A  S  M  -

4081  TGTGGCGAGCCCACGGGGTCGAGCCCGCCGCGGTCATCGGCCACTCCCAGGGCGAGATCG
      ----------+---------+---------+---------+---------+---------+  4140
        W  R  A  H  G  V  E  P  A  A  V  I  G  H  S  Q  G  E  I  A  -
```

```
4141 CCGCCGCGCTGCGTGCGGGGGCGCTCTCGCTGGACGACGCCGCGCGTGGTCGCGCTGC
        A  A  C  V  A  G  A  L  S  L  D  D  A  A  R  V  V  A  L  R  -    4200

4201 GCAGCCGGTCATCGCCACCATGCCCGGGAACAAGGGCATGGCCTCGATCGCCGCTCCGG
        S  R  V  I  A  T  M  P  G  N  K  G  M  A  S  I  A  A  P  A  -    4260

4261 CCGGCGAAGTCCGCGGCGCGAATCGGTGACCGCGTCGAGATCGCCGTCAACGGTCCGC
        G  E  V  R  A  R  I  G  D  R  V  E  I  A  A  V  N  G  P  R  -    4320

4321 GCTCGGTGGTGGTCGCGGGCGACAGCGACGAACTGGACCGGCTGGTCGCTTCCTGCACCA
        S  V  V  V  A  G  D  S  D  E  L  D  R  L  V  A  S  C  T  T  -    4380

4381 CCGAGTGCATCCGCGCCAAGCGGCTGGCCGTGGACTACGCGTCGCACTCCTCGCACGTCG
        E  C  I  R  A  K  R  L  A  V  D  Y  A  S  H  S  S  H  V  E  -    4440

4441 AGACGATCCGAGACGCACTGCACGCCGAGCTGGGAGAGGACTTCCACCCGCTGCCGGGGT
                                                                        4500
```

FIG. 2-13

```
        T   I   R   D   A   L   H   A   E   L   G   E   D   F   H   P   L   P   G   F   -
4501    TCGTGCCCTTCTCTCCACCGGTCACCGGGCGCTGGACGCAGCCGGACGAGCTCGACGCCG     4560

V   P   F   F   S   T   V   T   G   R   W   T   Q   P   D   E   L   D   A   G   -
4561    GGTACTGGTACCGGAACCTGCGCCGCACCGTGCGGTTCGCGGACGCCGTCCGTGCGCTCG     4620

Y   W   Y   R   N   L   R   R   T   V   R   F   A   D   A   V   R   A   L   A   -
4621    CCGAGCAGGGATATCGCACGTTCCTGGAGGTCAGCGCGCACCCGATCCTCACCGCCGCGA     4680

E   Q   G   Y   R   T   F   L   E   V   S   A   H   P   I   L   T   A   A   I   -
4681    TCGAGGAGATCGGGCGACGGATCGGGCGCCTCTCCGCCATCCATTCGTCTGCGCCGCG     4740

E   E   I   G   D   G   S   G   A   D   L   S   A   I   H   S   L   R   R   G   -
4741    GTGACGGCAGCCTCGCGGACTTCGGCGAAGCGCTCTCCCGCGTTCGCGGCCGGGTGTCG     4800

D   G   S   L   A   D   F   G   E   A   L   S   R   A   F   A   A   G   V   A   -
4801    CGGTGGACTGGGAGTCGGTGCACCTGGCACCGGAGCACGCCGGGTGCCCTTGCCCACCT     4860
```

```
              V  D  W  E  S  V  H  L  G  T  G  A  R  R  V  P  L  P  T  Y  -
       ACCCGTTCCAGCGCGAGCGCGTCTGGCTCGAACCGAAGCCGGTGGCGCCGGTCCACCG
4861   ------+---------+---------+---------+---------+---------+  4920

P  F  Q  R  E  R  V  W  L  E  P  K  P  V  A  R  R  S  T  E  -
       AGGTCGACGAGGTTTCCGCGCTGCGCTACCGCATCGAGTGGCGGCCCACCGGTGCCGGTG
4921   ------+---------+---------+---------+---------+---------+  4980

V  D  E  V  S  A  L  R  Y  R  I  E  W  R  P  T  G  A  G  E  -
       AACCCGCCCGGCTCGACGGCACCTGGCTGGTGGCGAAGTACGCCGGAACCGCGGACGAGA
4981   ------+---------+---------+---------+---------+---------+  5040

P  A  R  L  D  G  T  W  L  V  A  K  Y  A  G  T  A  D  E  T  -
       CGAGCACCGCGGGCTCGGAGGCCCTGGAGTCGGCGGGGGCGGTCCGCGAACTGGTCG
5041   ------+---------+---------+---------+---------+---------+  5100

S  T  A  A  R  E  A  L  E  S  A  G  A  R  V  R  E  L  V  V  -
       TGGACGCCCGCTGCGGTGCGCTCGGCGACGAACTCGCGGAGCGGCTTCGTTCGGTCGGAGGTGG
5101   ------+---------+---------+---------+---------+---------+  5160

```
5161  CAGGAGTGCTGTCCCTGCTCGCGGTGGACGAAGCCGAGGAGGCCGCTCGCC  5220
          G  V  L  S  L  L  A  V  D  E  A  E  P  E  E  A  P  L  A  L

5221  TGGCTTCGCTGGGACACGCTCAGCCTCGTGCAGGCGATGGTGTCGGCGAACTCGGAT  5280
          A  S  L  A  D  T  L  S  L  V  Q  A  M  V  S  A  E  L  G  C

5281  GTCCGCTGTGGACGGTGACGGAAAGCGCCGTCGCGACGGGCCGTTCGAACGCGTCCGCA  5340
          P  L  W  T  V  T  E  S  A  V  A  T  G  P  F  E  R  V  R  N

5341  ACGCCGCCCACGGCGCCCTGTGGGGCGTCGGGGGTCATCGCGCTGGAGAACCCCGCCG  5400
          A  A  H  G  A  L  W  G  V  G  R  V  I  A  L  E  N  P  A  V

5401  TGTGGGGCGCCCTGGTCGACGTGCCCGCCGGGTCGGTCGCCGAGCTGGCCCGGCACCTCG  5460
          W  G  L  V  D  V  P  A  G  S  V  A  E  L  A  R  H  L  A

5461  CGGCGGTCGTGTCCGGGGGCGCCGGTGAGGACCAGCTCGCGCTCCGCGCCGACGGGGTGT  5520
          A  V  V  S  G  G  A  G  E  D  Q  L  A  L  R  A  D  G  V  Y
```

FIG. 2-15

```
5521 ACGGACGCCGGTGGGTGCGCGGGCCCCGGCCGATGACGAGTGGAAACCCACCG 5580
      ---------+---------+---------+---------+---------+---------+
       G  R  R  W  V  R  A  A  A  P  A  T  D  D  E  W  K  P  T  G

5581 GAACCGTGCTGGTCACCGGTGGGGCGGTGTCGGGCAGATCGCGCGCTGGCTCG 5640
      ---------+---------+---------+---------+---------+---------+
       T  V  L  V  T  G  G  T  G  G  V  G  G  Q  I  A  R  W  L  A

5641 CCCGGGCGGCGCCCCACCTGCTCGTGGTGAGCCGCAGCCCGGACGGCGACGGCG 5700
      ---------+---------+---------+---------+---------+---------+
       R  R  G  A  P  H  L  L  V  S  R  S  G  P  D  A  D  G  A

5701 CCGGCGAACTGGTCGCCGAGCTCGGGTTCGGCGGCGCTGCTCGGGCCTGCG 5760
      ---------+---------+---------+---------+---------+---------+
       G  E  L  V  A  E  L  E  A  L  G  A  R  T  T  V  A  A  C  D

5761 ACGTGACCGACCGGGAGTCGGTTCGGCGAGCTGCTCGGCGCATCGGTGACGACGTCCCGC 5820
      ---------+---------+---------+---------+---------+---------+
       V  T  D  R  E  S  V  R  E  L  L  G  G  I  G  D  D  V  P  L

5821 TCTCGGGGTGTTCCACGCCGCCACGCGCTCGACGGCACCGTGGACACCCTCACCG 5880
      ---------+---------+---------+---------+---------+---------+
```

FIG. 2-16

```
        S   A   V   F   H   A   A   A   T   L   D   D   G   T   V   D   T   L   T   G   -
5881    GCGAGCGCATCGAGCGGGGCAAGTCGCGCCAAGGTGCTCGGCGCGCAACCTGCACGAGC        5940
        ------+---------+---------+---------+---------+---------+

E   R   I   E   R   A   S   R   A   K   V   L   G   A   R   N   L   H   E   L   -
5941    TGACGGCGCGAGCTGGACCTGACCGCCCTTCGTCGTGTTCTCGTCCTTCGCCTTCG            6000
        ------+---------+---------+---------+---------+---------+

T   R   E   L   D   L   T   A   F   V   L   F   S   S   F   A   S   A   F   G   -
6001    GCGCCCCCGGGCTCGGCGGCTACGCGCCCGGCAACGCCTACCTCGACGGCCTCGCCCAGC       6060
        ------+---------+---------+---------+---------+---------+

A   P   G   L   G   G   Y   A   P   G   N   A   Y   L   D   G   L   A   Q   Q   -
6061    AGCGGCGAGCGACGGACTCCCCGCGACCGCGTGGCCGTGGGGACGTGGGGCGGCAGCG         6120
        ------+---------+---------+---------+---------+---------+

R   R   S   D   G   L   P   A   T   A   V   A   W   G   T   W   A   G   S   G   -
6121    GGATGGCCGAAGGCGCGGGTGGCCCGACCGCTTCCGCAGGCACGCGTCATCGAGATGCCTC      6180
        ------+---------+---------+---------+---------+---------+

M   A   E   G   A   V   A   D   R   F   R   R   H   G   V   I   E   M   P   P   -
6181    CCGAGACGGCCTGCCGGCGTTGCAGAACGCGCTGGACCGCGAGGTCTGCCCGATCG           6240
        ------+---------+---------+---------+---------+---------+
```

```
      E  T  A  C  R  A  L  Q  N  A  L  D  R  A  E  V  C  P  I  V
6241  TCATCGACGTCAGGTGGGACCGGTTCCTGCTCGCCTACACCGGCCAGCGCCCGACCAGC  6300

I  D  V  R  W  D  R  F  L  L  A  Y  T  A  Q  R  P  T  R  L
6301  TCTTCGACGAGATCGACGACGCGCGGGCTGCGCCCGCAGGCGCCGGAACCGGCGGG     6360

F  D  E  I  D  D  A  R  R  A  A  P  Q  A  P  A  E  P  R  V
6361  TGGGCGCGCTGGCGTCGCTGCCCGGCGTCGCCGGAGCCGGAGGAAGCGCTGTTCGAGCTCGTGC  6420

G  A  L  A  S  L  P  A  P  E  R  E  E  A  L  F  E  L  V  R
6421  GCTCGCACGCGGCCGCCGTCCTCGGCCACGCCTCGGCGAGCCGGGTGCCCGCGACCAGG  6480

S  H  A  A  A  V  L  G  H  A  S  A  E  R  V  P  A  D  Q  A
6481  CCTTCGCGGAACTCGGCGTCGACTCGGCTCGTGTCGGCGCTTGAGCTGCGGCAACCGGCTCGGGCG  6540

F  A  E  L  G  V  D  S  L  S  A  L  E  L  R  N  R  L  G  A
      CCGCGACCGGTGTCCGCCTGCGACGACGACCGTCTTCGACCACCCCGACGTGCCGGACGC
```

```
6541  ------+---------+---------+---------+---------+---------+  6600
            A  T  G  V  R  L  P  T  T  V  F  D  H  P  D  V  R  T  L

TGGCGGGCCACCTGGCCCGCCGGAACTCGGGCGGTGCCGAGCAGGCCACCGG
6601  ------+---------+---------+---------+---------+---------+  6660
            A  A  H  L  A  A  E  L  G  G  A  T  G  A  E  Q  A  A  P  A

CGACCACGGCCCCCGTCGACGAGCCGATCGCGTCGGCATGGCGTGCCGCTGCCCG
6661  ------+---------+---------+---------+---------+---------+  6720
            T  T  A  P  V  D  E  P  I  A  I  V  G  M  A  C  R  L  P  G

GGGAGGTCGACTCCCCGGAGCGGCTGTGGGAGCTGATCACCTCGGGACGCGACTCCGCGG
6721  ------+---------+---------+---------+---------+---------+  6780
            E  V  D  S  P  E  R  L  W  E  L  I  T  S  G  R  D  S  A  A

CGGAGGTCCCCGATGACCGGGGCTGGGTCCCCGACGAGCTGATGGCCTCCGACGCGGGCGG
6781  ------+---------+---------+---------+---------+---------+  6840
            E  V  P  D  D  R  G  W  V  P  D  E  L  M  A  S  D  A  A  G

GAACCCGGCGCCACGGCAACTTCATGGCGGGCCGGTGACTTCGACGCGGCGGTTCTTCG
6841  ------+---------+---------+---------+---------+---------+  6900
            T  R  A  H  G  N  F  M  A  G  A  G  D  F  D  A  A  F  F  G
```

FIG. 2-19

```
6901 GGATCTCGCCGCGGAGGCGCTGGCGATGGACCCGCAGCAGCGCCAGGCGCTGGAGACGA 6960
       I  S  P  R  E  A  L  A  M  D  P  Q  Q  R  Q  A  L  E  T  T  -

6961 CGTGGGAGGCGCTGGAAAGCGCGGGCATCCCCACCGGAGACGTTGCGCGGCAGCGACACCG 7020
       W  E  A  L  E  S  A  G  I  P  P  E  T  L  R  G  S  D  T  G  -

7021 GCGTGTTCGTCGGCATGTCCCACCAGGGCTACGCGACCGGCCGTCCCCGCCCGGAGGACG 7080
       V  F  V  G  M  S  H  Q  G  Y  A  T  G  R  P  R  P  E  D  G  -

7081 GCGTCGACGGGTACCTGCTCACCGGCAACACCGCGAGCGTCGGGACGCATCGCCT 7140
       V  D  G  Y  L  L  T  G  N  T  A  S  V  A  S  G  R  I  A  Y  -

7141 ACGTGCTGGGGCTGGAAGGTCCCGCGCTGACGGTGGACACGGCGTGTTCGTCGTCGTTGG 7200
       V  L  G  L  E  G  P  A  L  T  V  D  T  A  C  S  S  S  L  V  -

7201 TGGCCGTTGCACACGGCGTGTGGGTCGTTGCGTGACGGTGACTGCGGTCTTGCGGTGCCG 7260
       A  L  H  T  A  C  G  S  L  R  D  G  D  C  G  L  A  V  A  G  -
```

FIG. 2-20

```
7261  GTGGTGTGTCGGTGATGGCGGGTCCGGAGGTGTTCACCGAGTTCTCCCGCCAGGGCGCGC
      ------+---------+---------+---------+---------+---------+ 7320
         G  V  S  V  M  A  G  P  E  V  F  T  E  F  S  R  Q  G  A  L  -

7321  TCTCGCCGGACGGCCGGTGCAAGCCCTTCTCGGACGAGGCCGACGGATTCGGTCTCGGGG
      ------+---------+---------+---------+---------+---------+ 7380
         S  P  D  G  R  C  K  P  F  S  D  E  A  D  G  F  G  L  G  E  -

7381  AGGGTTCGGCGTTCGTCGTGCTCCAGCGGTTGTCCGACGCCAGGCGGGAGGGCCGCCGCG
      ------+---------+---------+---------+---------+---------+ 7440
         G  S  A  F  V  V  L  Q  R  L  S  D  A  R  R  E  G  R  R  V  -

7441  TGCTCGGCGTGGTCGGGCCGGGTCCGGTGAACCAGGACGGCGAGCAACGGGCTCTCCG
      ------+---------+---------+---------+---------+---------+ 7500
         L  G  V  V  A  G  S  A  V  N  Q  D  G  A  S  N  G  L  S  A  -

7501  CTCCGAGCGGTCGCGCAGCAGCGGGTCATCCGCCGGGCGTGGGCGTGCGGGATCA
      ------+---------+---------+---------+---------+---------+ 7560
         P  S  G  V  A  Q  Q  R  V  I  R  R  A  W  A  R  A  G  I  T  -

7561  CGGGCGCGGATGTGGCCGTGGTGGAGGCGCATGGACCGGTACGCGGTGGGCTGGATCCGG
      ------+---------+---------+---------+---------+---------+ 7620
         G  A  D  V  A  V  V  E  A  H  G  T  G  T  R  L  G  D  P  V  -
```

```
7621 TGGAGGCGTCGGCGTTGCTGGCTACTTACGGCAAGTCGCGCGGGTCGTCGGGCCCGGTGC
     ----+----+----+----+----+----+----+----+----+----+----+----+ 7680
      E  A  S  A  L  L  A  T  Y  G  K  S  R  G  S  S  G  P  V  L

7681 TGCTGGGGTTCGGTGAAGTCGAACATCGGTCACGCGCAGGCCGCGGGTGTCGCGGGGGCG
     ----+----+----+----+----+----+----+----+----+----+----+----+ 7740
      L  G  S  V  K  S  N  I  G  H  A  Q  A  A  A  G  V  A  G  V

7741 TGATCAAGGTGCTGCTCGGCCTGGAACGCGGTGTGGTGCCCCCGATGCTGTGCCGGGGCG
     ----+----+----+----+----+----+----+----+----+----+----+----+ 7800
      I  K  V  L  L  G  L  E  R  G  V  V  P  P  M  L  C  R  G  E

7801 AGAGGTCGGGCCTCATCGACTGGTCCTCCGGCGAGATCGAGCTCGCAGACGGCGTGCGGG
     ----+----+----+----+----+----+----+----+----+----+----+----+ 7860
      R  S  G  L  I  D  W  S  S  G  E  I  E  L  A  D  G  V  R  E

7861 AGTGGTCGCCCGCCGCGGACGGGGTGCGCCGCGCCGGGGTGTCGGCGTTCGGGGTGAGCG
     ----+----+----+----+----+----+----+----+----+----+----+----+ 7920
      W  S  P  A  A  D  G  V  R  R  A  G  V  S  A  F  G  V  S  G

7921 GGACGAACGCGCACGTGATCATCGCCGAGCCCGGAACCGGAGCCCGTGCCGCAACCGC
     ----+----+----+----+----+----+----+----+----+----+----+----+ 7980
```

```
         T   N   A   H   V   I   I   A   E   P   P   E   P   V   P   Q   P   R
7981  GACGCATGCTGCCCCGCGACCGGGGTGTGCCGGTCGTGTCGGCCAGGACCGGGGCGG
      ---------+---------+---------+---------+---------+---------+  8040

R   M   L   P   A   T   G   V   V   P   V   V   L   S   A   R   T   G   A   A
8041  CGTTGCGGGGCGCAGGCCGGCAGGCTCGCCGACCACCTCGCCGCCATCCCGGATCGCAC
      ---------+---------+---------+---------+---------+---------+  8100

L   R   A   Q   A   G   R   L   A   D   H   L   A   A   H   P   G   I   A   P
8101  CGGCCCGAGCGTGAGCTGGACGATGGCCCGCCAGCACTTCGAGGAGCGGCCGCGG
      ---------+---------+---------+---------+---------+---------+  8160

A   D   V   S   W   T   M   A   R   Q   H   F   E   E   R   A   A   V
8161  TGCTCGCCGCCGACACCGGCCGAGGCCGTGCACCGGTTGCGCGGCCGACGGCGCGG
      ---------+---------+---------+---------+---------+---------+  8220

L   A   A   D   T   A   E   A   V   H   R   L   R   A   V   A   D   G   A   V
8221  TGGTTCCCGGTGTTGTCACCGGCCTCCGACGGTCGTTCAGTGTTCGTCTCCCTG
      ---------+---------+---------+---------+---------+---------+  8280

V   P   G   V   V   T   G   S   A   S   D   G   G   S   V   F   V   F   P   G
8281  GGCAGGGTGCCCAGTGGGAAGGCATGGCGCGGGAGTTGTTGCCGGTTCCCGTCTTCGCCG
      ---------+---------+---------+---------+---------+---------+  8340
```

FIG. 2-23

```
      Q  G  A  Q  W  E  G  M  A  R  E  L  L  P  V  P  V  F  A  E  -
      AGTCGATCGCCGAGTGCGATGCGGGTTGTCGGAGGTGGCCGGATTCTCGGTGTCCGAGG
8341  ---------+---------+---------+---------+---------+---------+  8400

S  I  A  E  C  D  A  V  L  S  E  V  A  G  F  S  V  S  E  V  -
      TGCTGGAGCCACGTCCGGACGCGCCGTCGCTGGAGGTCGACGTGGTGCAGCCGGTGC
8401  ---------+---------+---------+---------+---------+---------+  8460

L  E  P  R  P  D  A  P  S  L  E  R  V  D  V  V  Q  P  V  L  -
      TGTTCGCGGTGATGGTGTCGCTGGCGCGGTTGTGCCTGCCGGTGCCGTTCCTTCGG
8461  ---------+---------+---------+---------+---------+---------+  8520

F  A  V  M  V  S  L  A  R  L  W  R  A  C  G  A  V  P  S  A  -
      CCGTCATAGGGCACTCGCAGGGTGAGATCGCCGCCGCCGTGGTGGCGGAGCCGTTGTCGC
8521  ---------+---------+---------+---------+---------+---------+  8580

V  I  G  H  S  Q  G  E  I  A  A  A  V  V  A  G  A  L  S  L  -
      TGGAGGACGGCATGCGCGTCGTCGCCCGCCGGTCGAGGGCGTGCGTCGGGGCC
8581  ---------+---------+---------+---------+---------+---------+  8640

```
8641  GGGGAGCATGCTCTCGGTGCGCGGGCCGCTCCGACGTCGAGAAGCTGCTCGCCGACG  8700
           G  S  M  L  S  V  R  G  G  R  S  D  V  E  K  L  L  A  D  D

8701  ACAGCTGGACCGGCAGGCTGGAGGTCGCCGCGGTCAACGGCCCCGACGCCGTGGTGG  8760
           S  W  T  G  R  L  E  V  A  A  V  N  G  P  D  A  V  V  V  A

8761  CCGGTGACGCCCAGGCGGCGCGAGTTCCTCGAGTACTGCGAGGGCGTGGGCATCCGCG  8820
           G  D  A  Q  A  A  R  E  F  L  E  Y  C  E  G  V  G  I  R  A

8821  CCCGCGGCGATCCCGGTGGACTACGCCTCGCACACCGCGCACGTCGAGCCCGTGCCGACG  8880
           R  A  I  P  V  D  Y  A  S  H  T  A  H  V  E  P  V  R  D  E

8881  AACTGGTCCAGGCGCTGGCCGGGATCACCCCGCGACGGGCCGAGGTGCCGTTCTTCTCCA  8940
           L  V  Q  A  L  A  G  I  T  P  R  R  A  E  V  P  F  F  S  T

8941  CCCTGACCGGCGACTTCCTCGACGGCACCGAGCTGGACGCGGGCTACTGGTACCGCAACC  9000
           L  T  G  D  F  L  D  G  T  E  L  D  A  G  Y  W  Y  R  N  L
```

```
9001  TGCGTCACCCGGTGGAGTTCCACTCCGCCGTGCAGGCCGCTGACCGACCAGGGATACGCGA  9060
      ------+---------+---------+---------+---------+---------+----
       R  H  P  V  E  F  H  S  A  V  Q  A  L  T  D  Q  G  Y  A  T

9061  CGTTCATCGAGGTCAGCCCGCACCCCGGTGTCGCTGGCGTCCAGGAGACCCTCGACG     9120
      ------+---------+---------+---------+---------+---------+----
       F  I  E  V  S  P  H  P  V  L  A  S  S  V  Q  E  T  L  D  D

9121  ACGCCGAGTCGGACGCGGCGGTGCTCGGGACGCTGGAACGCGACGCGGGCGACGCCGACC  9180
      ------+---------+---------+---------+---------+---------+----
       A  E  S  D  A  A  V  L  G  T  L  E  R  D  A  G  D  A  D  R

9181  GCTTCCTCACGGCACTCGCCGACGCGCACACGCGCGGTGTCGCGGTCGACTGGGAAGCGG  9240
      ------+---------+---------+---------+---------+---------+----
       F  L  T  A  L  A  D  A  H  T  R  G  V  A  V  D  W  E  A  V

9241  TGCTCGGGCCTGGGCTACCCGTTCCAGGGCAAGCGGTTCT                      9300
      ------+---------+---------+---------+---------+---------+----
       L  G  R  A  G  L  V  D  L  P  G  Y  P  F  Q  G  K  R  F  W

9301  GGCTGCTGCCGGACCGCACCACCCCTCGTGACGAGCTCGACGGCTGGTTCTACCGGGTCG  9360
      ------+---------+---------+---------+---------+---------+----
```

```
       L  L  P  D  R  T  T  P  R  D  E  L  D  G  W  F  Y  R  V  D
       ACTGGACCGAGGTGCCGCGCGTTCCGAACCTGGAGCTGGACGGCTGGTTCTACCGCGTCGTGGACC  9420
9361   ---------+---------+---------+---------+---------+---------+

W  T  E  V  P  R  S  E  P  A  A  L  R  G  R  W  L  V  V
       TGCCCGAGGGCACGAGGAGGACGGCTGGACCGAGGTGCCGCGCTCGGAGCCGGCCGCTCTGCGCGGGCGCTGGCTCGTCGTCG  9480
9421   ---------+---------+---------+---------+---------+---------+

P  E  G  H  E  E  D  G  W  T  V  E  V  R  S  A  L  A  E  A
       CCGGAGGGGCACGAGGAGGACGGCTGGACCGTCGAGGTGCGCTCGGCGCTGGCGGAGGCG  9540
9481   ---------+---------+---------+---------+---------+---------+

G  A  E  P  E  V  T  R  G  V  G  G  L  V  G  D  C  A  G  V
       GGCGCCGAGCCCGAGGTCACGCGCGGCGTCGGCGGGCTGGTCGGCGACTGCGCGGGCGTG  9600
9541   ---------+---------+---------+---------+---------+---------+

V  S  L  L  A  L  E  G  D  D  G  A  V  Q  T  L  V  L  V  R  E
       GTGTCGCTGCTCGCCCTCGAGGGCGATGGCGCGGTGCAAACCCTGGTCCTCGTGCGGGAG  9660
9601   ---------+---------+---------+---------+---------+---------+

L  D  A  E  G  I  D  A  P  L  W  T  V  T  F  G  A  V  D  A
       CTCGACGCCGAGGGCATCGACGCGCCACTGTGGACGGTCACCTTCGGCGCGGTCGACGCG  9720
9661   ---------+---------+---------+---------+---------+---------+
```

FIG. 2-27

```
        G  S  P  V  A  R  P  D  Q  A  K  L  W  G  L  G  Q  V  A  S
        CCCTGGAACGCGGGCCCCGCTGGACCGGGCCTCGTCGACCTGCCGCACATGCCGGACCCGG
9721    ------+---------+---------+---------+---------+---------+  9780
                 L  E  R  G  P  R  W  T  G  L  V  D  L  P  H  M  P  D  P  E
        AACTGCGAGGCCGTCTCACCGGGTCTGGCCGGTGCTCGGAGGACCAGGTCGCGGTGCGCG
9781    ------+---------+---------+---------+---------+---------+  9840
                 L  R  G  R  L  T  A  V  L  A  G  S  E  D  Q  V  A  V  R  A
        CCGACGCCGTGCGTGCCGGGCGGCTTTCCCCGCCACGTCACCGCCACCTCGGAGTACG
9841    ------+---------+---------+---------+---------+---------+  9900
                 D  A  V  R  A  R  R  L  S  P  A  H  V  T  A  T  S  E  Y  A
        CGGTGCCGGCGGCACAATCCTGGTCACCGGTGGCACCGCCGGGCCTGGGCGCGGAGGTGG
9901    ------+---------+---------+---------+---------+---------+  9960
                 V  P  G  G  T  I  L  V  T  G  G  T  A  G  L  G  A  E  V  A
        CCCGGTGGCTCGCCGGCGCCGGCGAACACCTCGCGCTGGTCAGCCGGAGGCCCGG
9961    ------+---------+---------+---------+---------+---------+  10020
                 R  W  L  A  G  R  G  A  E  H  L  A  L  V  S  R  R  G  P  D
        ACACCGAGGGCGTCGGCCGACCTGACCGCCGAGCTGACCCGGCTCGGCCGCGGGTGTCGG
```

```
10021 TGCACGGCGTGCGACGTCAGCAGCCGCGAACCGGTGAGGAACTCGTGCACGGCCTGATCG 10080
        T  E  G  V  G  D  L  T  A  E  L  T  R  L  G  A  R  V  S  V

10081 AGCAGGGCGACGTCGTCCGGGTGTGGTGCACGCGGGACTGCCGCAGCAGGTCGCGA 10140
        H  A  C  D  V  S  S  R  E  P  V  R  E  L  V  H  G  L  I  E

10141 TCAACGACATGGACGAGGCCGCCTTCGACGAGGTGGTCGCGGCCAAGGCCGGGGCGCGG 10200
        Q  G  D  V  V  R  G  V  V  H  A  A  G  L  P  Q  Q  V  A  I

10201 TGCACCTGGACGAGCTGTGCTCGGACGCCGAGCTGTTCCTGCTGTTCTCCTCCGGGGCCG 10260
        N  D  M  D  E  A  A  F  D  E  V  V  A  A  K  A  G  G  A  V

10261 GGGTGTGGGGAAGCGCCCGCCAGGGCGCCTACGCCGCGGCAACGCGTTCCTGGACGCCT 10320
        H  L  D  E  L  C  S  D  A  E  L  F  L  L  F  S  S  G  A  G 10321                                                            10380
        V  W  G  S  A  R  Q  G  A  Y  A  A  G  N  A  F  L  D  A  F
```

```
10381  TCGCCCGGCACCGCCGGGGCCGCGGGCCCTGCCCGCCACGTCGTTGGGGTGTGGGGCTGTGGG
       ---------+---------+---------+---------+---------+---------+ 10440
        A  R  H  R  R  G  R  G  L  P  A  T  S  V  A  W  G  L  W  A

10441  CGGCGGCGGCATGACCGGCGACGAGGAGGCCGTGTCGTTCCTGCGCGAGCGCGGTGTGC
       ---------+---------+---------+---------+---------+---------+ 10500
        A  G  G  M  T  G  D  E  E  A  V  S  F  L  R  E  R  G  V  R

10501  GGGCGATGCCCGTACCGCGGCCCTGGCCGCGCTGGACAGGGTGCTGGCCTCCGGGGAGA
       ---------+---------+---------+---------+---------+---------+ 10560
        A  M  P  V  P  R  A  L  A  A  L  D  R  V  L  A  S  G  E  T

10561  CGGCGGTGGTCGTGACGGACGTGGACTGGCCCGCCTTCGCCGAGTCCTACACCGCGCCC
       ---------+---------+---------+---------+---------+---------+ 10620
        A  V  V  V  T  D  V  D  W  P  A  F  A  E  S  Y  T  A  A  R

10621  GGCCCCGGCCGTTGCTCGACCGCATCGTCACGACCGCCCCGAGCGAGCCCGGAGAAC
       ---------+---------+---------+---------+---------+---------+ 10680
        P  R  P  L  L  D  R  I  V  T  T  A  P  S  E  R  A  G  E  P

10681  CGGAGACGGAGAGCCTGCGCGACCGGCTGGCCGGGCTCTGCCGAGCGGACGGGCGG
       ---------+---------+---------+---------+---------+---------+ 10740
        E  T  E  S  L  R  D  R  L  A  G  L  P  R  A  E  R  T  A  E
```

FIG. 2-30

```
10741 AGCTGGTGCGGCCTGGTCCGGCACCAGCACCGGCGACCGTGCTGGGCCACGACGACCCGAAGG
      ----+----|----+----|----+----|----+----|----+----|----+----|  10800
       L  V  R  L  V  R  T  S  T  A  T  V  L  G  H  D  D  P  K  A  -

10801 CGGTGCGGCGACCACCGCCGTTCAAGGAGCTCGGGTTCGACTCGCTGGCGGCCGTCCGGC
      ----+----|----+----|----+----|----+----|----+----|----+----|  10860
       V  R  A  T  T  P  F  K  E  L  G  F  D  S  L  A  A  V  R  L  -

10861 TGCGCAACCTGCTCAACGCGGCCACCGGCCTCCGCCTGCCGTCGACGCTGGTCTTCGACC
      ----+----|----+----|----+----|----+----|----+----|----+----|  10920
       R  N  L  L  N  A  A  T  G  L  R  L  P  S  T  L  V  F  D  H  -

10921 ACCCGAACGCCTCCGCGGTCGCGGTTCCTCGACGCCGAGCTCGGCACCGAGGTCCGGG
      ----+----|----+----|----+----|----+----|----+----|----+----|  10980
       P  N  A  S  A  V  A  G  F  L  D  A  E  L  G  T  E  V  R  G  -

10981 GGGAGGCCGTCGGCCCTCGCGGGCTGGACGCGCTGGAAGGCGCCCTGCCCGAGGTGC
      ----+----|----+----|----+----|----+----|----+----|----+----|  11040
       E  A  P  S  A  L  A  G  L  D  A  L  E  G  A  L  P  E  V  P  -

11041 CCGCAACCGAGCGGGAAGAGCTGGTACAGCGCTTGGAACGGATGCTCGCCGCTACGCC
      ----+----|----+----|----+----|----+----|----+----|----+----|  11100
       A  T  E  R  E  E  L  V  Q  R  L  E  R  M  L  A  A  L  R  P  -
```

```
11101 CGGTCGCCCAGGCCGCCGACGCCTCCGGGACCGGCCAACCCGTCCGGGACGACCTGG 11160
            V  A  Q  A  A  D  A  S  G  T  G  A  N  P  S  G  D  D  L  G

11161 GCGAGGCGGTGGACGAACTGCTCGAAGCACTCGGCCGGGAGCTCGACGGCGATTGA 11219
            E  A  G  V  D  E  L  L  E  A  L  G  R  E  L  D  G  D  *

12643 CCGCCGATTGGAGAAAAGGTGACTGACAGCGAGAAGGTGGCGAGTACCTCCGTCGGGCG 12702
                  V  T  D  S  E  K  V  A  E  Y  L  R  R  A

12703 ACGCTCGACCTGCGCGTGCCCGGGCAGGCCGCATCCGCGAGCTGGAATCCGACCCGATCGCC 12762
            T  L  D  L  R  A  A  R  Q  R  I  R  E  L  E  S  D  P  I  A

12763 ATCGTCAGCATGGCCTGCCGCCTGCCCGGGGGTGAACACCCCGCAGCGGCTGTGTGGGAG 12822
            I  V  S  M  A  C  R  L  P  G  G  V  N  T  P  Q  R  L  W  E

CTGCTGCCGAGGGCGGTGAGACGCTGTCGGGCTTCCCCACCGACCGGGGCTGGGACCTG
```

```
12823  ------+---------+---------+---------+---------+---------+  12882
            GCGGGGCTGCACCACCCCGGAGACAACCCCGGTACCAGCTACGTCGACAAGGGCGGG
       L  L  R  E  G  G  E  T  L  S  G  F  P  T  D  R  G  W  D  L

12883  ------+---------+---------+---------+---------+---------+  12942
            TTCCTCGACGACGCGGGGCTTCGACGCGGAGTTCTTCGGCGTCTCGCCGCGAGGCC
       A  R  L  H  H  P  D  P  D  N  P  G  T  S  Y  V  D  K  G  G

12943  ------+---------+---------+---------+---------+---------+  13002
            GCGGCCATGGACCCCGCAGCAGCGGCTGCTGGAGACGAGCTGGTGGAGAAC
       F  L  D  D  A  A  G  F  D  A  E  F  F  G  V  S  P  R  E  A

13003  ------+---------+---------+---------+---------+---------+  13062
            GCCGGGCATCGACCCGCACTCGCTGCGCGGTACCGCGACCGGCGTCTTCCTCGGAGTGGCG
       A  A  M  D  P  Q  Q  R  L  L  L  E  T  S  W  E  L  V  E  N

13063  ------+---------+---------+---------+---------+---------+  13122
            AAGTTCGGCTACGGCGAGGACACCGCGGCGGCGGAGGACGTCGAGGGCTACTCGGTCACC
       A  G  I  D  P  H  S  L  R  G  T  A  T  G  V  F  L  G  V  A

```
13183  GGTGTGGCGCCCGCGGTCGCCTCCGGCCGCATCTCCTACACCATGGGCCTGGAGGGGCCG  13242
          ---------+---------+---------+---------+---------+---------+
        G  V  A  P  A  V  A  S  G  R  I  S  Y  T  M  G  L  E  G  P

13243  TCGATCAGCGTCGACACCGCGTGCTCGTCGTCGCTGGTGGCGCTGCACCTGGCGGTCGAG  13302
          ---------+---------+---------+---------+---------+---------+
        S  I  S  V  D  T  A  C  S  S  S  L  V  A  L  H  L  A  V  E

13303  TCGCTGCGCAAGGGCGAGTCGTCGATGGCGGTCGTCGGCGGTGCCGGTGATGGCGACC  13362
          ---------+---------+---------+---------+---------+---------+
        S  L  R  K  G  E  S  S  M  A  V  V  G  G  A  A  V  M  A  T

13363  CCGGGGGGTGTTCGTCGACTTCAGCCGGCAGCGCGCCCGGCTCGCCGACGGGCGGTCGAAG  13422
          ---------+---------+---------+---------+---------+---------+
        P  G  V  F  V  D  F  S  R  Q  R  A  L  A  A  D  G  R  S  K

13423  GCGTTCGGTGCCGGTGCCGACGGGTTCGGCTTCTCCGAAGGCGTCACCCTGGTCCTGCTC  13482
          ---------+---------+---------+---------+---------+---------+
        A  F  G  A  G  A  D  G  F  G  F  S  E  G  V  T  L  V  L  L

13483  GAGCGGCTGTCGGAGGCGCGGCGGAACGGGCACGAGGTGCTGGCGGTTCGGGGCTCG  13542
          ---------+---------+---------+---------+---------+---------+
        E  R  L  S  E  A  R  R  N  G  H  E  V  L  A  V  V  R  G  S
```

```
13543 GCGCTCAACCAGGAGACGGGGGCCAGCAACGGGCTTTCCGCGCGAGCGGGCCCGGCAGCGC 13602
       A  L  N  Q  D  G  A  S  N  G  L  S  A  P  S  G  P  A  Q  R

13603 AGGGTCATCCGGCAGGCCCTCGAGAGCTGGGGTCTGGAGCCCGGCGACGTCGACGCGGTG 13662
       R  V  I  R  Q  A  L  E  S  C  G  L  E  P  G  D  V  D  A  V

13663 GAGGCGCACGGCACCGGTACGGGCTCTCGGCGCCCGATCGAGGCGAACGCGCTGCTGGAC 13722
       E  A  H  G  T  G  T  A  L  G  D  P  I  E  A  N  A  L  L  D

13723 ACCTACGGCCGCGACCGCGCCGACCGGCCGCTCTGGCTCGGTGAAGTCCAAC 13782
       T  Y  G  R  D  R  D  A  D  R  P  L  W  L  G  S  V  K  S  N

13783 ATCGGCCACACCCAGGCGGCAGCGGCGGGCGTCACCGGCCTGCTGAAGGTGGTCCTGGCTG 13842
       I  G  H  T  Q  A  A  A  G  V  T  G  L  L  K  V  V  L  A  L

13843 CGCAACGGGGAACTGCCCGCGACCCTGCACGTCGAGGAGCCCACGCCCCACGTCGACTGG 13902
       R  N  G  E  L  P  A  T  L  H  V  E  E  P  T  P  H  V  D  W
```

FIG. 2-36

```
13903  TCGTCCGGCGGCGTGGCGCTGCTGGCGGCAACCAGCCGTGGCGGCGGGGCGAGCGGACT  13962
           S  S  G  G  V  A  L  L  A  G  N  Q  P  W  R  R  G  E  R  T

13963  CGGCGCGCCCGTGTTCCGCGATCAGCGGGACGAATGCCACGTGATCGTCGAG  14022
           R  R  A  R  V  S  A  F  G  I  S  G  T  N  A  H  V  I  V  E

14023  GAAGCTCCTGAGCGCGAGCACCGGGAGACCACCGCGCACGACGGCCGACCGGTTCCGCTG  14082
           E  A  P  E  R  E  H  R  E  T  T  A  H  D  G  R  P  V  P  L

14083  GTGGTGTCCGCGGCGCACGACGGCGTTGCGCAGGCCCAGATCGCCGAGCTG  14142
           V  V  S  A  R  T  T  A  A  L  R  A  Q  A  A  Q  I  A  E  L

14143  CTCGAACGCCCCGGACCTCGCGGGTCGGGCCTGGCCACGACCCGCGCC  14202
           L  E  R  P  D  A  D  L  A  G  V  G  L  G  L  A  T  T  R  A

14203  CGCCACGAGCACCGCGCCGTGGTGGCATCGACCCCGGAGGAAGCCGGTGCCGCGGACTG  14262
```

```
           R  H  E  H  R  A  A  V  V  A  S  T  R  E  E  A  V  R  G  L  -
         CGGGAGATCGCCGCCGGTGCGCCGGTGCCGCGACGGCCGTGGTCGAGGGCGTCACCGAGGTG
14263    ---------+---------+---------+---------+---------+---------+    14322
           R  E  I  A  A  G  A  A  T  A  D  A  V  V  E  G  V  T  E  V  -
         GACGGGCGCAACGTCGTCTTCCTGTTCCCGGGGCAGGGTTCGCAATGGGCCGGCATGGGT
14323    ---------+---------+---------+---------+---------+---------+    14382
           D  G  R  N  V  F  L  F  P  G  Q  G  S  Q  W  A  G  M  G  -
         GCCGAGCTGCTGTCGTCGCCGGTGTTCGCCGGGAAGATCCGGGCCTGCGACGAGTCG
14383    ---------+---------+---------+---------+---------+---------+    14442
           A  E  L  L  S  S  P  V  F  A  G  K  I  R  A  C  D  E  S  -
         ATGGCCCCGATGCAGGACTGGAAGGTCTCCGACGTGCTGCGTCAGGCGCCGGGCGCCG
14443    ---------+---------+---------+---------+---------+---------+    14502
           M  A  P  M  Q  D  W  K  V  S  D  V  L  R  Q  A  P  G  A  P  -
         GGCCTGGACCGGGTCGACGTGGTGCAGCCGGTGTTGTTCGCGGTGATGGTGTCGCTGGCG
14503    ---------+---------+---------+---------+---------+---------+    14562
           G  L  D  R  V  D  V  V  Q  P  V  L  F  A  V  M  V  S  L  A  -
         GAGCTGTGTGGGGCGCTCGTACGGCGTGGAGCCCGGCGTCGTGGGGCACTCGCCAGGGCGAG
14563    ---------+---------+---------+---------+---------+---------+    14622
```

```
          E   L   W   R   S   Y   G   V   E   P   A   A   V   V   G   H   S   Q   G   E
       ATCGCCGCGCGCACGTCGCCGGGCGCTCACGTTGGAGGACGGCGAAGCTCGTG
14623  ---------+---------+---------+---------+---------+---------+  14682
          I   A   A   H   V   A   G   A   L   T   L   E   D   A   A   K   L   V   V

GGCCGCAGCCGCCTGATGCGGTCGCTCTCCGGGGAGGGCGGCATGGCCGCCGTCGCGCTG
14683  ---------+---------+---------+---------+---------+---------+  14742
          G   R   S   R   L   M   R   S   L   S   G   E   G   G   M   A   A   V   A   L

GGCGAGGCCGCGGTGCGCGAGCGCCTGCGCCCGTGGCAGGACCGGCTCTCGGTGGCCGCG
14743  ---------+---------+---------+---------+---------+---------+  14802
          G   E   A   A   V   R   E   R   L   R   P   W   Q   D   R   L   S   V   A   A

GTCAACGGTCCCCGGTCGCGGTGTCGTGGTCTCCGGCGAGCCCGGCGCTGCGGGGTTTTCC
14803  ---------+---------+---------+---------+---------+---------+  14862
          V   N   G   P   R   S   V   V   V   S   G   E   P   G   A   L   R   A   F   S

GAGGACTGCGCGGCCGAGGGCATCCGCGTCCGCGACATCGACGTGGACTACGCCTCGCAC
14863  ---------+---------+---------+---------+---------+---------+  14922
          E   D   C   A   A   E   G   I   R   V   R   D   I   D   V   D   Y   A   S   H
```

```
14923  TCGCCCGAGATCGAGCGGGTCCGCGAGGAACTCCTCGAAACGACCGGCGACATCGCGCCG
       ------+---------+---------+---------+---------+---------+  14982
        S  P  Q  I  E  R  V  R  E  E  L  L  E  T  T  G  D  I  A  P

14983  CGCCGGCGCGGGTGACGTTCCACTCCACTGTGGAGTCGCGGTCTATGGACGGCACCGAG
       ------+---------+---------+---------+---------+---------+  15042
        R  P  A  R  V  T  F  H  S  T  V  E  S  R  S  M  D  G  T  E

15043  CTGGATGCCCGGTACTGGTACCGCAACCTGCGCGAGACGGTGCGCTTCGCCGACGCCGTG
       ------+---------+---------+---------+---------+---------+  15102
        L  D  A  R  Y  W  Y  R  N  L  R  E  T  V  R  F  A  D  A  V

15103  ACGCGGCTGGCCGAGTCGGGGATACGACGCGTTCATCGAGGTCAGCCCGCATCCGGTCGTG
       ------+---------+---------+---------+---------+---------+  15162
        T  R  L  A  E  S  G  Y  D  A  F  I  E  V  S  P  H  P  V  V

15163  GTCCAGGCCGTCGAGGAGGCGGTCGAAGAGGCTGACGGTGCCGAAGACGCGGTCGTAGTC
       ------+---------+---------+---------+---------+---------+  15222
        V  Q  A  V  E  E  A  V  E  E  A  D  G  A  E  D  A  V  V  V

15223  GGCTCGCTGCACCGCGACGGCGGGTGACCTCTCGGCCTTCCTGCGGTCGATGGCCACCGCG
       ------+---------+---------+---------+---------+---------+  15282
        G  S  L  H  R  D  G  G  D  L  S  A  F  L  R  S  M  A  T  A
```

FIG. 2-39

```
         CACGTGTCCGGTGTGGACATCAGGTGGGAGGTCGCTCTGCCCGGGCGCCGGCCCTTCGCG
15283    ------+---------+---------+---------+---------+---------+    15342
         H  V  S  G  V  D  I  R  W  D  V  A  L  P  G  A  A  P  F  A

CTGCCGACGTATCCGTTCCAGCGCAAGCGCTACTGGCTCCAGCCCGCCGCCCCGCCGCC
15343    ------+---------+---------+---------+---------+---------+    15402
         L  P  T  Y  P  F  Q  R  K  R  Y  W  L  Q  P  A  A  P  A  A

GCCTCCGACGAGCTGGCCTACCGCGTTTCCTGGACTCCGATCGAAAAGCCGGAGTCGGGA
15403    ------+---------+---------+---------+---------+---------+    15462
         A  S  D  E  L  A  Y  R  V  S  W  T  P  I  E  K  P  E  S  G

AACCTGGACGGCGACTGGTTGGTTGTCACACCCCTCATCAGTCCGGAGTGGACGGAAATG
15463    ------+---------+---------+---------+---------+---------+    15522
         N  L  D  G  D  W  L  V  V  T  P  L  I  S  P  E  W  T  E  M

CTGTGCGAGGCCATCAACGCCAACGGTGGCAGGGCGTTGCGCTGCGAGGTGGACACGTCC
15523    ------+---------+---------+---------+---------+---------+    15582
         L  C  E  A  I  N  A  N  G  G  R  A  L  R  C  E  V  D  T  S

GCTTCGCGCACTGAGATGGCCCAGGCCCGTCGCACAGGCCCGAACGGGATTCCGGGGCCTG
15583    ------+---------+---------+---------+---------+---------+    15642
```

FIG. 2-40

```
         A  S  R  T  E  M  A  Q  A  V  A  Q  A  G  T  G  F  R  G  V
      CTCTCGTTGCTGTCGTCGGACGAATCCGCCTGCCGTCCGGGGGTTCCTGCCGGTGCGGTC
15643 ------+---------+---------+---------+---------+---------+-- 15702

L  S  L  L  S  S  D  E  S  A  C  R  P  G  V  P  A  G  A  V
      GGCCTGCTCACCCTGGTCCAGGGCGCTGGGGCGCTGGGATGCCGGGGTCGACGCACCGGTGTGGTGC
15703 ------+---------+---------+---------+---------+---------+-- 15762

G  L  L  T  L  V  Q  A  L  G  D  D  A  G  V  D  A  P  V  W  C
      CTGACCCAGGGTGCGGTCCGCACTCCCGCCGACGACGACCTCGCCCGGCCTGCGCAGACC
15763 ------+---------+---------+---------+---------+---------+-- 15822

L  T  Q  G  A  V  R  T  P  A  D  D  D  L  A  R  P  A  Q  T
      ACCGCGCACGGCTTCGCGCAGGTCGCCGGGCTGGAGCTGCCGGGGCGCTGGGGCGGTGTG
15823 ------+---------+---------+---------+---------+---------+-- 15882

T  A  H  G  F  A  Q  V  A  G  L  E  L  P  G  R  W  G  G  V
      GTCGACCTGCCCGAATCGGTCGACGACGCGGCGCTGCGTCTGCTGGTGGCAGTCCTGCGC
15883 ------+---------+---------+---------+---------+---------+-- 15942

V  D  L  P  E  S  V  D  D  A  A  L  R  L  L  V  A  V  L  R
      GGCGGCGGCCGTGCCGAGGACCACCTCGCCGGTCCGGGACGGCCCTCCACGGCCGTCGC
15943 ------+---------+---------+---------+---------+---------+-- 16002
```

```
         G  G  G  R  A  E  D  H  L  A  V  R  D  G  R  L  H  G  R  R  -
         GTCGTCCGCGCAAGCCTGCCGCAGTCCGCGGCTCGCGGGAGCTGGACCCCGCACGGGACCGTG
16003    ----+----+----+----+----+----+----+----+----+----+----+----+    16062

V  V  R  A  S  L  P  Q  S  G  S  R  S  W  T  P  H  G  T  V  -
         CTGGTCACCGGCGGCGCGAGCCCCGTCGGCGAGCCCAACTGTGGTGGGTGGCTCGCCGACCGG
16063    ----+----+----+----+----+----+----+----+----+----+----+----+    16122

L  V  T  G  A  A  S  P  V  G  D  D  Q  L  V  R  W  L  A  D  R  -
         GGAGCCGAGCGGCTGGTGCTGGCCGGAGCCTGTCCGGGCGACGACCTGCTGGCCGCGGTC
16123    ----+----+----+----+----+----+----+----+----+----+----+----+    16182

G  A  E  R  L  V  L  A  G  A  C  P  G  D  D  L  L  A  A  V  -
         GAGGAAGCGGGGCGCATCGGCCGTGTGCGCCAGGACGCGGCGGCTGCCGAGGCG
16183    ----+----+----+----+----+----+----+----+----+----+----+----+    16242

E  E  A  G  A  S  A  V  V  C  A  Q  D  A  A  A  L  R  E  A  -
         CTCGGCGACGAGCCGGTGACCGCTCGTCACGCCCGGAACCCTGACGAACTTCGGCAGC
16243    ----+----+----+----+----+----+----+----+----+----+----+----+    16302

L  G  D  E  P  V  T  A  L  V  H  A  G  T  L  T  N  F  G  S  -
         ATCAGCGAAGTCGCACCGGAGGAGTTCGCCGAGACGATCGCGGGCCAAGACCGGTTGCTC
```

FIG. 2-43

```
16303 --------+---------+---------+---------+---------+---------+ 16362
         GCCGTGCTGGACGAAGTCCTCGGCGACCGGGCCGTCGAGCGGGAGGTCTACTGCTCGTCG
       I  S  E  V  A  P  E  E  F  A  E  T  I  A  A  K  T  A  L  L

16363 --------+---------+---------+---------+---------+---------+ 16422
         GTCGCCGGGATCTGGGGCGGCGCCGGGATGGCCGCCTACGCGGCAGGCAGCGCCTACCTC
       A  V  L  D  E  V  L  G  D  R  A  V  E  R  E  V  Y  C  S  S

16423 --------+---------+---------+---------+---------+---------+ 16482
         GACGCGCTGGCCGAGCACCACCGCGCGCGGGGCCGCTCGTGCACCTCGGTCGCCTGGACG
       V  A  G  I  W  G  G  A  G  M  A  A  Y  A  A  G  S  A  Y  L

16483 --------+---------+---------+---------+---------+---------+ 16542
         CCGTGGGCGCTGCCGGGCGGGGCGGTGGACGACGGGTACCTGCGGGAACGCGGACTGCGC
       D  A  L  A  E  H  H  R  A  R  G  R  S  C  T  S  V  A  W  T

16543 --------+---------+---------+---------+---------+---------+ 16602
         AGCCTCTCCGCCGACAGGGCGATGCGCACCTGGGAGCGGGTGCTGGCCGCCGGGCCGGTG
       P  W  A  L  P  G  G  A  V  D  D  G  Y  L  R  E  R  G  L  R

```
16663 TCGGTCGGCGGTGGCCGACGTGGACTGGCCGGTGCTCAGCGAAGGCTTCGCCGCCACCCGG 16722
      ------+---------+---------+---------+---------+---------+
      AGCCAGCCGCCACCGGCTGCACCTGACCGGCCACGAGTCGCTTCCGAAGCGGCGGTGGGCC
       S  V  A  V  D  V  D  W  P  V  L  S  E  G  F  A  A  T  R

16723 CCGACCGCGCTGTTCGCCGAACTCGCCGGCCGGGGCCAGGCGGAGGCCGAGCCGGAC 16782
      ------+---------+---------+---------+---------+---------+
       P  T  A  L  F  A  E  L  A  G  R  G  G  Q  A  E  A  E  P  D

16783 AGCGGACCGACCGGAGAGCCGGCACAACGGCTCGCCGGGCTTTCCCGACGAGCAGCAG 16842
      ------+---------+---------+---------+---------+---------+
       S  G  P  T  G  E  P  A  Q  R  L  A  G  L  S  P  D  E  Q  Q

16843 GAAAACCTGCTCGAACTCGTCGCGAACGCGGTTGCCGAGGTGCTTGGCCACGAGTCCGCC 16902
      ------+---------+---------+---------+---------+---------+
       E  N  L  L  E  L  V  A  N  A  V  A  E  V  L  G  H  E  S  A

16903 GCCGAGATCAACGTGCGCCGCGCGTTCAGCGAGCTCGGACTCGACTCGCTCAACGCGATG 16962
      ------+---------+---------+---------+---------+---------+
       A  E  I  N  V  R  R  A  F  S  E  L  G  L  D  S  L  N  A  M

16963 GCCCTGCGCAAGCGCCTGTCGGCGAGCACCGGCCTGCGCCTGCCCGCGTCGCTGGTGTTC 17022
      ------+---------+---------+---------+---------+---------+
       A  L  R  K  R  L  S  A  S  T  G  L  R  L  P  A  S  L  V  F
```

FIG. 2-45

```
17023 GACCACCCCACCGTCACCGGCTCGGCAGCACCTGCGCGCCCGGCTCGTCGGTGACGCC 17082
       D   H   P   T   V   T   A   L   A   Q   H   L   R   A   R   L   V   G   D   A

17083 GACCAGGCCGCGGTGCCGGGTGCCGTCGTCGGCGCCGCGGACGAGTCCGAGCCCATCGCCATCGTC 17142
       D   Q   A   A   V   R   V   V   G   A   A   D   E   S   E   P   I   A   I   V

17143 GGCATCGGCTGCCGTTCCCCGGCGGCATCGGCTCGCCCGAGCAGTTGTGGCGGGTGCTG 17202
       G   I   G   C   R   F   P   G   G   I   G   S   P   E   Q   L   W   R   V   L

17203 GCCGAGGGCGCGAACCTCACCACCGGCTTCCCCGGCCGACCGGGGCTGGGACATCGGGCGG 17262
       A   E   G   A   N   L   T   T   G   F   P   A   D   R   G   W   D   I   G   R

17263 CTCTACCACCCCGGACCCCGGACAACCCCGGCACCAGCTACGTGGACAAGGGCGGGTTCCTC 17322
       L   Y   H   P   D   P   D   N   P   G   T   S   Y   V   D   K   G   G   F   L

17323 ACCGACGCGGCGGATTTCGACCCCGGGCTTCTTCGGCATCACGCCCCGCGAAGGCGCTGGCG 17382
       T   D   A   A   D   F   D   P   G   F   F   G   I   T   P   R   E   A   L   A
```

FIG. 2-46

```
17383  ATGGACCCGCAGCAGCGCCTCATGCTGGAGACGGCGTGGGAGGCAGTGGAACGCGGGGC
       -------+---------+---------+---------+---------+---------+  17442
        M  D  P  Q  Q  R  L  M  L  E  T  A  W  E  A  V  E  R  A  G

17443  ATCGACCCCGACGCCCTGCGAGGCACCGACACCGGCGTCTTCGTCGGCATGAACGGCCAG
       -------+---------+---------+---------+---------+---------+  17502
        I  D  P  D  A  L  R  G  T  D  T  G  V  F  V  G  M  N  G  Q

17503  TCCTACATGCAGCTGCTGGCCGGTGAGGCCGAACGCGTCGACGGCTACCAGGGCCTCGGA
       -------+---------+---------+---------+---------+---------+  17562
        S  Y  M  Q  L  L  A  G  E  A  E  R  V  D  G  Y  Q  G  L  G

17563  AACTCCGCGAGCGTGCTCTCCGGGCGCATCGCCTACACCTTCGGCTGGGAGGGCCCGGCG
       -------+---------+---------+---------+---------+---------+  17622
        N  S  A  S  V  L  S  G  R  I  A  Y  T  F  G  W  E  G  P  A

17623  CTGACGGTGGACACCGCGTGCTCGTCCTCGCTGGTCGGCATCCACCTCGCGATGCAGGCG
       -------+---------+---------+---------+---------+---------+  17682
        L  T  V  D  T  A  C  S  S  S  L  V  G  I  H  L  A  M  Q  A

17683  CTGCGGGCGGGTGAGTGCTCCCTGGCCGGCGTCACGGTCATGTCCGACCCG
       -------+---------+---------+---------+---------+---------+  17742
```

```
         L   R   R   G   E   C   S   L   A   L   A   G   G   V   T   V   M   S   D   P   -
         TACACCTTCGTCGACTTCAGCACGCGCGGGCTCGCTGGCGGTGGCGGCGTCACGGTTGTCATGTCGGATCCG
17743    ---------+---------+---------+---------+---------+---------+    17802
         Y   T   F   V   D   F   S   T   Q   R   G   L   A   S   D   G   R   C   K   A   -
         TTCTCCGGCGCGGCCGACGGCTTCGCGCTGTCGGAAGGCGTCGCCGCGCTGGTGCTGGAG
17803    ---------+---------+---------+---------+---------+---------+    17862
         F   S   A   R   A   D   G   F   A   L   S   E   G   V   A   A   L   V   L   E   -
         CCGCTTTCCCGGGCGCGCGCCAACGGGCACCAGGTGCTGGCCGTGCTGCGCGGCAGCGCG
17863    ---------+---------+---------+---------+---------+---------+    17922
         P   L   S   R   A   R   A   N   G   H   Q   V   L   A   V   L   R   G   S   A   -
         GTCAACCAGGACGGTGCCAGCAACGGTCTCGCCGCTCCCAACGGCCCGTCGCAGGAGCGG
17923    ---------+---------+---------+---------+---------+---------+    17982
         V   N   Q   D   G   A   S   N   G   L   A   A   P   N   G   P   S   Q   E   R   -
         GTGATCCGGCAGGCGCTCGCCGCTTCGGGCGTGCCGGCCGCGGACGTCGTGGAG
17983    ---------+---------+---------+---------+---------+---------+    18042
         V   I   R   Q   A   L   A   A   S   G   V   P   A   A   D   V   D   V   V   E   -
```

FIG.2-47

```
18043 GCGCACGGGACGGGCACCGAGCTCGGCGACCCGATCGAGGCCGGCGCTCATCGCGACC 18102
        A  H  G  T  G  T  E  L  G  D  P  I  E  A  G  A  L  I  A  T

18103 TACGGCCAGGACCGGCCGCTGCGGCTCGGGTCGGTCAAGACCAACATCGGCCAC 18162
        Y  G  Q  D  R  P  L  R  L  G  S  V  K  T  N  I  G  H

18163 ACCCAGGCCGCGGCGGGCGCCGTGATCAAGGTCGTGCTGGCGATGCGGCACGGG 18222
        T  Q  A  A  A  G  A  V  I  K  V  V  L  A  M  R  H  G

18223 ATGCTGCCCCGGTCGTTGCACGCCGACGAGCTGTCCCCGCACATCGACTGGGAGTCGGGG 18282
        M  L  P  R  S  L  H  A  D  E  L  S  P  H  I  D  W  E  S  G

18283 GCCGTGGAGGTGCTGCGCGAGGAGGTGCCGTGGCCCGGTGAGCGCCCCCGGCGGGCG 18342
        A  V  E  V  L  R  E  E  V  P  W  P  A  G  E  R  P  R  R  A

18343 GGGGTGTCGTCCTTCGGCGTCAGCGGAACCAACGCGCACGTGATCGTCGAAGAGGCACCA 18402
        G  V  S  F  G  V  S  G  T  N  A  H  V  I  V  E  E  A  P
```

```
18403  GCAGAGCAGGAGGCCGCCCGCCACCGAGCGCGGTTCCGCCTGCCGTTCGTGCTGTCCGGCCGC  18462
          A  E  Q  E  A  A  R  T  E  R  G  P  L  P  F  V  L  S  G  R

18463  AGCCGAAGCCGTGGTCGCGGCCCAGGCCGCGCGCGCCCGAGCACCTGCGCGACACCCCG   18522
          S  E  A  V  V  A  A  Q  A  R  A  L  A  E  H  L  R  D  T  P

18523  GAGCTCGGCCTGACCGACGCGGCATGGACCCTCGCGACCGGCAGGGCGCGGTTCGACGTG   18582
          E  L  G  L  T  D  A  A  W  T  L  A  T  G  R  A  R  F  D  V

18583  CGAGCCGCGCCGTGCTCGGCGACGACCGCGCGGGCGTGTGCGCGGAGCTGGACGCGCTGGCC   18642
          R  A  A  V  L  G  D  D  R  A  G  V  C  A  E  L  D  A  L  A

18643  GAGGGCCGCCCGTCGGCCGACGCCGTCGCGCCGGTGACCTCCGCGCCAAGCCGGTC   18702
          E  G  R  P  S  A  D  A  V  A  P  V  T  S  A  P  R  K  P  V

18703  CTGGTCTTCCCCGGCCAGGGCGCGCAGTGGGTCGGCATGGCACGCGATCTGCTGGAATCC   18762
          L  V  F  P  G  Q  G  A  Q  W  V  G  M  A  R  D  L  L  E  S
```

FIG. 2-50

```
18763 TCCGAGGTGTTCGCCGAGTCGATGAGCCGGTGCGCCGAGGCGCTCTCGCCGCACACCGAC 18822
      AGGCTCCACAAGCGGCTCAGCTACTCGGCCACGCGGCTCCGCGAGAGCGGCGTGTGGCTG
       S   E   V   F   A   E   S   M   S   R   C   A   E   A   L   S   P   H   T   D

18823 TGGAAGTTGCTCGACGTCGTCCGGGGCGACGGGGGTCCCGACCCGCACGAGCGCGTCGAC 18882
      ACCTTCAACGAGCTGCAGCAGGCCCCGCTGCCCCCAGGGCTGGGCGTGCTCGCGCAGCTG
       W   K   L   L   D   V   V   R   G   D   G   G   P   D   P   H   E   R   V   D

18883 GTGCTCCAGCCGGTGCTCTTCTCGATCATGGTCTCGCTGGCCGAGCTGTGGCGCGCGCAC 18942
      CACGAGGTCGGCCACGAGAAGAGCTAGTACCAGAGCGACCGGCTCGACACCGCGCGCGTG
       V   L   Q   P   V   L   F   S   I   M   V   S   L   A   E   L   W   R   A   H

18943 GGCGTGACCCCGGCCGCCGTCGTCGGCCACTCGCAGGGCGAGATCGCCGCGGCCACGTG 19002
      CCGCACTGGGGCCGGCGGCAGCAGCCGGTGAGCGTCCCGCTCTAGCGGCGCCGGTGCAC
       G   V   T   P   A   A   V   V   G   H   S   Q   G   E   I   A   A   A   H   V

19003 GCGGGCGCGCTGTCGCTGGAAGCCGCCGCGAAGGTGGTGGCCCTGCGCAGCCAGGTGTTG 19062
      CGCCCGCGCGACAGCGACCTTCGGCGGCGCTTCCACCACCGGGACGCGTCGGTCCACAAC
       A   G   A   L   S   L   E   A   A   A   K   V   V   A   L   R   S   Q   V   L

19063 CGCGAGCTCGACGACCAGGGCGGCATGTGTCGGTCCCGCGACGAGCTGGAG 19122
      GCGCTCGAGCTGCTGGTCCCGCCGTACACAGCCAGGGCGCTGCTCGACCTC
```

```
       R   E   L   D   D   Q   G   G   M   V   S   V   G   A   S   R   D   E   L   E   -
       ACCGTGCTCGCGGCTGGACGGGCCGTGTCGCGGTGCCGCCGTGAACGGGCCTGGCACC         19182
19123  ------+---------+---------+---------+---------+---------+------

T   V   L   A   R   W   D   G   R   V   A   V   A   A   V   N   G   P   G   T   -
       AGCGTCGTTGCCGGGCCGACCGCGGAGCTGGACGAGTTCTTCGCCGAGGCCGAGGCGCGG       19242
19183  ------+---------+---------+---------+---------+---------+------

S   V   V   A   G   P   T   A   E   L   D   E   F   F   A   E   A   E   A   R   -
       GAGATGAAGCCGCGGCGCATCGCGGTGCGCTACGCCTCCCACTCCCCGGAGGTGGCGCGC       19302
19243  ------+---------+---------+---------+---------+---------+------

E   M   K   P   R   R   I   A   V   R   Y   A   S   H   S   P   E   V   A   R   -
       ATCGAGGACCGGCTCGCCGCCGAGCTGGGCACCATCACCGCCGTGCGGGGCTCGGTGCCG       19362
19303  ------+---------+---------+---------+---------+---------+------

I   E   D   R   L   A   A   E   L   G   T   I   T   A   V   R   G   S   V   P   -
       CTGCACTCCACGGTGACCGGCGAGGTCATCGACACCTCCGCGATGGACGCCTCCTACTGG     19422
19363  ------+---------+---------+---------+---------+---------+------

L   H   S   T   V   T   G   E   V   I   D   T   S   A   M   D   A   S   Y   W   -
       TACCGCAACCTGCGCCGACCAGTGCTCTTCGAGCAGGCGGTGCGCGGTCTGGTCGAGCAG      19482
19423  ------+---------+---------+---------+---------+---------+------
```

```
         Y   N   L   R   R   P   V   L   F   E   E   Q   A   V   R   G   L   V   E   Q   -
       GGCTTCGACACCTTCGTCGAGGTGAGCCCGGTGCTGCTGATGGCGGTCGAGGAG
19483  ---------+---------+---------+---------+---------+---------+  19542

G   F   D   T   F   V   E   V   S   P   H   P   V   L   L   M   A   V   E   E   -
       ACCGCCGAGCACGGCGCGGGGAAGTCACCTGCCGTGCCGACGCTGCGCGAGCAGAGC
19543  ---------+---------+---------+---------+---------+---------+  19602

T   A   E   H   A   G   A   E   V   T   C   V   P   T   L   R   R   E   Q   S   -
       GGACCGCACGAGTTCCTGCGCAACCTGCTGCGGGCTCACGTGCACGGCGTCGGCGCCGAC
19603  ---------+---------+---------+---------+---------+---------+  19662

G   P   H   E   F   L   R   N   L   L   R   A   H   V   H   G   V   G   A   D   -
       CTGCGTCCGGACGGGTGCCCGGGGACGGCCCGAGCTGCCCACCTACCCGTTCGAACAC
19663  ---------+---------+---------+---------+---------+---------+  19722

L   R   P   A   V   A   G   G   R   P   A   E   L   P   T   Y   P   F   E   H   -
       CAGCGCTTCTGGCCGCGGCCGCACCGGCCCGACGTCTCGGCGTGCGCGGC
19723  ---------+---------+---------+---------+---------+---------+  19782

Q   R   E   W   P   R   P   H   R   P   A   D   V   S   A   L   G   V   R   G   -
       GCGGAGCACCCGCTGCTCCGCGTTGCCGGTCGACGTTGCCGGCACGGCCGTGCGGTGTTC
```

FIG. 2-53

```
19783 ──────────┼──────────┼──────────┼──────────┼──────────┼──────────┼── 19842
       ACCGGAAGGCTTTCCACCGACGAGCCGTGGCTGGCCGAACACGTCGTGGGCGGCCGG
19843 ──────────┼──────────┼──────────┼──────────┼──────────┼──────────┼── 19902
         A  E  H  P  L  L  L  A  A  V  D  V  P  G  H  G  G  A  V  F

ACGCTGGTGCCGGGCAGCGTCCTGGTCGATCTCGCGCTCGCCGGGTGAGGACGTCGGG
19903 ──────────┼──────────┼──────────┼──────────┼──────────┼──────────┼── 19962
         T  G  R  L  S  T  D  E  Q  P  W  L  A  E  H  V  V  G  G  R

CTGCCGGTCCTGGAGGAACTGGTGTTGCAACGGCCGCTGGTCCTGGCCGGGGCGGGGCG
19963 ──────────┼──────────┼──────────┼──────────┼──────────┼──────────┼── 20022
         T  L  V  P  G  S  V  L  V  D  L  A  L  A  A  G  E  D  V  G

CTGCTGCGCATGTCGGTCGGGGCGCCCGACGAGTCGGGGCGGACGATCGACGTCCAC
20023 ──────────┼──────────┼──────────┼──────────┼──────────┼──────────┼── 20082
         L  P  V  L  E  E  L  V  L  Q  R  P  L  V  L  A  G  A  G  A

GCCGCCGAAGACGTGGCCGACCTCGCCGACGCGCAGTGGTCGCAGCACGCCACCGGGACG
20083 ──────────┼──────────┼──────────┼──────────┼──────────┼──────────┼── 20142
         L  L  R  M  S  V  G  A  P  D  E  S  G  R  R  T  I  D  V  H

A  A  E  D  V  A  D  L  A  D  A  Q  W  S  Q  H  A  T  G  T
```

```
                CTCGGCCAGGGGCGTCGCCGGCGGGTCCGAGGGATACCGAGCAGTGGCCGCCGGAGGACGCC
20143           ------------+------------+------------+------------+------------+------------ 20202
                 L  A  Q  G   V  A  A  G   P  R  D  T   E  Q  W  P   P  E  D  A

GTCCGGCATCCCCGCTCGACGACCACTACGACGGCCTCGCCGAGCAGGGCTACGAGTACGGA
20203           ------------+------------+------------+------------+------------+------------ 20262
                 V  R  I  P   L  D  D  H   Y  D  G  L   A  E  Q  G   Y  E  Y  G

CCGTCGTTCCAGGCCCTGCGCGAGCCGTGGCGCAAGGACGACTCGGTCTACGCCGAGGTG
20263           ------------+------------+------------+------------+------------+------------ 20322
                 P  S  F  Q   A  L  R  A   A  W  R  K   D  D  S  V   Y  A  E  V

TCCATCGCGGCGGACGAGGAAGGTTACGCCGTTCCACCCGGTGCTGCTCGACGCCGTGGCG
20323           ------------+------------+------------+------------+------------+------------ 20382
                 S  I  A  A   D  E  E  G   Y  A  F  H   P  V  L  L   D  A  V  A

CAGACGCTCAGCCTGGGCGCCCTCGGCGAGCCCGGGGGGAAAGCTGCCGTTCGGCGTGG
20383           ------------+------------+------------+------------+------------+------------ 20442
                 Q  T  L  S   L  G  A  L   G  E  P  G   G  G  K  L   P  F  A  W

AACACCGTGACCCTGCACGCCTCCGGGGCGACCTCGGTGCGTGTGGCGACGCCCGCC
20443           ------------+------------+------------+------------+------------+------------ 20502
                 N  T  V  T   L  H  A  S   G  A  T  S   V  R  V  V   A  T  P  A
```

```
20503 GGGGCGGGACGCGGATGGCCCTGCGGGTCACCGACCCGGCCAGGCCACCTGGTCGCCACGGTC 20562
       ---------+---------+---------+---------+---------+---------+
        G  A  D  A  M  A  L  R  V  T  D  P  A  G  H  L  V  A  T  V

20563 GACTCGCTGGTCGTCCGCAGCACCGGGGAGAAGTGGGAGCAGCCCGAACCGCGGTGGC 20622
       ---------+---------+---------+---------+---------+---------+
        D  S  L  V  V  R  S  T  G  E  K  W  E  Q  P  E  P  R  G  G

20623 GAGGGCGAGCTGCACGCTCTGGACTGGGGACGGCTAGCCGAGCCCGGCTCGACCGGTCGT 20682
       ---------+---------+---------+---------+---------+---------+
        E  G  E  L  H  A  L  D  W  G  R  L  A  E  P  G  S  T  G  R

20683 GTGGTCGCGGCCGATGCCTCGGACCTCGACGCCGTCCTGCGGTCCGGTGAACCCGAACCC 20742
       ---------+---------+---------+---------+---------+---------+
        V  V  A  A  D  A  S  D  L  D  A  V  L  R  S  G  E  P  E  P

20743 GACGCGGTCCTGGTCCGCTACGAACCCGAAGGCGACGACCCCCGCGCCGCCGCCCGCCAC 20802
       ---------+---------+---------+---------+---------+---------+
        D  A  V  L  V  R  Y  E  P  E  G  D  D  P  R  A  A  A  R  H

20803 GGCGTCCTCTGGCCGCTCGAACAGGAGGAGCTGCCGGGC 20862
       ---------+---------+---------+---------+---------+---------+
```

FIG. 2-56

```
           G  V  L  W  A  A  A  L  V  R  R  W  L  E  Q  E  E  L  P  G
        GCGACGCTGGTCATCGCCACGTCCGGCGGGTCACCGTGTCCGACGACGACAGCGTTCCC
20863   ---------+---------+---------+---------+---------+---------+   20922

A  T  L  V  I  A  T  S  G  A  V  T  V  S  D  D  D  S  V  P
        GAACCCGGCGCGCCGCCGCGATGTGGGGCGTGATCCGCTGTGCCAGGCCGAGTCGCCGGAC
20923   ---------+---------+---------+---------+---------+---------+   20982

E  P  G  A  A  A  M  W  G  V  I  R  C  A  Q  A  E  S  P  D
        CGGTTCGTGCTCCTCGACACCGACGCGGAACCTGGGATGCTGCCGGTTCCGGACAAC
20983   ---------+---------+---------+---------+---------+---------+   21042

R  F  V  L  L  D  T  D  A  E  P  G  M  L  P  A  V  P  D  N
        CCGCAGCTCGCGTTGCGCGGCGACGACGTCTTCGTGCCCCGTCTCGCCGCTCGCACCT
21043   ---------+---------+---------+---------+---------+---------+   21102

P  Q  L  A  L  R  G  D  D  V  F  V  P  R  L  S  P  L  A  P
        TCCGCGCTGACGCTTCCGGCACCGCAGGCCACCCAACGTCTCGTGCCGGGTGACGGGGCGATCGAC
21103   ---------+---------+---------+---------+---------+---------+   21162

S  A  L  T  L  P  A  G  T  Q  R  L  V  P  G  D  G  A  I  D
        TCCGTGGCCTTCGAGCCCGACCACCCGGAGCAGCCGACGTCGGGGGGCGAGGTCCGG
21163   ---------+---------+---------+---------+---------+---------+   21222
```

```
S   V   A   F   E   P   A   P   D   V   E   Q   P   L   R   A   G   E   V   R
       GTGGACGTGCGCGCCACCGGAGTCAACTTCCGCGACGTCCTCCTGGCACTCGGCATGTAT
21223  ------+---------+---------+---------+---------+---------+  21282

V   D   V   R   A   T   G   V   N   F   R   D   V   L   L   A   L   G   M   Y
       CCGCAGAAGGCGGACATGGGCACCGAGGCCGCCGGTGTCGTCACGGCCGTCGGACCGGAC
21283  ------+---------+---------+---------+---------+---------+  21342

P   Q   K   A   D   M   G   T   E   A   A   G   V   V   T   A   V   G   P   D
       GTGGACGCCTTCGCGCCGGGAGACCGGGTGCTCGGCCTGTTCCAGGGAGCCTTCGCGCCG
21343  ------+---------+---------+---------+---------+---------+  21402

V   D   A   F   A   P   G   D   R   V   L   G   L   F   Q   G   A   F   A   P
       ATCGCGGTCACCGATCACCGGCTCCTCGCACGAGTGCCGGACGGCTGGAGCGACGCCGAC
21403  ------+---------+---------+---------+---------+---------+  21462

I   A   V   T   D   H   R   L   L   A   R   V   P   D   G   W   S   D   A   D
       GCCGCGGCCGTGCCCATCGCCTACACCGCGCATTACGCGGCGCTGCACGATCTCGCGGGG
21463  ------+---------+---------+---------+---------+---------+  21522

A   A   V   P   I   A   Y   T   T   A   H   Y   A   L   H   D   L   A   G
       CTGCGCGGCGGGGTCAGTCGGTGCTCATCCACGCAGGCGGTGTGCGGCATGGGCGCC
21523  ------+---------+---------+---------+---------+---------+  21582
```

```
         L   R   A   G   Q   S   V   L   I   H   A   A   A   G   G   V   G   M   A   A
      GTCGGCGCTGGCCCCGCGCCGAGCGGCGGAGGTGTTGGCCACCGCCGGCCCGGCCAAGCAC
21583 ------+---------+---------+---------+---------+---------+ 21642

V   A   L   A   R   R   A   G   A   E   V   L   A   T   A   G   P   A   K   H
      GGGACGCTGCGGGCGCTCGGTCTCGACGAGCACATCGCTTCCTCCCGGAGACCGGT
21643 ------+---------+---------+---------+---------+---------+ 21702

G   T   L   R   A   L   G   L   D   D   E   H   I   A   S   S   R   E   T   G
      TTCGCCCGGAAGTTCCGGGAGCGCACCGGAGGCCGGGTGGACGTGGTGCTCAACTCG
21703 ------+---------+---------+---------+---------+---------+ 21762

F   A   R   K   F   R   E   R   T   G   G   R   G   V   D   V   V   L   N   S
      CTCACCGGGGAACTGCTCGACGAGTCCGCCGATCTGCTCGCCGAGGACGGCGTCTTCGTC
21763 ------+---------+---------+---------+---------+---------+ 21822

L   T   G   E   L   L   D   E   S   A   D   L   L   A   E   D   G   V   F   V
      GAGATGGGCAAGACCGACCTGCGGGACGCCGGGGACTTCCGGGGCCGATACGCCCCCGTC
21823 ------+---------+---------+---------+---------+---------+ 21882

E   M   G   K   T   D   L   R   D   A   G   D   F   R   G   R   Y   A   P   F
```

```
21883  GACCTCGGCGAGGCGGGTGACGACCGGCTCGGGGAGATCCTGCGCGAGGTCGTCGGCCTG  21942
         D   L   G   E   A   G   D   D   R   L   G   E   I   L   R   E   V   V   G   L

21943  CTGGGCGCCGGGGAGCTCGACCGGCTCCCCGTATCGGCGTGGGAGCTGGGATCCCGCGCCC  22002
         L   G   A   G   E   L   D   R   L   P   V   S   A   W   E   L   G   S   A   P

22003  GCGGCGTTGCAGCACATGAGCCGGGGCCGGCACGTCGGCAAGCTCGTGCTGACCCAGCCC  22062
         A   A   L   Q   H   M   S   R   G   R   H   V   G   K   L   V   L   T   Q   P

22063  GCGCCGGTGGACCCCGACGGCACGGTGCTGATCACGGGTGGCACCGGCACGCTCGGACGG  22122
         A   P   V   D   P   D   G   T   V   L   I   T   G   G   T   G   T   L   G   R

22123  CTGCTCGCGCGCCACCTCGTCACCGAGCACGGCGTGCGCCACCTGCTGCTGGTCAGCAGG  22182
         L   L   A   R   H   L   V   T   E   H   G   V   R   H   L   L   L   V   S   R

22183  CGCGGCGGCGACGCGCCGGTTCCGACGAGCTGCCGCGGAGATCGAGGACTTGGGGGCG  22242
```

FIG. 2-59

```
      R   G   A   D   A   P   G   S   D   E   L   R   A   E   I   E   D   L   G   A
      TCCGCGGAGATCGCGGGCTTGCGACACGCCGACCGCCGACGGCGCTTTCGGCGCTGCTGGAC
22243 ------+---------+---------+---------+---------+---------+---------+ 22302

S   A   E   I   A   A   C   D   T   A   D   R   D   A   L   S   A   L   L   D
      GGGCTGCCCCGGCTGACCGGTGTCGTGCACGGCGGGGTGTGCTGGCCGACGGGCTG
22303 ------+---------+---------+---------+---------+---------+ 22362

G   L   P   R   P   L   T   G   V   V   H   A   A   G   V   L   A   D   G   L
      GTCACCTCCATCGACGAGCCGGCCGTGGAGCAGGTGCTGCGCGCCAAGGTCGACGCGGGCG
22363 ------+---------+---------+---------+---------+---------+ 22422

V   T   S   I   D   E   P   A   V   E   Q   V   L   R   A   K   V   D   A   A
      TGGAACCTGCACGAGCTGACCGCGAACACCGGTCTGAGCTTCTTCGTGCTGTTCTCGTCC
22423 ------+---------+---------+---------+---------+---------+ 22482

W   N   L   H   E   L   T   A   N   T   G   L   S   F   F   V   L   F   S   S
      GCGGCGTCGGTGCTAGCCGGCCCGGGCCAGGGCGTGTACGCCGAACGAGTCGCTC
22483 ------+---------+---------+---------+---------+---------+ 22542

A   A   S   V   L   A   G   P   G   Q   G   V   Y   A   A   A   N   E   S   L
      AACGCCCTGGCTGCCCTCCGGAGGACGCGCCTTCCCGGAAGGCGCTCGGATGGGGA
22543 ------+---------+---------+---------+---------+---------+ 22602
```

```
              N   A   L   A   A   L   R   R   T   R   G   L   P   A   K   A   L   G   W   G    -
          CTGTGGGGCGCAGGCCAGCGAGATGACCAGCGGACTCGGCGACCGCATCGCCCGGACCGGG
22603     ------+---------+---------+---------+---------+---------+       22662

L   W   Q   A   S   E   M   T   S   G   L   G   D   R   I   A   R   T   G    -
          GTCGCCGCGCTGCCGACCGAGCGGGGCGCTCGCACTGTTCGACAGCGCCCTGCGCCGGC
22663     ------+---------+---------+---------+---------+---------+       22722

V   A   A   L   P   T   E   R   A   L   A   L   F   D   S   A   L   R   R   G    -
          GGTGAGGTCGTGTTCCCGGTCCATCAACCGTTCCGCGCTGCGCAGGGCCGAGTTCGTG
22723     ------+---------+---------+---------+---------+---------+       22782

G   E   V   V   F   P   L   S   I   N   R   S   A   L   R   R   A   E   F   V    -
          CCGGAGGTCCTGCGCGGCATGGTCAGGGCGAAGCTGCGCGCCGCAGGCCGAGGCG
22783     ------+---------+---------+---------+---------+---------+       22842

P   E   V   L   R   G   M   V   R   A   K   L   R   A   A   G   Q   A   E   A    -
          GCAGGGCCGAACGTGGTCGACCGGCTCGCCGGTCCGAGTCCGACCAGGTCGCCGGG
22843     ------+---------+---------+---------+---------+---------+       22902

A   G   P   N   V   V   D   R   L   A   G   R   S   E   S   D   Q   V   A   G    -
          CTGGCCGAACTGGTCGTTCACACGGTCTCCGGTACGGCTCGGCCGACCAG
22903     ------+---------+---------+---------+---------+---------+       22962
```

FIG. 2-62

```
            L  A  E  L  V  R  S  H  A  A  A  V  S  G  Y  Y  G  S  A  D  Q  -
         CTCCCCGAGCGCAAGGGCGTTCAAGGACCTCGGTTTCGACTCGCTGGCCGTGGAGCTG
22963    ---------+---------+---------+---------+---------+---------+  23022

L  P  E  R  K  A  F  K  D  L  G  F  D  S  L  A  A  V  E  L  -
         CGCAACCGCCTCGGTACCGCGACCGGCTGCCGGCCCAGCACGTTGGTGTTCGACCAC
23023    ---------+---------+---------+---------+---------+---------+  23082

R  N  R  L  G  T  A  T  G  V  R  L  P  S  T  L  V  F  D  H  -
         CCGACTCCGCTGGCGGTGGCCGAACACCTGCGGGACAGGCTGTTCGCGGCCTCACCGGCG
23083    ---------+---------+---------+---------+---------+---------+  23142

P  T  P  L  A  V  A  E  H  L  R  D  R  L  F  A  A  S  P  A  -
         GTGGACATCGGCGACCGGCTGGACGAGCTGGAGAAGGCGCTCGAAGCCCTGTCCGCCGAG
23143    ---------+---------+---------+---------+---------+---------+  23202

V  D  I  G  D  R  L  D  E  L  E  K  A  L  E  A  L  S  A  E  -
         GACGGGCACGACGACGTGGGCCAGCGCCTGGAGTCGCTGCTGCGCCGGTGGAACAGCAGG
23203    ---------+---------+---------+---------+---------+---------+  23262

D  G  H  D  D  V  G  Q  R  L  E  S  L  L  R  R  W  N  S  R  -
         CGGGCGGACGCCCCGAGCACGTCCGCGATCAGCGAGGACGCCAGTGACGACGAGCTGTTC
```

FIG. 2-63

```
23263 TCGATGCTCGACCAGCGGTTCGGCGGGGAGAGGACCTGTAGATGAGCGGTGACAACGGC 23322
       ---------+---------+---------+---------+---------+---------+
       R  A  D  A  P  S  T  S  A  I  S  E  D  A  S  D  D  E  L  F

23323 ATGACCGAGGAAAAGCTCCGGCGCTACCTCAAGCGCACCGTCACCGAGCTCGACTCGGTG 23382
       ---------+---------+---------+---------+---------+---------+
       S  M  L  D  Q  R  F  G  G  G  E  D  L  *  M  S  G  D  N  G

23383 ACCGCGCGCCTGCGTGAAGTCGAGCACCGGGCCGGTGAGCCGATCGCGATCGTCGGCATG 23442
       ---------+---------+---------+---------+---------+---------+
       M  T  E  E  K  L  R  R  Y  L  K  R  T  V  T  E  L  D  S  V

23443 GCGTGCCGGTTCCCCGGCGACGTGGACTCGCCGGAGTCGTTCTGGGAGTTCGTGTCCGGC 23502
       ---------+---------+---------+---------+---------+---------+
       T  A  R  L  R  E  V  E  H  R  A  G  E  P  I  A  I  V  G  M

23503 GCCTGCCGGTTCCCCGGCGACGTGGACTCGCCGGAGTCGTTCTGGGAGTTCGTGTCCGGC 23562
       ---------+---------+---------+---------+---------+---------+
       A  C  R  F  P  G  D  V  D  S  P  E  S  F  W  E  F  V  S  G

23563 GGCGGGGACGCCATCGCGGAGGCCCCGCGCCGACCGGGACCCCGACGCG 23622
       ---------+---------+---------+---------+---------+---------+
       G  G  D  A  I  A  E  A  P  A  D  R  G  W  E  P  D  P  D  A
```

```
23623 CGGCTGGGCGGGGATGCTCGCGGGCCGCGCGGGCGACTTCGACGCGGGCTTCTTCGGGATCTCG 23682
       -----+---------+---------+---------+---------+---------+---------+
        R   L   G   G   M   L   A   A   A   G   D   F   D   A   G   F   F   G   I   S

23683 CCGCGCGAGGCGCTGGCGATGGACCCGCAGCAGCGGATCATGCTGGAGATCTCGTGGGAG 23742
       -----+---------+---------+---------+---------+---------+---------+
        P   R   E   A   L   A   M   D   P   Q   Q   R   I   M   L   E   I   S   W   E

23743 GCGCTGGAGCGCGGCCACGATCCGGTGTCCCTGCGCGGCAGCGCGACCGGGGTGTTC 23802
       -----+---------+---------+---------+---------+---------+---------+
        A   L   E   R   A   G   H   D   P   V   S   L   R   G   S   A   T   G   V   F

23803 ACCGGTGTCGGCACCGTGGACTACGGGCCCCGACGAGGCCCCGACGAGGTCCTG 23862
       -----+---------+---------+---------+---------+---------+---------+
        T   G   V   G   T   V   D   Y   G   P   R   P   D   E   A   P   D   E   V   L

23863 GGCTACGTCGGCACCGCCTCCAGCGTCGCCTCCGGCGTCGCCTACTGCCTG 23922
       -----+---------+---------+---------+---------+---------+---------+
        G   Y   V   G   T   A   S   S   V   A   S   G   R   V   A   Y   C   L

23923 GGCCTGGAAGGCCCCGGCGATGACCGTCGACACCGCCTGTTCCTCCGGCTCACCGCCCTG 23982
       -----+---------+---------+---------+---------+---------+---------+
        G   L   E   G   P   A   M   T   V   D   T   A   C   S   S   G   L   T   A   L
```

```
23983  CACCTGGCGATGGAGTCGCTGCGCCGGGACGAGTGCGGCCTGGCGCTGGCCGGGGGCGTG  24042
         H  L  A  M  E  S  L  R  R  D  E  C  G  L  A  L  A  G  G  V

24043  ACGGTGATGAGCAGTCCCGGGGCGTTCACCGAGTTCCGCAGCCAGGGCGGGCTCGCCGCC  24102
         T  V  M  S  S  P  G  A  F  T  E  F  R  S  Q  G  G  L  A  A

24103  GACGGCCGCTGCAAGCCGTTCTCGAAGGCCGCCGACGGGTTCGGCCTGGCCGAGGGTGCC  24162
         D  G  R  C  K  P  F  S  K  A  A  D  G  F  G  L  A  E  G  A

24163  GGGGTCCTGGTGCTGCAACGGCTGTCGGCGGCGGCCAGGCGAGACCGGTGCTGGCC  24222
         G  V  L  V  L  Q  R  L  S  A  A  R  R  E  G  R  P  V  L  A

24223  GTGCTGCGGGGCTCGGCGGTCAACCAGGACGGCGCCAGCAACGGCTGACCGCCCGAGC  24282
         V  L  R  G  S  A  V  N  Q  D  G  A  S  N  G  L  T  A  P  S

24283  GGACCCGGCGCAGCAGGGGTCATCCCGCCTGGAGAACGCCGGTGTCCGGGGGC  24342
```

```
         G  P  A  Q  Q  R  V  I  R  R  A  L  E  N  A  G  V  R  A  G
         GACGTCGACTACGTGGAGGCCCACGGCACCGGCACCAGGCTGGGGCGACCCCATCGAGGTG
24343    ------+---------+---------+---------+---------+---------+   24402

D  V  D  Y  V  E  A  H  G  T  G  T  R  L  G  D  P  P  I  E  V
         CACGCGCTGCTCTCGACCTACGGCGCGGGAACGCGACCCGGAACGATCCACTGTGGATCGGT
24403    ------+---------+---------+---------+---------+---------+   24462

H  A  L  S  T  Y  G  A  E  R  D  P  D  D  D  P  L  W  I  G
         TCGGTCAAGTCCAACATTGGCCACCCAGGCCCGCCGCCGTCGCCGGGGTGATGAAG
24463    ------+---------+---------+---------+---------+---------+   24522

S  V  K  S  N  I  G  H  T  Q  A  A  A  G  V  A  G  V  M  K
         GCGGTGCTGGCGCTGCGCCACGGCGAGATGCCGCGCACGCTGCACTTCGACGAGCCCTCG
24523    ------+---------+---------+---------+---------+---------+   24582

A  V  L  A  L  R  H  G  E  M  P  R  T  L  H  F  D  E  P  S
         CCGCAGATCGAGTGGGACCTGGGCGCGGTGTCGGTGTGTCGCAGGCGCGTCGTGGCCC
24583    ------+---------+---------+---------+---------+---------+   24642

P  Q  I  E  W  D  L  G  A  V  S  V  V  S  Q  A  R  S  W  P
         GCCGGCGAGAGGCCCCAGGCCGTCTCCTCGTTCGGCATCAGCGGCACCAACGCG
24643    ------+---------+---------+---------+---------+---------+   24702
```

FIG. 2-66

```
         A  G  E  R  P  R  R  A  G  V  S  S  F  G  I  S  G  T  N  A
         CACGTCATCGTCGAAGAGGCGCCCGAGGCCCGACGAGAGCCGGCACCCGACTCGGGT
24703    ---------+---------+---------+---------+---------+---------+  24762

H  V  I  V  E  E  A  P  E  A  D  E  P  E  P  A  P  D  S  G
         CCGGTCCCGCTGGTGTTGTCCGGCCCCGACGAGCAGGCGATGCGGGCCAGGCGGGACGG
24763    ---------+---------+---------+---------+---------+---------+  24822

P  V  P  L  V  L  S  G  R  D  E  Q  A  M  R  A  Q  A  G  R
         CTGGCAGAGACCACCTCGCCGCCGAGCCGCGGAACTCGTTGCCGACACCGGTtTCACGCTG
24823    ---------+---------+---------+---------+---------+---------+  24882

L  A  D  H  L  A  R  E  P  R  N  S  L  R  D  T  G  F  T  L
         GCCACCCGCCGCAGCGGCGCGTGGGAGCACCGCGGTGGTCGGCGACGACGCC
24883    ---------+---------+---------+---------+---------+---------+  24942

A  T  R  R  S  A  W  E  H  R  A  V  V  V  G  D  R  D  D  A
         CTCGCCGGGCTGCGCGGCGGTGGCGGTGCCGACGGGCCGACGGCCACCGGGCAG
24943    ---------+---------+---------+---------+---------+---------+  25002

L  A  G  L  R  A  V  A  D  G  R  I  A  D  R  T  A  T  G  Q
         GCCCGAACTCGCCGGCGTCGGCGATGGTGTTCCCCGGCCAGGGGCGCAGTGGCAGGGGG
25003    ---------+---------+---------+---------+---------+---------+  25062
```

```
         A  R  T  R  R  G  V  A  M  V  F  P  G  Q  G  A  Q  W  Q  G
25063  ATGGCCCGCGACCTGCTGCGGGAGTCGCAGGTATTCGCCGACTCGATCCGCGACTGCGAG  25122
         -----+----+----+----+----+----+----+----+----+----+----+-----
         M  A  R  D  L  L  R  E  S  Q  V  F  A  D  S  I  R  D  C  E

R  A  L  A  P  H  V  D  W  S  L  T  D  L  L  S  G  A  R  P
25123  CGGGCGCTGGCCCCGCACGTCGACTGGTCGCTGACCGACCTGCTCAGCGGGGCGACCG   25182
         -----+----+----+----+----+----+----+----+----+----+----+-----
         R  A  L  A  P  H  V  D  W  S  L  T  D  L  L  S  G  A  R  P

L  D  R  V  D  V  V  Q  P  A  L  F  A  V  M  V  S  L  A  A
25183  CTGGACCGGGTCGACGTCGTCCAGCCCGCGCTCTTCGCCGTCATGGTGTCGCTGGGGCG   25242
         -----+----+----+----+----+----+----+----+----+----+----+-----
         L  D  R  V  D  V  V  Q  P  A  L  F  A  V  M  V  S  L  A  A

L  W  R  S  H  G  V  E  P  A  A  V  V  G  H  S  Q  G  E  I
25243  CTGTGGCGGTCTCCCACGGCGTCGAGCCCGCGGCCGTCGTCGGCCACTCGCAGGGCGAGATC  25302
         -----+----+----+----+----+----+----+----+----+----+----+-----
         L  W  R  S  H  G  V  E  P  A  A  V  V  G  H  S  Q  G  E  I

A  A  H  V  A  G  A  L  T  L  E  D  A  A  K  L  V  A  V
25303  GCCGCCGCGCACGTCGCCGGCGCTCACCCTGGAGGACGCCGCCAAGCTCGTCGCGGTC   25362
         -----+----+----+----+----+----+----+----+----+----+----+-----
         A  A  H  V  A  G  A  L  T  L  E  D  A  A  K  L  V  A  V
```

FIG. 2-69

```
25363 CGGAGCCGGGTCCTGGCCCGGCTCGGCGGGCCAGGGCGGCATGGGCGTCGTTCGGGCTGGGC
      -------+---------+---------+---------+---------+---------+ 25422
         R  S  R  V  L  A  R  L  G  G  Q  G  G  M  A  S  F  G  L  G

25423 ACCGAGCAGGCGGCCGAACGGATCGGGCGCTTCGCGGGCGCTCTCCATCGCCTCGGTC
      -------+---------+---------+---------+---------+---------+ 25482
         T  E  Q  A  A  E  R  I  G  R  F  A  G  A  L  S  I  A  S  V

25483 AACGGCCCCGGTCGTCGTCGCGGGGAGAGCGGGACCGCTGGACGAGCTGATCGCC
      -------+---------+---------+---------+---------+---------+ 25542
         N  G  P  R  S  V  V  V  A  G  E  S  G  P  L  D  E  L  I  A

25543 GAGTGCGAGGCCGAAGGCATAACGGCGCGCCATCCCCGTCGACTACGCCTCCCACTCA
      -------+---------+---------+---------+---------+---------+ 25602
         E  C  E  A  E  G  I  T  A  R  R  I  P  V  D  Y  A  S  H  S

25603 CCGCAGGTGGAGTCGCTGCGCGAGGAGCTGCTGACCGAGCTGGCCGGCATCTCCCCGGTG
      -------+---------+---------+---------+---------+---------+ 25662
         P  Q  V  E  S  L  R  E  E  L  L  T  E  L  A  G  I  S  P  V

25663 TCGGGCGACGTGGCGCTCTACTCGACCACGACCAGCCCGGCAGCCCATCGACACCGCCACGATG
      -------+---------+---------+---------+---------+---------+ 25722
```

```
         S   A   D   V   A   L   Y   S   T   T   T   G   Q   P   I   D   T   A   T   M   -
       GACACCGCCTACTGGTACGCCGAACCTGCGCGAGCAGGTTCCGCTTCCAGGACGCGACGCGG
25723  ------+---------+---------+---------+---------+---------+  25782

D   T   A   Y   W   Y   A   N   L   R   E   Q   V   R   F   Q   D   A   T   R   -
       CAGCTCGCCGAGGCGGGGGTTCGACGCGGTTCGTCGAGGTCAGCCCGCATCCGGTGCTGACC
25783  ------+---------+---------+---------+---------+---------+  25842

Q   L   A   E   A   G   F   D   A   F   V   E   V   S   P   H   P   V   L   T   -
       GTCGGCATCGAGGCCACGCTGGACTCCGCGCTCCCGGCCGACGCCGGCGCCTGCGTCGTG
25843  ------+---------+---------+---------+---------+---------+  25902

V   G   I   E   A   T   L   D   S   A   L   P   A   D   A   G   A   C   V   V   -
       GGCACCCTGCGCCGGGACCGCGGCGGCCTGGCCGACTTCCACACCGCGCTCGGCGAGGCG
25903  ------+---------+---------+---------+---------+---------+  25962

G   T   L   R   R   D   R   G   G   L   A   D   F   H   T   A   L   G   E   A   -
       TACGGCGCAGGGGCGTGGAGGTCGACTGGAGCCCGGCCTTCGCCGACGCGGGTCGAG
25963  ------+---------+---------+---------+---------+---------+  26022

Y   A   Q   G   V   E   V   D   W   S   P   A   F   A   D   A   R   P   V   E   -
       CTGCCCGTCTACCCGTTCCAGCGGCAGGGGTACTGGCCTGCCCATCCCACCGGGGGGGC
26023  ------+---------+---------+---------+---------+---------+  26082
```

FIG. 2-70

```
         L   P   V   Y   P   F   Q   R   Q   R   Y   W   L   P   I   P   T   G   G   R   -
         GCACGGGACGAGGACGACGACTGGCCGCTACCAGTCGTATGCGGGAAGCCGAGTGGGAG
26083    ---------+---------+---------+---------+---------+---------+   26142

A   R   D   E   D   D   D   W   R   Y   Q   V   V   W   R   E   A   E   W   E   -
         AGCCGCTTCGCTGGCCGGACGCCGTGCTGCTGGTGACCGGACCCGGGCCGTGCCGAGTTG
26143    ---------+---------+---------+---------+---------+---------+   26202

S   A   S   L   A   G   R   V   L   L   V   T   G   P   G   V   P   S   E   L   -
         TCGGACGCCATCCGAAGTGGAGCAGAGCCGGTGCGACGTCCTGACCTGCGACGTG
26203    ---------+---------+---------+---------+---------+---------+   26262

S   D   A   I   R   S   G   L   E   Q   S   G   A   T   V   L   T   C   D   V   -
         GAATCCCGTTCGACCATCGGCACCGCACTGGAGGCCGCCGACACCGACGCTCTGTCCACT
26263    ---------+---------+---------+---------+---------+---------+   26322

E   S   R   S   T   I   G   T   A   L   E   A   A   D   T   D   A   L   S   T   -
         GTGGTGTCGCTGCTGTCCCGCGACGGCGAGGCCCGTCGATCCGTCGGACGGCGCTCGCC
26323    ---------+---------+---------+---------+---------+---------+   26382

V   V   S   L   L   S   R   D   G   E   A   V   D   P   S   L   D   A   L   A   -
         CTGGTCCAGGCCCTCGGAGCCGGGGTCGAAGCACCGCTGTGGTGCTGACCCGCAAC
26383    ---------+---------+---------+---------+---------+---------+   26442
```

```
        L   V   Q   A   L   G   A   A   G   V   E   A   P   L   W   V   L   T   R   N
        GCCGTGCAGGTGGCCGACGGGCGAACTGGTCGATCCGGCGCAGGCCATGGTGGGCGTCTC
26443   ------+---------+---------+---------+---------+---------+---  26502
        A   V   Q   V   A   D   G   E   L   V   D   P   A   Q   A   M   V   G   G   L
        GGCCGCGTGGTCGGCATCGAGCAGCCCGGGCGCTGGGGCGGTCTGGTGGACCTGGTCGAC
26503   ------+---------+---------+---------+---------+---------+---  26562
        G   R   V   V   G   I   E   Q   P   G   R   W   G   G   L   V   D   L   V   D
        GCCGATGCCGCGTCGATCCGGTCGCTGGCCGCGGTGCTGGCCGACCCGCGCGGCGAGGAG
26563   ------+---------+---------+---------+---------+---------+---  26622
        A   D   A   A   S   I   R   S   L   A   A   V   L   A   D   P   R   G   E   E
        CAGGTCGCGCGATCCGGGGCGGACGGGATCAAGGTGGCCGAGGCTCGTGCCCCCCCCGC
26623   ------+---------+---------+---------+---------+---------+---  26682
        Q   V   A   I   R   A   D   G   I   K   V   A   R   L   V   P   A   P   A   R
        GCCGGCACGCACCCCGCTGGAGCCCTGGTGCTGGTTCACCGGGCACCGGAGGG
26683   ------+---------+---------+---------+---------+---------+---  26742
        A   A   R   T   R   W   S   P   R   G   T   V   L   V   T   G   G   T   G   G
        ATCGGCGGCACGTCGCCCGGCTGGCCCGGCCTGCTGGCCCGAGCACCTGGTGCTGCTG
```

GGCAGGGCGCGGTGCCGACGCACCCGGCCGTCCGAGCTGAGGGAGGAGCTGACCGCGCTC
26803 ----------------------------------------------------------- 26862
        G  R  R  G  A  D  A  P  G  A  S  E  L  R  E  E  L  T  A  L

GGCACGGGCGTGACCATCGCCGCCTGCGACGTCGCCGACCGGGCTCGCGAAGCGGTG
26863 ----------------------------------------------------------- 26922
        G  T  G  V  T  I  A  A  C  D  V  A  D  R  A  R  L  E  A  V

CTCGCCGCGGAGCGCGCCGAGGGACGCACGGTCAGCGCCGTGATGCACGCGGCGGGGGTT
26923 ----------------------------------------------------------- 26982
        L  A  A  E  R  A  E  G  R  T  V  S  A  V  M  H  A  A  G  V

TCCACGTCCACGCCCCTCGACGACCTCACCGAAGCCGAGTTCACCGAGATCGCCGACGTG
26983 ----------------------------------------------------------- 27042
        S  T  S  T  P  L  D  D  L  T  E  A  E  F  T  E  I  A  D  V

AAGGTGCGCGGCACCGTCAACCTGGACGAGCTCTGCCCCGGACCTCGACGCGTTCGTGTTG
27043 ----------------------------------------------------------- 27102
        K  V  R  G  T  V  N  L  D  E  L  C  P  D  L  D  A  F  V  L
```

```
27103  TTCTCCTCCAACGCGGGGCGTGTGGGCAGTCCGGGCTCGCCTCCTACGCGGGGCCAAC  27162
          F   S   S   N   A   G   V   W   G   S   P   G   L   A   S   Y   A   A   A   N

27163  GCCTTCCTCGACGGCTTCGCGCGGCGCCGGAGCGAGGGCGCCCGGTGACGTCCATC    27222
          A   F   L   D   G   F   A   R   R   R   S   E   G   A   P   V   T   S   I

27223  GCCTGGGGGCTCTGGGCCGGGCAGAACATGGCCGGGGACGAGGGCGGCGAGTACCTGCGC  27282
          A   W   G   L   W   A   G   Q   N   M   A   G   D   E   G   G   E   Y   L   R

27283  AGCCAGGGCCTGCGCGGGCCATGGACCCCGGATCGGGCCGTCGAGGAACTGCACATCACCCTC  27342
          S   Q   G   L   R   A   M   D   P   D   R   A   V   E   E   L   H   I   T   L

27343  GACCACGGTCAGACGTCCGTGTCGGTCGTGGACATGGATCGCAGGCGGTTCGTCGAGCTG    27402
          D   H   G   Q   T   S   V   S   V   V   D   M   D   R   R   R   F   V   E   L

27403  TTCACCGCGGCCCGGCACCGGCCGCTGTTCGACGAGATCGCCGGTGCCCGGGCGGGAAGCC  27462
          F   T   A   A   R   H   R   P   L   F   D   E   I   A   G   A   R   A   E   A
```

```
27463 CGGCAGAGCGAGGAGGGCCCGGCGCTCGCCCAGCGCCTCGCGGCGCTGTCGACGGCCGAG 27522
       R  Q  S  E  E  G  P  A  L  A  Q  R  L  A  A  L  S  T  A  E

27523 AGGCGGGAGCACCTCGCCCACCTGATCCGCGCCGAGGTCGCCGCGGTGCTCGGCCACGGC 27582
       R  R  E  H  L  A  H  L  I  R  A  E  V  A  A  V  L  G  H  G

27583 GACGACGCGGCGATCGACCGCGACCGCGCCTTCCGCGACCTCGGCTTCGACTCCATGACC 27642
       D  D  A  A  I  D  R  D  R  A  F  R  D  L  G  F  D  S  M  T

27643 GCCGTCGACCTGCGGAACCGGCTCGCCGCGGTGACCGGGGTGCGGGAAGCCGCGACGGTG 27702
       A  V  D  L  R  N  R  L  A  A  V  T  G  V  R  E  A  A  T  V

27703 GTCTTCGACCACCCGACCATCACCCGGCTCGCCGACCACTACCTGGAGCGGCTCGTCGGC 27762
       V  F  D  H  P  T  I  T  R  L  A  D  H  Y  L  E  R  L  V  G

27763 GCAGCAGAGGCGCAGCCCGCTCGTGCGCGAGGTGCCGAAGGATGCCGACGAC 27822
       A  A  E  A  Q  P  A  L  V  R  E  V  P  K  D  A  D  D
```

FIG. 2-76

```
27823 CCGATCGCGATCGTCGGCATGGCCTGCCGCTTCCCCGGCGTGCACAACCCCGGTGAG 27882
       ---------+---------+---------+---------+---------+---------+
         P   I   A   I   V   G   M   A   C   R   F   P   G   G   V   H   N   P   G   E

27883 CTGTGGGAGTTCATCGTCGGCCGCGGGGAGATGCCCACCGACCGCGGC 27942
       ---------+---------+---------+---------+---------+---------+
         L   W   E   F   I   V   G   R   G   D   A   V   T   E   M   P   T   D   R   G

27943 TGGGACCTCGACGCGCTGTTCGACCCCGACCCGCAGCGCCACGGAACCAGTACTCGCGA 28002
       ---------+---------+---------+---------+---------+---------+
         W   D   L   D   A   L   F   D   P   D   P   Q   R   H   G   T   S   Y   S   R

28003 CACGGCGCGTTCCTCGACGGGGCCGCCGACTTCGACGCGGCGTTCTTCGGGATCTCGCCG 28062
       ---------+---------+---------+---------+---------+---------+
         H   G   A   F   L   D   G   A   A   D   F   D   A   A   F   F   G   I   S   P

28063 CGCGAGGCGCTGGCGATGGACCCGCAGCAGCGCCAGGTCCTGGAAACGACGTGGGAGCTG 28122
       ---------+---------+---------+---------+---------+---------+
         R   E   A   L   A   M   D   P   Q   Q   R   Q   V   L   E   T   T   W   E   L

28123 TTCGAGAACGCCGGCATCGACCCGCACTCGCTGGGGCAGCGACACCGGCGTCTTCCTC 28182
       ---------+---------+---------+---------+---------+---------+
```

```
        F   E   N   A   G   I   D   P   H   S   L   R   G   S   D   T   G   V   F   L
        GGCGCCCGCGTACCAGGGCTACGGGCCAGGACGCGGTGGTGCCCGAGGACAGCGAGGGCTAC
28183   ------+---------+---------+---------+---------+---------+   28242

G   A   A   Y   Q   G   Y   G   Q   D   A   V   V   P   E   D   S   E   G   Y
        CTGCTCACCGGCAACTCCTCCGCCGTGGTGTCCGGCGTCGCCTACGTGCTGGGCTG
28243   ------+---------+---------+---------+---------+---------+   28302

L   L   T   G   N   S   S   A   V   V   S   G   R   V   A   Y   V   L   G   L
        GAAGGCCCCGCGGTCACGGTGGACACGGTCGTTCGTCGTTGGCCTTGCATTCG
28303   ------+---------+---------+---------+---------+---------+   28362

E   G   P   A   V   T   V   D   T   A   C   S   S   S   L   V   A   L   H   S
        GCGTGTGGGTCGTTGCGTGACGGTGACTGCGGTCTTGCGGTGGCCGGTGGTGTCGGTG
28363   ------+---------+---------+---------+---------+---------+   28422

A   C   G   S   L   R   D   G   D   C   G   L   A   V   A   G   G   V   S   V
        ATGGCGGGCCCGAGTTCTCCCGCCAGGCGCTTGGCCGTGACGGG
28423   ------+---------+---------+---------+---------+---------+   28482

M   A   G   P   E   V   F   T   E   F   S   R   Q   G   G   L   A   V   D   G
        CGCTGCAAGGCGTTCTCCGCGGAGGCCGACGGCTTCGGTTCGCCGAGGGCGTCGCGGTG
28483   ------+---------+---------+---------+---------+---------+   28542
```

FIG. 2-77

```
          R  C  K  A  F  S  A  E  A  D  G  F  G  F  A  E  G  V  A  V   -
         GTCCTGCTCCAGCGGTTGTCCGACGCCCGCAGGGCGTCGCCAGGTGCTCGGCGTGGTC       28602
28543    ---------+---------+---------+---------+---------+---------+--

V  L  L  Q  R  L  S  D  A  R  R  A  G  R  Q  V  L  G  V  V   -
         GCGGGCTCGGCGATCAACCAGGACGGCGAGCAACGGTCTCGGCGCCGAGCGGGCGTC         28662
28603    ---------+---------+---------+---------+---------+---------+--

A  G  S  A  I  N  Q  D  G  A  S  N  G  L  A  A  P  S  G  V   -
         GCCCAGCAGCGCGTGATCCGCAAGGCGTGGGCGCGGATCACCGGCGCGGATGTG           28722
28663    ---------+---------+---------+---------+---------+---------+--

A  Q  Q  R  V  I  R  K  A  W  A  R  A  G  I  T  G  A  D  V   -
         GCCGTGGTGGAGGCGCATGGGCACCGGTACGCGGCTGGGCGATCCGGTGAGGCGTCGGCG      28782
28723    ---------+---------+---------+---------+---------+---------+--

A  V  V  E  A  H  G  T  G  T  R  L  G  D  P  V  E  A  S  A   -
         TTGCTGGCTACTTACGGCAAGTCGCGCGGTCGTCGCTGCCCGGTTCGGTG              28842
28783    ---------+---------+---------+---------+---------+---------+--

```
28843  AAGTCGAACATCGGTCACGCGCAGGCGGCCCGCGGGTGTCGCGGGCGTGATCAAGGTGTC
       -----+---------+---------+---------+---------+---------+  28902
            K  S  N  I  G  H  A  Q  A  A  A  G  V  A  G  V  I  K  V  V

28903  CTGGGGTTGAACCGGGGCCTGGTGCCGCCGATGCTCTGCCGCGGGGAGCGGTCGCCGCTG
       -----+---------+---------+---------+---------+---------+  28962
            L  G  L  N  R  G  L  V  P  P  M  L  C  R  G  E  R  S  P  L

28963  ATCGAATGGTCCTCGGGTGGTGTGGAACTTGCCGAGGCCGTGAGCCCGTGGCCTCCGGCC
       -----+---------+---------+---------+---------+---------+  29022
            I  E  W  S  S  G  G  V  E  L  A  E  A  V  S  P  W  P  P  A

29023  GCGGACGGGGTGCGCCGGGCCGGTGTGTCGGCGTTCGGGGTGAGCGGACGAACGCGCAC
       -----+---------+---------+---------+---------+---------+  29082
            A  D  G  V  R  R  A  G  V  S  A  F  G  V  S  G  T  N  A  H

29083  GTGATCATCGCCGAGCCCCCGGAGCCCCTGCCCGAACCCGGACCCGGTGTGGGCGTG
       -----+---------+---------+---------+---------+---------+  29142
            V  I  I  A  E  P  P  E  P  L  P  E  P  G  P  V  G  V

29143  CTGGCCCGCTGCGAACTCGGTGCCCGTACTGCTGTCGGCCAGGACCGAGACCGGCGTTGGCA
       -----+---------+---------+---------+---------+---------+  29202
```

FIG. 2-79

```
                  L   A   A   A   N   S   V   P   V   L   L   S   A   R   T   E   T   A   L   A
         GCGCAGGGCCGGCGCTCCTGGAGTCCGCAGTGGACGACTCGGTTCCGTTGACGGCATTGGCT
29203    ------+---------+---------+---------+---------+---------+    29262
                  A   Q   A   R   L   L   E   S   A   V   D   D   D   S   V   P   L   T   A   L   A
         TCCGCGCTGGCCACCGGAGACGCGCCCCTGCCGCGTCGTGGCGGCGTTGCTGTGGCAGGCGAC
29263    ------+---------+---------+---------+---------+---------+    29322
                  S   A   L   A   T   G   R   A   H   L   P   R   R   A   A   L   L   A   G   D
         CACGAACAGCTCCGCGGGCAGTTGCGCGGGTCGCCGAGGGCGTTGCGGGCTCCCGGTGCC
29323    ------+---------+---------+---------+---------+---------+    29382
                  H   E   Q   L   R   G   Q   L   R   A   V   A   E   G   V   A   A   P   G   A
         ACCACCGGAACCGCCTCCGCGCCGGCGGTGTTTCGTCTTCCCAGTCAGGGTCAGGCTCAG
29383    ------+---------+---------+---------+---------+---------+    29442
                  T   T   G   T   A   S   A   G   G   V   V   F   V   F   P   G   Q   G   A   Q
         TGGGAGGGCATGGCCCGGGGCTTGCTCTCGGTCCCCGTCTTCGCCGAGTCGATCGCCGAG
29443    ------+---------+---------+---------+---------+---------+    29502
                  W   E   G   M   A   R   G   L   L   S   V   P   V   F   A   E   S   I   A   E
         TGCGATGCGGTGTTGTCGGAGGTGGCCGGGTTCTCGGCCTCCGAAGTGCTGGAGCAGCGT
29503    ------+---------+---------+---------+---------+---------+    29562
```

FIG.2-80

```
         C  D  A  V  L  S  E  V  A  G  F  S  A  S  E  V  L  E  Q  R
         CCGGACGCGGCCGTCGCTGGAGCGGGTCGACGTCGTACAGCCGGTCGTTGTTCTCCGTGATG
29563    ------+---------+---------+---------+---------+---------+    29622
         P  D  A  P  S  L  E  R  V  D  V  V  Q  P  V  L  F  S  V  M
         GTGTCGCTGGCGCGGGCTGTGGGGCGCTTGCGGAGTCAGCCCCTCGGCCGTCATCGGCCAT
29623    ------+---------+---------+---------+---------+---------+    29682
         V  S  L  A  R  L  W  G  A  C  G  V  S  P  S  A  V  I  G  H
         TCGCAGGGCGAGATCGCCGCCGCCGTGGCCGGGGTGTTGTCGCTGGAGGACGGCGTG
29683    ------+---------+---------+---------+---------+---------+    29742
         S  Q  G  E  I  A  A  A  V  V  A  G  V  L  S  L  E  D  G  V
         CGCGTCGTGGCCCTGCGCGCCAAGGCCGTTGCGTGGGCAAGGGCGGCATGGTC
29743    ------+---------+---------+---------+---------+---------+    29802
         R  V  V  A  L  R  A  K  A  L  R  A  L  A  G  K  G  G  M  V
         TCGTTGGCGGCTCCCCGGTGAACGCGCTGATCGCACCGTGGAGGACCGGATC
29803    ------+---------+---------+---------+---------+---------+    29862
         S  L  A  A  P  G  E  R  A  R  A  L  I  A  P  W  E  D  R  I
         TCCGTCGCGGGGTCAACTCCCCGGTCGTCTCCCGGATCCGGAGGCGCTG
29863    ------+---------+---------+---------+---------+---------+    29922
```

```
         S   V   A   A   V   N   S   P   S   S   V   V   V   S   G   D   P   E   A   L
29923  GCCGAACTCGTCGTTGCGAGGAACGAGGGCGTGCGGCGCCAAGACGCTCCCGGTGGAC  29982
       ------+---------+---------+---------+---------+---------+

A   E   L   V   A   R   C   E   D   E   G   V   R   A   K   T   L   P   V   D
29983  TACGCCTCGCACTCCCGCCACGTCGAGGAGATCCGGAGACGATCCTCGCCGACCTCGAC  30042
       ------+---------+---------+---------+---------+---------+

Y   A   S   H   S   R   H   V   E   E   I   R   E   T   I   L   A   D   L   D
30043  GGCATCTCCGCGCGGCGTGCCGCCATCCCGCTCTACTCCACGCTGCACGGGCGAACGGCGC  30102
       ------+---------+---------+---------+---------+---------+

G   I   S   A   R   R   A   A   I   P   L   Y   S   T   L   H   G   E   R   R
30103  GACGGCGCCGACATGGGTCCGCGGTACTGGTACGACAACCTGCGCTCCCAGGTGCGCTTC  30162
       ------+---------+---------+---------+---------+---------+

D   G   A   D   M   G   P   R   Y   W   Y   D   N   L   R   S   Q   V   R   F
30163  GACGAGGCGGTCTCGGCCGCCGTCGCCGACGGTCACGCCACCTTCGTCGAGATGAGCCCG  30222
       ------+---------+---------+---------+---------+---------+

D   E   A   V   S   A   A   V   A   D   G   H   A   T   F   V   E   M   S   P
       CACCCGGTGCTCACCGCGCAGGAGATCGCCGACGCCGTGGCCATCGGGTCG
```

FIG. 2-83

```
30223  CTGCACCGCGACACCGGCGAGGAGCACCTGATCGCCGAGCTCGCCCGGGCGCACGTGCAC 30282
       H  P  V  L  T  A  A  V  Q  E  I  A  A  D  A  V  A  I  G  S

30283 GGCGTGGCCGTGGACTGGCGGAACGTCTTCCCGGCGCACCTCCGTGGCCTGCCCAAC 30342
       L  H  R  D  T  A  E  E  H  L  I  A  E  L  A  R  A  H  V  H

30343 GGCGTGGCCGTGGACTGGCGGAACGTCTTCCCGGCGCACCTCCGTGGCCTGCCCAAC 30402
       G  V  A  V  D  W  R  N  V  F  P  A  A  P  P  V  A  L  P  N

30403 TACCCGTTCGAGCCCCAGCGCTACTGGCTCGCCGGAGGTGTCCGACCAGCTCGCCGAC 30462
       Y  P  F  E  P  Q  R  Y  W  L  A  P  E  V  S  D  Q  L  A  D

30463 AGCCGCTACCGCGTCGACTGGCGGCCACTGGCCACCACGCCGGTGGACCTGGAAGGCGGC 30522
       S  R  Y  R  V  D  W  R  P  L  A  T  T  P  V  D  L  E  G  G

30523 TTCCTGGTCCACGGGTCCGCACCGGAGTCGCTGACCAGCGCAGTCGAGAAGGCCGGAGGC 30582
       F  L  V  H  G  S  A  P  E  S  L  T  S  A  V  E  K  A  G  G
```

```
30583  CGCGTCGTGCCGGTCGCCTCGGCCGACCGCGAAGCCTCGGCGGCCCTGCGGGAGGTGCCG   30642
              R  V  V  P  V  A  S  A  D  R  E  A  S  A  A  L  R  E  V  P

30643  GGCGAGGTCGCCGGCGTGCTCTCGGTCCACACCGGCGCCGCAACGCACCTCGCGCTGCAC   30702
              G  E  V  A  G  V  L  S  V  H  T  G  A  A  T  H  L  A  L  H

30703  CAGTCGCTGGGTGAGGCCGGCGTGCGGGCCCCGCTCTGGCTGGTCACCAGCCGAGCGGTC   30762
              Q  S  L  G  E  A  G  V  R  A  P  L  W  L  V  T  S  R  A  V

30763  GCGCTCGGGGAGTCCGAGCCGGTCGATCCCGAGCAGGCGATGGTGTGGGGTCTCGGGCGC   30822
              A  L  G  E  S  E  P  V  D  P  E  Q  A  M  V  W  G  L  G  R

30823  GTCATGGGCCTGGAGACCCCCGGAACGGGTGTCTGTGGACCTGCCCGCCGAACCC   30882
              V  M  G  L  E  T  P  E  R  W  G  G  L  V  D  L  P  A  E  P

30883  GCGCCCGGGGACGGCGAGGCGTTCGTCGCCTGCCTCGGCCTGGACGGCCACGAGGACCAG   30942
              A  P  G  D  G  E  A  F  V  A  C  L  G  A  D  G  H  E  D  Q
```

FIG. 2-84

```
30943 GTCGCGATCCGTGACCACGCGCCCGCTACGGCCGCCGCCTCGTCCGCGCCCCGCTGGGCACC
      ----+----+----+----+----+----+----+----+----+----+----+----+ 31002
       V  A  I  R  D  H  A  R  Y  G  R  R  L  V  R  A  P  L  G  T

31003 CGGCGAGTCGAGCTGGGAGCCGGCGGGCACGGCGCTGGTCACCGGCGGCACCGGTGCGCTC
      ----+----+----+----+----+----+----+----+----+----+----+----+ 31062
       R  E  S  S  W  E  P  A  G  T  A  L  V  T  G  G  T  G  A  L

31063 GGCGGCCACGTCGCCCGCCACCTCGCCAGGTGCGGTGGAGGACCTGGTGCTGGTCAGC
      ----+----+----+----+----+----+----+----+----+----+----+----+ 31122
       G  G  H  V  A  R  H  L  A  R  C  G  V  E  D  L  V  L  V  S

31123 AGGCGCGGCGTCGACGCTCCCGGCGCCGAGCTGGAAGCCGAACTGGTCGCCCTCGGC
      ----+----+----+----+----+----+----+----+----+----+----+----+ 31182
       R  R  G  V  D  A  P  G  A  A  E  L  E  A  E  L  V  A  L  G

31183 GCGAAGACGACCATCACCGCGTGCGACGTGGCCGACCGCGAGCAGCTCTCCAAGCTGCTG
      ----+----+----+----+----+----+----+----+----+----+----+----+ 31242
       A  K  T  T  I  T  A  C  D  V  A  D  R  E  Q  L  S  K  L  L

31243 GAAGAACTGCGCGGCAGGGACGTCCGGTGCGTGCACACCGGCGGGGTGCCC
      ----+----+----+----+----+----+----+----+----+----+----+----+ 31302
```

FIG. 2-85

```
       E  E  L  R  G  Q  G  R  P  V  R  T  V  V  H  T  A  G  V  P
       GAATCGAGGCCGCTGCACGAGATCGGCGAGCTGGAGTCGGTCGCGGCGAAGGTGACC
31303  ----+----+----+----+----+----+----+----+----+----+----+  31362

E  S  R  P  L  H  E  I  G  E  L  E  S  V  C  A  A  K  V  T
       GGGGCCCGGCTGCTCGACGAGCTGTGCCCCGAGACCTTCGTCCTGTTCTCGTCC
31363  ----+----+----+----+----+----+----+----+----+----+----+  31422

G  A  R  L  L  D  E  L  C  P  D  A  E  T  F  V  L  F  S  S
       GGAGCGGGGGTGTGGGGCAGTGCGCAACCTCGGCGCCTACTCCGGCCAACGCCTACCTC
31423  ----+----+----+----+----+----+----+----+----+----+----+  31482

G  A  G  V  W  G  S  A  N  L  G  A  Y  S  A  A  N  A  Y  L
       GACGCGCTGGCCCACCGCGCCCGTGCGAAGGCCCGTCGCGGCACGTCCGTCGGGGC
31483  ----+----+----+----+----+----+----+----+----+----+----+  31542

D  A  L  A  H  R  R  R  A  E  G  R  A  A  T  S  V  A  W  G
       GCCTGGGCGGGCGAGGGCATGGCCACCGGCGACCTCGAGGGCTCACCCGGCGCCCTG
31543  ----+----+----+----+----+----+----+----+----+----+----+  31602

A  W  A  G  E  G  M  A  T  G  D  L  E  G  L  T  R  R  G  L
       CGCCCGATGGCGCCCGAGCCGCGGCCGATCCGCGCTGCACCAGGCGCTGGACAACGGGGAC
31603  ----+----+----+----+----+----+----+----+----+----+----+  31662
```

FIG. 2-86

```
        R   P   M   A   P   E   R   A   I   R   A   L   H   Q   A   L   D   N   G   D
        ACGTGCGTTTCGATCGCCGACGTGACTGGGAGGCCTTCGGGTCGGCTTCACCGCCGCC
31663   ---+---------+---------+---------+---------+---------+---------+  31722

T   C   V   S   I   A   D   V   D   W   E   A   F   A   V   G   F   T   A   A
        CGGCCGCCGTCCGCTGGACGAGCTCGTCACGCCGGTGGGGCCGTCCCCGCGGTG
31723   ---+---------+---------+---------+---------+---------+---------+  31782

R   P   R   P   L   L   D   E   L   V   T   P   A   V   G   A   V   P   A   V
        CAGGCGGCCCCGGCGCGGGAGATGACGTCGCAGGAGTTGCTGGAGTTCACGCACTCGCAC
31783   ---+---------+---------+---------+---------+---------+---------+  31842

Q   A   A   P   A   R   E   M   T   S   Q   E   L   L   E   F   T   H   S   H
        GTCGCGGGCGATCCTCGGGCATTCCAGCCCGGACGCGGTCGGGCAGGACCAGCCGTTCACC
31843   ---+---------+---------+---------+---------+---------+---------+  31902

V   A   A   I   L   G   H   S   S   P   D   A   V   G   Q   D   Q   P   F   T
        GAGCTCGGCTTCGACTCGCTGACCGCGGTCGGGCTGCGCAACCAGCTCCAGCAGGCCACC
31903   ---+---------+---------+---------+---------+---------+---------+  31962

E   L   G   F   D   S   L   T   A   V   G   L   R   N   Q   L   Q   Q   A   T
        GGGCTCGGCGCTGCCCCGGACCCTGGTGTTCGAGCACCCCACGGTCCGCAGGTTGGCCGAC
31963   ---+---------+---------+---------+---------+---------+---------+  32022
```

```
              G  L  A  L  P  A  T  L  V  F  E  H  P  T  V  R  R  L  A  D    -
         CACATAGGACACAGCTCGACAGCGGGACTCCCGCCCGGAAGCGAGCAGCGCTCTTCGC               32082
32023    ----+----+----+----+----+----+----+----+----+----+----+----+
              H  I  G  Q  Q  L  D  S  G  T  P  A  R  E  A  S  S  A  L  R    -
         GACGGCTACCGGCAGGCGGGGCCGTGTCGGGCAGGGTCCGGTCCTACCTGACCTGCTGGCG               32142
32083    ----+----+----+----+----+----+----+----+----+----+----+----+
              D  G  Y  R  Q  A  G  V  S  G  R  V  R  S  Y  L  D  L  L  A    -
         GGGCTGTCGGACTTCCGCGAGCACTTCGACGGTCTCCGACGGTTCTCCCTCGATCTCGTG               32202
32143    ----+----+----+----+----+----+----+----+----+----+----+----+
              G  L  S  D  F  R  E  H  F  D  G  S  D  G  F  S  L  D  L  V    -
         GACATGGCCGACGGTCCCGGAGAGGTCACGGTGATCTGCTGCGCGGGAACGGGCGGCGATC               32262
32203    ----+----+----+----+----+----+----+----+----+----+----+----+
              D  M  A  D  G  P  G  E  V  T  V  I  C  C  A  G  T  A  A  I    -
         TCCGGTCCGGCACGAGTTCACCCGGCTCGCCGGGGCGCTGCGCGGAATCGCTCCGGTTCGG               32322
32263    ----+----+----+----+----+----+----+----+----+----+----+----+
              S  G  P  H  E  F  T  R  L  A  G  A  L  R  G  I  A  P  V  R    -
```

```
32323  GCCGTGCCCCAGCCCGGCTACGAGGAGGGGGAACCTCTGCCGTCGTCGATGGCGGCGGTG  32382
            A  V  P  Q  P  G  Y  E  E  G  E  P  L  P  S  S  M  A  A  V

32383  GCGGGGGTGCAGGCCGATGCGGTCATCAGGACACAGGGGGACAAGCCGTTCGTGGTGGCC  32442
            A  A  V  Q  A  D  A  V  I  R  T  Q  G  D  K  P  F  V  V  A

32443  GGTCACTCCGCGGGGCACTGATGGCCTACGCGCTGGCGACCGAACTGCTCGATCGCGGG   32502
            G  H  S  A  G  A  L  M  A  Y  A  L  A  T  E  L  L  D  R  G

32503  CACCCGCCACGCGGTGTCGTCCTGATCGACGTCTACCCGCCGGTCACCAGGACGCGGATG  32562
            H  P  P  R  G  V  V  L  I  D  V  Y  P  P  G  H  Q  D  A  M

32563  AACGCCTGGCTGGAGGAGCTGACCGCCACGCTGTTCGACCGCGAGACGGTGCGGATGGAC  32622
            N  A  W  L  E  E  L  T  A  T  L  F  D  R  E  T  V  R  M  D

32623  GACACCAGGCTCACCGGCCTACGACCGCCTCACCGGTCAGTGGCGACCCCGG          32682
            D  T  R  L  T  G  A  Y  D  R  L  T  G  Q  W  R  P  R
```

FIG. 2-89

```
32683 GAAACCGGGCTGCCGACGCTGCTGGTCAGCGCCGGCGAGCCGATGGGTCCGTGGCCCGAC
      ------+---------+---------+---------+---------+---------+ 32742
      E  T  G  L  P  T  L  L  V  S  A  G  E  P  M  G  P  W  P  D

32743 GACAGCTGGAAGCCGACGTGGCCCTTCGAGCACGACACCGTCGCCGTCCCCGGCGACCAC
      ------+---------+---------+---------+---------+---------+ 32802
      D  S  W  K  P  T  W  P  F  E  H  D  T  V  A  V  P  G  D  H

32803 TTCACGATGGTGCAGGAACACGCCGATGCGGCGATCGCGCGGCACATCGACGCCTGGCTGGGC
      ------+---------+---------+---------+---------+---------+ 32862
      F  T  M  V  Q  E  H  A  D  A  A  I  A  R  H  I  D  A  W  L  G

32863 GGAGGGAATTCATGA
      ------+-------- 32877
      G  G  N  S  *
```

FIG. 2-90

| NUMBER | SITE | DISTANCE (Kb)[a] |
|---|---|---|
| 1 | BamHI | −3.60 |
| 2 | PvuII | −3.50 |
| 3 | PvuII | −3.40 |
| 4 | PstI | −3.05 |
| 5 | BamHI | −2.95 |
| 6 | XhoI | −2.80 |
| 7 | PstI | −2.00 |
| 8 | HindII | −1.60 |
| 9 | SphI | −1.55 |
| 10 | EcoRI | −1.50 |
| 11 | KpnI | −1.35 |
| 12 | EcoRI | −1.05 |
| 13 | SmaI[b] | −0.90 |
| 14 | SphI | −0.75 |
| 15 | KpnI | −0.65 |
| 16 | SmaI | −0.20 |

FIG. 4

METHOD OF DIRECTING BIOSYNTHESIS OF SPECIFIC POLYKETIDES

This application is a divisional of U.S. Ser. No. 07/642,734, filed Jan. 17, 1991, issued as U.S. Pat. No. 5,824,513 on Oct. 20, 1998.

FIELD OF THE INVENTION

The present invention relates to a method for directing the biosynthesis of specific polyketide analogs by genetic manipulation. In particular, polyketide biosynthetic genes are manipulated to produce precise, novel polyketides of predicted structure.

BACKGROUND OF THE INVENTION

Polyketides are a large class of natural products that includes many important antibiotics and immunosuppressants such as erythromycins, tetracyclines, and rapamycins. Their synthesis proceeds by an ordered condensation of acyl esters to generate carbon chains of varying length and substitution pattern that are later converted to mature polyketides. This process has long been recognized as resembling fatty acid biosynthesis, but with important differences. Unlike a fatty acid synthase, a typical polyketide synthase is programmed to make many choices during carbon chain assembly: For example, the choice of "starter" and "extender" units, which are often selected from acetate, propionate or butyrate residues in a defined sequence. The choice of using a full cycle of reduction-dehydration-reduction after some condensation steps, omitting it completely, or using one of two incomplete cycles (reduction alone or reduction followed by dehydration), which determines the pattern of keto or hydroxyl groups and the degree of saturation at different points in the chain is additionally programed. Finally the choice of stereochemistry for the substituents at many of the carbon atoms is programmed by the polyketide synthase.

Because of the commercial significance of Streptomyces, a great amount of effort has been expended in the study of Streptomyces genetics. Consequently much is known about Streptomyces and several cloning vectors exist for transformations of the organism.

Although many polyketides have been identified, there remains the need to obtain novel polyketide structures with enhanced properties. Current methods of obtaining such molecules include screening of natural isolates and chemical modification of existing polyketides, both of which are costly and time consuming. Current screening methods are based on gross properties of the molecule, i.e. antibacterial, antifungal activity, etc., and both a priori knowledge of the structure of the molecules obtained or predetermination of enhanced properties are virtually impossible. Chemical modification of preexisting structures has been successfully employed, but it still suffers from practical limitations to the type of compounds obtainable, largely connected to the poor yield of multistep syntheses and available chemistry to effect modifications. The following modifications are extremely difficult or inefficient at the present time: change of the stereochemistry of the side chains in the completed polyketide; change of the length of the polyketide by removal or addition of carbon units from the interior of the acyl chain; and dehydroxylation at unique positions in the acyl chain. Accordingly, there exists the need to obtain molecules wherein such changes can be specified and performed and would represent an improvement in the technology to produce altered polyketide molecules with predicted structure.

SUMMARY OF THE INVENTION

The present invention provides a method to produce novel structures from designing and introducing specified changes in the DNA governing the synthesis of the polyketide. According to the method of the present invention, the biosynthesis of specific polyketide analogs is accomplished by genetic manipulation of a polyketide-producing microorganism comprising the steps of:

(1) isolating a polyketide biosynthetic gene-containing DNA sequence;

(2) identifying enzymatic activities associated within said DNA sequence;

(3) introducing one or more specified changes into said DNA sequence which codes for one of said enzymatic activities which results in an altered DNA sequence;

(4) introducing said altered DNA sequence into the polyketide-producing microorganism to replace the original sequence;

(5) growing a culture of the altered microorganism under conditions suitable for the formation of the specific polyketide analog; and (6) isolating said specific polyketide analog from the culture.

The present method is most useful when the segment of the chromosome modified is involved in an enzymatic activity associated with polyketide biosynthesis. The present invention is especially useful in manipulating polyketide biosynthetic genes from Streptomyces, an organism which provides over one-half of the clinically useful antibiotics.

BRIEF DESCRIPTION OF THE DRAWINGS

FIG. 2. illustrates the nucleotide sequence of eryA with corresponding translation of the three open reading frames. Standard one letter codes for the amino acids appear beneath their respective nucleic acid codons. The standard one letter codes for the amino acid sequences are as follows:

Figure 3:
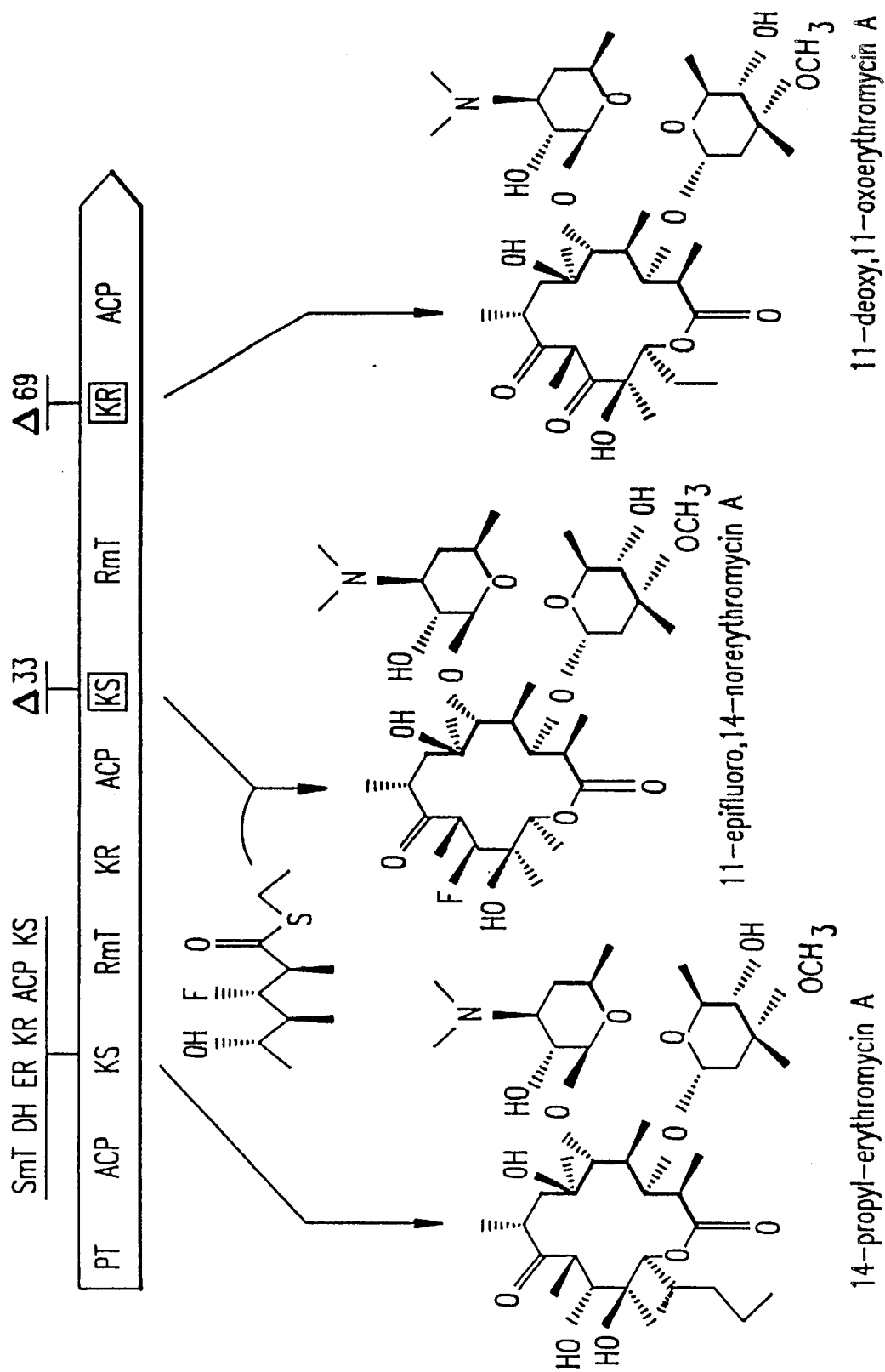

A—alanine
R—arginine
N—asparagine
D—aspartic acid
C—cysteine
Q—glutamine
E—glutamic acid
G—glycine
H—histidine
I—isoleucine
L—leucine
K—lysine M—methionine (start)
F—phenylalanine
P—proline
S—serine
T—threonine
W—tryptophan
Y—tyrosine
V—valine FIG. 3. is a schematic representation of Type I, Type II and Type III changes in eryA and structures of corresponding novel polyketides produced. Δ69 (Type I) and Δ33 (Type II) represent in-frame deletions of the base pairs in the DNA segments corresponding to the KR of module 2 and the β-ketoacyl ACP synthase of module 2, respectively. Insertion of a complete copy of module 4 within module 1 is also shown. Production of 11-epifluoro-15-norerythromycin in strain that carries Δ33 occurs when substrate analog (2S,3S,4S,5S)2,4-dimethyl-3-fluoro-5-hydroxyhexanoic acid-ethyl thioester is fed.

FIG. 4 illustrates the restriction site coordinates of cosmid pR1 5' to the sequence of eryA (FIG. 2).

DETAILED DESCRIPTION OF THE INVENTION

For the purposes of the present invention as disclosed and claimed herein, the following terms are defined.

The term "polyketide" as used refers to a large and diverse class of natural products, including antibiotics, pigments, and immunosuppressants. Antibiotics include, but are not limited to anthracyclines, tetracyclines, polyethers, ansamycins, macrolides of different types (polyenes and avermectins as well as classical macrolides such as erythromycins).

The term "polyketide-producing microorganism" as used herein includes any Actinomycetales which can produced a polyketide. Examples of Actinomycetes that produce polyketides include but are not limited to *Micromonospora rosaria, Micromonospora megalomicea, Sacharapolyspora erythraea, Streptomyces antibioticus, Streptomyces albireticuli, Streptomyces ambofasciens, Streptomyces avermitilis, Streptomyces fradiae, Streptomyces hygroscopicus, Streptomyces tsukubaensis, Streptomyces griseus, Streptomyces mycarofasciens, Streptomyces platensis, Streptomyces venezuelae, Streptomyces violaceoniger,* and various Actinomadura, Dactylosporangium and Nocardia strains that produce polyether type of polyketides.

The term "polyketide synthase" as used herein refers to the complex of enzymatic activities responsible for the biosynthesis of polyketides which include but are not limited to β-ketoreductase, dehydratase, acyl carrier protein, enoylreductase, β-ketoacyl ACP synthase, and acyltransferase.

The term "extender" as used herein refers to a coenzyme A thioester of a dicarboxylate which is incorporated into a polyketide by a polyketide synthase.

The term "starter" as used herein refers to a coenzyme A thioester of a carboxylic acid which is used by the polyketide synthase as the first building block of the polyketide.

The term "eryA" as used herein refers to the genes involved in the formation of the polyketide moiety of erythromycin.

The term "condensation" as used herein refers to the addition of an extender unit out to the nascent polyketide chain and requires the action of β-ketoacyl ACP synthase, acyltransferase, and acyl carrier protein.

The term "β-carbonyl processing" as used herein refers to changes effecting the carbonyl group of the growing polyketide via β-ketoreductase, dehydratase, and enoylreductase.

The term "module" as used herein refers to the genetic element encoding one condensation step, as defined above, and one β-carbonyl processing step, as defined herein.

The term "Type I change" as used herein refers to changes in DNA sequence which will result in the production of polyketide rings of length identical to that of 6-deoxyerythronolide A, but with altered functional groups at specific ring positions.

The term "Type II change" as used herein refers to alterations which will result in the production of macrolide rings only when fed exogenously with substrate analogs, e.g. thioesters of appropriate acyl compounds of various length. Thus Type II mutants are erythromycin non-producing (Ery⁻) mutants. The structure of the resulting macrolides will depend on the substrate employed.

The term "Type III change" as used herein refers to alterations which will result in the biosynthesis of macrolide rings of length reduced (deletion) or increased (insertion) by two carbon units, or macrolide rings altered in specific portions of the chain (replacement).

Figure 1:
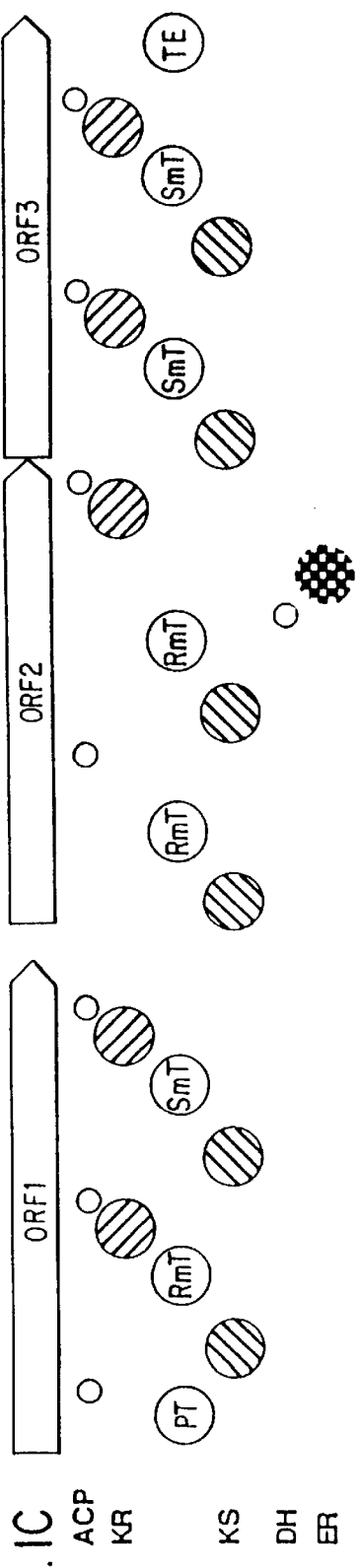
FIG. 1 illustrates the organization of gene encoding polyketide synthase and designated eryA as follows: (a) Map coordinates of the DNA; (b) DOTPLOT of the output of COMPARE (window=50, stringency=32) program (Sequence Analysis Software Package of the Genetics Computer Group, University of Wisconsin, Biotechnology Center, 1710 University Avenue, Madison, Wisconsin 53705 of eryA segment (x-axis) vs. subsegment of eryA comprises between 23–27.5 sequence coordinates (y-axis) [see FIG. 2]; (c) Open reading frame organization of eryA and enzymatic activities encoded. PT=propionyltransferase; ACP=acyl carrier protein; KS=$\beta$-ketoacyl ACP synthase; RmT=(2R) methylmalonyl CoA transferase; KR=$\beta$-ketoreductase; SmT=(2S) methylmalonyl CoA transferase; DH=dehydratase; ER=enoylreductase; TE=thioesterase; and (d) Schematic diagram showing the extent of each of the six modules in eryA.

In its broadest sense, the present invention entails a general procedure for producing novel polyketide structures in vivo by selectively altering the genetic information of the organism that naturally produces a related polyketide. A set of examples described herein are a series of novel polyketides that make use of the genetic information for the biosynthesis of the polyketide portion of the macrolide antibiotic erythromycin. The organization of the segment of the *Saccharapolyspora erythraea* chromosome, designated eryA, and the corresponding polypeptides which it encodes that determine the biosynthesis of the polyketide segment of erythromycin, are shown in FIG. 1. It is seen that eryA is organized in modules, as shown, and that each module takes care of one condensation step, through the action of the β-ketoacyl ACP synthase specified within, wherein an extender unit, methylmalonyl CoA, is added first to the starter unit, propionyl CoA, and then to the successively growing acyl chain. The precise succession of elongation steps is dictated by the genetic order of the six modules: module 1 determines the first condensation; module 2, the second; module 3, the third, and so on until the sixth condensation step has occurred. Furthermore, the processing of the growing chain after each condensation is also determined by the information within each module. Thus β-ketoreduction of the β-carbonyl takes place after each step except for step 3, as determined by the presence of a functional β-ketoreductase in all modules except module 3, whereas dehydration and enoylreduction only take place after the fourth extender unit is added to the growing acyl chain, as determined by the presence of dehydratase and enoylreductase in module 4. Furthermore, the choice of the correct enantiomer (2R or 2S) of methylmalonyl-CoA as the extender unit employed at each condensation is specified by the acyltransferase function determined by each module (FIG. 1C).

In the present invention, novel polyketide molecules of desired structure are produced by the introduction of specific genetic alterations of the eryA sequence into the *Sac. erythraea* chromosome. The complete nucleotide sequence of the eryA segment of the *Sac. erythraea* chromosome and the sequence of the corresponding polypeptides are shown in FIG. 2. Three types of alterations to the eryA DNA sequence are described: (i) those inactivating a single function in a module which does not arrest acyl chain growth (β-ketoreductase, dehydratase, or enoylreductase); (ii) those inactivating a single function in a module which does arrest chain growth (β-ketoacyl ACP synthase, acyltransferase or acyl carrier protein); and (iii) those affecting an entire module (deletion, insertion, or replacement). The novel polyketides produced by strains carrying these types of mutations can be classified accordingly. Type I changes will result in the production of polyketide rings of length identical to that of 6-deoxyerythronolide A, but with altered functional groups at specific ring positions. Strains carrying type II alterations will result in the production of macrolide rings only when fed exogenously with substrate analogs, e.g. thioesters of appropriate acyl compounds of various length. Thus Type II mutants are erythromycin non-producing (Ery⁻) mutants. The structure of the resulting macrolides will depend on the substrate employed. Type III changes will result in the biosynthesis of macrolide rings of length reduced (deletion) or increased (insertion) by two carbon units, or macrolide rings altered in specific portions of the chain (replacement). A schematic representation of some examples of Type I, Type II and Type III alterations in eryA and the corresponding novel polyketides produced in hosts that carry such alterations is shown in FIG. 3.

In the examples described herein, specific mutations in the eryA region of the *Sac. erythraea* chromosome are introduced by a simple two-step approach: 1) introduction of a specified change in a cloned DNA segment; 2) exchange of the wild type allele with the mutated one. Step 1 requires standard recombinant DNA manipulations employing *E. coli* as the host. Step 2 requires one or more plasmids out of the several *E. coli-Sac. erythraea* shuttle vectors available and a simple screening procedure for the presence of the colony carrying the altered gene. Two methods are used to introduce the altered allele into the chromosome to replace the wild type allele. The first employs gene replacement, described in Examples 7, 11, 15, 19 and 24, wherein the gene to be altered, along with adjacent upstream and downstream DNA, is mutated and cloned into a *Sac. erythraea* non-replicating vector. The plasmid carrying the altered allele is then introduced into the host strain by transformation of protoplasts employing selection for a plasmid marker. Since the plasmid does not replicate, regenerated cells that carry the marker have undergone a single homologous recombination between one of the two segments flanking the mutation on the plasmid and its homologous counterpart in the chromosome. Some of the colonies that have subsequently lost the marker will have undergone a second recombination between the other plasmid borne adjacent DNA segment and its homologous chromosomal counterpart resulting in the retention of the mutation in the chromosome, replacing the normal allele with the mutant one. The second method to introduce an altered allele into the chromosome employs gene conversion, described in Examples 37 and 43. In this method, an Ery⁻ *Sac. erythraea* strain carrying a deletion of a specified region of the eryA segment of the chromosome is used as a host. Into a *Sac. erythraea* multicopy plasmid that carries a selectable marker is cloned the wild type counterpart (segment 1) of the eryA segment mutant in the host. Subsequently, the desired homologous or heterologous DNA segment to be introduced (segment 2) is cloned within the portion of segment 1 which is deleted in the mutant strain. The resulting plasmid is then introduced into the host employing selection for the marker. Among the transformants will be a population that have integrated segments 1 and 2 from the plasmid by the process of gene conversion which can be verified by examination of the DNA among the colonies that have recovered the ability to produce erythromycin.

Two examples each of Types I, II and III alterations to the eryA DNA sequence and the resultant novel polyketides produced are described in the examples described herein. Examples 1 through 8, 9 through 12 and 13 through 16 describe the construction and effect of three Type I mutants. Examples 17 through 22 and 23 through 27 describe the construction of two Type II mutants and the effects of feeding two different synthetic substrates to the mutant strains. Examples 28 through 38 and 39 through 44 outline the steps in constructing Type III changes and their respective effects on the structure of the novel polyketides produced. In Examples 1 through 7 a plasmid that contains a substantial deletion of the segment of the gene corresponding to the b-ketoreductase of module 5 is created, the altered gene is inserted into the *Sac. erythraea* chromosome to replace the wild type allele and the new strain carrying the altered gene is identified and isolated. In Example 8, the new strain is fermented and the novel polyketide 5-oxo-5,6-dideoxy-3α-mycarosyl erythronolide B that results from the introduction of the mutant allele is isolated. In Examples 9 through 11, a mutation is introduced into the β-ketoreductase of module 2 and the mutated allele is then used to replace the wild type allele in the chromosome. In Example 12, the strain carrying the altered allele is fermented and the novel compound 11-oxo-11-deoxyerythromycin A is isolated. Similarly, in Examples 13 through 16 a mutation is introduced into the dehydratase of module 4 and the mutated allele is then used to replace the wild type allele in the chromosome. The strain carrying this altered allele is then fermented and the novel products 7-hydroxyerythromycin A and 6-deoxy-7-hydroxyerythromycin A are isolated. In Examples 17 through 21, a mutation is made in the DNA corresponding to the β-ketoacyl-ACP synthase of module 1 and introduced into the chromosome to replace the wild type allele. This mutation has the effect of arresting the synthesis of the polyketide chain and results in the Ery⁻ phenotype. The synthetic substrate (2S,3R,4S,5S)3,5-dihydroxy-2,4-dimethylhexanoic acid-ethyl ester is then made and fed to the mutant resulting in the production of the novel compound (14S,15S)14(1-hydroxyethyl)erythromycin. Similarly, in Examples 22 through 24, a mutation is created in the β-ketoacyl-ACP synthase of module 2 and introduced into the chromosome to replace the wild type allele. In Example 25 and 26, the synthetic substrate (2S,3S,4S,5S)2,4-dimethyl-3-fluoro-5-hydroxyhexanoic acid-ethyl thioester is made and fed to the NRRL module 2β-ketoacyl-ACP synthase mutant and the resulting novel compound 11-epifluoro-15-norerythromycin is isolated. In Examples 27 through 38, a copy of the DNA sequence corresponding to module 4 is introduced into the deleted segment of the β-ketoacyl-ACP synthase of module 1 resulting in the production of the novel compound 14(1-propyl)erythromycin. In Examples 40 through 44, a copy of the DNA sequence corresponding to module 5 is introduced into the deleted segment of the β-ketoacyl ACP synthase of module 1 resulting in the production of the novel compound 14[1(1-hydroxypropyl)]erythromycin.

GENERAL METHODS

Materials, Plasmids and Bacterial Strains

Restriction endonucleases, T4 DNA ligase, nick-translation kit, competent *E. coli* DH5α cells, X-gal, IPTG, and plasmids pUC19 and pUC12 are purchased from Bethesda Research Laboratories (BRL), Gaithersburg, Md. [α-$^{32}$P]dCTP and Hybond N are from Amersham Corp., Chicago, Ill. Seakem LE agarose and Seaplaque low gelling temperature agarose are from FMC Bioproducts, Rockland, Me. *E. coli* K12 strains carrying the *E. coli*-Sac. shuttle plasmids pWHM3 or pWHM4 (Vara et al., *J. Bacteriol.*, 171: 5872 (1989)) or the cosmids pS1 (Tuan et al., *Gene* 90: 21 (1990)) and *Sac. erythraea* strain NRRL2338 have been deposited in the culture collection of the Agricultural Research Laboratories, Peoria, Ill. and are available under the NRRL accession numbers B-30055, B-30054, and B-30056 respectively. *Staphylococcus aureus* Th$^R$ (thiostrepton resistant) is obtained by plating $10^8$ cells of *S. aureus* on agar medium containing 10 mg/ml thiostrepton and picking a survivor after 48 hr growth at 37° C. Thiostrepton is obtained from Squibb-Bristol Myers, New Brunswick, N.J. All other chemical and reagents are from standard commercial sources unless specified otherwise.

DNA Manipulations

Standard conditions (Maniatis et al., *Molecular Cloning, A Laboratory Manual*, Cold Spring Harbor Laboratory, Cold Spring Harbor, N.Y., 1982) are employed for restriction endonuclease digestion, agarose gel-electrophoresis, nick translation of DNA to make $^{32}$P-labeled probes, DNA ligation, and transformation of *E. coli* employing selection for ampicillin resistance (Ap$^R$) on LB agar plates. Plasmid DNA is isolated from minipreps of *E. coli* transformants by the boiling method (Maniatis et al., 1982, supra). DNA fragments are recovered from low melting agarose gels using the method of Langridge et al., 1980. Total DNA from *Sac. erythraea* strains is prepared according to described procedures (Hopwood et al., *Genetic Manipulation of Streptomyces, A Laboratory Manual*, John Innes Foundation, Norwich, U.K., 1985). DNA is transferred from agarose gels onto Hybond N following the manufacturer's instructions. Hybridizations are performed in sealed bags containing 10–20 ml of [1×NET (20×NET=3 M NaCl, 0.3 M TrisHCl, 20 mM Na$_2$EDTA, pH 8.0), 5×Denhardt's solution (Maniatis et al, 1982, supra), 0.2 mg/ml denatured calf thymus DNA, 0.2% SDS, and $0.5-2\times10^7$ cpm of the nick-translated probe] for 16–20 hr at 65° C. Filters are washed three times in 1×NET/0.1% SDS for 20 min each at room temperature, and once in 0.05×NET/0.1% SDS for 20 min at 70° C. Filters are reused as described (Donadio et al., 1990).

Amplification of DNA Fragments

Synthetic deoxyoligonucleotides are synthesized on an ABI Model 380A synthesizer (Applied Biosystems, Foster City, Calif.) following the manufacturer's recommendations. Amplification of DNA fragments is performed by the polymerase chain reaction (PCR) employing a Coy thermocycler. Reactions contain 100 pmol of each primer, 1 µg of template DNA (cosmid pS1 carrying the eryA segment from *Sac. erythraea* strain NRRL 2338), and 2.5 units of *Thermus aquaticus* DNA polymerase in a 100 ml volume of PCR buffer [50 mM KCl, 10 mM TrisHCl (pH 8.0) 2 mM MgCl$_2$, 0.01% gelatin) containing 200 mM of the 4 dNTPs. The above reagents are from Perkin Elmer Cetus, Norwalk, Conn. The reaction mixture is overlaid with a drop of paraffin oil and subjected to 30–50 cycles. Each cycle consists of one 94° C., one 55° C. and one 72° C. period, each of the duration of 3 min. The progress of the amplification is monitored by agarose gel-electrophoresis. The PCR primers described in the examples below are derived from the nucleotide sequence of eryA of FIG. 2.

Gene Replacement and Gene Conversion

Protoplasts of *Sac. erythraea* strains are prepared and transformed with miniprep DNA isolated from *E. coli* according to published procedures (Yamamoto et al., 1986). Integrative transformants, in the case of pWHM3 derivatives, are selected after one round of non-selective growth of the primary Th$^R$ transformants as described by Weber et. al, *Gene,* 68: 173 (1988). Loss of the Th$^R$ phenotype is monitored by plating serial dilutions of a Th$^R$ integrant on non-selective medium, followed by replica-plating on thiostrepton-containing medium. Th$^S$ (thiostrepton-sensitive) colonies arise at a frequency of $10^{-2}$ (Donadio et al., 1990). The retention of the mutant allele is established by Southern hybridization of a few Th$^S$ colonies.

A few hundred Th$^R$ colonies obtained by transformation of an eryA strain with pWHM4 derivatives are screened for antibiotic production by the agar-plug assay employing *Staphylococcus aureus* as Th$^R$ organism as described (Tuan et al., *Gene,* 90: 21 (1990)). The frequency of gene conversion between a 5 kb segment of homologous sequence and a strain carrying a small deletion is >25% (Tuan et al., *Gene,* 90: 21 (1990)). Colonies found to produce antibiotic activity are inoculated in SGGP (Yamamoto et al., 1986), protoplasts are prepared, and the regenerated protoplasts are scored for loss of the plasmid by replica-plating on non-selective medium. Th$^S$ colonies are then rechecked for antibiotic production, and six producers are analyzed on Southern blots.

Fermentation

*Sac. erythraea* cells are inoculated into 100 ml SCM medium (1.5% soluble starch, 2.0% Soytone [Difco], 0.15% Yeast Extract [Difco], 0.01% CaCl$_2$) and allowed to grow at 32° C. for 3 to 6 days. The entire culture is then inoculated into 10 liters of fresh SCM medium. The fermenter is operated for a period of 7 days at 32° C. maintaining constant aeration and pH at 7.0. After fermentation is complete, the cells are removed by centrifugation at 4° C. and the fermentation beer is kept in the cold until further use.

The present invention will now be illustrated, but is not intended to be limited, by the following examples:

EXAMPLE 1

Construction of Plasmid pABX9

The 9.6 kb BamHI-XhoI segment comprised between sequence coordinates 21.96 and 31.52 was isolated from cosmid pS1 and ligated to SalI-digested pUC19 DNA. The resulting mixture contained the desired plasmid pABX9.

EXAMPLE 2

Construction of *E. coli* K12 DH5α/pABX9

Approximately 10 ng of plasmid pABX9, prepared as described in Example 1, were transformed into *E. coli* K12 DH5α and a few of the resulting white Ap$^R$ colonies that appeared on the LB-agar plates containing X-gal and ampicillin were analyzed for their plasmid content. One colony was found to carry pABX9, as verified by the observation of fragments of 3.93, 3.39, 2.01, 1.56, 0.87, and 0.48 kb in size upon agarose gel electrophoresis after SmaI digestion of the plasmid.

EXAMPLE 3

Construction of Plasmid pABX9DN

Plasmid pABX9, isolated from *E. coli* K12 DH5α/pABX9, was digested with NcoI and then treated with T4 DNA ligase. The resulting mixture contained the desired plasmid pABX9DN.

EXAMPLE 4

Construction of E. coli K12 DH5α/pABX9DN

Approximately 10 ng of plasmid pABX9DN, prepared as described in Example 3, were transformed into E. coli K12 DH5α and a few of the resulting white Ap$^R$ colonies that appeared on the LB-agar plates containing X-gal and ampicillin were analyzed for their plasmid content. Colonies carrying pABX9DN exhibited a single NcoI fragment of 11.5 kb visible by agarose gel electrophoresis, confirming that the 813 bp NcoI—NcoI fragment from pABX9 has been deleted in pABX9DN.

EXAMPLE 5

Construction of Plasmid pABX95DN

Plasmid pABX95DN was digested with EcoRI and HindIII and ligated to pWHM3 digested with the same two enzymes. The resulting mixture contained the desired plasmid pABX95DN.

EXAMPLE 6

Construction of E. coli K12 DH5α/pABX95DN

Approximately 10 ng of plasmid pABX95DN, prepared as described in Example 5, were transformed into E. coli K12 DH5a and a few of the resulting white Ap$^R$ colonies that appeared on the LB-agar plates containing X-gal and ampicillin were analyzed for their plasmid content. Colonies carrying pABX95DN exhibited fragments of 8.8 and 7.2 kb visible in agarose gels after EcoRI and HindIII digestion.

EXAMPLE 7

Construction of Sac. erythraea AKR5 Carrying the eryAKR5 Allele by Gene Replacement Approximately 1 mg of plasmid pABX95DN, isolated from E. coli K12 DH5α/pABX95DN, was transformed into Sac. erythraea NRRL 2338 and stable Th$^R$ colonies were isolated. Serial dilutions of one of these colonies were screened for the loss of the antibiotic resistance marker and total DNA from 5 Th$^S$ colonies as well as from untransformed Sac. erythraea NRRL 2338 was digested with SstI and analyzed by Southern hybridization employing the 0.8 kb SalI fragment between sequence coordinates 24.26 and 25.06 (from pABX9) as probe. Whereas NRRL 2338 showed one SstI band of 3.7 kb that hybridized to the probe, samples from four of the Th$^S$ strains exhibited a SstI-hybridizing band of 6.1 kb indicating the presence of the mutant allele. One of these colonies was kept and designated strain AKR5. It carries a deletion of 813 bp in the KR5 segment of eryA and is designated the eryAKR5 allele.

EXAMPLE 8

Isolation, Purification and Properties of 5-oxo-5,6-dideoxy-3-a-mycarosyl erythronolide B from Sac. erythraea AKR5

A 10-liter fermentation of Sac. erythrea AKR5 carrying the eryAKR5 allele in a Biolafitte fermentor using SNC Media. The fermentor was inoculated with 100 ml of a 3 day old seed. The pO$_2$ was initially 80 ppm and the temperature was maintained at 32° C. The pH was controlled to 7.0±0.2 by addition of propionic acid or potassium hydroxide as needed. At harvest (3 days), the whole broth was extracted three times with 4-liter portions of ethylacetate. The combined extracts were concentrated under reduced pressure and the residue was chromatographed on a column (50×5 cm) of silica gel packed and loaded in toluene and eluted with a stepwise gradient of increasing concentration of isopropanol in toluene. Fractions were analyzed by TLC and spots were detected by spraying with anisaldehyde sulfuric acid spray reagent and heating. A major component giving blue colored spots eluted with approximately 7% isopropanol. Fractions containing this material were combined and concentrated to a residue (800 mg). This was further chromatographed on a column (100×3 cm) of Sephadex LH-20 in chloroform-heptane-ethanol, 10:10:1, v/v/v. Fractions were analyzed as above, early fractions (9–13) yielded 5,6-dideoxy-3-a-mycarosyl-5-oxoerythronolide B (45 mg) which was crystallized from heptane/ethylacetate mixture to mp 163–164° C.

CMR spectrum in CDCl$_3$ (ppm downfield from TMS)

| | | |
|---|---|---|
| 8.6 | 37.9 | 70.0 |
| 9.9 | 38.7 | 76.2 |
| 9.9 | 40.4 | 76.4 |
| 10.4 | 40.7 | 80.4 |
| 14.5 | 43.3 | 100.4 |
| 15.2 | 45.8 | 175.8 |
| 17.1 | 46.8 | 210.8 |
| 17.7 | 48.9 | 217.7 |
| 25.3 | 66.5 | |
| 25.5 | 69.4 | |

Structure was determined by single crystal X-ray diffraction.

Later fractions (15–17) yielded 5,6-dideoxy-5-oxoerythronolide B (10 mg) and still later fractions yielded 5,6-dideoxy-6,6a-epoxy-5-oxoerythronolide B (2.8 mg).

EXAMPLE 9

Construction of Plasmid pALeryAKR2

The 1.3 kb DNA segment comprised between coordinates 8.63–9.93 (fragment 1) is amplified by PCR employing two oligodeoxynucleotides, 1a (5'-GGGAGCATGCTCTCGGTGCGCGGCGGCCGC-3') [SEQ ID NO:6] and 1b (5'-GCCCTGCAGCGCGTACTCCGAGGTGGCGGT-3') [SEQ ID NO:7]. Similarly, the 1.3 kb DNA segment between coordinates 9.99–11.26 (fragment 2) is PCR-amplified employing primers 2a (5'-TGGTCTGCAGGCGAGGCCGGACACCGAGG-3') [SEQ ID NO:8] and 2b (5'-GGAAGAAGTCAAAGTTCCTCGGTCCCTTCT-3') [SEQ ID NO:9]. After digestion with SphI+PstI (fragment 1) and PstI+EcoRI (fragment 2), the two fragments are ligated to EcoRI+SphI-digested pWHM3. The resultant mixture contains the desired plasmid pALeryAKR2.

EXAMPLE 10

Construction of E. coli K12 DH5/pALeryAKR2

Approximately 10 ng of plasmid pALeryAKR2, prepared as described in Example 9, are transformed into E. coli K12 DH5α, and a few of the resulting white Ap$^R$ colonies that appear on the LB-agar plates containing X-gal and ampicillin are analyzed for their plasmid content. The identity of plasmid pALeryA2KR2, 9.8 kb in size, and carrying a 2.6 kb EcoRI-SphI insert with an internal PstI site, is verified by SalI digestion (fragments at 2.91, 2.21, 1.61, 1.42, 1.08, 0.29, 0.12 and 0.10 kb are released, visible by agarose gel electrophoresis). pALeryAKR2 contains an in-frame deletion of 102 base pairs of the corresponding segment of the wild type eryA chromosomal DNA. The cloned segment in pALeryAKR2 is designated the eryAKR2 allele.

EXAMPLE 11

Construction of *Sac. erythraea* AKR2 Carrying the eryAKR2 allele by Gene Replacement Approximately 1 mg of plasmid pALeryAKR2, isolated from *E. coli* K12 DH5α/pALeryAKR2, is transformed into *Sac. erythraea* protoplasts and stable Th$^R$ colonies are isolated. Serial dilutions of one of these colonies are screened for loss of the antibiotic resistance marker, and six Th$^S$ colonies are analyzed for their genotype by Southern hybridization. Total DNA from the six Th$^S$ colonies and from untransformed *Sac. erythraea* NRRL2338 is digested with PstI and with SalI and is then examined by Southern hybridization using the 2.6 kb EcoRI-SphI insert from pALeryAKR2 as probe. Whereas NRRL2338 contains a 39 kb PstI hybridizing band, colonies in which the mutation in KR2 has been introduced (strain AKR2) exhibit two bands of approximately equal intensity, one at 27 kb and the other at 12 kb. The SalI digest, with bands at 1.04, 0.75, 0.29, 0.12 and 0.10 kb common to NRRL2338 and AKR2, but with the 1.16 kb band in NRRL2338 replaced by the 1.06 kb band in AKR2, confirms that the only change introduced into strain AKR2 is the deletion of the 102 bp segment from KR2, resulting in a strain carrying the eryAKR2 allele.

EXAMPLE 12

Isolation and Purification of 11-deoxy-11-oxoerythromycin A

The fermentation beer of strain AKR2, cooled to 4° C. is adjusted to pH 8.0 and is extracted sequentially with three equal volumes of methylene chloride. The combined methylene extracts are concentrated to an oily residue and partitioned between heptane and methanol. The methanol layer is removed, washed once with heptane and concentrated to a residue. The residue is digested in methylene chloride and washed once with potassium phosphate buffer pH 7.8 and once with water. The methylene chloride layer is concentrated to a residue and digested in the lower phase (1:1:1, v/v/v) of a carbon tetrachloride; methanol; aqueous phosphate buffer (0.05 M, pH 7.0) system and chromatographed on an Ito Coil Planet Centrifuge in the same system. Fractions containing the desired 11-oxo-11-deoxyerythromycin A were combined, concentrated, digested in methylene chloride, washed well with water and concentrated on rotary evaporator under reduced pressure to yield 11-deoxy-11-oxoerythromycin A as an off-white solid froth. Its identity is confirmed by comparison with antibiotic L53-18A. 11-Deoxy-11-oxoerythromycin A is dissolved in tetrahydrofuran and the solution is diluted with an equal volume of water. This is then acidified to pH 4.0 and allowed to stand at room temperature for 4 hours. The pH is adjusted to 9.0 and the solution is diluted with an equal volume of water and extracted with two volumes of methylene chloride. The combined methylene chloride extracts were evaporated to dryness under reduced pressure to yield antibiotic L53-18A as a white solid.

EXAMPLE 13

Construction of Plasmid pALeryADH4

Primers 3a (GCGCGAGCTCGACGACCAGGGCGGCATGGT) [SEQ ID NO:10] and 3b (GGTGGCATGCTGCGACCACTGCGCGTCGGC) [SEQ ID NO:11] are used to PCR-amplify the 1.05 kb eryA segment of the *Sac. erythraea* chromosome between sequence coordinates 18.47–20.07 (fragment 3), and primers 4a (AGCTGCATGCTCTGGACTGGGGACGGCTAG) [SEQ ID NO:12] and 4b (CGCGGGATCCCAGCTCCCACGCCGATACCG) [SEQ ID NO:13] are used to amplify the 1.35 kb segment between sequence coordinates 20.58–21.96 (fragment 4) as described in Example 1. Fragment 3 and 4, after digestion with SstI+SphI and with SphI+BamHI, respectively, are ligated to SstI-, BamHI-digested pWHM3. The resulting ligation mixture contains the desired plasmid pALeryADH4.

EXAMPLE 14

Construction of *E. coli* K12 DH5a/pALeryADH4

Approximately 10 ng of pALeryADH4, prepared as described in Example 13, are transformed transformed into *E. coli* K12 DH5α, and a few of the resulting white Ap$^R$ colonies that appear on the LB-agar plates containing X-gal and ampicillin are analyzed for their plasmid content. The identity of plasmid pALeryADH4, 9.6 kb in size, is verified by SphI+EcoRI digestion (fragments at 7.2, 1.35 and 1.05 kb are released). pALeryADH4 carries a 498 base pair in-frame deletion of the corresponding segment of the wild type eryA DNA. The cloned segment in pALeryADH4 is designated the eryADH4 allele.

EXAMPLE 15

Construction of *Sac. erythraea* ADH4 Carrying the eryADH4 allele by Gene Replacement Approximately 1 mg of plasmid pALeryADH4, isolated from *E. coli* K12 DH5α/pALeryADH4, is used for transformation into *Sac. erythraea* protoplasts and stable Th$^R$ colonies are isolated. Serial dilutions of one of these colonies are screened for loss of the antibiotic resistance marker, and six Th$^S$ colonies are analyzed for their genotype by Southern hybridization. Total DNA from the six Th$^S$ colonies and from untransformed *Sac. erythraea* NRRL2338 is digested with SphI and with SstI and examined by Southern hybridization using the 2.4 kb SstI-BamHI insert from pALeryADH4 as probe. Strains in which the wild type allele has been replaced by the mutated copy show two SphI bands, one at 13.5 kb and the other at 12.4 kb, whereas the wild type strain exhibits a single band at 26 kb. The SstI pattern, with the 2.9 kb band from NRRL2338 being replaced in ADH4 by a 2.5 kb band, confirms that the 487 bp deletion created in plasmid pALeryADH4 has been transferred into the chromosome of ADH4. Strains that carry the eryADH4 allele in place of the wild type sequence are designated *Sac. erythraea* ADH4.

EXAMPLE 16

Isolation and Characterization of 7-hydroxyerythromycin A and 6-deoxy-7-hydroxyerythromycin A The fermentation beer of strain ADH4 is cooled to 4° C. and the pH is adjusted to 5.0. The mixture is extracted once with an equal volume of methylene chloride. The pH of the aqueous layer is readjusted to 9.0 and two further methylene chloride extracts are carried out. These two extracts are combined, washed with water and concentrated to a residue. This is digested in 10 ml of the upper phase of a (3:7:5, v/v/v) mixture of hexane, ethylacetate, aqueous phosphate buffer (0.05 M, pH 7.5) and chromatographed on an Ito Coil Planet Centrifuge in the same system. Fractions containing the desired 7-hydroxyerythromycin were combined, concentrated, and partitioned between methylene chloride and dilute (pH 9.5) ammonium hydroxide solution. Fractions containing the desired 6-deoxy-7-hydroxyerythromycin were combined, concentrated, and partitioned between methylene chloride and dilute (pH 9.5) ammonium hydroxide solution. The methylene chloride layers are washed with water and then concentrated to yield the desired 7-hydroxyerythromycin A and 6-deoxy-7-hydroxyerythromycin A as white foams.

EXAMPLE 17

Construction of Plasmid pALeryAKS1

The 1.4 kb segment of eryA, between sequence coordinates 1.11–2.54 (fragment 5) and the 1.5 kb segment between sequence coordinates 2.88–4.37 (fragment 6) are PCR-amplified using primers 5a (TGCAGAATTCGCTGGCCGCGCTCTGGCGCT) [SEQ ID NO:14] and 5b (GAGAGCTGCAGCATGAGCCGCTGCTGCGGG) [SEQ ID NO:15], and 6a (CATGCTGCAGGACTTCAGCCGGATGAACTC) [SEQ ID NO:16] and 6b (GAGGAAGCTTCCAGCCGGTCCAGTTCGTCC) [SEQ ID NO:17], respectively, as described in Example 9. After digestion with EcoRI+PstI (fragment 5) and PstI+HindIII (fragment 6), the two fragments are ligated to EcoRI+HindIII-digested pWHM3. The resulting mixture contains the desired plasmid pALeryAKS1.

EXAMPLE 18

Construction of E. coli K12 DH5a/pALeryAKS1

Approximately 10 ng of pALeryAKS1, prepared as described in Example 17, are transformed into E. coli K12 DH5α, and a few of the resulting white $Ap^R$ colonies that appear on the LB-agar plates containing X-gal and ampicillin are analyzed for their plasmid content. The identity of plasmid pALeryAKS1, 10.1 kb in size, is verified by digestion with PstI+HindIII (fragments of 8.6 and 1.5 kb are observed by agarose gel electrophoresis) and with SalI (fragments of 2.93, 2.21, 1.42, 1.37, 0.86, 0.54, 0.27, 0.14, 0.13, and 0.10 kb are observed). pALeryAKS1 carries an in-frame deletion of 282 base pairs of the corresponding wild type eryA DNA. The cloned insert in plasmid pALeryAKS1 is designated the eryAKS1 allele.

EXAMPLE 19

Construction of Sac. erythraea AKS1 Carrying the eryAKS1 allele by Gene Replacement Approximately 1 mg of plasmid pALeryAKS1, isolated from E. coli K12 DH5α/pALeryAKS1, is used for transformation into Sac. erythraea protoplasts and stable $Th^R$ colonies are isolated. Serial dilutions of one of these colonies are screened for loss of the antibiotic resistance marker, and six $Th^S$ colonies are analyzed for their genotype by Southern hybridization. Total DNA from the six $Th^S$ colonies and from untransformed Sac. erythraea NRRL2338 is digested with PstI and with SmaI and examined in Southern hybridization employing the 2.9 kb EcoRI-HindII insert from pALeryAKS1 as probe. Colonies in which the wild type allele has been replaced by the mutated copy (strain AKS1) show two PstI bands, one at 34.5 and the other at 4.4 kb, whereas the wild type strain exhibits a single band at 39 kb. The SmaI pattern, with the 2.9 kb band from NRRL2338 being replaced in AKS1 by a 2.6 kb band, confirms that the 282 bp created in plasmid pALeryAKS1 has been transferred into strain AKS1. Strains that carry the eryAKS1 allele are designated Sac. erythraea AKS1.

EXAMPLE 20

Synthesis of (2S,3R,4S,5S)3,5-dihydroxy-2,4-dimethylhexanoic acid n-butyl thioester A convenient source of this compound in chiral purity is the antibiotic oleandomycin. Oleandomycin (5 g) is dissolved in an aprotic solvent such as toluene and treated with diazabicyclo[5.4.0]undecene-5 (1 g) and heated for one hour. The resulting solution is poured into iced water, agitated well and the organic layer is drawn off and concentrated to a residue. The residue is digested in methylene chloride and treated exhaustively with a solution of ozone. The resulting ozonide is oxidatively decomposed with dilute hydrogen peroxide in sufficient aqueous ethanol to yield a monophasic mixture. This is further diluted with water and made 0.1 N with sodium hydroxide. The mixture is warmed for one hour at 70° C. and then cooled before being acidified to pH 2.5 with dilute sulfuric acid. The mixture is then exhaustively extracted with methylene chloride. The combined extracts are concentrated to an oily residue and the desired lactone is recovered by chromatography on silica gel eluted with a gradient of toluene-isopropanol.

The δ-lactone is converted to the butyl thioester before feeding to Sac. erythrea AKS1 by refluxing with n-butylthiol in the presence of a catalytic amount of triethylamine.

EXAMPLE 21

Isolation of (14S,15S)14(1-hydroxyethyl) erythromycin A

The fermentation broth of AKS1 is cooled to 4° C. and adjusted to pH 4.0 and extracted once with methylene chloride. The aqueous layer is readjusted to pH 9.0 and extracted twice with methylene chloride and the combined extracts are concentrated to a solid residue. This is digested in methanol and chromatographed over a column of Sephadex LH-20 in methanol. Fractions are tested for bioactivity against a sensitive organism, such as Staphylococcus aureus $Th^R$, and active fractions are combined. The combined fractions are concentrated and the residue is digested in 10 ml of the upper phase of a solvent system consisting of n-heptane, benzene, acetone, isopropanol, 0.05 M, pH 7.0 aqueous phosphate buffer (5:10:3:2:5, v/v/v/v/v), and chromatographed on an Ito Coil Planet Centrifuge in the same system. Active fractions are combined, concentrated and partitioned between methylene chloride and dilute ammonium hydroxide (pH 9.0). The methylene chloride layer is separated and concentrated to yield the desired product as a white foam.

EXAMPLE 22

Construction of Plasmid pALeryAKS2

Primers 7a (CGCCCGAATTCGAGGCGCTGGGCGCCCGGAC) [SEQ ID NO:18] and 7b (CCACCTGCAGCGCGGGACCTTCCAGCCCC) [SEQ ID NO:19], and primers 8a (GTGGGTCGCTGCAGACGGTGACTGCGG) [SEQ ID NO:20] and 8b (GGTCAAGCTTCGTCGGCGAGCAGCTTCTC) [SEQ ID NO:21] are used to PCR-amplify the 1.45 kb eryA segment between sequence coordinates 5.71–7.16 (fragment 7) and the 1.5 kb eryA segment between sequence coordinates 7.22–8.70 (fragment 8), respectively. After digestion with EcoRI+PstI (fragment 7) and with PstI+HindIII (fragment 8), the two fragments are ligated to pWHM3 cut with EcoRI+HindIII. The resulting mixture contains the desired plasmid pALeryAKS2.

EXAMPLE 23

Construction of E. coli K12 DH5a/pALeryAKS2

Approximately 10 ng of pALeryAKS2, prepared as described in Example 22, are transformed into E. coli K12 DH5α, and a few of the resulting white $Ap^R$ colonies that appear on the LB-agar plates containing X-gal and ampicillin are analyzed for their plasmid content. The identity of plasmid pALeryAKS2, 10.1 kb in size, is verified by digestion with PstI+HindIII (fragments of 8.6 and 1.5 kb are observed by agarose gel electrophoresis) and with SstII (fragments of 4.0, 2.3, 2.0, 0.72, 0.43, 0.40, 0.20, 0.18, 0.13 and 0.11 kb observed). Plasmid pALeryAKS2 carries an in-frame deletion of 60 base pairs of the corresponding wild type eryA DNA. This deletion removes the active site cysteine from KS2. The cloned insert in plasmid pALeryAKS2 is designated the eryAKS2 allele.

EXAMPLE 24

Construction of Sac. erythraea AKS2 Carrying the eryAKS2 allele by Gene Replacement Approximately 1 mg of plasmid pALeryAKS2, isolated from E. coli K12 DH5α/pALeryAKS2, is used for transformation into Sac. erythraea protoplasts and stable $Th^R$ colonies are isolated. Serial dilutions of one of these colonies are screened for loss of the antibiotic resistance marker, and six $Th^S$ colonies are analyzed for their genotype by Southern hybridization. Total DNA from the six $Th^S$ colonies and from untransformed Sac. erythraea NRRL2338 is digested with PstI and with SstII and examined in Southern hybridization employing the 2.9 kb EcoRI-HindII insert from pALeryAKS2 as probe. Colonies in which the wild type allele has been replaced by the mutated copy (strain AKS2) show two PstI bands, one at 34.5 and the other at 4.4 kb, whereas the wild type strain exhibits a single band at 39 kb. The SstII pattern, with the 0.78 kb band from NRRL2338 being replaced in AKS2 by a 0.72 kb band, confirms that the 60 bp created in plasmid pALeryAKS2 has been transferred into strain AKS2. Strains that carry the eryAKS2 allele are designated Sac. erythraea AKS2.

EXAMPLE 25

Synthesis of (2R,3R,4S,5R)2,4-dimethyl-3-fluoro-5-hydroxyhexanoic acid n-butyl thioester (2R,3S,4S,5R)3,5-Dihydroxy-2,4-dimethylhexanoic acid-δ-lactone (1 g) from Example 20 is digested in 10 ml of pyridine and treated with p-toluenesulfonyl chloride (1.3 g) and allowed to stand at room temperature overnight. The mixture is poured into iced water and extracted with methylene chloride and the methylene chloride is concentrated to the crude sulfonate ester. This is digested in acetonitrile (100 ml) and heated under reflux after the addition of tetrabutylammonium fluoride (1.75 g). After 6 hours the mixture is cooled, poured over iced water (300 ml) and extracted three times with 200 ml portions of methylene chloride. The combined methylene chloride extracts were concentrated and the residue was chromatographed on a column of silica gel eluted with a stepwise gradient of isopropanol (0 to 50%) in toluene. Fractions containing (2R,3R,4S,5R)2,4-dimethyl-3-fluoro-5-hydroxyhexanoic acid d-lactone were combined and concentrated to a white solid. The lactone is then converted to the n-butyl thioester by refluxing in n-butyl thiol with a catalytic amount of triethylamine. Solvent is removed and the residue is digested in DMSO before feeding to fermentations of Sac. erythraea AKS2.

EXAMPLE 26

Isolation and Purification of 11-epifluoro-15-norerythromycin A

The fermentation broth of strain AKS2 is cooled to 4° C. and adjusted to pH 4.0 and extracted once with ethylacetate. The aqueous layer is adjusted to pH 9.0 and extracted twice with methylene chloride and the combined extracts are concentrated to a white solid. This is chromatographed over a column of Sephadex LH-20 in a mixture of heptane, chloroform, ethanol (10:10:1, v/v/v) and fractions containing the desired product are combined and concentrated to a solid residue. This is further purified by countercurrent chromatography on an Ito Coil Planet Centrifuge on a system composed of carbon tetrachloride; methanol; 0.05 M; pH 7.0 aqueous potassium phosphate buffer (1:1:1, v/v/v). Fractions containing the desired 11-epifluoro-15-norerythromycin were combined, and concentrated to a residue. This was digested in methylene chloride and dilute (pH 9.5) ammonium hydroxide and the methylene chloride layer was separated, washed with water and concentrated to yield the desired 11-epifluoro-15-norerythromycin A as white solid.

EXAMPLE 27

Construction of Plasmid pALeryAM4.1

Primers 9a (GCGCCGAATTCTCGAGACGGCGTGGGAGGCA) [SEQ ID NO:22] and 9b (TTGCGGTACCAGTAGGAGGCGTCCATCGCG) [SEQ ID NO:23] are employed to PCR-amplify the 2.0 kb eryA segment between sequence coordinates 17.35–19.38 (fragment 9). After digestion with EcoRI+KpnI, fragment 9 is ligated to pUC19 cut with the same two enzymes The resulting mixture contains the desired plasmid pALeryAM4.1.

EXAMPLE 28

Construction of E. coli K12 DH5a/pALeryAM4.1

Approximately 10 ng of pALeryAM4.1, prepared as described in Example 27, are transformed into E. coli K12 DH5a, and a few of the resulting white $Ap^R$ colonies that appear on the LB-agar plates containing X-gal and ampicillin are analyzed for their plasmid content. The identity of plasmid pALeryAM4.1, 4.7 kb in size, is verified by digestion with SalI (fragments of 2.8, 0.85, 0.53, 0.27 and 0.22 kb are observed by agarose gel electrophoresis).

EXAMPLE 29

Construction of Plasmid pALeryAM4.2

Primers 10a (GCTGGGATCCCGCGGCGCGGGTTGCAGCAC) [SEQ ID NO:24] and 10b (CGGAACTCGGTGAGCATGCCGGGACTGCTC) [SEQ ID NO:25] are used to PCR-amplify the 2.1 kb eryA segment between sequence coordinates 21.94–24.00 (fragment 10). The 2.6 kb fragment KpnI(96)-BamHI(102) from cosmid clone pR1, and fragment 10 cut with BamHI+SphI, are ligated to pALeryAM4.1 cut with KpnI+SphI. The resulting mixture contains the desired plasmid pALeryAM4.2.

EXAMPLE 30

Construction of E. coli K12 DH5a/pALeryAM4.2

Approximately 10 ng of pALeryAM4.2, prepared as described in Example 29, are transformed into E. coli K12 DH5a, and a few of the resulting white $Ap^R$ colonies that appear on the LB-agar plates containing X-gal and ampicillin are analyzed for their plasmid content. The identity of plasmid pALeryAM4.2, 9.3 kb in size, is verified by digestion with XhoI+SphI (to ensure that the entire 6.65 kb insert is released) and with SalI, with fragments of 2.8, 1.82, 1.09, 0.94, 0.85, 0.75, 0.45, 0.27, 0.22 and 0.13 kb are observed by agarose gel electrophoresis).

EXAMPLE 31

Construction of Plasmid pALeryAM1

The 2.9 kb SmaI(4)-SmaI(20) fragment from cosmid clone pR1 is ligated to pUC12 cut with SmaI. The resulting mixture contains plasmid pALeryAM1.

EXAMPLE 32

Construction of E. coli K12 DH5αa/pALeryAM1

Approximately 10 ng of pALeryAM1, prepared as described in Example 31, are transformed into E. coli K12 DH5α, and a few of the resulting white $Ap^R$ colonies that appear on the LB-agar plates containing X-gal and ampicillin are analyzed for their plasmid content. The identity of plasmid pALeryAM1, 5.6 kb in size, is verified by digestion with SmaI (the 2.9 kb insert is released) and with SphI, with release of one 4.4 and one 1.07 kb bands. Both orientations of the insert in plasmid pALeryAM1 are useful.

EXAMPLE 33

Construction of Plasmid pALeryAM4.3

Plasmid pALeryAM1 is cut with XhoI to completion, partially with SphI, and the resulting 5.25 kb band, isolated from an agarose gel, is ligated to the 6.65 kb insert released from pALeryAM4.2 by XhoI+SphI digestion The resulting mixture contains the desired plasmid pALeryAM4.3.

EXAMPLE 34

Construction of E. coli K12 DH5a/pALeryAM4.3

Approximately 10 ng of pALeryAM4.3, prepared as described in Example 33, are transformed into E. coli K12 DH5α, and a few of the resulting white $Ap^R$ colonies that appear on the LB-agar plates containing X-gal and ampicillin are analyzed for their plasmid content. The identity of plasmid pALeryAM4.1, 11.9 kb in size, is verified by XhoI+SphI digestion (fragments of 6.65 and 5.25 kb are visible by agarose gel-electrophoresis). Plasmid pALeryAM4.3 carries the entire eryA module 4 inserted into the KS region of module 1. The cloned insert in pALeryAM4.3 is degnated the eryAM412 allele.

EXAMPLE 35

Construction of Plasmid pALeryAM4.4

Plasmid pALeryAM4.3 is cut with EcoRI+HindIII, and the resulting 9.2 kb band, recovered from an agarose gel, is ligated to pWHM4 cut with the same two enzymes. The resulting mixture contains the desired plasmid pALeryAM4.4.

EXAMPLE 36

Construction of E. coli K12 DH5α/pALeryAM4.4

Approximately 10 ng of pALeryAM4.4, prepared as described in Example 35, are transformed into E. coli K12 DH5α, and a few of the resulting white $Ap^R$ colonies that appear on the LB-agar plates containing X-gal and ampicillin are analyzed for their plasmid content. The identity of plasmid pALeryAM4.1, 16.5 kb in size, is verified by EcoRI+HindIII digestion, with fragments of 9.2 and 7.3 kb released. Plasmid pALeryAM4.4 carries the eryAM412 allele on the Sac. erythraea multicopy vector pWHM4.

EXAMPLE 37

Construction of Sac. erythraea AM412 Carrying the eryAM412 allele by Gene Conversion Approximately 1 mg of plasmid pALeryAM4.4, isolated from E. coli K12 DH5α/pALeryAM4.4, is used for transformation into Sac. erythraea strain AKS1 protoplasts. A few hundred transformants are screened for antibiotic production by the agar-plug assay, and one of the colonies found to produce antimicrobial activity is cured of pALeryAM4.4 by protoplast formation and regeneration as described in General Methods. Total DNA from six antibiotic-producing, $Th^S$ colonies (strain AM412) and from strain AKS1 is digested with SphI and with XhoI and the resulting Southern blot is hybridized first to the 2.9 kb insert from pALeryAM1, and then to the 2.9 kb SstI(95)-SstI(101) fragment from plasmid pALeryAM4.2. With the first probe, the SphI band at 0.8 kb in strain AKS1 is seen to be replaced by a 7.5 kb band in strain AM412, whereas the other two bands at 2.4 kb and 5.2 kb are unaffected. In the XhoI digest, the AKS1 band at 2.9 kb is replaced by a 9.6 kb band in AM412, with the other band at 5.2 kb conserved in both strains. Using the SstI(95)-SstI(101) fragment as probe, strain AKS1 exhibits one band at 25.5 kb and one at 17.9 kb in the SphI and XhoI digests, respectively, whereas, in addition to these bands, strain AM412 shows one SphI band at 7.5 kb and one XhoI band at 9.6 kb. In this way, it is established that the eryAKS1 allele has been converted into the eryAM412 allele in strain AM412.

EXAMPLE 38

Isolation and Purification of 14-(1-propyl) erythromycin A

At harvest the fermentation is adjusted to pH 9.5 and extracted twice with equal volumes of methylene chloride.

The combined extracts are washed once with water and concentrated to an oily residue. This is partitioned in a heptane methanol water (5:5:1, v/v/v) system and the lower layer is washed once with heptane and then concentrated to a semisolid residue. This is digested in methanol and chromatographed over a column of Sephadex LH-20 in methanol. Fractions are tested for bioactivity in an agar diffusion assay on plates seeded with the macrolide-sensitive strain Staphylococcus aureus Th$^R$. Active fractions are combined and further purified by chromatography over silica gel a chloroform:methanol gradient containing 0.1% triethylamine. Fractions containing the desired 14-(1-propyl) erythromycin A are combined and concentrated to yield the product as a white solid.

EXAMPLE 39

Construction of Plasmid pALeryAM5.1

The 4.7 kb eryA fragment between sequence coordinates 23.65–28.36 (fragment 11) is PCR-amplified employing primers 11a (ATGCTCGAGATCTCGTGGGAGGCGCTGGA) [SEQ ID NO:26] and 1b (AGAACTCGGTGAGCATGCCCGGGCCCGCCA) [SEQ ID NO:27]. Fragment 11, after digestion with XhoI+SphI, is ligated to the 5.25 kb fragment resulting from complete XhoI and partial SphI digestion of pALeryAM1, as in Example 33. The resulting mixture contains the desired plasmid pALeryAM5.1.

EXAMPLE 40

Construction of E. coli K12 DH5α/pALeryAM5.1

Approximately 10 ng of pALeryAM5.1, prepared as described in Example 39, are transformed into E. coli K12 DH5α, and a few of the resulting white Ap$^R$ colonies that appear on the LB-agar plates containing X-gal and ampicillin are analyzed for their plasmid content. The identity of plasmid pALeryAM5.1, 9.95 kb in size, is verified by SphI+XhoI digestion, with fragments of 5.25 and 4.7 kb released, and by SmaI digestion where fragments of 3.39, 2.68 and 1.94 (doublet) kb are observed. Plasmid pALeryAM5.1 carries the entire eryA module 5 inserted into the β-ketoacyl ACP synthase region of module 1. The cloned insert in plasmid pALeryAM5.1 is designated the eryA512 allele.

EXAMPLE 41

Construction of Plasmid pALeryAM5.2

Plasmid pALeryAM5.1 is cut with EcoRI+HindIII and the resulting 6.3 kb fragment, recovered from an agarose gel, is ligated to pWHM4 cut with the same two enzymes. The resulting mixture contains the desired plasmid pALeryAM5.2.

EXAMPLE 42

Construction of E. coli K12 DH5α/pALeryAM5.2

Approximately 10 ng of pALeryAM5.2, prepared as described in Example 41, are transformed into E. coli K12 DH5α, and a few of the resulting white Ap$^R$ colonies that appear on the LB-agar plates containing X-gal and ampicillin are analyzed for their plasmid content. The identity of plasmid pALeryAM5.2, 13.6 kb in size, is verified by digestion with EcoRI+HindIII, with fragments of 7.3 and 6.3 kb released. Plasmid pALeryAM5.2 contains the eryAM512 allele on the Sac. erythraea multicopy vector pWHM4.

EXAMPLE 43

Construction of Sac. erythraea AM512 Carrying the eryAM512 allele by Gene Conversion Approximately 1 mg of plasmid pALeryAM5.2, isolated from E. coli K12 DH5α/pALeryAM5.2, is used for transformation into Sac. erythraea strain AKS1 protoplasts. A few hundred transformants are screened for antibiotic production by the agar-plug assay, and one of the colonies found to produce antimicrobial activity is cured of pALeryAM5.2 by protoplast formation and regeneration as described in General Methods. Total DNA from six antibiotic-producing, Th$^S$ colonies (strain AM512) and from strain AKS1 is digested with SphI and with XhoI and the resulting Southern blot is hybridized first to the 2.9 kb insert from pALeryAM1, and then to the 0.8 kb NcoI(119)-NcoI(123) fragment from plasmid pALeryAM5.1. With the first probe, the SphI band at 0.8 kb in strain AKS1 is replaced by a 5.5 kb band in strain AM512, whereas the other two bands at 2.4 kb and 5.2 kb are unaffected. In the XhoI digest, the AKS1 band at 2.9 kb is replaced by a 7.6 kb band in AM512, with the other band at 5.2 kb conserved in both strains. Using the NcoI(119)-NcoI(123) fragment as probe, strain AKS1 exhibits one band at 25.5 kb and one at 17.9 kb in the SphI and XhoI digests, respectively, whereas, in addition to these bands, strain AM512 shows one SphI band at 5.5 kb and one XhoI band at 7.6 kb. In this way, it is established that the eryAKS1 allele has been converted into the eryAM512 allele in strain AM512.

EXAMPLE 44

Isolation and Purification of 14[1(1-hydroxypropyl)]erythromycin A

At harvest the pH of the fermentation of AM512 is adjusted to 9.5 and the mixture is extracted twice with equal volumes of ethylacetate. The combined ethylacetate extracts are washed with water, dried and partitioned in a heptane, methanol, water (5:5:1, v/v/v) system. The lower (methanolic phase) is washed with an equal volume of heptane and is concentrated to a residue. This is chromatographed on a Sephadex LH-20 column in methanol and fractions containing the desired 14[1(1-hydroxypropyl)] erythromycin A are concentrated and further purified by chromatography on an Ito Coil Planet Centrifuge in a system consisting of n-heptane, benzene, acetone, isopropanol, 0.65 M, pH 7.0 aqueous potassium phosphate buffer (5:10:2:3:5, v/v/v/v/v). Fractions containing the desired product are concentrated to a solid residue and partitioned between methylene chloride and dilute (pH 9.5) ammonium hydroxide. The organic layer is washed with water and concentrated to yield 14[1(1-hydroxypropyl)]erythromycin A as a white solid.

Although the present invention is described in the Examples listed above in terms of preferred embodiments, they are not to be regarded as limiting the scope of the invention. The above descriptions serve to illustrate the principles and methodologies involved in creating the three types of mutations that can be introduced into the eryA segment of the Sac. erythraea chromosome that result in the synthesis of novel polyketide products. Although single Type I alterations, leading to the production of 5-oxo-5,6,-dideoxy-3α-mycorosyl erythronolide B, 11-oxo-11- deoxyerythromycin A, 7-hydroxyerythromycin A, 7-oxo-7deoxyerythromycin A, 5-desosaminyl-3-oxo-3-deoxyerythronolide A, and Δ-6,7-anhydro-6-deoxyerythromycin A are specified herein, it is obvious that other Type I changes can be introduced into the eryA segment leading to novel polyketide structures. Among the additional Type I alterations that can be obtained are those in which two or more modules are affected leading to the synthesis of novel polyketides. Examples of combinations of two Type I alterations leading to useful compounds include but are not limited to: mutants of the the β-ketoreductase of module 2 (KR2) and the β-ketoreductase of module 4 (KR4) leading to the formation of 7,11-dioxo-7,11-dideoxyerythromycin A; mutants of KR2 and the β-ketoreductase of module 6 (KR6) leading to the formation of 3,11-dioxo-3,11-dideoxy-5-desosaminylerythronolide A; mutants of KR2 and the dehydratase of module 4 (DH4) leading to the synthesis of 7-hydroxy-11-oxo-11-deoxyerythromycin A; mutants of KR2 and the enoylreductase of module 4 (ER4) leading to the synthesis of Δ-6,7-anhydro-11-oxo- 11-deoxyerythromycin A; mutants of KR4 and KR6 leading to the synthesis of 3,7-dioxo-3,7-dideoxy-5-desosaminylerythronolide A; mutants of KR6 and DH4 leading to the synthesis of 3-oxo-3-deoxy-5-desosaminyl-7-hydroxyerythronolide A; mutants of KR6 and ER4 leading to the synthesis of 3-oxo-3-deoxy-5-desosaminyl-Δ-6,7-anhydroerythronolide A. Examples of combinations of three Type I alterations leading to the synthesis of novel polyketides include but are not limited to: mutants of KR2, KR4 and KR6 leading to the synthesis of 3,7,11-trioxo-3,7, 11-trideoxy-5-desosaminylerythronolide A; mutants of KR2, KR6 and DH4 leading to the synthesis of 3,11-dioxo-3,11-dideoxy-5-desosaminyl-7-hydroxyerythronolide A; mutants of KR2, KR6 and ER4 leading to the synthesis of 3,11-dioxo-3,11-dideoxy-5-desosaminyl-D-6,7-anhydroerythronolide A. All combinations of two or three Type I mutants, the Sac. erythraea strains that carry said combinations and the corresponding polyketides produced from said strains, therefore, are included within the scope of the present invention.

Although the Type II mutants specified herein have been constructed in the β-ketoacyl ACP synthase of module 1 (KS1) and the β-ketoacyl ACP synthase of module 2 (KS2), other Type II mutants can be constructed in other domains to result in the synthesis of novel polyketide structures upon feeding with appropriate substrate analogs. Other Type II mutants include but are not limited to: inactivation of the either of the acyltransferases or acyl carrier proteins of module 1, or the acyltransferase or acyl carrier protein of module 2, the δ-ketoacyl ACP synthase, acyltransferase or acyl carrier protein of module 3, module 4 or module 5. Furthermore, compounds other than (2S,3R,4S,5S)3,5-dihydroxy-2,4-dimethylhexanoic acid-ethyl thioester and (2S,3S,4S,5S)2,4-dimethyl-3-fluoro-5-hydroxyhexanoic acid-ethyl thioester specified herein can be synthesized and fed to strains AKS1 or AKS2 specified herein or other strains that carry other Type II mutations to result in the creation of novel polyketides that are within the scope of the present invention.

Although two examples of Type III alterations are specified herein, it is apparent to those skilled in the art that many other examples of Type III changes are possible. Strains of Sac. erythraea carrying changes of this type offer the very high potential for the production of novel polyketides of specified structure, since they do not require synthetic substrates as do Type II mutants and they are not limited to the formation of derivatives of erythromycin, as in the case of Type I mutants. In the embodiments of Type III mutants specified herein, we have illustrated how a second copy of a complete module can be introduced at a desired position by gene conversion to result in the synthesis of 14-(1-propyl) erythromycin A or 14-[1(1-hydroxypropyl])erythromycin A. These alterations make use of the high conservation and simultaneous lack of specificity of the β-ketoacyl ACP synthases of modules 1 and 2, thereby making possible the construction of hybrid β-ketoacyl ACP synthase functions consisting of portions of proteins derived from different modules. Those skilled in the art understand, therefore, that it is possible, as exemplified for KS1 and KS2, to delete a small portion of the δ-ketoacyl ACP synthase of other modules and to construct strains carrying such alterations which can then be employed as hosts for introducing at the deleted β-ketoacyl ACP synthase location a second copy of any homologous module. Furthermore, as exemplified herein, it is also possible to delete any segment of eryA by ligation of two non-contiguous PCR-generated fragments and to subsequently construct strains, therefore, devoid of any or all portions of any module. Such strains deleted of a full module can be employed for reintroduction of either the same or a different module at a different location. It is possible, therefore, to determine the novel structures desired and then create a series of Sac. erythraea strains containing the corresponding arrangements of eryA modules that would produce said novel structures that are included within the scope of the present invention. Additional examples of novel compounds produced from the construction of Type III alterations include but are not limited to 11-deoxyerythromycin, resulting from the insertion of the eryA segment encoding DH4 and ER4 in module 2.

Moreover, it will also be apparent that two or more modules can be excised and introduced into various sites of the Sac. erythraea chromosome to produce novel polyketides of predicted structure such as the introduction of the eryA segment encoding DH4 and ER4 in both module 1 and module 2 to result in the production of 14(R)[1-hydroxypropyl]11-deoxyerythromycin A. All combinations, therefore, of Type III alterations and the strains of Sac. erythraea that carry said alterations as well as the polyketides produced from said strains are included within the scope of the present invention.

In addition, it is also possible to create combinations of Type I, Type II and Type III alterations and insert such alterations into Sac. erythraea to produce novel polyketides. Examples of such combinations include but are not limited to the following. The combination of a Type I alteration, such as an alteration in DH4 and a Type II alteration, such as a mutation in the KS1 to result in the formation of (14S,15S)14-[1-hydroxyethyl]-7-hydroxyerythromycin A when the strain of Sac. erythraea carrying such alterations is fed with the compound (2S,3R,4S,5S)3,5-dihydroxy-2,4-dimethylhexanoic acid ethyl ester. The combination of a Type I alteration, such as an alteration in DH4 and a Type III alteration, such as found in Sac. erythraea strain AM412, wherein a copy of the DNA segment of module 4 is introduced in module 1, such that the Sac. erythraea strain so constructed produces the compound 7-hydroxy-14-propylerythromycin A. All combinations of two or more alterations of Type I, Type II and Type III alterations, the Sac. erythraea strains that carry such alterations, and the polyketides produced from such strains are included within the scope of the present invention. It will also occur to those skilled in the art that novel structures can be produced by altering the specificity of the acyltransferase functions in any module. Examples include: replacement of the acyltransferase domains of modules 1, 2, 3, 4, 5,or 6 in eryA with those of modules 4, 4, 2, 2, 2, and 4, respectively, to result in the production of 12-epierythromycin A, 10-epierythromycin A, 8-epierythromycin A, 6-epierythromycin A, 4-epierythromycin A and 2-epierythromycin A, respectively, that are included within the scope of the present invention.

It should be emphasized that the introduction of an entire eryA module at a different location, as exemplified for the construction of Sac. erythraea strains AM412 and AM512 in Examples 29 and 35, respectively, does not rely on homologous recombination between the incoming eryA module and the host chromosome. Rather, gene conversion of the host allele with the eryA allele residing on the multicopy plasmid requires DNA sequences homologous to the host allele flanking the incoming module. Thus, any module carrying the desired specificities, either from homologous or heterologous sources, can be employed in gene conversion of the host allele, provided that is flanked by segments of homology. It will occur to those skilled in the art, therefore, that, given the large number of natural polyketide molecules existing, a wide variety of additional novel molecules of predicted structure can be produced in Type III mutants containing an additional module of desired specificities or where an endogenous module is replaced by an exogenous one. The length of the acyl chain can be easily controlled by suitably changing the number of modules involved in its synthesis. Similarly, the introduction of keto, hydroxy, enoyl, or methylene groups at specific points along the acyl chain can be easily achieved by introducing the proper b-carbon processing functions (β-ketoreductase, dehydratase and enoylreductase) in the required modules. Exogenous modules constitute the source of specificities for starter and extender units other than those employed by Sac. erythraea for erythromycin biosynthesis, making it thereby possible to employ, for example, malonylCoA or (2R)- or (2S)ethylmalonylCoA, etc. as extender units, and acetyl CoA, butyryl CoA, etc. as the starter unit. The result will be the formation of erythromycin analogs containing the desired functional groups and side chains with the desired stereochemistry. As an extension of the examples reported with eryA, the construction of a Sac. erythraea strain carrying a heterologous module inserted into eryA requires: (i) cloning of the genes from any other Actinomyces producing a polyketide with desired structural features; (ii) mapping of the modular organization of the cloned genes by low stringency hybridization and restriction analysis; (iii) locating the module carrying the desired specificities by partial sequencing; (iv) precise excision of the desired genetic element and cloning into a vector suitable for gene conversion; (v) construction and transformation of a Sac. erythraea strain suitable for gene conversion and screening for the novel compound. Any module, or portion thereof, can thus be precisely excised from the genome of a polyketide-producing microorganism and introduced into suitable Sac. erythraea strains to create a novel polyketide of predicted structure. Thus, replacement of the acyltransferase segments of modules 1, 2, 3, 4, 5,or 6 in eryA with the acyltransferase segment specific for malonyl CoA, such as can be found in the polyketide synthase genes for the synthesis of pikromycin in Streptomyces venezuelae, to result in the synthesis of 12-norerythromycin A, 10-norerythromycin A, 8-norerythromycin A, 6-norerythromycin A, 4-norerythromycin A and 2-norerythromycin A, respectively, that are included within the scope of the present invention. In addition, replacement of the acyltransferase segments of modules 1, 2, 3, 4, 5, or 6 in eryA with an acyltransferase specific for (2R)-ethylmalonyl CoA, such as can be found in the polyketide synthase genes for the synthesis of spiramycin in Streptomyces ambofasciens, will result in the formation of 12-homoerythromycin A, 10-homoerythromycin A, 8-epihomoerythromycin A, 6-epihomoerythromycin A, 4-epihomoerythromycin A and 2-homoerythromycin A, respectively, all of which are included within the scope of the present invention. Similarly, introduction of acyltransferase segments carrying desired specificities for the starter or extender unit into eryA DNA that results in the synthesis of novel compounds are included within the scope of the present invention. The erythromycin analogs produced by the method of this invention are structurally similar to known antibacterial and prokinetic agents.

It will also occur to those skilled in the art that genetic manipulations described herein need not be limited to Sac. erythraea. Suitable hosts are any other polyketide-producing Actinomyces where DNA can be precisely inserted into the chromosome. Hence, the choice of a convenient host is based solely on the relatedness of the novel polyketide to a natural counterpart so as to minimize the number of module rearrangements required for its biosynthesis. Therefore, Type I, Type II and Type III alterations can be constructed in other Actinomyces employing either endogenous or exogenous modules to produce novel polyketides employing strategies analogous to those described herein for Sac. erythraea. Thus all Type I, Type II or Type III mutations or various combinations thereof constructed in other actinomycetes according to the principles described herein, and the respective polyketides produced from such strains, are included within the scope of the present invention. Examples of polyketides that can be altered by creating Type I, Type II or Type III changes in the producing microorganisms include, but are not limited to macrolide antibiotics such as erythromycin, tylosin, spiramycin, etc.; ansamacrolides such as rifamycins, maytansines, etc.; polyketide antibiotics such as tetracycline; polyethers such as monesin, salinomycin, etc.; polyenes such as candicidin, amphothericins; immunosuppressants such as FK506, ascomycin, rapamycin, etc. and other complex polyketides such as avermectin.

Whereas the novel derivatives or modifications of erythromycin described herein have been specified as the A derivatives, such as 7-hydroxyerythromycin A, 11-oxo-11-deoxyerythromycin A, 14[1(1-hydroxypropyl)] erythromycin A, etc., those skilled in the art understand that the wild type strain of Sac. erythraea produces a family of erythromycin compounds, including erythromycin A, erythromycin B, erythromycin C and erythromycin D. Thus, modified strains of Sac. erythraea, such as strain AKR2, for example, would be expected to produce the corresponding members of the 11-oxo-11-deoxyerythromycin family, including 11-oxo-11-deoxyerythromycin A, 11-oxo-11-deoxyerythromycin B, 11-oxo-11-deoxyerythromycin C, and 11-oxo-11-deoxyerythromycin D. Similarly, strain AM412 would be expected to produce not only 14(1-propyl)erythromycin A but also the other members of the 14(1-propyl)erythromycin family including 14(1-propyl) erythromycin B, 14(1-propyl)erythromycin C and 14(1-propyl)erythromycin D. Similarly, all other modified strains of Sac. erythraea described herein that produce novel erythromycin derivatives would be expected to produce the A, B, C, and D forms of said derivatives. Therefore, all members of the family of each of the novel polyketides described herein are included within the scope of the present invention.

Variations and modifications of the methods for obtaining the desired plasmids, hosts for cloning and choices of vectors and segments of eryA DNA to clone and modify, other than those described herein that result in substantially the same strains and same products as those described herein will occur to those skilled in the art. For example, although we have described the use of the plasmids pWH3 and pWHM4 as *E. coli-Sac. erythraea* shuttle vectors, other vectors can be employed wherein all or part of pWHM3 or pWHM4 is replaced by other DNA segments that function in a similar manner, such as replacing the pUC19 component of pWHM3 and pWHM4 with pBR322, available from BRL, employing different segments of the pIJ101 or pJV1 replicons in pWHM3 and pWHM4, respectively, or employing selectable markers other than thiostrepton- and ampicillin-resistance. These are just few of a long list of possible examples all of which are included within the scope of the present invention. Similarly, the segments of the eryA locus subcloned into pWHM3 for generating strains AKS1, AKS2, etc. specified herein can readily be substituted for other segments of different length encoding the same functions, either produced by PCR-amplification of genomic DNA or of an isolated clone, or by isolating suitable restriction fragments from *Sac. erythraea*. In the same way, it is possible to create eryA strains carrying mutations functionally equivalent to those described herein by deleting different portions of the corresponding genes, by creating insertions into them, or by site-directed mutagenesis of specific nucleotide residues. Moreover, *Sac. erythraea* strains with mutant alleles other than the β-ketoacyl ACP synthase portions of eryA can be employed as hosts for gene conversion; Type III mutants can be constructed by double reciprocal crossover as exemplified for Type I and Type II mutants rather than by the gene conversion method described herein. Additional modifications include changes in the restriction sites used for cloning or in the general methodologies described above. All such changes are included in the scope of the invention. It will also occur to those skilled in the art that different methods are available to ferment *Sac. erythraea*, to extract the novel polyketides specified herein, and to synthesize substrate analogs, and that all such methods are also included within the scope of the present invention.

It will be apparent that many modifications and variations of the invention as set forth herein are possible without departing from the spirit and scope thereof, and that, accordingly, such limitations are imposed only as indicated by the appended claims.

What is claimed is:

1. A method for directing the biosynthesis of specific macrolide polyketide analogs by genetic manipulation of a polyketide-producing microorganism, said method comprising the steps of:
   (1) isolating a macrolide polyketide biosynthetic gene-containing DNA sequence;
   (2) identifying enzymatic activities associated within said gene-containing DNA sequence;
   (3) introducing one or more specified changes into said gene-containing DNA sequence which codes for one of said enzymatic activities resulting in an altered DNA sequence;
   (4) introducing said altered DNA sequence into a polyketide-producing microorganism to replace the original sequence;
   (5) growing a culture of the altered microorganism under conditions suitable for the formation of the specific macrolide polyketide analog; and
   (6) isolating said specific macrolide polyketide analog from the culture.

2. An isolated polynucleotide segment that encodes a biologically active 6-deoxyerythronolide B synthase from *Saccharopolyspora erythraea*.

3. The polynucleotide segment of claim 2 wherein said 6-deoxyerythronolide B synthase possesses one or more enzymatic activities associated with the production of 6-deoxyerythronolide B.

4. The polynucleotide segment of claim 3 wherein said enzymatic activities are selected from the group consisting of β-ketoreductase, dehydratase, enoylreductase, acyl carrier protein, β-ketoacyl ACP and acyltransferase.

5. The polynucleotide segment of claim 3 selected from the group consisting of SEQ ID NO:1 and SEQ ID NO:3.

6. The polynucleotide segment of claim 4 wherein said polynucleotide segment is from about nucleotide position 2250 to about nucleotide position 3626 of SEQ ID NO:1.

7. The polynucleotide segment of claim 4 wherein said polynucleotide segment is from about nucleotide position 3831 to about nucleotide position 4814 of SEQ ID NO:1.

8. The polynucleotide segment of claim 4 wherein said polynucleotide segment is from about nucleotide position 5574 to about nucleotide position 6125 of SEQ ID NO:1.

9. The polynucleotide segment of claim 4 wherein said polynucleotide segment is from about nucleotide position 6369 to about nucleotide position 6626 of SEQ ID NO:1.

10. The polynucleotide segment of claim 4 wherein said polynucleotide segment is from about nucleotide position 6675 to about nucleotide position 8057 of SEQ ID NO:1.

11. The polynucleotide segment of claim 4 wherein said polynucleotide segment is from about nucleotide position 8262 to about nucleotide position 9236 of SEQ ID NO:1.

12. The polynucleotide segment of claim 4 wherein said polynucleotide segment is from about nucleotide position 9906 to about nucleotide position 10454 of SEQ ID NO:1.

13. The polynucleotide segment of claim 4 wherein said polynucleotide segment is from about nucleotide position 10707 to about nucleotide position 10964 of SEQ ID NO:1.

14. The polynucleotide segment of claim 4 wherein said polynucleotide segment is from about nucleotide position 103 to about nucleotide position 1482 of SEQ ID NO:3.

15. The polynucleotide segment of claim 4 wherein said polynucleotide segment is from about nucleotide position 1693 to about nucleotide position 2670 of SEQ ID NO:3.

16. The polynucleotide segment of claim 4 wherein said polynucleotide segment is from about nucleotide position 3406 to about nucleotide position 3921 of SEQ ID NO:3.

17. The polynucleotide segment of claim 4 wherein said polynucleotide segment is from about nucleotide position 4171 to about nucleotide position 4428 of SEQ ID NO:3.

18. The polynucleotide segment of claim 4 wherein said polynucleotide segment is from about nucleotide position 4477 to about nucleotide position 5847 of SEQ ID NO:3.

19. The polynucleotide segment of claim 4 wherein said polynucleotide segment is from about nucleotide position 6055 to about nucleotide position 7026 of SEQ ID NO:3.

20. The polynucleotide segment of claim 4 wherein said polynucleotide segment is from about nucleotide position 7165 to about nucleotide position 7638 of SEQ ID NO:3.

21. The polynucleotide segment of claim 4 wherein said polynucleotide segment is from about nucleotide position 9433 to about nucleotide position 9984 of SEQ ID NO:3.

22. The polynucleotide segment of claim 4 wherein said polynucleotide segment is from about nucleotide position 10225 to about nucleotide position 10482 of SEQ ID NO:3.

23. The polynucleotide segment of claim 4 wherein said polynucleotide segment is from about nucleotide position 10831 to about nucleotide position 12174 of SEQ ID NO:3.

24. The polynucleotide segment of claim 4 wherein said polynucleotide segment is from about nucleotide position 12379 to about nucleotide position 13350 of SEQ ID NO:3.

25. The polynucleotide segment of claim 4 wherein said polynucleotide segment is from about nucleotide position 14062 to about nucleotide position 14610 of SEQ ID NO:3.

26. The polynucleotide segment of claim 4 wherein said polynucleotide segment is from about nucleotide position 14857 to about nucleotide position 15114 of SEQ ID NO:3.

27. The polynucleotide segment of claim 4 wherein said polynucleotide segment is from about nucleotide position 15172 to about nucleotide position 16569 of SEQ ID NO:3.

28. The polynucleotide segment of claim 4 wherein said polynucleotide segment is from about nucleotide position 16768 to about nucleotide position 17721 of SEQ ID NO:3.

29. The polynucleotide segment of claim 4 wherein said polynucleotide segment is from about nucleotide position 18379 to about nucleotide position 18921 of SEQ ID NO:3.

30. The polynucleotide segment of claim 4 wherein said polynucleotide segment is from about nucleotide position 19141 to about nucleotide position 19398 of SEQ ID NO:3.

31. A vector comprising a polynucleotide segment that encodes a biologically active 6-deoxyerythronolide B synthase from *Saccharopolyspora erythraea*.

32. The vector of claim 31 wherein said 6-deoxyerythronolide B synthase possesses one or more enzymatic activities associated with the production of 6-deoxyerythronolide B.

33. The vector of claim 32 wherein said enzymatic activities are selected from the group consisting of β-ketoreductase, dehydratase, enoylreductase, acyl carrier protein, β-ketoacyl ACP and acyltransferase.

34. A host cell comprising the vector of claim 31.

35. A host cell comprising the vector of claim 32.

36. A host cell comprising the vector of claim 33.

37. An isolated polypeptide having the biological activity of 6-deoxyerythronolide B synthase from *Saccharopolyspora erythraea*.

38. The polypeptide of claim 37 wherein said 6-deoxyerythronolide B synthase possesses one or more enzymatic activities associated with the production of 6-deoxyerythronolide B.

39. The polypeptide of claim 38 wherein said enzymatic activities are selected from the group consisting of β-ketoreductase, dehydratase, enoylreductase, acyl carrier protein, β-ketoacyl ACP and acyltransferase.

* * * * *

```
                           SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
         (A) LENGTH: 11219 base pairs
         (B) TYPE: nucleic acid
         (C) STRANDEDNESS: double
         (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
         (A) ORGANISM: Saccharopolyspora erythraea
         (B) STRAIN: NRRL 2338

(ix) FEATURE:
         (A) NAME/KEY: misc_feature
         (B) LOCATION: 744..6659
         (D) OTHER INFORMATION: /function= "APPROXIMATE SPAN OF
             MODULE 1"
             /label= FUNCTION (ix) FEATURE:
         (A) NAME/KEY: CDS
         (B) LOCATION: 744..11219
         (D) OTHER INFORMATION: /function= "gene= "eryA""
             /product= ""ORF1 encoding modules 1 & 2 for
             6-deoxyerythronolide B""

(ix) FEATURE:
         (A) NAME/KEY: misc_feature
         (B) LOCATION: 744..1868
         (D) OTHER INFORMATION: /function= "approximate span of
             acyltransferase domain 1 of module 1"

(ix) FEATURE:
         (A) NAME/KEY: misc_feature
         (B) LOCATION: 1998..2198
         (D) OTHER INFORMATION: /function= "approximate span of
``` acyl carrier domain 1 of module 1"

(ix) FEATURE:
    (A) NAME/KEY: misc_feature
    (B) LOCATION: 2250..3626
    (D) OTHER INFORMATION: /function= "approximate span of beta-ketoacylACP synthase domain/module1"

(ix) FEATURE:
    (A) NAME/KEY: misc_feature
    (B) LOCATION: 3831..4811
    (D) OTHER INFORMATION: /function= "approximate span of acyltransferase 2 domain of module 1"

(ix) FEATURE:
    (A) NAME/KEY: misc_feature
    (B) LOCATION: 5574..6125
    (D) OTHER INFORMATION: /function= "approximate span of beta-ketoreductase domain of module 1"

(ix) FEATURE:
    (A) NAME/KEY: misc_feature
    (B) LOCATION: 6369..6626
    (D) OTHER INFORMATION: /function= "approximate span of acyl carrier domain 2 of module 1"

(ix) FEATURE:
    (A) NAME/KEY: misc_feature
    (B) LOCATION: 6678..11219
    (D) OTHER INFORMATION: /function= "approximate span of module 2"

(ix) FEATURE:
    (A) NAME/KEY: misc_feature
    (B) LOCATION: 6678..8066
    (D) OTHER INFORMATION: /function= "approximate span of beta-ketoacyl ACPsynthase of module 2"

(ix) FEATURE:
    (A) NAME/KEY: misc_feature
    (B) LOCATION: 8262..9305
    (D) OTHER INFORMATION: /function= "approximate span of acyltransferase domain of module 2"

(ix) FEATURE:
    (A) NAME/KEY: misc_feature
    (B) LOCATION: 9906..10454
    (D) OTHER INFORMATION: /function= "approximate span of beta-ketoreductase domain of module 2"

(ix) FEATURE:
    (A) NAME/KEY: misc_feature
    (B) LOCATION: 10707..10964
    (D) OTHER INFORMATION: /function= "approximate span of acyl carrier domain of module 2"

(xi) SEQUENCE DESCRIPTION: SEQ ID NO:1:

```
GTCGACCTGC GGCGATCGTG CAGCGCGCCG ACGAGGTCGT GCATCAGGCC GACGTTGACC      60

CGCTCGGCTT CCGGGTCGGA GGTGGCGCTG CGCCAGGTGG AACCGCCCGC TGCGTGCGCC     120

ACCAGGTGCA CGATCACGTC GGCGTCCTCG ATCGCGGCGG CGGCCCGGCC CGGTTCCAGC     180

AGGTCGGCGC GCAGGTCCTC GACCTCCGCG GCGCCGGGCG GAACCGCGGG CGCTCCGCCG     240

CGGGACACCG CGCGCAGCCG GACCGGGTGG TCGCGCAGCT CGCGCAGAAC CGCGCTCCCG     300

ACGAAGCCGG AAGCGCCCAG AAGGGTGATC AATTGACGCG GGGAATCACT GATCCCATTC     360

ACCGGAGCAT TTGCTCGCTT TCCAGGTCGG TGCTACGGGC GAAATTCAAA GAATCTCCCC     420

AGCGCGATGT GCGGCAACCC GTCACTGGGC CACCACAGTA GGTAGCCGCC GTTGATCTTG     480

TCAACATGCA GATGTTCACA GGTTCGTTGG CTCGACGAGG CGATGTCAAC CTCTTGATCC     540

TTCCTATATT GTTCGCCCAT TGCGTGGTCG TCGAGTAGGG GGACGCGTGG CGGACCTGTC     600

AAAGCTCTCC GACAGTCGGA CTGCACAACC TGGGAGGATC GTTCGTCCGT GGCCCCTGTC     660
```

-continued

```
GGGGTGCAAT GAATCCGCCT TGCGGGCCCG TGCGCGCCAA TTGCGTGCAC ATCTCGATCG        720

ATTTCCCGAT GCCGGTGTCG AAG GTG TCG GGG CCG CGC TCG CGC ACG ACG          770
                         Val Ser Gly Pro Arg Ser Arg Thr Thr
                          1               5

AGC AGG CGG ACG CCG GTC CGC ATC GGC GCG GTC GTC GTC GCC TCC TCG        818
Ser Arg Arg Thr Pro Val Arg Ile Gly Ala Val Val Val Ala Ser Ser
 10              15                  20                  25

ACC TCC GAG CTG CTC GAC GGC CTG GCC GCC GTC GCC GAC GGC CGG CCG        866
Thr Ser Glu Leu Leu Asp Gly Leu Ala Ala Val Ala Asp Gly Arg Pro
                 30                  35                  40

CAC GCC TCG GTG GTC CGC GGC GTG GCC CGG CCG TCC GCG CCG GTG GTG        914
His Ala Ser Val Val Arg Gly Val Ala Arg Pro Ser Ala Pro Val Val
             45                  50                  55

TTC GTC TTC CCG GGC CAG GGC GCG CAA TGG GCC GGG ATG GCG GGC GAA        962
Phe Val Phe Pro Gly Gln Gly Ala Gln Trp Ala Gly Met Ala Gly Glu
         60                  65                  70

CTC CTC GGC GAG TCA AGG GTT TTC GCC GCC GCG ATG GAC GCG TGC GCG       1010
Leu Leu Gly Glu Ser Arg Val Phe Ala Ala Ala Met Asp Ala Cys Ala
     75                  80                  85

CGG GCG TTC GAG CCC GTG ACC GAC TGG ACG CTG GCG CAG GTC CTG GAC       1058
Arg Ala Phe Glu Pro Val Thr Asp Trp Thr Leu Ala Gln Val Leu Asp
 90                  95                 100                 105

TCT CCC GAG CAG TCG CGC CGC GTC GAG GTC GTC CAG CCC GCC CTG TTC       1106
Ser Pro Glu Gln Ser Arg Arg Val Glu Val Val Gln Pro Ala Leu Phe
                110                 115                 120

GCG GTG CAG ACG TCG CTG GCC GCG CTC TGG CGC TCC TTC GGC GTG ACC       1154
Ala Val Gln Thr Ser Leu Ala Ala Leu Trp Arg Ser Phe Gly Val Thr
            125                 130                 135

CCC GAC GCC GTG GTG GGC CAC AGC ATC GGC GAG CTG GCC GCC GCG CAC       1202
Pro Asp Ala Val Val Gly His Ser Ile Gly Glu Leu Ala Ala Ala His
        140                 145                 150

GTG TGC GGT GCG GCC GGT GCC GCC GAC GCC GCG CGC GCC GCC GCG CTG       1250
Val Cys Gly Ala Ala Gly Ala Ala Asp Ala Ala Arg Ala Ala Ala Leu
    155                 160                 165

TGG AGC CGC GAG ATG ATT CCG TTG GTG GGC AAC GGC GAC ATG GCA GCC       1298
Trp Ser Arg Glu Met Ile Pro Leu Val Gly Asn Gly Asp Met Ala Ala
170                 175                 180                 185

GTC GCG CTC TCC GCC GAC GAG ATC GAG CCG CGC ATC GCC CGG TGG GAC       1346
Val Ala Leu Ser Ala Asp Glu Ile Glu Pro Arg Ile Ala Arg Trp Asp
                190                 195                 200

GAC GAC GTG GTG CTG GCC GGG GTC AAC GGT CCG CGC TCG GTT CTG CTG       1394
Asp Asp Val Val Leu Ala Gly Val Asn Gly Pro Arg Ser Val Leu Leu
            205                 210                 215

ACC GGG TCG CCG GAA CCG GTC GCG CGC CGG GTC CAG GAG CTC TCG GCC       1442
Thr Gly Ser Pro Glu Pro Val Ala Arg Arg Val Gln Glu Leu Ser Ala
        220                 225                 230

GAG GGG GTC CGC GCA CAG GTC ATC AAT GTG TCG ATG GCG GCG CAC TCG       1490
Glu Gly Val Arg Ala Gln Val Ile Asn Val Ser Met Ala Ala His Ser
235                 240                 245

GCG CAG GTC GAC GAC ATC GCC GAG GGG ATG CGC TCG GCC CTG GCG TGG       1538
Ala Gln Val Asp Asp Ile Ala Glu Gly Met Arg Ser Ala Leu Ala Trp
250                 255                 260                 265

TTC GCG CCC GGT GGC TCG GAG GTG CCC TTC TAC GCC AGC CTC ACC GGA       1586
Phe Ala Pro Gly Gly Ser Glu Val Pro Phe Tyr Ala Ser Leu Thr Gly
                270                 275                 280

GGT GCG GTC GAC ACG CGG GAG CTG GTG GCC GAC TAC TGG CGC CGC AGC       1634
Gly Ala Val Asp Thr Arg Glu Leu Val Ala Asp Tyr Trp Arg Arg Ser
            285                 290                 295

TTC CGG CTG CCG GTG CGC TTC GAC GAG GCG ATC CGG TCC GCC CTG GAG       1682
Phe Arg Leu Pro Val Arg Phe Asp Glu Ala Ile Arg Ser Ala Leu Glu
```

|     |     |     |     |     |     |     |     |     |     |     |     |     |     |     |     |      |
|---|---|---|---|---|---|---|---|---|---|---|---|---|---|---|---|---|
| | | 300 | | | | | 305 | | | | | 310 | | | | |
| GTC | GGT | CCC | GGC | ACG | TTC | GTC | GAA | GCG | AGC | CCG | CAC | CCG | GTG | CTG | GCC | 1730 |
| Val | Gly | Pro | Gly | Thr | Phe | Val | Glu | Ala | Ser | Pro | His | Pro | Val | Leu | Ala | |
| | 315 | | | | | 320 | | | | | 325 | | | | | |
| GCC | GCG | CTC | CAG | CAG | ACG | CTC | GAC | GCC | GAG | GGC | TCC | TCG | GCC | GCG | GTG | 1778 |
| Ala | Ala | Leu | Gln | Gln | Thr | Leu | Asp | Ala | Glu | Gly | Ser | Ser | Ala | Ala | Val | |
| 330 | | | | | 335 | | | | | 340 | | | | | 345 | |
| GTC | CCG | ACG | CTG | CAA | CGC | GGG | CAG | GGC | GGC | ATG | CGG | CGG | TTC | CTG | CTG | 1826 |
| Val | Pro | Thr | Leu | Gln | Arg | Gly | Gln | Gly | Gly | Met | Arg | Arg | Phe | Leu | Leu | |
| | | | | 350 | | | | | 355 | | | | | 360 | | |
| GCC | GCG | GCC | CAG | GCG | TTC | ACC | GGC | GGC | GTG | GCC | GTC | GAC | TGG | ACC | GCC | 1874 |
| Ala | Ala | Ala | Gln | Ala | Phe | Thr | Gly | Gly | Val | Ala | Val | Asp | Trp | Thr | Ala | |
| | | | 365 | | | | | 370 | | | | | 375 | | | |
| GCC | TAC | GAC | GAC | GTG | GGG | CCG | AAC | CCG | GCT | CTC | TGC | CGG | AGT | TCG | CGC | 1922 |
| Ala | Tyr | Asp | Asp | Val | Gly | Pro | Asn | Pro | Ala | Leu | Cys | Arg | Ser | Ser | Arg | |
| | | 380 | | | | | 385 | | | | | 390 | | | | |
| CGG | CCG | AGG | AGG | AAG | ACG | AGC | CGG | CCG | AGT | CCG | GCG | TCG | ACT | GGA | ACG | 1970 |
| Arg | Pro | Arg | Arg | Lys | Thr | Ser | Arg | Pro | Ser | Pro | Ala | Ser | Thr | Gly | Thr | |
| | 395 | | | | | 400 | | | | | 405 | | | | | |
| CGC | CAC | CGC | ACG | TGC | TGC | GAG | CGG | CTG | CTC | GCG | GTC | GTC | AAC | GGC | GAG | 2018 |
| Arg | His | Arg | Thr | Cys | Cys | Glu | Arg | Leu | Leu | Ala | Val | Val | Asn | Gly | Glu | |
| 410 | | | | | 415 | | | | | 420 | | | | | 425 | |
| ACC | GCC | GCG | TTG | GCG | GGC | CGC | GAA | GCC | GAC | GCC | GAG | GCC | ACG | TTC | CGC | 2066 |
| Thr | Ala | Ala | Leu | Ala | Gly | Arg | Glu | Ala | Asp | Ala | Glu | Ala | Thr | Phe | Arg | |
| | | | | 430 | | | | | 435 | | | | | 440 | | |
| GAG | CTG | GGG | CTG | GAC | TCG | GTG | CTG | GCC | GCG | CAG | CTG | CGC | GCC | AAG | GTG | 2114 |
| Glu | Leu | Gly | Leu | Asp | Ser | Val | Leu | Ala | Ala | Gln | Leu | Arg | Ala | Lys | Val | |
| | | | 445 | | | | | 450 | | | | | 455 | | | |
| AGC | GCC | GCG | ATC | GGG | CGC | GAG | GTC | AAC | ATC | GCC | CTG | CTC | TAC | GAC | CAC | 2162 |
| Ser | Ala | Ala | Ile | Gly | Arg | Glu | Val | Asn | Ile | Ala | Leu | Leu | Tyr | Asp | His | |
| | | 460 | | | | | 465 | | | | | 470 | | | | |
| CCG | ACT | CCG | CGT | GCG | CTC | GCG | GAA | GCA | CTC | GCG | GCG | GGA | ACC | GAG | GTC | 2210 |
| Pro | Thr | Pro | Arg | Ala | Leu | Ala | Glu | Ala | Leu | Ala | Ala | Gly | Thr | Glu | Val | |
| | 475 | | | | | 480 | | | | | 485 | | | | | |
| GCA | CAA | CGG | GAA | ACC | CGC | GCG | CGG | ACC | AAC | GAA | GCG | GCG | CCC | GGC | GAA | 2258 |
| Ala | Gln | Arg | Glu | Thr | Arg | Ala | Arg | Thr | Asn | Glu | Ala | Ala | Pro | Gly | Glu | |
| 490 | | | | | 495 | | | | | 500 | | | | | 505 | |
| CCG | GTC | GCG | GTC | GTC | GCG | ATG | GCC | TGC | CGG | CTG | CCC | GGC | GGT | GTG | AGC | 2306 |
| Pro | Val | Ala | Val | Val | Ala | Met | Ala | Cys | Arg | Leu | Pro | Gly | Gly | Val | Ser | |
| | | | | 510 | | | | | 515 | | | | | 520 | | |
| ACC | CCG | GAG | GAG | TTC | TGG | GAG | CTG | CTG | TCG | GAG | GGC | CGC | GAC | GCG | GTC | 2354 |
| Thr | Pro | Glu | Glu | Phe | Trp | Glu | Leu | Leu | Ser | Glu | Gly | Arg | Asp | Ala | Val | |
| | | | 525 | | | | | 530 | | | | | 535 | | | |
| GCG | GGA | CTG | CCG | ACC | GAC | CGC | GGC | TGG | GAC | CTG | GAC | TCG | CTG | TTC | CAC | 2402 |
| Ala | Gly | Leu | Pro | Thr | Asp | Arg | Gly | Trp | Asp | Leu | Asp | Ser | Leu | Phe | His | |
| | | 540 | | | | | 545 | | | | | 550 | | | | |
| CCC | GAC | CCC | ACG | CGC | TCG | GGC | ACC | GCG | CAC | CAG | CGC | GGC | GGT | GGT | TTC | 2450 |
| Pro | Asp | Pro | Thr | Arg | Ser | Gly | Thr | Ala | His | Gln | Arg | Gly | Gly | Gly | Phe | |
| | 555 | | | | | 560 | | | | | 565 | | | | | |
| CTG | ACC | GAG | GCG | ACC | GCG | TTC | GAC | CCG | GCC | TTC | TTC | GGC | ATG | TCC | CCG | 2498 |
| Leu | Thr | Glu | Ala | Thr | Ala | Phe | Asp | Pro | Ala | Phe | Phe | Gly | Met | Ser | Pro | |
| 570 | | | | | 575 | | | | | 580 | | | | | 585 | |
| CGC | GAG | GCG | CTG | GCC | GTC | GAC | CCG | CAG | CAG | CGG | CTC | ATG | CTC | GAG | CTC | 2546 |
| Arg | Glu | Ala | Leu | Ala | Val | Asp | Pro | Gln | Gln | Arg | Leu | Met | Leu | Glu | Leu | |
| | | | | 590 | | | | | 595 | | | | | 600 | | |
| TCC | TGG | GAA | GTG | CTG | GAA | CGG | GCG | GGA | ATC | CCG | CCG | ACC | TCG | TTG | CAG | 2594 |
| Ser | Trp | Glu | Val | Leu | Glu | Arg | Ala | Gly | Ile | Pro | Pro | Thr | Ser | Leu | Gln | |
| | | | 605 | | | | | 610 | | | | | 615 | | | |
| GCC | TCG | CCC | ACT | GGC | GTG | TTC | GTC | GGC | CTG | ATC | CCG | CAG | GAG | TAC | GGC | 2642 |
| Ala | Ser | Pro | Thr | Gly | Val | Phe | Val | Gly | Leu | Ile | Pro | Gln | Glu | Tyr | Gly | |

```
                  620                 625                 630
CCG CGG CTG GCC GAG GGC GGC GAA GGC GTC GAG GGC TAC CTG ATG ACC                    2690
Pro Arg Leu Ala Glu Gly Gly Glu Gly Val Glu Gly Tyr Leu Met Thr
    635                 640                 645

GGT ACG ACC ACG AGC GTC GCC TCC GGC CGC ATC GCC TAC ACG CTC GGC                    2738
Gly Thr Thr Thr Ser Val Ala Ser Gly Arg Ile Ala Tyr Thr Leu Gly
650                 655                 660                 665

CTG GAG GGC CCG GCG ATC AGC GTG GAC ACC GCG TGC TCG TCC TCG CTG                    2786
Leu Glu Gly Pro Ala Ile Ser Val Asp Thr Ala Cys Ser Ser Ser Leu
                    670                 675                 680

GTC GCG GTG CAC CTG GCG TGC CAG TCG CTG CGG CGC GGC GAG TCG TCG                    2834
Val Ala Val His Leu Ala Cys Gln Ser Leu Arg Arg Gly Glu Ser Ser
                685                 690                 695

CTG GCG ATG GCA GGC GGT GTC ACG GTG ATG CCG ACG CCC GGC ATG CTG                    2882
Leu Ala Met Ala Gly Gly Val Thr Val Met Pro Thr Pro Gly Met Leu
            700                 705                 710

GTG GAC TTC AGC CGG ATG AAC TCG CTG GCG CCG GAC GGC CGG TGC AAG                    2930
Val Asp Phe Ser Arg Met Asn Ser Leu Ala Pro Asp Gly Arg Cys Lys
    715                 720                 725

GCT TTC TCC GCC GGC GCC AAC GGT TTC GGC ATG GCC GAG GGC GCC GGG                    2978
Ala Phe Ser Ala Gly Ala Asn Gly Phe Gly Met Ala Glu Gly Ala Gly
730                 735                 740                 745

ATG CTC CTG CTG GAG CGG CTT TCG GAC GCC CGC CGC AAC GGC CAC CCG                    3026
Met Leu Leu Leu Glu Arg Leu Ser Asp Ala Arg Arg Asn Gly His Pro
                    750                 755                 760

GTG CTC GCC GTG CTC AGG GGG ACG GCG GTC AAC TCC GAC GGC GCG AGC                    3074
Val Leu Ala Val Leu Arg Gly Thr Ala Val Asn Ser Asp Gly Ala Ser
                765                 770                 775

AAC GGG CTG TCG GCG CCC AAC GGG CGG GCG CAG GTG CGG GTC ATC CAG                    3122
Asn Gly Leu Ser Ala Pro Asn Gly Arg Ala Gln Val Arg Val Ile Gln
            780                 785                 790

CAG GCG CTG GCA GAG TCC GGT CTC GGG CCC GCC GAC ATC GAC GCC GTC                    3170
Gln Ala Leu Ala Glu Ser Gly Leu Gly Pro Ala Asp Ile Asp Ala Val
    795                 800                 805

GAG GCG CAC GGC ACC GGT ACC CGA CTC GGC GAC CCG ATC GAG GCG CGG                    3218
Glu Ala His Gly Thr Gly Thr Arg Leu Gly Asp Pro Ile Glu Ala Arg
810                 815                 820                 825

GCG CTG TTC GAG GCG TAC GGG CGC GAC CGC GAG CAG CCG CTG CAC CTG                    3266
Ala Leu Phe Glu Ala Tyr Gly Arg Asp Arg Glu Gln Pro Leu His Leu
                    830                 835                 840

GGC TCG GTC AAG TCC AAC CTC GGC CAC ACC CAG GCG GCC GCC GGT GTT                    3314
Gly Ser Val Lys Ser Asn Leu Gly His Thr Gln Ala Ala Ala Gly Val
                845                 850                 855

GCC GGC GTG ATC AAG ATG GTG CTG GCG ATG CGC GCG GGC ACC CTT CCC                    3362
Ala Gly Val Ile Lys Met Val Leu Ala Met Arg Ala Gly Thr Leu Pro
            860                 865                 870

CGC ACT CTG CAC GCA TCG GAG CGG TCG AAG GAG ATC GAC TGG TCA TCC                    3410
Arg Thr Leu His Ala Ser Glu Arg Ser Lys Glu Ile Asp Trp Ser Ser
    875                 880                 885

GGT GCG ATC AGC CTG CTC GAC GAG CCG GAG CCG TGG CCC GCC GGC GCG                    3458
Gly Ala Ile Ser Leu Leu Asp Glu Pro Glu Pro Trp Pro Ala Gly Ala
890                 895                 900                 905

CGA CCG CGC CGG GCG GGG GTC TCG TCG TTC GGC ATC AGC GGC ACC AAC                    3506
Arg Pro Arg Arg Ala Gly Val Ser Ser Phe Gly Ile Ser Gly Thr Asn
                    910                 915                 920

GCG CAC GCC ATC ATC GAG GAA GCT CCG CAG GTC GTC GAA GGC GAG CGG                    3554
Ala His Ala Ile Ile Glu Glu Ala Pro Gln Val Val Glu Gly Glu Arg
                925                 930                 935

GTC GAG GCC GGC GAC GTC GTG GCG CCC TGG GTG CTT TCG GCG AGC AGC                    3602
Val Glu Ala Gly Asp Val Val Ala Pro Trp Val Leu Ser Ala Ser Ser
```

-continued

```
              940                 945                 950
GCG GAA GGT CTG CGC GCC CAG GCG GCG CGG CTG GCC GCG CAC CTG CGC         3650
Ala Glu Gly Leu Arg Ala Gln Ala Ala Arg Leu Ala Ala His Leu Arg
    955                 960                 965

GAG CAC CCC GGT CAG GAC CCG CGC GAC ATC GCG TAC TCG CTC GCG ACG         3698
Glu His Pro Gly Gln Asp Pro Arg Asp Ile Ala Tyr Ser Leu Ala Thr
970                 975                 980                 985

GGA CGG GCC GCG CTG CCC CAC CGC GCC GCC TTC GCC CCC GTC GAC GAG         3746
Gly Arg Ala Ala Leu Pro His Arg Ala Ala Phe Ala Pro Val Asp Glu
                990                 995                 1000

TCC GCC GCG CTG CGC GTG CTC GAC GGT CTC GCG ACG GGA AAC GCC GAC         3794
Ser Ala Ala Leu Arg Val Leu Asp Gly Leu Ala Thr Gly Asn Ala Asp
    1005                1010                1015

GGT GCC GCC GTT GGA ACG AGC CGG GCG CAG CAG CGC GCC GTC TTC GTC         3842
Gly Ala Ala Val Gly Thr Ser Arg Ala Gln Gln Arg Ala Val Phe Val
    1020                1025                1030

TTC CCC GGG CAG GGT TGG CAG TGG GCG GGC ATG GCC GTC GAC CTG CTC         3890
Phe Pro Gly Gln Gly Trp Gln Trp Ala Gly Met Ala Val Asp Leu Leu
    1035                1040                1045

GAC ACC TCC CCG GTT TTC GCA GCC GCG TTG CGC GAG TGC GCC GAC GCG         3938
Asp Thr Ser Pro Val Phe Ala Ala Ala Leu Arg Glu Cys Ala Asp Ala
1050                1055                1060                1065

CTC GAA CCG CAT CTG GAC TTC GAG GTG ATC CCG TTC CTG CGC GCG GAA         3986
Leu Glu Pro His Leu Asp Phe Glu Val Ile Pro Phe Leu Arg Ala Glu
                1070                1075                1080

GCC GCG AGG CGG GAG CAG GAC GCG GCG CTG TCG ACC GAG CGC GTG GAC         4034
Ala Ala Arg Arg Glu Gln Asp Ala Ala Leu Ser Thr Glu Arg Val Asp
                1085                1090                1095

GTG GTG CAG CCC GTG ATG TTC GCG GTC ATG GTC TCG CTG GCG TCG ATG         4082
Val Val Gln Pro Val Met Phe Ala Val Met Val Ser Leu Ala Ser Met
    1100                1105                1110

TGG CGA GCC CAC GGC GTC GAG CCG GCC GCG GTC ATC GGG CAC TCC CAG         4130
Trp Arg Ala His Gly Val Glu Pro Ala Ala Val Ile Gly His Ser Gln
    1115                1120                1125

GGC GAG ATC GCC GCC GCG TGC GTC GCG GGC GCG CTC TCG CTG GAC GAC         4178
Gly Glu Ile Ala Ala Ala Cys Val Ala Gly Ala Leu Ser Leu Asp Asp
1130                1135                1140                1145

GCC GCG CGC GTG GTC GCG CTG CGC AGC CGC GTC ATC GCC ACC ATG CCC         4226
Ala Ala Arg Val Val Ala Leu Arg Ser Arg Val Ile Ala Thr Met Pro
                1150                1155                1160

GGG AAC AAG GGC ATG GCC TCG ATC GCC GCT CCG GCC GGC GAA GTC CGC         4274
Gly Asn Lys Gly Met Ala Ser Ile Ala Ala Pro Ala Gly Glu Val Arg
                1165                1170                1175

GCG CGA ATC GGT GAC CGC GTC GAG ATC GCC GCC GTC AAC GGT CCG CGC         4322
Ala Arg Ile Gly Asp Arg Val Glu Ile Ala Ala Val Asn Gly Pro Arg
    1180                1185                1190

TCG GTG GTG GTC GCC GGC GAC AGC GAC GAA CTG GAC CGG CTG GTC GCT         4370
Ser Val Val Val Ala Gly Asp Ser Asp Glu Leu Asp Arg Leu Val Ala
    1195                1200                1205

TCC TGC ACC ACC GAG TGC ATC CGC GCC AAG CGG CTG GCC GTG GAC TAC         4418
Ser Cys Thr Thr Glu Cys Ile Arg Ala Lys Arg Leu Ala Val Asp Tyr
1210                1215                1220                1225

GCG TCG CAC TCC TCG CAC GTC GAG ACG ATC CGA GAC GCA CTG CAC GCC         4466
Ala Ser His Ser Ser His Val Glu Thr Ile Arg Asp Ala Leu His Ala
                1230                1235                1240

GAG CTG GGA GAG GAC TTC CAC CCG CTG CCG GGG TTC GTG CCC TTC TTC         4514
Glu Leu Gly Glu Asp Phe His Pro Leu Pro Gly Phe Val Pro Phe Phe
                1245                1250                1255

TCC ACC GTC ACC GGG CGC TGG ACG CAG CCG GAC GAG CTC GAC GCC GGG         4562
Ser Thr Val Thr Gly Arg Trp Thr Gln Pro Asp Glu Leu Asp Ala Gly
```

-continued

```
          1260                1265                1270
TAC TGG TAC CGG AAC CTG CGC CGC ACC GTG CGG TTC GCG GAC GCC GTC        4610
Tyr Trp Tyr Arg Asn Leu Arg Arg Thr Val Arg Phe Ala Asp Ala Val
    1275                1280                1285

CGT GCG CTC GCC GAG CAG GGA TAT CGC ACG TTC CTG GAG GTC AGC GCG        4658
Arg Ala Leu Ala Glu Gln Gly Tyr Arg Thr Phe Leu Glu Val Ser Ala
1290                1295                1300                1305

CAC CCG ATC CTC ACC GCC GCG ATC GAG GAG ATC GGC GAC GGA TCG GGC        4706
His Pro Ile Leu Thr Ala Ala Ile Glu Glu Ile Gly Asp Gly Ser Gly
            1310                1315                1320

GCC GAC CTC TCC GCC ATC CAT TCG CTG CGC CGC GGT GAC GGC AGC CTC        4754
Ala Asp Leu Ser Ala Ile His Ser Leu Arg Arg Gly Asp Gly Ser Leu
        1325                1330                1335

GCG GAC TTC GGC GAA GCG CTC TCC CGC GCG TTC GCC GCC GGT GTC GCG        4802
Ala Asp Phe Gly Glu Ala Leu Ser Arg Ala Phe Ala Ala Gly Val Ala
    1340                1345                1350

GTG GAC TGG GAG TCG GTG CAC CTG GGC ACC GGA GCA CGC CGG GTG CCC        4850
Val Asp Trp Glu Ser Val His Leu Gly Thr Gly Ala Arg Arg Val Pro
1355                1360                1365

TTG CCC ACC TAC CCG TTC CAG CGC GAG CGC GTC TGG CTC GAA CCG AAG        4898
Leu Pro Thr Tyr Pro Phe Gln Arg Glu Arg Val Trp Leu Glu Pro Lys
1370                1375                1380                1385

CCG GTG GCG CGC CGG TCC ACC GAG GTC GAC GAG GTT TCC GCG CTG CGC        4946
Pro Val Ala Arg Arg Ser Thr Glu Val Asp Glu Val Ser Ala Leu Arg
            1390                1395                1400

TAC CGC ATC GAG TGG CGG CCC ACC GGT GCC GGT GAA CCC GCC CGG CTC        4994
Tyr Arg Ile Glu Trp Arg Pro Thr Gly Ala Gly Glu Pro Ala Arg Leu
        1405                1410                1415

GAC GGC ACC TGG CTG GTG GCG AAG TAC GCC GGA ACC GCG GAC GAG ACG        5042
Asp Gly Thr Trp Leu Val Ala Lys Tyr Ala Gly Thr Ala Asp Glu Thr
    1420                1425                1430

AGC ACC GCG GCT CGG GAG GCC CTG GAG TCG GCC GGG GCG CGG GTC CGC        5090
Ser Thr Ala Ala Arg Glu Ala Leu Glu Ser Ala Gly Ala Arg Val Arg
1435                1440                1445

GAA CTG GTC GTG GAC GCC CGC TGC GGT CGC GAC GAA CTC GCG GAG CGG        5138
Glu Leu Val Val Asp Ala Arg Cys Gly Arg Asp Glu Leu Ala Glu Arg
1450                1455                1460                1465

CTT CGT TCG GTC GGC GAG GTG GCA GGA GTG CTG TCC CTG CTC GCG GTG        5186
Leu Arg Ser Val Gly Glu Val Ala Gly Val Leu Ser Leu Leu Ala Val
            1470                1475                1480

GAC GAA GCG GAG CCG GAG GAG GCG CCG CTC GCG CTG GCT TCG CTG GCG        5234
Asp Glu Ala Glu Pro Glu Glu Ala Pro Leu Ala Leu Ala Ser Leu Ala
        1485                1490                1495

GAC ACG CTC AGC CTC GTG CAG GCG ATG GTG TCG GCC GAA CTC GGA TGT        5282
Asp Thr Leu Ser Leu Val Gln Ala Met Val Ser Ala Glu Leu Gly Cys
    1500                1505                1510

CCG CTG TGG ACG GTG ACG GAA AGC GCC GTC GCG ACG GGG CCG TTC GAA        5330
Pro Leu Trp Thr Val Thr Glu Ser Ala Val Ala Thr Gly Pro Phe Glu
1515                1520                1525

CGC GTC CGC AAC GCC GCC CAC GGC GCC CTG TGG GGC GTC GGG CGG GTC        5378
Arg Val Arg Asn Ala Ala His Gly Ala Leu Trp Gly Val Gly Arg Val
1530                1535                1540                1545

ATC GCG CTG GAG AAC CCC GCC GTG TGG GGC GGC CTG GTC GAC GTG CCC        5426
Ile Ala Leu Glu Asn Pro Ala Val Trp Gly Gly Leu Val Asp Val Pro
            1550                1555                1560

GCG GGG TCG GTC GCC GAG CTG GCC CGG CAC CTC GCG GCG GTC GTG TCC        5474
Ala Gly Ser Val Ala Glu Leu Ala Arg His Leu Ala Ala Val Val Ser
        1565                1570                1575

GGC GGC GCC GGT GAG GAC CAG CTC GCG CTG CGC GCC GAC GGG GTG TAC        5522
Gly Gly Ala Gly Glu Asp Gln Leu Ala Leu Arg Ala Asp Gly Val Tyr
```

-continued

```
              1580                1585                1590
GGA CGC CGG TGG GTG CGC GCG GCG GCC CCG GCG ACC GAT GAC GAG TGG         5570
Gly Arg Arg Trp Val Arg Ala Ala Ala Pro Ala Thr Asp Asp Glu Trp
        1595                1600                1605

AAA CCC ACC GGA ACC GTG CTG GTC ACC GGT GGC ACG GGC GGT GTC GGC         5618
Lys Pro Thr Gly Thr Val Leu Val Thr Gly Gly Thr Gly Gly Val Gly
1610                1615                1620                1625

GGG CAG ATC GCG CGC TGG CTC GCC CGG CGG GGC GCG CCC CAC CTG CTG         5666
Gly Gln Ile Ala Arg Trp Leu Ala Arg Arg Gly Ala Pro His Leu Leu
                1630                1635                1640

CTG GTG AGC CGC AGC GGG CCG GAC GCG GAC GGC GCC GGC GAA CTG GTC         5714
Leu Val Ser Arg Ser Gly Pro Asp Ala Asp Gly Ala Gly Glu Leu Val
            1645                1650                1655

GCC GAG CTC GAG GCG CTG GGC GCC CGG ACG ACC GTC GCG GCC TGC GAC         5762
Ala Glu Leu Glu Ala Leu Gly Ala Arg Thr Thr Val Ala Ala Cys Asp
        1660                1665                1670

GTG ACC GAC CGC GAG TCG GTT CGC GAG CTG CTC GGC GGC ATC GGT GAC         5810
Val Thr Asp Arg Glu Ser Val Arg Glu Leu Leu Gly Gly Ile Gly Asp
    1675                1680                1685

GAC GTC CCG CTC TCG GCG GTG TTC CAC GCC GCC GCC ACG CTC GAC GAC         5858
Asp Val Pro Leu Ser Ala Val Phe His Ala Ala Ala Thr Leu Asp Asp
1690                1695                1700                1705

GGC ACC GTG GAC ACC CTC ACC GGC GAG CGC ATC GAG CGG GCA AGT CGC         5906
Gly Thr Val Asp Thr Leu Thr Gly Glu Arg Ile Glu Arg Ala Ser Arg
                1710                1715                1720

GCC AAG GTG CTC GGC GCG CGC AAC CTG CAC GAG CTG ACG CGC GAG CTG         5954
Ala Lys Val Leu Gly Ala Arg Asn Leu His Glu Leu Thr Arg Glu Leu
            1725                1730                1735

GAC CTG ACC GCC TTC GTG CTG TTC TCG TCC TTC GCC TCG GCC TTC GGC         6002
Asp Leu Thr Ala Phe Val Leu Phe Ser Ser Phe Ala Ser Ala Phe Gly
        1740                1745                1750

GCC CCC GGG CTC GGC GGC TAC GCG CCC GGC AAC GCC TAC CTC GAC GGC         6050
Ala Pro Gly Leu Gly Gly Tyr Ala Pro Gly Asn Ala Tyr Leu Asp Gly
    1755                1760                1765

CTC GCC CAG CAG CGG CGG AGC GAC GGA CTC CCC GCG ACC GCC GTG GCG         6098
Leu Ala Gln Gln Arg Arg Ser Asp Gly Leu Pro Ala Thr Ala Val Ala
1770                1775                1780                1785

TGG GGG ACG TGG GCG GGC AGC GGG ATG GCC GAA GGC GCG GTG GCC GAC         6146
Trp Gly Thr Trp Ala Gly Ser Gly Met Ala Glu Gly Ala Val Ala Asp
                1790                1795                1800

CGC TTC CGC AGG CAC GGC GTC ATC GAG ATG CCT CCC GAG ACG GCC TGC         6194
Arg Phe Arg Arg His Gly Val Ile Glu Met Pro Pro Glu Thr Ala Cys
            1805                1810                1815

CGG GCG TTG CAG AAC GCG CTG GAC CGC GCC GAG GTC TGC CCG ATC GTC         6242
Arg Ala Leu Gln Asn Ala Leu Asp Arg Ala Glu Val Cys Pro Ile Val
        1820                1825                1830

ATC GAC GTC AGG TGG GAC CGG TTC CTG CTC GCC TAC ACC GCG CAG CGC         6290
Ile Asp Val Arg Trp Asp Arg Phe Leu Leu Ala Tyr Thr Ala Gln Arg
    1835                1840                1845

CCG ACC AGG CTC TTC GAC GAG ATC GAC GAC GCG CGG CGG GCT GCG CCG         6338
Pro Thr Arg Leu Phe Asp Glu Ile Asp Asp Ala Arg Arg Ala Ala Pro
1850                1855                1860                1865

CAG GCG CCG GCC GAA CCG CGG GTG GGC GCG CTG GCG TCG CTG CCC GCG         6386
Gln Ala Pro Ala Glu Pro Arg Val Gly Ala Leu Ala Ser Leu Pro Ala
                1870                1875                1880

CCG GAG CGC GAG GAA GCG CTG TTC GAG CTC GTG CGC TCG CAC GCG GCC         6434
Pro Glu Arg Glu Glu Ala Leu Phe Glu Leu Val Arg Ser His Ala Ala
            1885                1890                1895

GCC GTC CTC GGC CAC GCC TCG GCC GAG CGG GTG CCC GCC GAC CAG GCC         6482
Ala Val Leu Gly His Ala Ser Ala Glu Arg Val Pro Ala Asp Gln Ala
```

```
                  1900                1905               1910
TTC GCG AAA CTC GGC GTC GAC TCG CTG TCG GCG CTT GAG CTG CGC AAC           6530
Phe Ala Glu Leu Gly Val Asp Ser Leu Ser Ala Leu Glu Leu Arg Asn
    1915                1920                1925

CGG CTC GGC GCC GCG ACC GGT GTC CGC CTG CCG ACG ACG ACC GTC TTC           6578
Arg Leu Gly Ala Ala Thr Gly Val Arg Leu Pro Thr Thr Thr Val Phe
1930                1935                1940                1945

GAC CAC CCC GAC GTG CGG ACG CTG GCG GCG CAC CTG GCC GCC GAA CTC           6626
Asp His Pro Asp Val Arg Thr Leu Ala Ala His Leu Ala Ala Glu Leu
                1950                1955                1960

GGC GGT GCG ACC GGA GCC GAG CAG GCG GCA CCG GCG ACC ACG GCC CCC           6674
Gly Gly Ala Thr Gly Ala Glu Gln Ala Ala Pro Ala Thr Thr Ala Pro
            1965                1970                1975

GTC GAC GAG CCG ATC GCG ATC GTC GGC ATG GCG TGC CGG CTG CCC GGG           6722
Val Asp Glu Pro Ile Ala Ile Val Gly Met Ala Cys Arg Leu Pro Gly
        1980                1985                1990

GAG GTC GAC TCC CCG GAG CGG CTG TGG GAG CTG ATC ACC TCG GGA CGC           6770
Glu Val Asp Ser Pro Glu Arg Leu Trp Glu Leu Ile Thr Ser Gly Arg
    1995                2000                2005

GAC TCC GCG GCG GAG GTC CCC GAT GAC CGG GGC TGG GTC CCC GAC GAG           6818
Asp Ser Ala Ala Glu Val Pro Asp Asp Arg Gly Trp Val Pro Asp Glu
2010                2015                2020                2025

CTG ATG GCC TCC GAC GCG GCG GGA ACC CGC GCC CAC GGC AAC TTC ATG           6866
Leu Met Ala Ser Asp Ala Ala Gly Thr Arg Ala His Gly Asn Phe Met
                2030                2035                2040

GCG GGC GCC GGT GAC TTC GAC GCG GCG TTC TTC GGG ATC TCG CCG CGC           6914
Ala Gly Ala Gly Asp Phe Asp Ala Ala Phe Phe Gly Ile Ser Pro Arg
            2045                2050                2055

GAG GCG CTG GCG ATG GAC CCG CAG CAG CGC CAG GCG CTG GAG ACG ACG           6962
Glu Ala Leu Ala Met Asp Pro Gln Gln Arg Gln Ala Leu Glu Thr Thr
        2060                2065                2070

TGG GAG GCG CTG GAA AGC GCG GGC ATC CCA CCG GAG ACG TTG CGC GGC           7010
Trp Glu Ala Leu Glu Ser Ala Gly Ile Pro Pro Glu Thr Leu Arg Gly
    2075                2080                2085

AGC GAC ACC GGC GTG TTC GTC GGC ATG TCC CAC CAG GGC TAC GCG ACC           7058
Ser Asp Thr Gly Val Phe Val Gly Met Ser His Gln Gly Tyr Ala Thr
2090                2095                2100                2105

GGG CGT CCG CGC CCG GAG GAC GGC GTC GAC GGG TAC CTG CTC ACC GGC           7106
Gly Arg Pro Arg Pro Glu Asp Gly Val Asp Gly Tyr Leu Leu Thr Gly
                2110                2115                2120

AAC ACC GCG AGC GTC GCG TCG GGA CGC ATC GCC TAC GTG CTG GGG CTG           7154
Asn Thr Ala Ser Val Ala Ser Gly Arg Ile Ala Tyr Val Leu Gly Leu
            2125                2130                2135

GAA GGT CCC GCG CTG ACG GTG GAC ACG GCG TGT TCG TCG TCG TTG GTG           7202
Glu Gly Pro Ala Leu Thr Val Asp Thr Ala Cys Ser Ser Ser Leu Val
        2140                2145                2150

GCG TTG CAC ACG GCG TGT GGG TCG TTG CGT GAC GGT GAC TGC GGT CTT           7250
Ala Leu His Thr Ala Cys Gly Ser Leu Arg Asp Gly Asp Cys Gly Leu
    2155                2160                2165

GCG GTG GCC GGT GGT GTG TCG GTG ATG GCG GGT CCG GAG GTG TTC ACC           7298
Ala Val Ala Gly Gly Val Ser Val Met Ala Gly Pro Glu Val Phe Thr
2170                2175                2180                2185

GAG TTC TCC CGC CAG GGC GCG CTC TCG CCG GAC GGC CGG TGC AAG CCC           7346
Glu Phe Ser Arg Gln Gly Ala Leu Ser Pro Asp Gly Arg Cys Lys Pro
                2190                2195                2200

TTC TCG GAC GAG GCC GAC GGA TTC GGT CTC GGG GAG GGT TCG GCG TTC           7394
Phe Ser Asp Glu Ala Asp Gly Phe Gly Leu Gly Glu Gly Ser Ala Phe
            2205                2210                2215

GTC GTG CTC CAG CGG TTG TCC GAC GCC AGG CGG GAG GGC CGC CGC GTG           7442
Val Val Leu Gln Arg Leu Ser Asp Ala Arg Arg Glu Gly Arg Arg Val
```

-continued

```
            2220                2225                2230
CTC GGC GTG GTG GCC GGG TCC GCG GTG AAC CAG GAC GGC GCG AGC AAC       7490
Leu Gly Val Val Ala Gly Ser Ala Val Asn Gln Asp Gly Ala Ser Asn
    2235                2240                2245

GGG CTC TCC GCT CCG AGC GGC GTC GCG CAG CAG CGG GTC ATC CGC CGG       7538
Gly Leu Ser Ala Pro Ser Gly Val Ala Gln Gln Arg Val Ile Arg Arg
2250                2255                2260                2265

GCG TGG GCG CGT GCG GGG ATC ACG GGC GCG GAT GTG GCC GTG GTG GAG       7586
Ala Trp Ala Arg Ala Gly Ile Thr Gly Ala Asp Val Ala Val Val Glu
        2270                2275                2280

GCG CAT GGG ACC GGT ACG CGG CTG GGC GAT CCG GTG GAG GCG TCG GCG       7634
Ala His Gly Thr Gly Thr Arg Leu Gly Asp Pro Val Glu Ala Ser Ala
    2285                2290                2295

TTG CTG GCT ACT TAC GGC AAG TCG CGC GGG TCG TCG GGC CCG GTG CTG       7682
Leu Leu Ala Thr Tyr Gly Lys Ser Arg Gly Ser Ser Gly Pro Val Leu
2300                2305                2310

CTG GGT TCG GTG AAG TCG AAC ATC GGT CAC GCG CAG GCG GCC GCG GGT       7730
Leu Gly Ser Val Lys Ser Asn Ile Gly His Ala Gln Ala Ala Ala Gly
        2315                2320                2325

GTC GCG GGC GTG ATC AAG GTG CTC CTC GGC CTG GAA CGC GGT GTG GTG       7778
Val Ala Gly Val Ile Lys Val Leu Leu Gly Leu Glu Arg Gly Val Val
    2330                2335                2340                2345

CCC CCG ATG CTG TGC CGG GGC GAG AGG TCG GGC CTC ATC GAC TGG TCC       7826
Pro Pro Met Leu Cys Arg Gly Glu Arg Ser Gly Leu Ile Asp Trp Ser
                2350                2355                2360

TCC GGC GAG ATC GAG CTC GCA GAC GGC GTG CGG GAG TGG TCG CCC GCC       7874
Ser Gly Glu Ile Glu Leu Ala Asp Gly Val Arg Glu Trp Ser Pro Ala
            2365                2370                2375

GCG GAC GGG GTG CGC CGG GCA GGT GTG TCG GCG TTC GGG GTG AGC GGG       7922
Ala Asp Gly Val Arg Arg Ala Gly Val Ser Ala Phe Gly Val Ser Gly
        2380                2385                2390

ACG AAC GCG CAC GTG ATC ATC GCC GAG CCG CCG GAA CCG GAG CCC GTG       7970
Thr Asn Ala His Val Ile Ile Ala Glu Pro Pro Glu Pro Glu Pro Val
    2395                2400                2405

CCG CAA CCG CGA CGC ATG CTG CCC GCG ACC GGG GTG GTG CCG GTC GTG       8018
Pro Gln Pro Arg Arg Met Leu Pro Ala Thr Gly Val Val Pro Val Val
2410                2415                2420                2425

CTG TCG GCC AGG ACC GGG GCG GCG TTG CGG GCG CAG GCC GGC AGG CTC       8066
Leu Ser Ala Arg Thr Gly Ala Ala Leu Arg Ala Gln Ala Gly Arg Leu
                2430                2435                2440

GCC GAC CAC CTC GCC GCG CAT CCC GGG ATC GCA CCG GCC GAC GTG AGC       8114
Ala Asp His Leu Ala Ala His Pro Gly Ile Ala Pro Ala Asp Val Ser
            2445                2450                2455

TGG ACG ATG GCG CGG GCC CGC CAG CAC TTC GAG GAG CGG GCC GCG GTG       8162
Trp Thr Met Ala Arg Ala Arg Gln His Phe Glu Glu Arg Ala Ala Val
        2460                2465                2470

CTC GCC GCC GAC ACC GCC GAG GCC GTG CAC CGG TTG CGG GCG GTG GCC       8210
Leu Ala Ala Asp Thr Ala Glu Ala Val His Arg Leu Arg Ala Val Ala
    2475                2480                2485

GAC GGC GCG GTG GTT CCC GGT GTT GTC ACC GGC AGT GCC TCC GAC GGT       8258
Asp Gly Ala Val Val Pro Gly Val Val Thr Gly Ser Ala Ser Asp Gly
2490                2495                2500                2505

GGT TCA GTG TTC GTC TTC CCT GGG CAG GGT GCC CAG TGG GAA GGC ATG       8306
Gly Ser Val Phe Val Phe Pro Gly Gln Gly Ala Gln Trp Glu Gly Met
                2510                2515                2520

GCG CGG GAG TTG TTG CCG GTT CCC GTC TTC GCC GAG TCG ATC GCC GAG       8354
Ala Arg Glu Leu Leu Pro Val Pro Val Phe Ala Glu Ser Ile Ala Glu
            2525                2530                2535

TGC GAT GCG GTG TTG TCG GAG GTG GCC GGA TTC TCG GTG TCC GAG GTG       8402
Cys Asp Ala Val Leu Ser Glu Val Ala Gly Phe Ser Val Ser Glu Val
```

-continued

```
                 2540                2545                2550
CTG GAG CCA CGT CCG GAC GCG CCG TCG CTG GAG CGG GTC GAC GTG GTG           8450
Leu Glu Pro Arg Pro Asp Ala Pro Ser Leu Glu Arg Val Asp Val Val
            2555                2560                2565

CAG CCG GTG CTG TTC GCG GTG ATG GTG TCG CTG GCG CGG TTG TGG CGT           8498
Gln Pro Val Leu Phe Ala Val Met Val Ser Leu Ala Arg Leu Trp Arg
2570                2575                2580                2585

GCC TGC GGT GCC GTT CCT TCG GCC GTC ATA GGG CAC TCG CAG GGT GAG           8546
Ala Cys Gly Ala Val Pro Ser Ala Val Ile Gly His Ser Gln Gly Glu
                2590                2595                2600

ATC GCC GCC GCG GTG GTG GCG GGA GCG TTG TCG CTG GAG GAC GGC ATG           8594
Ile Ala Ala Ala Val Val Ala Gly Ala Leu Ser Leu Glu Asp Gly Met
            2605                2610                2615

CGC GTC GTC GCC CGC CGG TCG AGG GCG GTG CGT GCG GTC GCG GGC CGG           8642
Arg Val Val Ala Arg Arg Ser Arg Ala Val Arg Ala Val Ala Gly Arg
        2620                2625                2630

GGG AGC ATG CTC TCG GTG CGC GGC GGC CGC TCC GAC GTC GAG AAG CTG           8690
Gly Ser Met Leu Ser Val Arg Gly Gly Arg Ser Asp Val Glu Lys Leu
    2635                2640                2645

CTC GCC GAC GAC AGC TGG ACC GGC AGG CTG GAG GTC GCC GCG GTC AAC           8738
Leu Ala Asp Asp Ser Trp Thr Gly Arg Leu Glu Val Ala Ala Val Asn
2650                2655                2660                2665

GGC CCC GAC GCC GTG GTG GTG GCC GGT GAC GCC CAG GCG GCG CGC GAG           8786
Gly Pro Asp Ala Val Val Val Ala Gly Asp Ala Gln Ala Ala Arg Glu
                2670                2675                2680

TTC CTG GAG TAC TGC GAG GGC GTG GGC ATC CGC GCC CGC GCG ATC CCG           8834
Phe Leu Glu Tyr Cys Glu Gly Val Gly Ile Arg Ala Arg Ala Ile Pro
            2685                2690                2695

GTG GAC TAC GCC TCG CAC ACC GCG CAC GTC GAG CCC GTG CGC GAC GAA           8882
Val Asp Tyr Ala Ser His Thr Ala His Val Glu Pro Val Arg Asp Glu
        2700                2705                2710

CTG GTC CAG GCG CTG GCC GGG ATC ACC CCG CGA CGG GCC GAG GTG CCG           8930
Leu Val Gln Ala Leu Ala Gly Ile Thr Pro Arg Arg Ala Glu Val Pro
    2715                2720                2725

TTC TTC TCC ACC CTG ACC GGC GAC TTC CTC GAC GGC ACC GAG CTG GAC           8978
Phe Phe Ser Thr Leu Thr Gly Asp Phe Leu Asp Gly Thr Glu Leu Asp
2730                2735                2740                2745

GCG GGC TAC TGG TAC CGC AAC CTG CGT CAC CCG GTG GAG TTC CAC TCC           9026
Ala Gly Tyr Trp Tyr Arg Asn Leu Arg His Pro Val Glu Phe His Ser
                2750                2755                2760

GCC GTG CAG GCG CTG ACC GAC CAG GGA TAC GCG ACG TTC ATC GAG GTC           9074
Ala Val Gln Ala Leu Thr Asp Gln Gly Tyr Ala Thr Phe Ile Glu Val
            2765                2770                2775

AGC CCG CAC CCG GTG CTG GCG TCG AGC GTC CAG GAG ACC CTC GAC GAC           9122
Ser Pro His Pro Val Leu Ala Ser Ser Val Gln Glu Thr Leu Asp Asp
        2780                2785                2790

GCC GAG TCG GAC GCG GCG GTG CTC GGG ACG CTG GAA CGC GAC GCG GGC           9170
Ala Glu Ser Asp Ala Ala Val Leu Gly Thr Leu Glu Arg Asp Ala Gly
    2795                2800                2805

GAC GCC GAC CGC TTC CTC ACG GCA CTC GCC GAC GCG CAC ACG CGC GGT           9218
Asp Ala Asp Arg Phe Leu Thr Ala Leu Ala Asp Ala His Thr Arg Gly
2810                2815                2820                2825

GTC GCG GTC GAC TGG GAA GCG GTG CTC GGC CGG GCC GGA CTG GTC GAC           9266
Val Ala Val Asp Trp Glu Ala Val Leu Gly Arg Ala Gly Leu Val Asp
                2830                2835                2840

CTG CCG GGT TAT CCT TTC CAG GGC AAG CGG TTC TGG CTG CTG CCG GAC           9314
Leu Pro Gly Tyr Pro Phe Gln Gly Lys Arg Phe Trp Leu Leu Pro Asp
            2845                2850                2855

CGC ACC ACC CCT CGT GAC GAG CTC GAC GGC TGG TTC TAC CGG GTC GAC           9362
Arg Thr Thr Pro Arg Asp Glu Leu Asp Gly Trp Phe Tyr Arg Val Asp
```

```
                    2860                 2865                      2870
TGG ACC GAG GTG CCG CGC TCC GAA CCT GCC GCG CTG CGC GGC CGT TGG               9410
Trp Thr Glu Val Pro Arg Ser Glu Pro Ala Ala Leu Arg Gly Arg Trp
    2875                2880                     2885

CTC GTG GTG GTG CCC GAG GGG CAC GAG GAG GAC GGC TGG ACC GTC GAG               9458
Leu Val Val Val Pro Glu Gly His Glu Glu Asp Gly Trp Thr Val Glu
2890                     2895                    2900                    2905

GTG CGG TCC GCG CTC GCC GAG GCC GGC GCC GAA CCG GAG GTC ACG CGC               9506
Val Arg Ser Ala Leu Ala Glu Ala Gly Ala Glu Pro Glu Val Thr Arg
            2910                    2915                    2920

GGC GTC GGC GGG CTG GTC GGT GAC TGC GCG GGC GTG GTG TCG TTG CTC               9554
Gly Val Gly Gly Leu Val Gly Asp Cys Ala Gly Val Val Ser Leu Leu
                2925                    2930                    2935

GCC CTC GAG GGC GAT GGT GCG GTG CAA ACC CTT GTG CTG GTG CGG GAA               9602
Ala Leu Glu Gly Asp Gly Ala Val Gln Thr Leu Val Leu Val Arg Glu
        2940                    2945                    2950

CTC GAC GCC GAG GGC ATC GAC GCG CCA CTG TGG ACG GTC ACC TTC GGC               9650
Leu Asp Ala Glu Gly Ile Asp Ala Pro Leu Trp Thr Val Thr Phe Gly
            2955                    2960                    2965

GCG GTC GAC GCG GGC AGT CCG GTG GCC CGC CCG GAC CAG GCG AAG CTG               9698
Ala Val Asp Ala Gly Ser Pro Val Ala Arg Pro Asp Gln Ala Lys Leu
2970                    2975                    2980                    2985

TGG GGG CTG GGC CAG GTC GCG TCC CTG GAA CGC GGG CCC CGC TGG ACC               9746
Trp Gly Leu Gly Gln Val Ala Ser Leu Glu Arg Gly Pro Arg Trp Thr
                2990                    2995                    3000

GGC CTC GTC GAC CTG CCG CAC ATG CCG GAC CCG GAA CTG CGA GGC CGT               9794
Gly Leu Val Asp Leu Pro His Met Pro Asp Pro Glu Leu Arg Gly Arg
            3005                    3010                    3015

CTC ACC GCG GTG CTG GCC GGC TCG GAG GAC CAG GTC GCG GTG CGC GCC               9842
Leu Thr Ala Val Leu Ala Gly Ser Glu Asp Gln Val Ala Val Arg Ala
        3020                    3025                    3030

GAC GCC GTG CGT GCG CGG CGG CTT TCC CCC GCC CAC GTC ACC GCC ACC               9890
Asp Ala Val Arg Ala Arg Arg Leu Ser Pro Ala His Val Thr Ala Thr
            3035                    3040                    3045

TCG GAG TAC GCG GTG CCG GGC GGC ACA ATC CTG GTC ACC GGT GGC ACC               9938
Ser Glu Tyr Ala Val Pro Gly Gly Thr Ile Leu Val Thr Gly Gly Thr
3050                    3055                    3060                    3065

GCC GGC CTG GGC GCG GAG GTG GCC CGG TGG CTC GCC GGT CGC GGC GCC               9986
Ala Gly Leu Gly Ala Glu Val Ala Arg Trp Leu Ala Gly Arg Gly Ala
                3070                    3075                    3080

GAA CAC CTC GCG CTG GTC AGC AGG CGA GGC CCG GAC ACC GAG GGC GTC              10034
Glu His Leu Ala Leu Val Ser Arg Arg Gly Pro Asp Thr Glu Gly Val
            3085                    3090                    3095

GGC GAC CTG ACC GCC GAG CTG ACC CGG CTC GGC GCG CGG GTG TCG GTG              10082
Gly Asp Leu Thr Ala Glu Leu Thr Arg Leu Gly Ala Arg Val Ser Val
        3100                    3105                    3110

CAC GCG TGC GAC GTC AGC AGC CGC GAA CCG GTG AGG GAA CTC GTG CAC              10130
His Ala Cys Asp Val Ser Ser Arg Glu Pro Val Arg Glu Leu Val His
            3115                    3120                    3125

GGC CTG ATC GAG CAG GGC GAC GTC GTC CGC GGT GTG GTG CAC GCG GCG              10178
Gly Leu Ile Glu Gln Gly Asp Val Val Arg Gly Val Val His Ala Ala
3130                    3135                    3140                    3145

GGA CTG CCG CAG CAG GTC GCG ATC AAC GAC ATG GAC GAG GCC GCC TTC              10226
Gly Leu Pro Gln Gln Val Ala Ile Asn Asp Met Asp Glu Ala Ala Phe
                3150                    3155                    3160

GAC GAG GTG GTC GCG GCC AAG GCC GGG GGC GCG GTG CAC CTG GAC GAG              10274
Asp Glu Val Val Ala Ala Lys Ala Gly Gly Ala Val His Leu Asp Glu
            3165                    3170                    3175

CTG TGC TCG GAC GCC GAG CTG TTC CTG CTG TTC TCC TCC GGG GCC GGG              10322
Leu Cys Ser Asp Ala Glu Leu Phe Leu Leu Phe Ser Ser Gly Ala Gly
```

```
                3180              3185              3190
GTG TGG GGA AGC GCC CGC CAG GGC GCC TAC GCC GCG GGC AAC GCG TTC    10370
Val Trp Gly Ser Ala Arg Gln Gly Ala Tyr Ala Ala Gly Asn Ala Phe
    3195              3200              3205

CTG GAC GCC TTC GCC CGG CAC CGC CGG GGC CGC GGC CTG CCC GCC ACG    10418
Leu Asp Ala Phe Ala Arg His Arg Arg Gly Arg Gly Leu Pro Ala Thr
3210              3215              3220              3225

TCG GTG GCG TGG GGG CTG TGG GCG GCG GGC GGC ATG ACC GGC GAC GAG    10466
Ser Val Ala Trp Gly Leu Trp Ala Ala Gly Gly Met Thr Gly Asp Glu
        3230              3235              3240

GAG GCC GTG TCG TTC CTG CGC GAG CGC GGT GTG CGG GCG ATG CCC GTA    10514
Glu Ala Val Ser Phe Leu Arg Glu Arg Gly Val Arg Ala Met Pro Val
            3245              3250              3255

CCG CGC GCC CTC GCC GCC CTG GAC AGG GTG CTG GCC TCC GGG GAG ACG    10562
Pro Arg Ala Leu Ala Ala Leu Asp Arg Val Leu Ala Ser Gly Glu Thr
3260              3265              3270

GCG GTG GTC GTG ACG GAC GTG GAC TGG CCC GCC TTC GCC GAG TCC TAC    10610
Ala Val Val Val Thr Asp Val Asp Trp Pro Ala Phe Ala Glu Ser Tyr
    3275              3280              3285

ACC GCC GCC CGG CCC CGG CCG TTG CTC GAC CGC ATC GTC ACG ACC GCG    10658
Thr Ala Ala Arg Pro Arg Pro Leu Leu Asp Arg Ile Val Thr Thr Ala
3290              3295              3300              3305

CCG AGC GAG CGG GCC GGA GAA CCG GAG ACG GAG AGC CTG CGC GAC CGG    10706
Pro Ser Glu Arg Ala Gly Glu Pro Glu Thr Glu Ser Leu Arg Asp Arg
            3310              3315              3320

CTG GCG GGT CTG CCG CGT GCC GAG CGG ACG GCG GAG CTG GTG CGC CTG    10754
Leu Ala Gly Leu Pro Arg Ala Glu Arg Thr Ala Glu Leu Val Arg Leu
        3325              3330              3335

GTC CGC ACC AGC ACC GCG ACC GTG CTG GGC CAC GAC GAC CCG AAG GCG    10802
Val Arg Thr Ser Thr Ala Thr Val Leu Gly His Asp Asp Pro Lys Ala
    3340              3345              3350

GTG CGC GCG ACC ACG CCG TTC AAG GAG CTC GGG TTC GAC TCG CTG GCG    10850
Val Arg Ala Thr Thr Pro Phe Lys Glu Leu Gly Phe Asp Ser Leu Ala
    3355              3360              3365

GCC GTC CGG CTG CGC AAC CTG CTC AAC GCG GCC ACC GGG CTC CGC CTG    10898
Ala Val Arg Leu Arg Asn Leu Leu Asn Ala Ala Thr Gly Leu Arg Leu
3370              3375              3380              3385

CCG TCG ACG CTG GTC TTC GAC CAC CCG AAC GCC TCC GCG GTC GCC GGT    10946
Pro Ser Thr Leu Val Phe Asp His Pro Asn Ala Ser Ala Val Ala Gly
            3390              3395              3400

TTC CTC GAC GCC GAG CTC GGC ACC GAG GTC CGG GGG GAG GCG CCG TCG    10994
Phe Leu Asp Ala Glu Leu Gly Thr Glu Val Arg Gly Glu Ala Pro Ser
        3405              3410              3415

GCC CTC GCC GGG CTG GAC GCG CTG GAA GGC GCC CTG CCC GAG GTG CCC    11042
Ala Leu Ala Gly Leu Asp Ala Leu Glu Gly Ala Leu Pro Glu Val Pro
    3420              3425              3430

GCA ACC GAG CGG GAA GAG CTG GTA CAG CGC TTG GAA CGG ATG CTC GCC    11090
Ala Thr Glu Arg Glu Glu Leu Val Gln Arg Leu Glu Arg Met Leu Ala
    3435              3440              3445

GCG CTA CGC CCG GTC GCC CAG GCC GCC GAC GCC TCC GGG ACC GGC GCC    11138
Ala Leu Arg Pro Val Ala Gln Ala Ala Asp Ala Ser Gly Thr Gly Ala
3450              3455              3460              3465

AAC CCG TCC GGC GAC GAC CTG GGC GAG GCG GGC GTG GAC GAA CTG CTC    11186
Asn Pro Ser Gly Asp Asp Leu Gly Glu Ala Gly Val Asp Glu Leu Leu
            3470              3475              3480

GAA GCA CTC GGC CGG GAG CTC GAC GGC GAT TGA                        11219
Glu Ala Leu Gly Arg Glu Leu Asp Gly Asp
        3485              3490
```

(2) INFORMATION FOR SEQ ID NO:2:

(i) SEQUENCE CHARACTERISTICS:
    (A) LENGTH: 3491 amino acids
    (B) TYPE: amino acid
    (D) TOPOLOGY: linear (ii) MOLECULE TYPE: protein (xi) SEQUENCE DESCRIPTION: SEQ ID NO:2:

```
Val Ser Gly Pro Arg Ser Arg Thr Thr Ser Arg Arg Thr Pro Val Arg
 1               5                  10                  15

Ile Gly Ala Val Val Ala Ser Ser Thr Ser Glu Leu Leu Asp Gly
            20                  25                  30

Leu Ala Ala Val Ala Asp Gly Arg Pro His Ala Ser Val Val Arg Gly
            35                  40                  45

Val Ala Arg Pro Ser Ala Pro Val Val Phe Val Phe Pro Gly Gln Gly
            50                  55                  60

Ala Gln Trp Ala Gly Met Ala Gly Glu Leu Leu Gly Glu Ser Arg Val
 65              70                  75                  80

Phe Ala Ala Ala Met Asp Ala Cys Ala Arg Ala Phe Glu Pro Val Thr
                85                  90                  95

Asp Trp Thr Leu Ala Gln Val Leu Asp Ser Pro Glu Gln Ser Arg Arg
                100                 105                 110

Val Glu Val Val Gln Pro Ala Leu Phe Ala Val Gln Thr Ser Leu Ala
            115                 120                 125

Ala Leu Trp Arg Ser Phe Gly Val Thr Pro Asp Ala Val Val Gly His
130                 135                 140

Ser Ile Gly Glu Leu Ala Ala Ala His Val Cys Gly Ala Ala Gly Ala
145                 150                 155                 160

Ala Asp Ala Ala Arg Ala Ala Ala Leu Trp Ser Arg Glu Met Ile Pro
                165                 170                 175

Leu Val Gly Asn Gly Asp Met Ala Ala Val Ala Leu Ser Ala Asp Glu
                180                 185                 190

Ile Glu Pro Arg Ile Ala Arg Trp Asp Asp Asp Val Val Leu Ala Gly
                195                 200                 205

Val Asn Gly Pro Arg Ser Val Leu Leu Thr Gly Ser Pro Glu Pro Val
            210                 215                 220

Ala Arg Arg Val Gln Glu Leu Ser Ala Glu Gly Val Arg Ala Gln Val
225                 230                 235                 240

Ile Asn Val Ser Met Ala Ala His Ser Ala Gln Val Asp Asp Ile Ala
                245                 250                 255

Glu Gly Met Arg Ser Ala Leu Ala Trp Phe Ala Pro Gly Gly Ser Glu
                260                 265                 270

Val Pro Phe Tyr Ala Ser Leu Thr Gly Gly Ala Val Asp Thr Arg Glu
            275                 280                 285

Leu Val Ala Asp Tyr Trp Arg Ser Phe Arg Leu Pro Val Arg Phe
            290                 295                 300

Asp Glu Ala Ile Arg Ser Ala Leu Glu Val Gly Pro Gly Thr Phe Val
305                 310                 315                 320

Glu Ala Ser Pro His Pro Val Leu Ala Ala Leu Gln Gln Thr Leu
                325                 330                 335

Asp Ala Glu Gly Ser Ser Ala Ala Val Val Pro Thr Leu Gln Arg Gly
                340                 345                 350

Gln Gly Gly Met Arg Arg Phe Leu Leu Ala Ala Ala Gln Ala Phe Thr
                355                 360                 365

Gly Gly Val Ala Val Asp Trp Thr Ala Ala Tyr Asp Asp Val Gly Pro
```

```
            370                 375                 380
Asn Pro Ala Leu Cys Arg Ser Ser Arg Arg Pro Arg Lys Thr Ser
385                 390                 395                 400

Arg Pro Ser Pro Ala Ser Thr Gly Thr Arg His Arg Thr Cys Cys Glu
                405                 410                 415

Arg Leu Leu Ala Val Val Asn Gly Glu Thr Ala Ala Leu Ala Gly Arg
                420                 425                 430

Glu Ala Asp Ala Glu Ala Thr Phe Arg Glu Leu Gly Leu Asp Ser Val
                435                 440                 445

Leu Ala Ala Gln Leu Arg Ala Lys Val Ser Ala Ala Ile Gly Arg Glu
450                 455                 460

Val Asn Ile Ala Leu Leu Tyr Asp His Pro Thr Pro Arg Ala Leu Ala
465                 470                 475                 480

Glu Ala Leu Ala Ala Gly Thr Glu Val Ala Gln Arg Glu Thr Arg Ala
                485                 490                 495

Arg Thr Asn Glu Ala Ala Pro Gly Glu Pro Val Ala Val Ala Met
                500                 505                 510

Ala Cys Arg Leu Pro Gly Gly Val Ser Thr Pro Glu Glu Phe Trp Glu
                515                 520                 525

Leu Leu Ser Glu Gly Arg Asp Ala Val Ala Gly Leu Pro Thr Asp Arg
530                 535                 540

Gly Trp Asp Leu Asp Ser Leu Phe His Pro Asp Pro Thr Arg Ser Gly
545                 550                 555                 560

Thr Ala His Gln Arg Gly Gly Phe Leu Thr Glu Ala Thr Ala Phe
                565                 570                 575

Asp Pro Ala Phe Phe Gly Met Ser Pro Arg Glu Ala Leu Ala Val Asp
                580                 585                 590

Pro Gln Gln Arg Leu Met Leu Glu Leu Ser Trp Glu Val Leu Glu Arg
                595                 600                 605

Ala Gly Ile Pro Pro Thr Ser Leu Gln Ala Ser Pro Thr Gly Val Phe
610                 615                 620

Val Gly Leu Ile Pro Gln Glu Tyr Gly Pro Arg Leu Ala Glu Gly Gly
625                 630                 635                 640

Glu Gly Val Glu Gly Tyr Leu Met Thr Gly Thr Thr Thr Ser Val Ala
                645                 650                 655

Ser Gly Arg Ile Ala Tyr Thr Leu Gly Leu Glu Gly Pro Ala Ile Ser
                660                 665                 670

Val Asp Thr Ala Cys Ser Ser Leu Val Ala Val His Leu Ala Cys
                675                 680                 685

Gln Ser Leu Arg Arg Gly Glu Ser Ser Leu Ala Met Ala Gly Gly Val
                690                 695                 700

Thr Val Met Pro Thr Pro Gly Met Leu Val Asp Phe Ser Arg Met Asn
705                 710                 715                 720

Ser Leu Ala Pro Asp Gly Arg Cys Lys Ala Phe Ser Ala Gly Ala Asn
                725                 730                 735

Gly Phe Gly Met Ala Glu Gly Ala Gly Met Leu Leu Leu Glu Arg Leu
                740                 745                 750

Ser Asp Ala Arg Arg Asn Gly His Pro Val Leu Ala Val Leu Arg Gly
                755                 760                 765

Thr Ala Val Asn Ser Asp Gly Ala Ser Asn Gly Leu Ser Ala Pro Asn
                770                 775                 780

Gly Arg Ala Gln Val Arg Val Ile Gln Gln Ala Leu Ala Glu Ser Gly
785                 790                 795                 800
```

-continued

```
Leu Gly Pro Ala Asp Ile Asp Ala Val Glu Ala His Gly Thr Gly Thr
            805                 810                 815
Arg Leu Gly Asp Pro Ile Glu Ala Arg Ala Leu Phe Glu Ala Tyr Gly
        820                 825                 830
Arg Asp Arg Glu Gln Pro Leu His Leu Gly Ser Val Lys Ser Asn Leu
    835                 840                 845
Gly His Thr Gln Ala Ala Ala Gly Val Ala Gly Val Ile Lys Met Val
850                 855                 860
Leu Ala Met Arg Ala Gly Thr Leu Pro Arg Thr Leu His Ala Ser Glu
865                 870                 875                 880
Arg Ser Lys Glu Ile Asp Trp Ser Ser Gly Ala Ile Ser Leu Leu Asp
            885                 890                 895
Glu Pro Glu Pro Trp Pro Ala Gly Ala Arg Pro Arg Arg Ala Gly Val
        900                 905                 910
Ser Ser Phe Gly Ile Ser Gly Thr Asn Ala His Ala Ile Ile Glu Glu
    915                 920                 925
Ala Pro Gln Val Val Glu Gly Glu Arg Val Glu Ala Gly Asp Val Val
930                 935                 940
Ala Pro Trp Val Leu Ser Ala Ser Ser Ala Glu Gly Leu Arg Ala Gln
945                 950                 955                 960
Ala Ala Arg Leu Ala Ala His Leu Arg Glu His Pro Gly Gln Asp Pro
            965                 970                 975
Arg Asp Ile Ala Tyr Ser Leu Ala Thr Gly Arg Ala Ala Leu Pro His
        980                 985                 990
Arg Ala Ala Phe Ala Pro Val Asp Glu Ser Ala Ala Leu Arg Val Leu
    995                 1000                1005
Asp Gly Leu Ala Thr Gly Asn Ala Asp Gly Ala Ala Val Gly Thr Ser
1010                1015                1020
Arg Ala Gln Gln Arg Ala Val Phe Val Phe Pro Gly Gln Gly Trp Gln
1025                1030                1035                1040
Trp Ala Gly Met Ala Val Asp Leu Leu Asp Thr Ser Pro Val Phe Ala
            1045                1050                1055
Ala Ala Leu Arg Glu Cys Ala Asp Ala Leu Glu Pro His Leu Asp Phe
        1060                1065                1070
Glu Val Ile Pro Phe Leu Arg Ala Glu Ala Ala Arg Glu Gln Asp
    1075                1080                1085
Ala Ala Leu Ser Thr Glu Arg Val Asp Val Val Gln Pro Val Met Phe
1090                1095                1100
Ala Val Met Val Ser Leu Ala Ser Met Trp Arg Ala His Gly Val Glu
1105                1110                1115                1120
Pro Ala Ala Val Ile Gly His Ser Gln Gly Glu Ile Ala Ala Ala Cys
            1125                1130                1135
Val Ala Gly Ala Leu Ser Leu Asp Asp Ala Ala Arg Val Ala Leu
        1140                1145                1150
Arg Ser Arg Val Ile Ala Thr Met Pro Gly Asn Lys Gly Met Ala Ser
    1155                1160                1165
Ile Ala Ala Pro Ala Gly Glu Val Arg Ala Arg Ile Gly Asp Arg Val
    1170                1175                1180
Glu Ile Ala Ala Val Asn Gly Pro Arg Ser Val Val Ala Gly Asp
1185                1190                1195                1200
Ser Asp Glu Leu Asp Arg Leu Val Ala Ser Cys Thr Thr Glu Cys Ile
            1205                1210                1215
Arg Ala Lys Arg Leu Ala Val Asp Tyr Ala Ser His Ser Ser His Val
        1220                1225                1230
```

```
Glu Thr Ile Arg Asp Ala Leu His Ala Glu Leu Gly Glu Asp Phe His
    1235                1240                1245

Pro Leu Pro Gly Phe Val Pro Phe Phe Ser Thr Val Thr Gly Arg Trp
    1250                1255                1260

Thr Gln Pro Asp Glu Leu Asp Ala Gly Tyr Trp Tyr Arg Asn Leu Arg
1265                1270                1275                1280

Arg Thr Val Arg Phe Ala Asp Ala Val Arg Ala Leu Ala Glu Gln Gly
            1285                1290                1295

Tyr Arg Thr Phe Leu Glu Val Ser Ala His Pro Ile Leu Thr Ala Ala
            1300                1305                1310

Ile Glu Glu Ile Gly Asp Gly Ser Gly Ala Asp Leu Ser Ala Ile His
            1315                1320                1325

Ser Leu Arg Arg Gly Asp Gly Ser Leu Ala Asp Phe Gly Glu Ala Leu
            1330                1335                1340

Ser Arg Ala Phe Ala Ala Gly Val Ala Val Asp Trp Glu Ser Val His
1345                1350                1355                1360

Leu Gly Thr Gly Ala Arg Arg Val Pro Leu Pro Thr Tyr Pro Phe Gln
            1365                1370                1375

Arg Glu Arg Val Trp Leu Glu Pro Lys Pro Val Ala Arg Arg Ser Thr
            1380                1385                1390

Glu Val Asp Glu Val Ser Ala Leu Arg Tyr Arg Ile Glu Trp Arg Pro
            1395                1400                1405

Thr Gly Ala Gly Glu Pro Ala Arg Leu Asp Gly Thr Trp Leu Val Ala
            1410                1415                1420

Lys Tyr Ala Gly Thr Ala Asp Glu Thr Ser Thr Ala Ala Arg Glu Ala
1425                1430                1435                1440

Leu Glu Ser Ala Gly Ala Arg Val Arg Glu Leu Val Val Asp Ala Arg
            1445                1450                1455

Cys Gly Arg Asp Glu Leu Ala Glu Arg Leu Arg Ser Val Gly Glu Val
            1460                1465                1470

Ala Gly Val Leu Ser Leu Leu Ala Val Asp Glu Ala Glu Pro Glu Glu
            1475                1480                1485

Ala Pro Leu Ala Leu Ala Ser Leu Ala Asp Thr Leu Ser Leu Val Gln
            1490                1495                1500

Ala Met Val Ser Ala Glu Leu Gly Cys Pro Leu Trp Thr Val Thr Glu
1505                1510                1515                1520

Ser Ala Val Ala Thr Gly Pro Phe Glu Arg Val Arg Asn Ala Ala His
            1525                1530                1535

Gly Ala Leu Trp Gly Val Gly Arg Val Ile Ala Leu Glu Asn Pro Ala
            1540                1545                1550

Val Trp Gly Gly Leu Val Asp Val Pro Ala Gly Ser Val Ala Glu Leu
            1555                1560                1565

Ala Arg His Leu Ala Ala Val Val Ser Gly Gly Ala Gly Glu Asp Gln
            1570                1575                1580

Leu Ala Leu Arg Ala Asp Gly Val Tyr Gly Arg Arg Trp Val Arg Ala
1585                1590                1595                1600

Ala Ala Pro Ala Thr Asp Asp Glu Trp Lys Pro Thr Gly Thr Val Leu
            1605                1610                1615

Val Thr Gly Gly Thr Gly Gly Val Gly Gly Gln Ile Ala Arg Trp Leu
            1620                1625                1630

Ala Arg Arg Gly Ala Pro His Leu Leu Leu Val Ser Arg Ser Gly Pro
            1635                1640                1645

Asp Ala Asp Gly Ala Gly Glu Leu Val Ala Glu Leu Glu Ala Leu Gly
```

-continued

```
              1650                1655                1660

Ala Arg Thr Thr Val Ala Ala Cys Asp Val Thr Asp Arg Glu Ser Val
1665                1670                1675                1680

Arg Glu Leu Leu Gly Gly Ile Gly Asp Asp Val Pro Leu Ser Ala Val
                1685                1690                1695

Phe His Ala Ala Ala Thr Leu Asp Asp Gly Thr Val Asp Thr Leu Thr
                1700                1705                1710

Gly Glu Arg Ile Glu Arg Ala Ser Arg Ala Lys Val Leu Gly Ala Arg
                1715                1720                1725

Asn Leu His Glu Leu Thr Arg Glu Leu Asp Leu Thr Ala Phe Val Leu
                1730                1735                1740

Phe Ser Ser Phe Ala Ser Ala Phe Gly Ala Pro Gly Leu Gly Gly Tyr
1745                1750                1755                1760

Ala Pro Gly Asn Ala Tyr Leu Asp Gly Leu Ala Gln Gln Arg Arg Ser
                1765                1770                1775

Asp Gly Leu Pro Ala Thr Ala Val Ala Trp Gly Thr Trp Ala Gly Ser
                1780                1785                1790

Gly Met Ala Glu Gly Ala Val Ala Asp Arg Phe Arg Arg His Gly Val
                1795                1800                1805

Ile Glu Met Pro Pro Glu Thr Ala Cys Arg Ala Leu Gln Asn Ala Leu
                1810                1815                1820

Asp Arg Ala Glu Val Cys Pro Ile Val Ile Asp Val Arg Trp Asp Arg
1825                1830                1835                1840

Phe Leu Leu Ala Tyr Thr Ala Gln Arg Pro Thr Arg Leu Phe Asp Glu
                1845                1850                1855

Ile Asp Asp Ala Arg Arg Ala Ala Pro Gln Ala Pro Ala Glu Pro Arg
                1860                1865                1870

Val Gly Ala Leu Ala Ser Leu Pro Ala Pro Glu Arg Glu Glu Ala Leu
                1875                1880                1885

Phe Glu Leu Val Arg Ser His Ala Ala Val Leu Gly His Ala Ser
                1890                1895                1900

Ala Glu Arg Val Pro Ala Asp Gln Ala Phe Ala Glu Leu Gly Val Asp
1905                1910                1915                1920

Ser Leu Ser Ala Leu Glu Leu Arg Asn Arg Leu Gly Ala Ala Thr Gly
                1925                1930                1935

Val Arg Leu Pro Thr Thr Thr Val Phe Asp His Pro Asp Val Arg Thr
                1940                1945                1950

Leu Ala Ala His Leu Ala Ala Glu Leu Gly Gly Ala Thr Gly Ala Glu
                1955                1960                1965

Gln Ala Ala Pro Ala Thr Thr Ala Pro Val Asp Glu Pro Ile Ala Ile
                1970                1975                1980

Val Gly Met Ala Cys Arg Leu Pro Gly Glu Val Asp Ser Pro Glu Arg
1985                1990                1995                2000

Leu Trp Glu Leu Ile Thr Ser Gly Arg Asp Ser Ala Ala Glu Val Pro
                2005                2010                2015

Asp Asp Arg Gly Trp Val Pro Asp Glu Leu Met Ala Ser Asp Ala Ala
                2020                2025                2030

Gly Thr Arg Ala His Gly Asn Phe Met Ala Gly Ala Gly Asp Phe Asp
                2035                2040                2045

Ala Ala Phe Phe Gly Ile Ser Pro Arg Glu Ala Leu Ala Met Asp Pro
                2050                2055                2060

Gln Gln Arg Gln Ala Leu Glu Thr Thr Trp Glu Ala Leu Glu Ser Ala
2065                2070                2075                2080
```

```
Gly Ile Pro Pro Glu Thr Leu Arg Gly Ser Asp Thr Gly Val Phe Val
            2085                2090                2095

Gly Met Ser His Gln Gly Tyr Ala Thr Gly Arg Pro Arg Pro Glu Asp
            2100                2105                2110

Gly Val Asp Gly Tyr Leu Leu Thr Gly Asn Thr Ala Ser Val Ala Ser
            2115                2120                2125

Gly Arg Ile Ala Tyr Val Leu Gly Leu Glu Gly Pro Ala Leu Thr Val
            2130                2135                2140

Asp Thr Ala Cys Ser Ser Leu Val Ala Leu His Thr Ala Cys Gly
2145                2150                2155                2160

Ser Leu Arg Asp Gly Asp Cys Gly Leu Ala Val Ala Gly Gly Val Ser
            2165                2170                2175

Val Met Ala Gly Pro Glu Val Phe Thr Glu Phe Ser Arg Gln Gly Ala
            2180                2185                2190

Leu Ser Pro Asp Gly Arg Cys Lys Pro Phe Ser Asp Glu Ala Asp Gly
            2195                2200                2205

Phe Gly Leu Gly Glu Gly Ser Ala Phe Val Val Leu Gln Arg Leu Ser
            2210                2215                2220

Asp Ala Arg Arg Glu Gly Arg Arg Val Leu Gly Val Val Ala Gly Ser
2225                2230                2235                2240

Ala Val Asn Gln Asp Gly Ala Ser Asn Gly Leu Ser Ala Pro Ser Gly
            2245                2250                2255

Val Ala Gln Gln Arg Val Ile Arg Arg Ala Trp Ala Arg Ala Gly Ile
            2260                2265                2270

Thr Gly Ala Asp Val Ala Val Val Glu Ala His Gly Thr Gly Thr Arg
            2275                2280                2285

Leu Gly Asp Pro Val Glu Ala Ser Ala Leu Leu Ala Thr Tyr Gly Lys
            2290                2295                2300

Ser Arg Gly Ser Ser Gly Pro Val Leu Leu Gly Ser Val Lys Ser Asn
2305                2310                2315                2320

Ile Gly His Ala Gln Ala Ala Gly Val Ala Gly Val Ile Lys Val
            2325                2330                2335

Leu Leu Gly Leu Glu Arg Gly Val Val Pro Pro Met Leu Cys Arg Gly
            2340                2345                2350

Glu Arg Ser Gly Leu Ile Asp Trp Ser Ser Gly Glu Ile Glu Leu Ala
            2355                2360                2365

Asp Gly Val Arg Glu Trp Ser Pro Ala Ala Asp Gly Val Arg Arg Ala
            2370                2375                2380

Gly Val Ser Ala Phe Gly Val Ser Gly Thr Asn Ala His Val Ile Ile
2385                2390                2395                2400

Ala Glu Pro Pro Glu Pro Glu Pro Val Pro Gln Pro Arg Arg Met Leu
            2405                2410                2415

Pro Ala Thr Gly Val Val Pro Val Leu Ser Ala Arg Thr Gly Ala
            2420                2425                2430

Ala Leu Arg Ala Gln Ala Gly Arg Leu Ala Asp His Leu Ala Ala His
            2435                2440                2445

Pro Gly Ile Ala Pro Ala Asp Val Ser Trp Thr Met Ala Arg Ala Arg
            2450                2455                2460

Gln His Phe Glu Glu Arg Ala Ala Val Leu Ala Ala Asp Thr Ala Glu
2465                2470                2475                2480

Ala Val His Arg Leu Arg Ala Val Ala Asp Gly Ala Val Val Pro Gly
            2485                2490                2495

Val Val Thr Gly Ser Ala Ser Asp Gly Gly Ser Val Phe Val Phe Pro
            2500                2505                2510
```

```
Gly Gln Gly Ala Gln Trp Glu Gly Met Ala Arg Glu Leu Leu Pro Val
        2515                2520                2525

Pro Val Phe Ala Glu Ser Ile Ala Glu Cys Asp Ala Val Leu Ser Glu
        2530                2535                2540

Val Ala Gly Phe Ser Val Ser Glu Val Leu Glu Pro Arg Pro Asp Ala
2545                2550                2555                2560

Pro Ser Leu Glu Arg Val Asp Val Val Gln Pro Val Leu Phe Ala Val
        2565                2570                2575

Met Val Ser Leu Ala Arg Leu Trp Arg Ala Cys Gly Ala Val Pro Ser
        2580                2585                2590

Ala Val Ile Gly His Ser Gln Gly Glu Ile Ala Ala Val Val Ala
        2595                2600                2605

Gly Ala Leu Ser Leu Glu Asp Gly Met Arg Val Val Ala Arg Arg Ser
        2610                2615                2620

Arg Ala Val Arg Ala Val Ala Gly Arg Gly Ser Met Leu Ser Val Arg
2625                2630                2635                2640

Gly Gly Arg Ser Asp Val Glu Lys Leu Leu Ala Asp Asp Ser Trp Thr
        2645                2650                2655

Gly Arg Leu Glu Val Ala Ala Val Asn Gly Pro Asp Ala Val Val Val
        2660                2665                2670

Ala Gly Asp Ala Gln Ala Ala Arg Glu Phe Leu Glu Tyr Cys Glu Gly
        2675                2680                2685

Val Gly Ile Arg Ala Arg Ala Ile Pro Val Asp Tyr Ala Ser His Thr
        2690                2695                2700

Ala His Val Glu Pro Val Arg Asp Glu Leu Val Gln Ala Leu Ala Gly
2705                2710                2715                2720

Ile Thr Pro Arg Arg Ala Glu Val Pro Phe Phe Ser Thr Leu Thr Gly
        2725                2730                2735

Asp Phe Leu Asp Gly Thr Glu Leu Asp Ala Gly Tyr Trp Tyr Arg Asn
        2740                2745                2750

Leu Arg His Pro Val Glu Phe His Ser Ala Val Gln Ala Leu Thr Asp
        2755                2760                2765

Gln Gly Tyr Ala Thr Phe Ile Glu Val Ser Pro His Pro Val Leu Ala
        2770                2775                2780

Ser Ser Val Gln Glu Thr Leu Asp Asp Ala Glu Ser Asp Ala Ala Val
2785                2790                2795                2800

Leu Gly Thr Leu Glu Arg Asp Ala Gly Asp Ala Asp Arg Phe Leu Thr
        2805                2810                2815

Ala Leu Ala Asp Ala His Thr Arg Gly Val Ala Val Asp Trp Glu Ala
        2820                2825                2830

Val Leu Gly Arg Ala Gly Leu Val Asp Leu Pro Gly Tyr Pro Phe Gln
        2835                2840                2845

Gly Lys Arg Phe Trp Leu Leu Pro Asp Arg Thr Thr Pro Arg Asp Glu
        2850                2855                2860

Leu Asp Gly Trp Phe Tyr Arg Val Asp Trp Thr Glu Val Pro Arg Ser
2865                2870                2875                2880

Glu Pro Ala Ala Leu Arg Gly Arg Trp Leu Val Val Pro Glu Gly
        2885                2890                2895

His Glu Glu Asp Gly Trp Thr Val Glu Val Arg Ser Ala Leu Ala Glu
        2900                2905                2910

Ala Gly Ala Glu Pro Glu Val Thr Arg Gly Val Gly Gly Leu Val Gly
        2915                2920                2925

Asp Cys Ala Gly Val Val Ser Leu Leu Ala Leu Glu Gly Asp Gly Ala
```

-continued

```
         2930                2935                2940
Val Gln Thr Leu Val Leu Val Arg Glu Leu Asp Ala Glu Gly Ile Asp
2945                2950                2955                2960

Ala Pro Leu Trp Thr Val Thr Phe Gly Ala Val Asp Ala Gly Ser Pro
                2965                2970                2975

Val Ala Arg Pro Asp Gln Ala Lys Leu Trp Gly Leu Gly Gln Val Ala
                2980                2985                2990

Ser Leu Glu Arg Gly Pro Arg Trp Thr Gly Leu Val Asp Leu Pro His
        2995                3000                3005

Met Pro Asp Pro Glu Leu Arg Gly Arg Leu Thr Ala Val Leu Ala Gly
        3010                3015                3020

Ser Glu Asp Gln Val Ala Val Arg Ala Asp Ala Val Arg Ala Arg Arg
3025                3030                3035                3040

Leu Ser Pro Ala His Val Thr Ala Thr Ser Glu Tyr Ala Val Pro Gly
                3045                3050                3055

Gly Thr Ile Leu Val Thr Gly Gly Thr Ala Gly Leu Gly Ala Glu Val
                3060                3065                3070

Ala Arg Trp Leu Ala Gly Arg Gly Ala Glu His Leu Ala Leu Val Ser
                3075                3080                3085

Arg Arg Gly Pro Asp Thr Glu Gly Val Gly Asp Leu Thr Ala Glu Leu
        3090                3095                3100

Thr Arg Leu Gly Ala Arg Val Ser Val His Ala Cys Asp Val Ser Ser
3105                3110                3115                3120

Arg Glu Pro Val Arg Glu Leu Val His Gly Leu Ile Glu Gln Gly Asp
                3125                3130                3135

Val Val Arg Gly Val Val His Ala Ala Gly Leu Pro Gln Gln Val Ala
                3140                3145                3150

Ile Asn Asp Met Asp Glu Ala Ala Phe Asp Glu Val Val Ala Ala Lys
                3155                3160                3165

Ala Gly Gly Ala Val His Leu Asp Glu Leu Cys Ser Asp Ala Glu Leu
        3170                3175                3180

Phe Leu Leu Phe Ser Ser Gly Ala Gly Val Trp Gly Ser Ala Arg Gln
3185                3190                3195                3200

Gly Ala Tyr Ala Ala Gly Asn Ala Phe Leu Asp Ala Phe Ala Arg His
                3205                3210                3215

Arg Arg Gly Arg Gly Leu Pro Ala Thr Ser Val Ala Trp Gly Leu Trp
                3220                3225                3230

Ala Ala Gly Gly Met Thr Gly Asp Glu Ala Val Ser Phe Leu Arg
        3235                3240                3245

Glu Arg Gly Val Arg Ala Met Pro Val Pro Arg Ala Leu Ala Ala Leu
        3250                3255                3260

Asp Arg Val Leu Ala Ser Gly Glu Thr Ala Val Val Val Thr Asp Val
3265                3270                3275                3280

Asp Trp Pro Ala Phe Ala Glu Ser Tyr Thr Ala Ala Arg Pro Arg Pro
                3285                3290                3295

Leu Leu Asp Arg Ile Val Thr Thr Ala Pro Ser Glu Arg Ala Gly Glu
                3300                3305                3310

Pro Glu Thr Glu Ser Leu Arg Asp Arg Leu Ala Gly Leu Pro Arg Ala
        3315                3320                3325

Glu Arg Thr Ala Glu Leu Val Arg Leu Val Arg Thr Ser Thr Ala Thr
        3330                3335                3340

Val Leu Gly His Asp Asp Pro Lys Ala Val Arg Ala Thr Thr Pro Phe
3345                3350                3355                3360
```

-continued

```
Lys Glu Leu Gly Phe Asp Ser Leu Ala Ala Val Arg Leu Arg Asn Leu
            3365                3370                3375

Leu Asn Ala Ala Thr Gly Leu Arg Leu Pro Ser Thr Leu Val Phe Asp
        3380                3385                3390

His Pro Asn Ala Ser Ala Val Ala Gly Phe Leu Asp Ala Glu Leu Gly
        3395                3400                3405

Thr Glu Val Arg Gly Glu Ala Pro Ser Ala Leu Ala Gly Leu Asp Ala
        3410                3415                3420

Leu Glu Gly Ala Leu Pro Glu Val Pro Ala Thr Glu Arg Glu Leu
3425                3430                3435                3440

Val Gln Arg Leu Glu Arg Met Leu Ala Ala Leu Arg Pro Val Ala Gln
            3445                3450                3455

Ala Ala Asp Ala Ser Gly Thr Gly Ala Asn Pro Ser Gly Asp Asp Leu
            3460                3465                3470

Gly Glu Ala Gly Val Asp Glu Leu Leu Glu Ala Leu Gly Arg Glu Leu
            3475                3480                3485

Asp Gly Asp
    3490
```

(2) INFORMATION FOR SEQ ID NO:3:

(i) SEQUENCE CHARACTERISTICS:
      (A) LENGTH: 20235 base pairs
      (B) TYPE: nucleic acid
      (C) STRANDEDNESS: double
      (D) TOPOLOGY: unknown (ii) MOLECULE TYPE: DNA (genomic)

(iii) HYPOTHETICAL: NO (iv) ANTI-SENSE: NO (vi) ORIGINAL SOURCE:
      (A) ORGANISM: Saccharopolyspora erythraea
      (B) STRAIN: NRRL 238

(ix) FEATURE:
      (A) NAME/KEY: CDS
      (B) LOCATION: 19..10722
      (D) OTHER INFORMATION: /codon_start= 19
          /function= "gene eryA"
          /product= "eryA ORF2 encoding modules 3 & 4 for
          6-deoxyerythronolide B"

(ix) FEATURE:
      (A) NAME/KEY: misc_feature
      (B) LOCATION: 19..4470
      (D) OTHER INFORMATION: /function= "approximate span of
         module 3"

(ix) FEATURE:
      (A) NAME/KEY: misc_feature
      (B) LOCATION: 97..1482
      (D) OTHER INFORMATION: /function= "approximate span of
         beta-ketoacyl ACP synthase of module 3"

(ix) FEATURE:
      (A) NAME/KEY: misc_feature
      (B) LOCATION: 1693..2670
      (D) OTHER INFORMATION: /function= "approximate span of
         acyltransferase domain module 3"

(ix) FEATURE:
      (A) NAME/KEY: misc_feature
      (B) LOCATION: 3406..3921
      (D) OTHER INFORMATION: /function= "approximate span of
         beta-ketoreductase domain of module 3"

(ix) FEATURE:
      (A) NAME/KEY: misc_feature

-continued

```
        (B) LOCATION: 4171..4428
        (D) OTHER INFORMATION: /function= "approximate span of
            acyl carrier domain of module 3"

(ix) FEATURE:
        (A) NAME/KEY: misc_feature
        (B) LOCATION: 4471..10722
        (D) OTHER INFORMATION: /function= "approximate span of
            module 4"

(ix) FEATURE:
        (A) NAME/KEY: misc_feature
        (B) LOCATION: 4471..5847
        (D) OTHER INFORMATION: /function= "approximate span of
            beta-ketoacylACPsynhase domain of module"

(ix) FEATURE:
        (A) NAME/KEY: misc_feature
        (B) LOCATION: 6054..7026
        (D) OTHER INFORMATION: /function= "approximate span of
            acyltransferase domain of module 4"

(ix) FEATURE:
        (A) NAME/KEY: misc_feature
        (B) LOCATION: 7165..9216
        (D) OTHER INFORMATION: /function= "approximate span of
            dehydratase and enoylreductase domains m"

(ix) FEATURE:
        (A) NAME/KEY: misc_feature
        (B) LOCATION: 9433..9984
        (D) OTHER INFORMATION: /function= "approximate span
            beta-ketoreductase of module 4"

(ix) FEATURE:
        (A) NAME/KEY: misc_feature
        (B) LOCATION: 10225..10483
        (D) OTHER INFORMATION: /function= "approximate span of
            acyl carrier domain of module 4"

(ix) FEATURE:
        (A) NAME/KEY: CDS
        (B) LOCATION: 10723..20235
        (D) OTHER INFORMATION: /codon_start= 10723
            /function= "gene =eryA"
            /product= "orf3 encoding modules 5 & 6
            6-deoxyerythronolide B formatio"

(ix) FEATURE:
        (A) NAME/KEY: misc_feature
        (B) LOCATION: 10723..15165
        (D) OTHER INFORMATION: /function= "approximate span of
            module 5"

(ix) FEATURE:
        (A) NAME/KEY: misc_feature
        (B) LOCATION: 10831..12174
        (D) OTHER INFORMATION: /function= "approximate span of
            beta-ketoacylACPsynthase domain of modul"

(ix) FEATURE:
        (A) NAME/KEY: misc_feature
        (B) LOCATION: 12379..13350
        (D) OTHER INFORMATION: /function= "approximatr span of
            acyltransferase domain of module 5"

(ix) FEATURE:
        (A) NAME/KEY: misc_feature
        (B) LOCATION: 14062..14610
        (D) OTHER INFORMATION: /function= "approximate span of
            beta-ketoreductase of module 5"

(ix) FEATURE:
        (A) NAME/KEY: misc_feature
        (B) LOCATION: 14857..15114
        (D) OTHER INFORMATION: /function= "approximate span of
            acyl carrier domain of module 5"

(ix) FEATURE:
        (A) NAME/KEY: misc_feature
```

(B) LOCATION: 15166..20235
(D) OTHER INFORMATION: /function= "approximate span of module 6"

(ix) FEATURE:
(A) NAME/KEY: misc_feature
(B) LOCATION: 15172..16569
(D) OTHER INFORMATION: /function= "approximate span of beta-ketoacylACPsynthase domain of modul"

(ix) FEATURE:
(A) NAME/KEY: misc_feature
(B) LOCATION: 16768..17721
(D) OTHER INFORMATION: /function= "approximate span of acyltransferase domain of module 6"

(ix) FEATURE:
(A) NAME/KEY: misc_feature
(B) LOCATION: 18379..18921
(D) OTHER INFORMATION: /function= "approximate span of beta-ketoreductase domain of module 6"

(ix) FEATURE:
(A) NAME/KEY: misc_feature
(B) LOCATION: 19149..19398
(D) OTHER INFORMATION: /function= "approximate span of acyl carrier domain of module 6"

(ix) FEATURE:
(A) NAME/KEY: misc_feature
(B) LOCATION: 19492..20235
(D) OTHER INFORMATION: /function= "approximate span of thioesterase domain of module 6"

(xi) SEQUENCE DESCRIPTION: SEQ ID NO:3:

```
CCGCCGATTG GAGAAAAG GTG ACT GAC AGC GAG AAG GTG GCG GAG TAC CTC         51
                    Val Thr Asp Ser Glu Lys Val Ala Glu Tyr Leu
                     1           5                  10

CGT CGG GCG ACG CTC GAC CTG CGT GCC GCC CGG CAG CGC ATC CGC GAG         99
Arg Arg Ala Thr Leu Asp Leu Arg Ala Ala Arg Gln Arg Ile Arg Glu
         15              20                  25

CTG GAA TCC GAC CCG ATC GCC ATC GTC AGC ATG GCC TGC CGC CTG CCG        147
Leu Glu Ser Asp Pro Ile Ala Ile Val Ser Met Ala Cys Arg Leu Pro
             30              35                  40

GGC GGG GTG AAC ACC CCG CAG CGG CTG TGG GAG CTG CTG CGC GAG GGC        195
Gly Gly Val Asn Thr Pro Gln Arg Leu Trp Glu Leu Leu Arg Glu Gly
         45              50                  55

GGT GAG ACG CTG TCG GGC TTC CCC ACC GAC CGG GGC TGG GAC CTG GCG        243
Gly Glu Thr Leu Ser Gly Phe Pro Thr Asp Arg Gly Trp Asp Leu Ala
 60              65                  70                  75

CGG CTG CAC CAC CCC GAC CCG GAC AAC CCC GGT ACC AGC TAC GTC GAC        291
Arg Leu His His Pro Asp Pro Asp Asn Pro Gly Thr Ser Tyr Val Asp
             80              85                  90

AAG GGC GGG TTC CTC GAC GAC GCG GCG GGC TTC GAC GCG GAG TTC TTC        339
Lys Gly Gly Phe Leu Asp Asp Ala Ala Gly Phe Asp Ala Glu Phe Phe
             95             100                 105

GGC GTC TCG CCG CGC GAG GCC GCG GCC ATG GAC CCG CAG CAG CGG CTG        387
Gly Val Ser Pro Arg Glu Ala Ala Ala Met Asp Pro Gln Gln Arg Leu
        110             115                 120

CTG CTG GAG ACG AGC TGG GAG CTG GTG GAG AAC GCC GGC ATC GAC CCG        435
Leu Leu Glu Thr Ser Trp Glu Leu Val Glu Asn Ala Gly Ile Asp Pro
125             130                 135

CAC TCG CTG CGC GGT ACC GCG ACC GGC GTC TTC CTC GGA GTG GCG AAG        483
His Ser Leu Arg Gly Thr Ala Thr Gly Val Phe Leu Gly Val Ala Lys
140             145                 150                 155

TTC GGC TAC GGC GAG GAC ACC GCC GCG GCG GAG GAC GTC GAG GGC TAC        531
Phe Gly Tyr Gly Glu Asp Thr Ala Ala Ala Glu Asp Val Glu Gly Tyr
                160                 165                 170
```

```
TCG GTC ACC GGT GTG GCG CCC GCG GTC GCC TCC GGC CGC ATC TCC TAC       579
Ser Val Thr Gly Val Ala Pro Ala Val Ala Ser Gly Arg Ile Ser Tyr
            175                 180                 185

ACC ATG GGC CTG GAG GGG CCG TCG ATC AGC GTC GAC ACC GCG TGC TCG       627
Thr Met Gly Leu Glu Gly Pro Ser Ile Ser Val Asp Thr Ala Cys Ser
            190                 195                 200

TCG TCG CTG GTG GCG CTG CAC CTG GCG GTC GAG TCG CTG CGC AAG GGC       675
Ser Ser Leu Val Ala Leu His Leu Ala Val Glu Ser Leu Arg Lys Gly
            205                 210                 215

GAG TCG TCG ATG GCG GTC GTC GGC GGT GCC GCG GTG ATG GCG ACC CCG       723
Glu Ser Ser Met Ala Val Val Gly Gly Ala Ala Val Met Ala Thr Pro
220                 225                 230                 235

GGG GTG TTC GTC GAC TTC AGC CGG CAG CGC GCG CTC GCC GCC GAC GGG       771
Gly Val Phe Val Asp Phe Ser Arg Gln Arg Ala Leu Ala Ala Asp Gly
                240                 245                 250

CGG TCG AAG GCG TTC GGT GCC GGC GCC GAC GGG TTC GGC TTC TCC GAA       819
Arg Ser Lys Ala Phe Gly Ala Gly Ala Asp Gly Phe Gly Phe Ser Glu
            255                 260                 265

GGC GTC ACC CTG GTC CTG CTC GAG CGG CTG TCG GAG GCG CGG CGA AAC       867
Gly Val Thr Leu Val Leu Leu Glu Arg Leu Ser Glu Ala Arg Arg Asn
            270                 275                 280

GGG CAC GAG GTG CTG GCG GTG GTT CGC GGC TCG GCG CTC AAC CAG GAC       915
Gly His Glu Val Leu Ala Val Val Arg Gly Ser Ala Leu Asn Gln Asp
            285                 290                 295

GGG GCC AGC AAC GGG CTT TCC GCG CCG AGC GGG CCC GCG CAG CGC AGG       963
Gly Ala Ser Asn Gly Leu Ser Ala Pro Ser Gly Pro Ala Gln Arg Arg
300                 305                 310                 315

GTC ATC CGG CAG GCC CTC GAG AGC TGC GGT CTG GAG CCC GGC GAC GTC      1011
Val Ile Arg Gln Ala Leu Glu Ser Cys Gly Leu Glu Pro Gly Asp Val
                320                 325                 330

GAC GCG GTG GAG GCG CAC GGC ACC GGT ACG GCG CTC GGC GAC CCG ATC      1059
Asp Ala Val Glu Ala His Gly Thr Gly Thr Ala Leu Gly Asp Pro Ile
            335                 340                 345

GAG GCG AAC GCG CTG CTG GAC ACC TAC GGC CGC GAC CGC GAC GCC GAC      1107
Glu Ala Asn Ala Leu Leu Asp Thr Tyr Gly Arg Asp Arg Asp Ala Asp
            350                 355                 360

CGG CCG CTC TGG CTG GGC TCG GTG AAG TCC AAC ATC GGC CAC ACC CAG      1155
Arg Pro Leu Trp Leu Gly Ser Val Lys Ser Asn Ile Gly His Thr Gln
365                 370                 375

GCG GCA GCG GGC GTC ACC GGC CTG CTG AAG GTG GTC CTG GCG CTG CGC      1203
Ala Ala Ala Gly Val Thr Gly Leu Leu Lys Val Val Leu Ala Leu Arg
380                 385                 390                 395

AAC GGG GAA CTG CCC GCG ACC CTG CAC GTC GAG GAG CCC ACG CCG CAC      1251
Asn Gly Glu Leu Pro Ala Thr Leu His Val Glu Glu Pro Thr Pro His
                400                 405                 410

GTC GAC TGG TCG TCC GGC GGC GTG GCG CTG CTG GCG GGC AAC CAG CCG      1299
Val Asp Trp Ser Ser Gly Gly Val Ala Leu Leu Ala Gly Asn Gln Pro
            415                 420                 425

TGG CGG CGC GGC GAG CGG ACT CGG CGC GCC CGT GTT TCC GCG TTC GGG      1347
Trp Arg Arg Gly Glu Arg Thr Arg Arg Ala Arg Val Ser Ala Phe Gly
            430                 435                 440

ATC AGC GGG ACG AAT GCG CAC GTG ATC GTC GAG GAA GCT CCT GAG CGC      1395
Ile Ser Gly Thr Asn Ala His Val Ile Val Glu Glu Ala Pro Glu Arg
445                 450                 455

GAG CAC CGG GAG ACC ACC GCG CAC GAC GGC CGA CCG GTT CCG CTG GTG      1443
Glu His Arg Glu Thr Thr Ala His Asp Gly Arg Pro Val Pro Leu Val
460                 465                 470                 475

GTG TCC GCG CGC ACG ACG GCG GCG TTG CGG GCG CAG GCC GCC CAG ATC      1491
Val Ser Ala Arg Thr Thr Ala Ala Leu Arg Ala Gln Ala Ala Gln Ile
                480                 485                 490
```

```
GCC GAG CTG CTC GAA CGC CCG GAC GCC GAC CTC GCC GGG GTC GGG CTG      1539
Ala Glu Leu Leu Glu Arg Pro Asp Ala Asp Leu Ala Gly Val Gly Leu
            495                 500                 505

GGC CTG GCC ACG ACC CGC GCC CGC CAC GAG CAC CGC GCC GCC GTG GTG      1587
Gly Leu Ala Thr Thr Arg Ala Arg His Glu His Arg Ala Ala Val Val
            510                 515                 520

GCA TCG ACC CGC GAG GAA GCG GTG CGC GGA CTG CGG GAG ATC GCC GCC      1635
Ala Ser Thr Arg Glu Glu Ala Val Arg Gly Leu Arg Glu Ile Ala Ala
525                 530                 535

GGT GCC GCG ACG GCC GAC GCC GTG GTC GAG GGC GTC ACC GAG GTG GAC      1683
Gly Ala Ala Thr Ala Asp Ala Val Val Glu Gly Val Thr Glu Val Asp
540                 545                 550                 555

GGG CGC AAC GTC GTC TTC CTG TTC CCG GGG CAG GGT TCG CAA TGG GCC      1731
Gly Arg Asn Val Val Phe Leu Phe Pro Gly Gln Gly Ser Gln Trp Ala
                560                 565                 570

GGC ATG GGT GCC GAG CTG CTG TCG TCG TCG CCG GTG TTC GCC GGG AAG      1779
Gly Met Gly Ala Glu Leu Leu Ser Ser Ser Pro Val Phe Ala Gly Lys
            575                 580                 585

ATC CGG GCC TGC GAC GAG TCG ATG GCC CCG ATG CAG GAC TGG AAG GTC      1827
Ile Arg Ala Cys Asp Glu Ser Met Ala Pro Met Gln Asp Trp Lys Val
            590                 595                 600

TCC GAC GTG CTG CGT CAG GCG CCG GGG GCG CCG GGC CTG GAC CGG GTC      1875
Ser Asp Val Leu Arg Gln Ala Pro Gly Ala Pro Gly Leu Asp Arg Val
605                 610                 615

GAC GTG GTG CAG CCG GTG TTG TTC GCG GTG ATG GTG TCG CTG GCG GAG      1923
Asp Val Val Gln Pro Val Leu Phe Ala Val Met Val Ser Leu Ala Glu
620                 625                 630                 635

CTG TGG CGC TCG TAC GGC GTG GAG CCC GCG GCG GTC GTG GGG CAC TCG      1971
Leu Trp Arg Ser Tyr Gly Val Glu Pro Ala Ala Val Val Gly His Ser
                640                 645                 650

CAG GGC GAG ATC GCC GCC GCG CAC GTC GCC GGG GCG CTC ACG TTG GAG      2019
Gln Gly Glu Ile Ala Ala Ala His Val Ala Gly Ala Leu Thr Leu Glu
            655                 660                 665

GAC GCG GCG AAG CTC GTC GTG GGC CGC AGC CGC CTG ATG CGG TCG CTC      2067
Asp Ala Ala Lys Leu Val Val Gly Arg Ser Arg Leu Met Arg Ser Leu
            670                 675                 680

TCC GGG GAG GGC GGC ATG GCC GCC GTC GCG CTG GGC GAG GCC GCG GTG      2115
Ser Gly Glu Gly Gly Met Ala Ala Val Ala Leu Gly Glu Ala Ala Val
            685                 690                 695

CGC GAG CGC CTG CGG CCG TGG CAG GAC CGG CTC TCG GTG GCC GCG GTC      2163
Arg Glu Arg Leu Arg Pro Trp Gln Asp Arg Leu Ser Val Ala Ala Val
700                 705                 710                 715

AAC GGT CCC CGG TCG GTC GTG GTC TCC GGC GAG CCC GGC GCG CTG CGG      2211
Asn Gly Pro Arg Ser Val Val Val Ser Gly Glu Pro Gly Ala Leu Arg
                720                 725                 730

GCG TTT TCC GAG GAC TGC GCG GCC GAG GGC ATC CGC GTC CGC GAC ATC      2259
Ala Phe Ser Glu Asp Cys Ala Ala Glu Gly Ile Arg Val Arg Asp Ile
            735                 740                 745

GAC GTG GAC TAC GCC TCG CAC TCG CCG CAG ATC GAG CGG GTC CGC GAG      2307
Asp Val Asp Tyr Ala Ser His Ser Pro Gln Ile Glu Arg Val Arg Glu
            750                 755                 760

GAA CTC CTC GAA ACG ACC GGC GAC ATC GCG CCG CGC CCG GCG CGG GTG      2355
Glu Leu Leu Glu Thr Thr Gly Asp Ile Ala Pro Arg Pro Ala Arg Val
765                 770                 775

ACG TTC CAC TCC ACT GTG GAG TCG CGG TCT ATG GAC GGC ACC GAG CTG      2403
Thr Phe His Ser Thr Val Glu Ser Arg Ser Met Asp Gly Thr Glu Leu
780                 785                 790                 795

GAT GCC CGG TAC TGG TAC CGC AAC CTG CGC GAG ACG GTG CGC TTC GCC      2451
Asp Ala Arg Tyr Trp Tyr Arg Asn Leu Arg Glu Thr Val Arg Phe Ala
                800                 805                 810
```

-continued

| | |
|---|---|
| GAC GCC GTG ACG CGG CTG GCG GAG TCG GGA TAC GAC GCG TTC ATC GAG<br>Asp Ala Val Thr Arg Leu Ala Glu Ser Gly Tyr Asp Ala Phe Ile Glu<br>815                         820                     825 | 2499 |
| GTC AGC CCG CAT CCG GTC GTG GTC CAG GCC GTC GAG GAG GCG GTC GAA<br>Val Ser Pro His Pro Val Val Val Gln Ala Val Glu Glu Ala Val Glu<br>830                        835                    840 | 2547 |
| GAG GCT GAC GGT GCC GAA GAC GCG GTC GTA GTC GGC TCG CTG CAC CGC<br>Glu Ala Asp Gly Ala Glu Asp Ala Val Val Val Gly Ser Leu His Arg<br>845                        850                    855 | 2595 |
| GAC GGC GGT GAC CTC TCG GCC TTC CTG CGG TCG ATG GCC ACC GCG CAC<br>Asp Gly Gly Asp Leu Ser Ala Phe Leu Arg Ser Met Ala Thr Ala His<br>860                  865                  870                  875 | 2643 |
| GTG TCC GGT GTG GAC ATC AGG TGG GAC GTC GCT CTG CCC GGC GCC GCG<br>Val Ser Gly Val Asp Ile Arg Trp Asp Val Ala Leu Pro Gly Ala Ala<br>                    880                    885                  890 | 2691 |
| CCC TTC GCG CTG CCG ACG TAT CCG TTC CAG CGC AAG CGC TAC TGG CTC<br>Pro Phe Ala Leu Pro Thr Tyr Pro Phe Gln Arg Lys Arg Tyr Trp Leu<br>              895                    900                  905 | 2739 |
| CAG CCC GCC GCA CCC GCC GCC GCC TCC GAC GAG CTG GCC TAC CGC GTT<br>Gln Pro Ala Ala Pro Ala Ala Ala Ser Asp Glu Leu Ala Tyr Arg Val<br>           910                    915                  920 | 2787 |
| TCC TGG ACT CCG ATC GAA AAG CCG GAG TCG GGA AAC CTG GAC GGC GAC<br>Ser Trp Thr Pro Ile Glu Lys Pro Glu Ser Gly Asn Leu Asp Gly Asp<br>925                        930                    935 | 2835 |
| TGG TTG GTT GTC ACA CCC CTC ATC AGT CCG GAG TGG ACG GAA ATG CTG<br>Trp Leu Val Val Thr Pro Leu Ile Ser Pro Glu Trp Thr Glu Met Leu<br>940                        945                    950                  955 | 2883 |
| TGC GAG GCC ATC AAC GCC AAC GGT GGC AGG GCG TTG CGC TGC GAG GTG<br>Cys Glu Ala Ile Asn Ala Asn Gly Gly Arg Ala Leu Arg Cys Glu Val<br>                    960                    965                  970 | 2931 |
| GAC ACG TCC GCT TCG CGC ACT GAG ATG GCC CAG GCC GTC GCA CAG GCC<br>Asp Thr Ser Ala Ser Arg Thr Glu Met Ala Gln Ala Val Ala Gln Ala<br>            975                    980                  985 | 2979 |
| GGA ACG GGA TTC CGG GGC GTG CTC TCG TTG CTG TCG TCG GAC GAA TCC<br>Gly Thr Gly Phe Arg Gly Val Leu Ser Leu Leu Ser Ser Asp Glu Ser<br>           990                    995                 1000 | 3027 |
| GCC TGC CGT CCG GGG GTT CCT GCC GGT GCG GTC GGC CTG CTC ACC CTG<br>Ala Cys Arg Pro Gly Val Pro Ala Gly Ala Val Gly Leu Leu Thr Leu<br>1005                    1010                 1015 | 3075 |
| GTC CAG GCG CTG GGC GAT GCC GGG GTC GAC GCA CCG GTG TGG TGC CTG<br>Val Gln Ala Leu Gly Asp Ala Gly Val Asp Ala Pro Val Trp Cys Leu<br>1020                    1025                 1030                1035 | 3123 |
| ACC CAG GGT GCG GTC CGC ACT CCC GCC GAC GAC GAC CTC GCC CGG CCT<br>Thr Gln Gly Ala Val Arg Thr Pro Ala Asp Asp Asp Leu Ala Arg Pro<br>           1040                  1045                 1050 | 3171 |
| GCG CAG ACC ACC GCG CAC GGC TTC GCG CAG GTC GCC GGG CTG GAG CTG<br>Ala Gln Thr Thr Ala His Gly Phe Ala Gln Val Ala Gly Leu Glu Leu<br>              1055                 1060                 1065 | 3219 |
| CCG GGC CGC TGG GGC GGT GTG GTC GAC CTG CCC GAA TCG GTC GAC GAC<br>Pro Gly Arg Trp Gly Gly Val Val Asp Leu Pro Glu Ser Val Asp Asp<br>           1070                  1075                 1080 | 3267 |
| GCG GCG CTG CGT CTG CTC GTG GCA GTC CTG CGC GGC GGC GGC CGT GCC<br>Ala Ala Leu Arg Leu Leu Val Ala Val Leu Arg Gly Gly Gly Arg Ala<br>1085                    1090                 1095 | 3315 |
| GAG GAC CAC CTC GCG GTC CGG GAC GGC CGC CTC CAC GGC CGT CGC GTC<br>Glu Asp His Leu Ala Val Arg Asp Gly Arg Leu His Gly Arg Arg Val<br>1100                    1105                 1110                1115 | 3363 |
| GTC CGC GCA AGC CTG CCG CAG TCC GGC TCG CGG AGC TGG ACC CCG CAC<br>Val Arg Ala Ser Leu Pro Gln Ser Gly Ser Arg Ser Trp Thr Pro His<br>              1120                 1125                 1130 | 3411 |

-continued

| | |
|---|---|
| GGG ACC GTG CTG GTC ACC GGC GCG GCG AGC CCC GTC GGC GAC CAA CTG<br>Gly Thr Val Leu Val Thr Gly Ala Ala Ser Pro Val Gly Asp Gln Leu<br>　　　　　　1135　　　　　　　　　　1140　　　　　　　　　　1145 | 3459 |
| GTG CGG TGG CTC GCC GAC CGG GGA GCC GAG CGG CTG GTG CTG GCC GGA<br>Val Arg Trp Leu Ala Asp Arg Gly Ala Glu Arg Leu Val Leu Ala Gly<br>1150　　　　　　　　　　1155　　　　　　　　　　1160 | 3507 |
| GCC TGT CCG GGC GAC GAC CTG CTG GCC GCG GTC GAG GAA GCG GGC GCA<br>Ala Cys Pro Gly Asp Asp Leu Leu Ala Ala Val Glu Glu Ala Gly Ala<br>1165　　　　　　　　　　1170　　　　　　　　　　1175 | 3555 |
| TCG GCC GTC GTG TGC GCC CAG GAC GCG GCG GCG CTG CGC GAG GCG CTC<br>Ser Ala Val Val Cys Ala Gln Asp Ala Ala Ala Leu Arg Glu Ala Leu<br>1180　　　　　　　　　　1185　　　　　　　　　　1190　　　　　　　　　　1195 | 3603 |
| GGC GAC GAG CCG GTG ACC GCG CTC GTG CAC GCC GGA ACC CTG ACG AAC<br>Gly Asp Glu Pro Val Thr Ala Leu Val His Ala Gly Thr Leu Thr Asn<br>　　　　　　　　　　1200　　　　　　　　　　1205　　　　　　　　　　1210 | 3651 |
| TTC GGC AGC ATC AGC GAA GTC GCA CCG GAG GAG TTC GCC GAG ACG ATC<br>Phe Gly Ser Ile Ser Glu Val Ala Pro Glu Glu Phe Ala Glu Thr Ile<br>　　　　　　1215　　　　　　　　　　1220　　　　　　　　　　1225 | 3699 |
| GCG GCC AAG ACC GCG TTG CTC GCC GTG CTG GAC GAA GTC CTC GGC GAC<br>Ala Ala Lys Thr Ala Leu Leu Ala Val Leu Asp Glu Val Leu Gly Asp<br>　　　　　　1230　　　　　　　　　　1235　　　　　　　　　　1240 | 3747 |
| CGG GCC GTC GAG CGG GAG GTC TAC TGC TCG TCG GTC GCC GGG ATC TGG<br>Arg Ala Val Glu Arg Glu Val Tyr Cys Ser Ser Val Ala Gly Ile Trp<br>　　　　　　1245　　　　　　　　　　1250　　　　　　　　　　1255 | 3795 |
| GGC GGC GCC GGG ATG GCC GCC TAC GCG GCA GGC AGC GCC TAC CTC GAC<br>Gly Gly Ala Gly Met Ala Ala Tyr Ala Ala Gly Ser Ala Tyr Leu Asp<br>1260　　　　　　　　　　1265　　　　　　　　　　1270　　　　　　　　　　1275 | 3843 |
| GCG CTG GCC GAG CAC CAC CGC GCG CGG GGC CGC TCG TGC ACC TCG GTC<br>Ala Leu Ala Glu His His Arg Ala Arg Gly Arg Ser Cys Thr Ser Val<br>　　　　　　　　　　1280　　　　　　　　　　1285　　　　　　　　　　1290 | 3891 |
| GCC TGG ACG CCG TGG GCG CTG CCG GGC GGG GCG GTG GAC GAC GGC TAC<br>Ala Trp Thr Pro Trp Ala Leu Pro Gly Gly Ala Val Asp Asp Gly Tyr<br>　　　　　　1295　　　　　　　　　　1300　　　　　　　　　　1305 | 3939 |
| CTG CGG GAA CGC GGA CTG CGC AGC CTC TCC GCC GAC AGG GCG ATG CGC<br>Leu Arg Glu Arg Gly Leu Arg Ser Leu Ser Ala Asp Arg Ala Met Arg<br>　　　　　　1310　　　　　　　　　　1315　　　　　　　　　　1320 | 3987 |
| ACC TGG GAG CGG GTG CTG GCC GCC GGG CCG GTG TCG GTC GCG GTG GCC<br>Thr Trp Glu Arg Val Leu Ala Ala Gly Pro Val Ser Val Ala Val Ala<br>　　　　　　1325　　　　　　　　　　1330　　　　　　　　　　1335 | 4035 |
| GAC GTG GAC TGG CCG GTG CTC AGC GAA GGC TTC GCC GCC ACC CGG CCG<br>Asp Val Asp Trp Pro Val Leu Ser Glu Gly Phe Ala Ala Thr Arg Pro<br>1340　　　　　　　　　　1345　　　　　　　　　　1350　　　　　　　　　　1355 | 4083 |
| ACC GCG CTG TTC GCC GAA CTC GCC GGC CGC GGC GGA CAG GCG GAG GCC<br>Thr Ala Leu Phe Ala Glu Leu Ala Gly Arg Gly Gly Gln Ala Glu Ala<br>　　　　　　　　　　1360　　　　　　　　　　1365　　　　　　　　　　1370 | 4131 |
| GAG CCG GAC AGC GGA CCG ACC GGC GAG CCG GCA CAA CGG CTC GCG GGG<br>Glu Pro Asp Ser Gly Pro Thr Gly Glu Pro Ala Gln Arg Leu Ala Gly<br>　　　　　　1375　　　　　　　　　　1380　　　　　　　　　　1385 | 4179 |
| CTT TCC CCG GAC GAG CAG CAG GAA AAC CTG CTC GAA CTC GTC GCG AAC<br>Leu Ser Pro Asp Glu Gln Gln Glu Asn Leu Leu Glu Leu Val Ala Asn<br>　　　　　　1390　　　　　　　　　　1395　　　　　　　　　　1400 | 4227 |
| GCG GTT GCC GAG GTG CTT GGC CAC GAG TCC GCC GCC GAG ATC AAC GTG<br>Ala Val Ala Glu Val Leu Gly His Glu Ser Ala Ala Glu Ile Asn Val<br>　　　　　　1405　　　　　　　　　　1410　　　　　　　　　　1415 | 4275 |
| CGC CGC GCG TTC AGC GAG CTC GGA CTC GAC TCG CTC AAC GCG ATG GCC<br>Arg Arg Ala Phe Ser Glu Leu Gly Leu Asp Ser Leu Asn Ala Met Ala<br>1420　　　　　　　　　　1425　　　　　　　　　　1430　　　　　　　　　　1435 | 4323 |
| CTG CGC AAG CGC CTG TCG GCG AGC ACC GGC CTG CGG CTG CCC GCG TCG<br>Leu Arg Lys Arg Leu Ser Ala Ser Thr Gly Leu Arg Leu Pro Ala Ser<br>　　　　　　　　　　1440　　　　　　　　　　1445　　　　　　　　　　1450 | 4371 |

```
CTG GTG TTC GAC CAC CCC ACC GTC ACC GCG CTC GCG CAG CAC CTG CGC         4419
Leu Val Phe Asp His Pro Thr Val Thr Ala Leu Ala Gln His Leu Arg
             1455                1460                1465

GCC CGG CTC GTC GGT GAC GCC GAC CAG GCC GCG GTG CGC GTC GTC GGC         4467
Ala Arg Leu Val Gly Asp Ala Asp Gln Ala Ala Val Arg Val Val Gly
     1470                1475                1480

GCG GCC GAC GAG TCC GAG CCC ATC GCC ATC GTC GGC ATC GGC TGC CGT         4515
Ala Ala Asp Glu Ser Glu Pro Ile Ala Ile Val Gly Ile Gly Cys Arg
 1485                1490                1495

TTC CCC GGC GGC ATC GGC TCG CCC GAG CAG TTG TGG CGG GTG CTG GCC         4563
Phe Pro Gly Gly Ile Gly Ser Pro Glu Gln Leu Trp Arg Val Leu Ala
1500                1505                1510                1515

GAG GGC GCG AAC CTC ACC ACC GGC TTC CCG GCC GAC CGG GGC TGG GAC         4611
Glu Gly Ala Asn Leu Thr Thr Gly Phe Pro Ala Asp Arg Gly Trp Asp
             1520                1525                1530

ATC GGG CGG CTC TAC CAC CCG GAC CCG GAC AAC CCC GGC ACC AGC TAC         4659
Ile Gly Arg Leu Tyr His Pro Asp Pro Asp Asn Pro Gly Thr Ser Tyr
     1535                1540                1545

GTG GAC AAG GGC GGG TTC CTC ACC GAC GCG GCG GAT TTC GAC CCG GGC         4707
Val Asp Lys Gly Gly Phe Leu Thr Asp Ala Ala Asp Phe Asp Pro Gly
 1550                1555                1560

TTC TTC GGC ATC ACG CCC CGC GAA GCG CTG GCG ATG GAC CCG CAG CAG         4755
Phe Phe Gly Ile Thr Pro Arg Glu Ala Leu Ala Met Asp Pro Gln Gln
1565                1570                1575

CGC CTC ATG CTG GAG ACG GCG TGG GAG GCA GTG GAA CGC GCG GGC ATC         4803
Arg Leu Met Leu Glu Thr Ala Trp Glu Ala Val Glu Arg Ala Gly Ile
1580                1585                1590                1595

GAC CCC GAC GCC CTG CGA GGC ACC GAC ACC GGC GTC TTC GTC GGC ATG         4851
Asp Pro Asp Ala Leu Arg Gly Thr Asp Thr Gly Val Phe Val Gly Met
             1600                1605                1610

AAC GGC CAG TCC TAC ATG CAG CTG CTG GCC GGT GAG GCC GAA CGC GTC         4899
Asn Gly Gln Ser Tyr Met Gln Leu Leu Ala Gly Glu Ala Glu Arg Val
     1615                1620                1625

GAC GGC TAC CAG GGC CTC GGA AAC TCC GCG AGC GTG CTC TCC GGG CGC         4947
Asp Gly Tyr Gln Gly Leu Gly Asn Ser Ala Ser Val Leu Ser Gly Arg
 1630                1635                1640

ATC GCC TAC ACC TTC GGC TGG GAG GGC CCG GCG CTG ACG GTG GAC ACC         4995
Ile Ala Tyr Thr Phe Gly Trp Glu Gly Pro Ala Leu Thr Val Asp Thr
1645                1650                1655

GCG TGC TCG TCC TCG CTG GTC GGC ATC CAC CTC GCG ATG CAG GCG CTG         5043
Ala Cys Ser Ser Ser Leu Val Gly Ile His Leu Ala Met Gln Ala Leu
1660                1665                1670                1675

CGG CGC GGT GAG TGC TCC CTG GCG CTG GCC GGC GGC GTC ACG GTC ATG         5091
Arg Arg Gly Glu Cys Ser Leu Ala Leu Ala Gly Gly Val Thr Val Met
             1680                1685                1690

TCC GAC CCG TAC ACC TTC GTC GAC TTC AGC ACG CAG CGC GGG CTC GCC         5139
Ser Asp Pro Tyr Thr Phe Val Asp Phe Ser Thr Gln Arg Gly Leu Ala
     1695                1700                1705

TCC GAC GGT CGC TGC AAG GCG TTC TCC GCG CGG GCC GAC GGC TTC GCG         5187
Ser Asp Gly Arg Cys Lys Ala Phe Ser Ala Arg Ala Asp Gly Phe Ala
 1710                1715                1720

CTG TCG GAA GGC GTC GCC GCG CTG GTG CTG GAG CCG CTT TCC CGG GCG         5235
Leu Ser Glu Gly Val Ala Ala Leu Val Leu Glu Pro Leu Ser Arg Ala
1725                1730                1735

CGC GCC AAC GGG CAC CAG GTG CTG GCC GTG CTG CGC GGC AGC GCG GTC         5283
Arg Ala Asn Gly His Gln Val Leu Ala Val Leu Arg Gly Ser Ala Val
1740                1745                1750                1755

AAC CAG GAC GGT GCC AGC AAC GGT CTC GCC GCT CCC AAC GGC CCG TCG         5331
Asn Gln Asp Gly Ala Ser Asn Gly Leu Ala Ala Pro Asn Gly Pro Ser
             1760                1765                1770
```

```
CAG GAG CGG GTG ATC CGG CAG GCG CTC GCC GCT TCG GGC GTG CCG GCC       5379
Gln Glu Arg Val Ile Arg Gln Ala Leu Ala Ala Ser Gly Val Pro Ala
            1775                1780                1785

GCG GAC GTC GAC GTC GTG GAG GCG CAC GGG ACG GGC ACC GAG CTC GGC       5427
Ala Asp Val Asp Val Val Glu Ala His Gly Thr Gly Thr Glu Leu Gly
        1790                1795                1800

GAC CCG ATC GAG GCC GGC GCG CTC ATC GCG ACC TAC GGC CAG GAC CGC       5475
Asp Pro Ile Glu Ala Gly Ala Leu Ile Ala Thr Tyr Gly Gln Asp Arg
    1805                1810                1815

GAC CGG CCG CTG CGG CTC GGC TCG GTG AAG ACC AAC ATC GGC CAC ACC       5523
Asp Arg Pro Leu Arg Leu Gly Ser Val Lys Thr Asn Ile Gly His Thr
1820                1825                1830                1835

CAG GCC GCG GCG GGC GCC GCG GGC GTG ATC AAG GTC GTG CTG GCG ATG       5571
Gln Ala Ala Ala Gly Ala Ala Gly Val Ile Lys Val Val Leu Ala Met
                1840                1845                1850

CGG CAC GGG ATG CTG CCC CGG TCG TTG CAC GCC GAC GAG CTG TCC CCG       5619
Arg His Gly Met Leu Pro Arg Ser Leu His Ala Asp Glu Leu Ser Pro
            1855                1860                1865

CAC ATC GAC TGG GAG TCG GGC GCC GTG GAG GTG CTG CGC GAG GAG GTG       5667
His Ile Asp Trp Glu Ser Gly Ala Val Glu Val Leu Arg Glu Glu Val
        1870                1875                1880

CCG TGG CCG GCG GGT GAG CGC CCC CGG CGG GCG GGG GTG TCG TCC TTC       5715
Pro Trp Pro Ala Gly Glu Arg Pro Arg Arg Ala Gly Val Ser Ser Phe
    1885                1890                1895

GGC GTC AGC GGA ACC AAC GCG CAC GTG ATC GTC GAA GAG GCA CCA GCA       5763
Gly Val Ser Gly Thr Asn Ala His Val Ile Val Glu Glu Ala Pro Ala
1900                1905                1910                1915

GAG CAG GAG GCC GCC CGC ACC GAG CGC GGT CCG CTG CCG TTC GTG CTG       5811
Glu Gln Glu Ala Ala Arg Thr Glu Arg Gly Pro Leu Pro Phe Val Leu
                1920                1925                1930

TCC GGC CGC AGC GAA GCC GTG GTC GCG GCC CAG GCC CGC GCG CTC GCC       5859
Ser Gly Arg Ser Glu Ala Val Val Ala Ala Gln Ala Arg Ala Leu Ala
            1935                1940                1945

GAG CAC CTG CGC GAC ACC CCG GAG CTC GGC CTG ACC GAC GCG GCG TGG       5907
Glu His Leu Arg Asp Thr Pro Glu Leu Gly Leu Thr Asp Ala Ala Trp
        1950                1955                1960

ACG CTC GCG ACC GGC AGG GCG CGG TTC GAC GTG CGA GCC GCC GTG CTC       5955
Thr Leu Ala Thr Gly Arg Ala Arg Phe Asp Val Arg Ala Ala Val Leu
    1965                1970                1975

GGC GAC GAC CGC GCG GGC GTG TGC GCG GAG CTG GAC GCG CTG GCC GAG       6003
Gly Asp Asp Arg Ala Gly Val Cys Ala Glu Leu Asp Ala Leu Ala Glu
1980                1985                1990                1995

GGC CGC CCG TCG GCC GAC GCC GTC GCG CCG GTG ACC TCC GCG CCG CGC       6051
Gly Arg Pro Ser Ala Asp Ala Val Ala Pro Val Thr Ser Ala Pro Arg
                2000                2005                2010

AAG CCG GTC CTG GTC TTC CCC GGC CAG GGC GCG CAG TGG GTC GGC ATG       6099
Lys Pro Val Leu Val Phe Pro Gly Gln Gly Ala Gln Trp Val Gly Met
            2015                2020                2025

GCA CGC GAT CTG CTG GAA TCC TCC GAG GTG TTC GCC GAG TCG ATG AGC       6147
Ala Arg Asp Leu Leu Glu Ser Ser Glu Val Phe Ala Glu Ser Met Ser
        2030                2035                2040

CGG TGC GCC GAG GCG CTC TCG CCG CAC ACC GAC TGG AAG TTG CTC GAC       6195
Arg Cys Ala Glu Ala Leu Ser Pro His Thr Asp Trp Lys Leu Leu Asp
    2045                2050                2055

GTC GTC CGC GGC GAC GGC GGT CCC GAC CCG CAC GAG CGC GTC GAC GTG       6243
Val Val Arg Gly Asp Gly Gly Pro Asp Pro His Glu Arg Val Asp Val
2060                2065                2070                2075

CTC CAG CCG GTG CTC TTC TCG ATC ATG GTC TCG CTG GCC GAG CTG TGG       6291
Leu Gln Pro Val Leu Phe Ser Ile Met Val Ser Leu Ala Glu Leu Trp
                2080                2085                2090
```

```
CGC GCG CAC GGC GTG ACC CCG GCC GCC GTC GTC GGC CAC TCG CAG GGC      6339
Arg Ala His Gly Val Thr Pro Ala Ala Val Val Gly His Ser Gln Gly
             2095                2100                2105

GAG ATC GCC GCG GCG CAC GTG GCG GGC GCG CTG TCG CTG GAA GCC GCC      6387
Glu Ile Ala Ala Ala His Val Ala Gly Ala Leu Ser Leu Glu Ala Ala
         2110                2115                2120

GCG AAG GTG GTG GCC CTG CGC AGC CAG GTG TTG CGC GAG CTC GAC GAC      6435
Ala Lys Val Val Ala Leu Arg Ser Gln Val Leu Arg Glu Leu Asp Asp
     2125                2130                2135

CAG GGC GGC ATG GTG TCG GTC GGC GCG TCC CGC GAC GAG CTG GAG ACC      6483
Gln Gly Gly Met Val Ser Val Gly Ala Ser Arg Asp Glu Leu Glu Thr
2140                2145                2150                2155

GTG CTC GCG CGC TGG GAC GGC CGT GTC GCG GTG GCC GCC GTG AAC GGG      6531
Val Leu Ala Arg Trp Asp Gly Arg Val Ala Val Ala Ala Val Asn Gly
             2160                2165                2170

CCT GGC ACC AGC GTC GTT GCC GGG CCG ACC GCG GAG CTG GAC GAG TTC      6579
Pro Gly Thr Ser Val Val Ala Gly Pro Thr Ala Glu Leu Asp Glu Phe
         2175                2180                2185

TTC GCC GAG GCC GAG GCG CGG GAG ATG AAG CCG CGC CGG ATC GCC GTG      6627
Phe Ala Glu Ala Glu Ala Arg Glu Met Lys Pro Arg Arg Ile Ala Val
     2190                2195                2200

CGC TAC GCC TCC CAC TCC CCG GAG GTG GCG CGC ATC GAG GAC CGG CTC      6675
Arg Tyr Ala Ser His Ser Pro Glu Val Ala Arg Ile Glu Asp Arg Leu
 2205                2210                2215

GCG GCC GAG CTG GGC ACC ATC ACC GCC GTG CGG GGC TCG GTG CCG CTG      6723
Ala Ala Glu Leu Gly Thr Ile Thr Ala Val Arg Gly Ser Val Pro Leu
2220                2225                2230                2235

CAC TCC ACG GTG ACC GGC GAG GTC ATC GAC ACC TCC GCG ATG GAC GCC      6771
His Ser Thr Val Thr Gly Glu Val Ile Asp Thr Ser Ala Met Asp Ala
             2240                2245                2250

TCC TAC TGG TAC CGC AAC CTG CGC CGA CCA GTG CTC TTC GAG CAG GCG      6819
Ser Tyr Trp Tyr Arg Asn Leu Arg Arg Pro Val Leu Phe Glu Gln Ala
         2255                2260                2265

GTG CGC GGT CTG GTC GAG CAG GGC TTC GAC ACC TTC GTC GAG GTG AGC      6867
Val Arg Gly Leu Val Glu Gln Gly Phe Asp Thr Phe Val Glu Val Ser
     2270                2275                2280

CCG CAC CCG GTG CTG CTG ATG GCG GTC GAG GAG ACC GCC GAG CAC GCG      6915
Pro His Pro Val Leu Leu Met Ala Val Glu Glu Thr Ala Glu His Ala
 2285                2290                2295

GGC GCG GAA GTC ACC TGC GTG CCG ACG CTG CGC CGC GAG CAG AGC GGA      6963
Gly Ala Glu Val Thr Cys Val Pro Thr Leu Arg Arg Glu Gln Ser Gly
2300                2305                2310                2315

CCG CAC GAG TTC CTG CGC AAC CTG CTG CGG GCT CAC GTG CAC GGC GTC      7011
Pro His Glu Phe Leu Arg Asn Leu Leu Arg Ala His Val His Gly Val
             2320                2325                2330

GGC GCC GAC CTG CGT CCG GCG GTG GCC GGG GGA CGG CCG GCC GAG CTG      7059
Gly Ala Asp Leu Arg Pro Ala Val Ala Gly Gly Arg Pro Ala Glu Leu
         2335                2340                2345

CCC ACC TAC CCG TTC GAA CAC CAG CGC TTC TGG CCG CGG CCG CAC CGG      7107
Pro Thr Tyr Pro Phe Glu His Gln Arg Phe Trp Pro Arg Pro His Arg
     2350                2355                2360

CCC GCC GAC GTC TCG GCG CTG GGC GTG CGC GGC GCG GAG CAC CCG CTG      7155
Pro Ala Asp Val Ser Ala Leu Gly Val Arg Gly Ala Glu His Pro Leu
 2365                2370                2375

CTG CTC GCC GCG GTC GAC GTG CCG GGC CAC GGC GGT GCG GTG TTC ACC      7203
Leu Leu Ala Ala Val Asp Val Pro Gly His Gly Gly Ala Val Phe Thr
2380                2385                2390                2395

GGA AGG CTT TCC ACC GAC GAG CAG CCG TGG CTG GCC GAA CAC GTC GTG      7251
Gly Arg Leu Ser Thr Asp Glu Gln Pro Trp Leu Ala Glu His Val Val
             2400                2405                2410
```

-continued

```
GGC GGC CGG ACG CTG GTG CCG GGC AGC GTC CTG GTC GAT CTC GCG CTC        7299
Gly Gly Arg Thr Leu Val Pro Gly Ser Val Leu Val Asp Leu Ala Leu
            2415                2420                2425

GCC GCG GGT GAG GAC GTC GGG CTG CCG GTC CTG GAG GAA CTG GTG TTG        7347
Ala Ala Gly Glu Asp Val Gly Leu Pro Val Leu Glu Glu Leu Val Leu
    2430                2435                2440

CAA CGG CCG CTG GTG CTG GCC GGG GCG GGG GCG CTG CTG CGC ATG TCG        7395
Gln Arg Pro Leu Val Leu Ala Gly Ala Gly Ala Leu Leu Arg Met Ser
2445                2450                2455

GTC GGC GCG CCC GAC GAG TCG GGG CGG CGG ACG ATC GAC GTC CAC GCC        7443
Val Gly Ala Pro Asp Glu Ser Gly Arg Arg Thr Ile Asp Val His Ala
        2460                2465                2470                2475

GCC GAA GAC GTG GCC GAC CTC GCC GAC GCG CAG TGG TCG CAG CAC GCC        7491
Ala Glu Asp Val Ala Asp Leu Ala Asp Ala Gln Trp Ser Gln His Ala
                2480                2485                2490

ACC GGG ACG CTC GCG CAG GGC GTC GCC GCG GGT CCG AGG GAT ACC GAG        7539
Thr Gly Thr Leu Ala Gln Gly Val Ala Ala Gly Pro Arg Asp Thr Glu
    2495                2500                2505

CAG TGG CCG CCG GAG GAC GCC GTC CGC ATC CCG CTC GAC GAC CAC TAC        7587
Gln Trp Pro Pro Glu Asp Ala Val Arg Ile Pro Leu Asp Asp His Tyr
2510                2515                2520

GAC GGC CTC GCC GAG CAG GGC TAC GAG TAC GGA CCG TCG TTC CAG GCC        7635
Asp Gly Leu Ala Glu Gln Gly Tyr Glu Tyr Gly Pro Ser Phe Gln Ala
        2525                2530                2535

CTG CGA GCC GCG TGG CGC AAG GAC GAC TCG GTC TAC GCC GAG GTG TCC        7683
Leu Arg Ala Ala Trp Arg Lys Asp Asp Ser Val Tyr Ala Glu Val Ser
2540                2545                2550                2555

ATC GCG GCG GAC GAG GAA GGT TAC GCG TTC CAC CCG GTG CTG CTC GAC        7731
Ile Ala Ala Asp Glu Glu Gly Tyr Ala Phe His Pro Val Leu Leu Asp
                2560                2565                2570

GCC GTG GCG CAG ACG CTC AGC CTG GGC GCC CTC GGC GAG CCG GGC GGG        7779
Ala Val Ala Gln Thr Leu Ser Leu Gly Ala Leu Gly Glu Pro Gly Gly
    2575                2580                2585

GGA AAG CTG CCG TTC GCG TGG AAC ACC GTG ACC CTG CAC GCC TCC GGG        7827
Gly Lys Leu Pro Phe Ala Trp Asn Thr Val Thr Leu His Ala Ser Gly
        2590                2595                2600

GCG ACC TCG GTG CGG GTC GTG GCG ACG CCC GCC GGG GCG GAC GCG ATG        7875
Ala Thr Ser Val Arg Val Val Ala Thr Pro Ala Gly Ala Asp Ala Met
2605                2610                2615

GCC CTG CGG GTC ACC GAC CCG GCA GGC CAC CTG GTC GCC ACG GTC GAC        7923
Ala Leu Arg Val Thr Asp Pro Ala Gly His Leu Val Ala Thr Val Asp
2620                2625                2630                2635

TCG CTG GTC GTC CGC AGC ACC GGG GAG AAG TGG GAG CAG CCC GAA CCG        7971
Ser Leu Val Val Arg Ser Thr Gly Glu Lys Trp Glu Gln Pro Glu Pro
                2640                2645                2650

CGC GGT GGC GAG GGC GAG CTG CAC GCT CTG GAC TGG GGA CGG CTA GCC        8019
Arg Gly Gly Glu Gly Glu Leu His Ala Leu Asp Trp Gly Arg Leu Ala
    2655                2660                2665

GAG CCC GGC TCG ACC GGT CGT GTG GTC GCG GCC GAT GCC TCG GAC CTC        8067
Glu Pro Gly Ser Thr Gly Arg Val Val Ala Ala Asp Ala Ser Asp Leu
        2670                2675                2680

GAC GCC GTC CTG CGG TCC GGT GAA CCC GAA CCC GAC GCG GTC CTG GTC        8115
Asp Ala Val Leu Arg Ser Gly Glu Pro Glu Pro Asp Ala Val Leu Val
2685                2690                2695

CGC TAC GAA CCC GAA GGC GAC GAC CCC CGC GCC GCG GCC CGC CAC GGC        8163
Arg Tyr Glu Pro Glu Gly Asp Asp Pro Arg Ala Ala Ala Arg His Gly
2700                2705                2710                2715

GTC CTC TGG GCC GCC GCG CTC GTG CGC CGC TGG CTC GAA CAG GAG GAG        8211
Val Leu Trp Ala Ala Ala Leu Val Arg Arg Trp Leu Glu Gln Glu Glu
                2720                2725                2730
```

| | | |
|---|---|---|
| CTG CCG GGC GCG ACG CTG GTC ATC GCC ACG TCC GGC GCG GTC ACC GTG<br>Leu Pro Gly Ala Thr Leu Val Ile Ala Thr Ser Gly Ala Val Thr Val<br>　　　　　2735　　　　　　　　　2740　　　　　　　　　2745 | 8259 | |
| TCC GAC GAC GAC AGC GTT CCC GAA CCC GGC GCC GCC GCG ATG TGG GGC<br>Ser Asp Asp Asp Ser Val Pro Glu Pro Gly Ala Ala Ala Met Trp Gly<br>　　　　　2750　　　　　　　　　2755　　　　　　　　　2760 | 8307 | |
| GTG ATC CGC TGT GCG CAG GCC GAG TCG CCG GAC CGG TTC GTG CTC CTC<br>Val Ile Arg Cys Ala Gln Ala Glu Ser Pro Asp Arg Phe Val Leu Leu<br>　　　　　2765　　　　　　　　　2770　　　　　　　　　2775 | 8355 | |
| GAC ACC GAC GCG GAA CCT GGG ATG CTG CCT GCG GTT CCG GAC AAC CCG<br>Asp Thr Asp Ala Glu Pro Gly Met Leu Pro Ala Val Pro Asp Asn Pro<br>2780　　　　　　　　　2785　　　　　　　　　2790　　　　　　　　　2795 | 8403 | |
| CAG CTC GCG TTG CGC GGC GAC GAC GTC TTC GTG CCG CGC CTC TCG CCG<br>Gln Leu Ala Leu Arg Gly Asp Asp Val Phe Val Pro Arg Leu Ser Pro<br>　　　　　　　　　2800　　　　　　　　　2805　　　　　　　　　2810 | 8451 | |
| CTC GCA CCT TCC GCG CTG ACG CTT CCG GCA GGC ACC CAA CGT CTC GTG<br>Leu Ala Pro Ser Ala Leu Thr Leu Pro Ala Gly Thr Gln Arg Leu Val<br>　　　　　2815　　　　　　　　　2820　　　　　　　　　2825 | 8499 | |
| CCG GGT GAC GGG GCG ATC GAC TCC GTG GCC TTC GAG CCC GCA CCC GAC<br>Pro Gly Asp Gly Ala Ile Asp Ser Val Ala Phe Glu Pro Ala Pro Asp<br>　　　　　2830　　　　　　　　　2835　　　　　　　　　2840 | 8547 | |
| GTC GAG CAG CCG CTC CGG GCG GGC GAG GTC CGG GTG GAC GTG CGC GCC<br>Val Glu Gln Pro Leu Arg Ala Gly Glu Val Arg Val Asp Val Arg Ala<br>　　　　　2845　　　　　　　　　2850　　　　　　　　　2855 | 8595 | |
| ACC GGA GTC AAC TTC CGC GAC GTC CTC CTC GCA CTC GGC ATG TAT CCG<br>Thr Gly Val Asn Phe Arg Asp Val Leu Leu Ala Leu Gly Met Tyr Pro<br>2860　　　　　　　　　2865　　　　　　　　　2870　　　　　　　　　2875 | 8643 | |
| CAG AAG GCG GAC ATG GGC ACC GAG GCC GCC GGT GTC GTC ACG GCG GTC<br>Gln Lys Ala Asp Met Gly Thr Glu Ala Ala Gly Val Val Thr Ala Val<br>　　　　　　　　　2880　　　　　　　　　2885　　　　　　　　　2890 | 8691 | |
| GGA CCG GAC GTG GAC GCC TTC GCG CCG GGA GAC CGG GTG CTC GGC CTG<br>Gly Pro Asp Val Asp Ala Phe Ala Pro Gly Asp Arg Val Leu Gly Leu<br>　　　　　2895　　　　　　　　　2900　　　　　　　　　2905 | 8739 | |
| TTC CAG GGA GCC TTC GCG CCG ATC GCG GTC ACC GAT CAC CGG CTC CTC<br>Phe Gln Gly Ala Phe Ala Pro Ile Ala Val Thr Asp His Arg Leu Leu<br>　　　　　2910　　　　　　　　　2915　　　　　　　　　2920 | 8787 | |
| GCA CGA GTG CCG GAC GGC TGG AGC GAC GCC GAC GCC GCG GCC GTG CCC<br>Ala Arg Val Pro Asp Gly Trp Ser Asp Ala Asp Ala Ala Ala Val Pro<br>　　　　　2925　　　　　　　　　2930　　　　　　　　　2935 | 8835 | |
| ATC GCC TAC ACC ACG GCG CAT TAC GCG CTG CAC GAT CTC GCG GGG CTG<br>Ile Ala Tyr Thr Thr Ala His Tyr Ala Leu His Asp Leu Ala Gly Leu<br>2940　　　　　　　　　2945　　　　　　　　　2950　　　　　　　　　2955 | 8883 | |
| CGC GCG GGT CAG TCG GTG CTC ATC CAC GCA GCG GCA GGC GGT GTC GGC<br>Arg Ala Gly Gln Ser Val Leu Ile His Ala Ala Ala Gly Gly Val Gly<br>　　　　　　　　　2960　　　　　　　　　2965　　　　　　　　　2970 | 8931 | |
| ATG GCG GCC GTC GCG CTG GCC CGC CGA GCG GGG GCG GAG GTG TTG GCC<br>Met Ala Ala Val Ala Leu Ala Arg Arg Ala Gly Ala Glu Val Leu Ala<br>　　　　　2975　　　　　　　　　2980　　　　　　　　　2985 | 8979 | |
| ACC GCC GGC CCG GCC AAG CAC GGG ACG CTG CGG GCG CTC GGT CTC GAC<br>Thr Ala Gly Pro Ala Lys His Gly Thr Leu Arg Ala Leu Gly Leu Asp<br>　　　　　2990　　　　　　　　　2995　　　　　　　　　3000 | 9027 | |
| GAC GAG CAC ATC GCT TCC TCC CGG GAG ACC GGT TTC GCC CGG AAG TTC<br>Asp Glu His Ile Ala Ser Ser Arg Glu Thr Gly Phe Ala Arg Lys Phe<br>　　　　　3005　　　　　　　　　3010　　　　　　　　　3015 | 9075 | |
| CGG GAG CGC ACC GGA GGC CGC GGC GTG GAC GTG GTG CTC AAC TCG CTC<br>Arg Glu Arg Thr Gly Gly Arg Gly Val Asp Val Val Leu Asn Ser Leu<br>3020　　　　　　　　　3025　　　　　　　　　3030　　　　　　　　　3035 | 9123 | |
| ACC GGG GAA CTG CTC GAC GAG TCC GCG GAT CTG CTC GCC GAG GAC GGC<br>Thr Gly Glu Leu Leu Asp Glu Ser Ala Asp Leu Leu Ala Glu Asp Gly<br>　　　　　3040　　　　　　　　　3045　　　　　　　　　3050 | 9171 | |

| | |
|---|---|
| GTC TTC GTC GAG ATG GGC AAG ACC GAC CTG CGG GAC GCC GGG GAC TTC<br>Val Phe Val Glu Met Gly Lys Thr Asp Leu Arg Asp Ala Gly Asp Phe<br>                  3055                          3060                        3065 | 9219 |
| CGG GGC CGA TAC GCC CCG TTC GAC CTC GGC GAG GCG GGT GAC GAC CGG<br>Arg Gly Arg Tyr Ala Pro Phe Asp Leu Gly Glu Ala Gly Asp Asp Arg<br>                  3070                          3075                        3080 | 9267 |
| CTC GGG GAG ATC CTG CGC GAG GTC GTC GGC CTG CTG GGC GCC GGG GAG<br>Leu Gly Glu Ile Leu Arg Glu Val Val Gly Leu Leu Gly Ala Gly Glu<br>3085                          3090                        3095 | 9315 |
| CTC GAC CGG CTC CCG GTA TCG GCG TGG GAG CTG GGA TCC GCG CCC GCG<br>Leu Asp Arg Leu Pro Val Ser Ala Trp Glu Leu Gly Ser Ala Pro Ala<br>3100                    3105                        3110                    3115 | 9363 |
| GCG TTG CAG CAC ATG AGC CGG GGC AGG CAC GTC GGC AAG CTC GTG CTG<br>Ala Leu Gln His Met Ser Arg Gly Arg His Val Gly Lys Leu Val Leu<br>                        3120                        3125                        3130 | 9411 |
| ACC CAG CCC GCG CCG GTG GAC CCG GAC GGC ACG GTG CTG ATC ACG GGT<br>Thr Gln Pro Ala Pro Val Asp Pro Asp Gly Thr Val Leu Ile Thr Gly<br>                  3135                          3140                        3145 | 9459 |
| GGC ACC GGC ACG CTC GGA CGG CTG CTC GCG CGC CAC CTC GTC ACC GAG<br>Gly Thr Gly Thr Leu Gly Arg Leu Leu Ala Arg His Leu Val Thr Glu<br>              3150                        3155                        3160 | 9507 |
| CAC GGC GTG CGG CAC CTG CTG CTG GTC AGC AGG CGC GGC GCG GAC GCG<br>His Gly Val Arg His Leu Leu Leu Val Ser Arg Arg Gly Ala Asp Ala<br>                  3165                        3170                        3175 | 9555 |
| CCG GGT TCC GAC GAG CTG CGC GCG GAG ATC GAG GAC TTG GGC GCG TCC<br>Pro Gly Ser Asp Glu Leu Arg Ala Glu Ile Glu Asp Leu Gly Ala Ser<br>3180                        3185                        3190                    3195 | 9603 |
| GCG GAG ATC GCG GCT TGC GAC ACC GCC GAC CGC GAC GCG CTT TCG GCG<br>Ala Glu Ile Ala Ala Cys Asp Thr Ala Asp Arg Asp Ala Leu Ser Ala<br>                      3200                        3205                        3210 | 9651 |
| CTG CTG GAC GGG CTG CCC CGG CCG CTG ACC GGT GTC GTG CAC GCG GCG<br>Leu Leu Asp Gly Leu Pro Arg Pro Leu Thr Gly Val Val His Ala Ala<br>              3215                        3220                        3225 | 9699 |
| GGT GTG CTG GCC GAC GGG CTG GTC ACC TCC ATC GAC GAG CCG GCG GTG<br>Gly Val Leu Ala Asp Gly Leu Val Thr Ser Ile Asp Glu Pro Ala Val<br>                  3230                        3235                        3240 | 9747 |
| GAG CAG GTG CTG CGC GCC AAG GTC GAC GCG GCG TGG AAC CTG CAC GAG<br>Glu Gln Val Leu Arg Ala Lys Val Asp Ala Ala Trp Asn Leu His Glu<br>            3245                        3250                        3255 | 9795 |
| CTG ACC GCG AAC ACC GGT CTG AGC TTC TTC GTG CTG TTC TCG TCC GCG<br>Leu Thr Ala Asn Thr Gly Leu Ser Phe Phe Val Leu Phe Ser Ser Ala<br>3260                        3265                        3270                    3275 | 9843 |
| GCG TCG GTG CTA GCC GGC CCG GGG CAG GGC GTG TAC GCG GCC GCG AAC<br>Ala Ser Val Leu Ala Gly Pro Gly Gln Gly Val Tyr Ala Ala Ala Asn<br>                    3280                        3285                    3290 | 9891 |
| GAG TCG CTC AAC GCG CTG GCT GCC CTC CGG AGG ACG CGC GGC CTT CCC<br>Glu Ser Leu Asn Ala Leu Ala Ala Leu Arg Arg Thr Arg Gly Leu Pro<br>                3295                        3300                        3305 | 9939 |
| GCG AAG GCG CTC GGA TGG GGA CTG TGG GCG CAG GCC AGC GAG ATG ACC<br>Ala Lys Ala Leu Gly Trp Gly Leu Trp Ala Gln Ala Ser Glu Met Thr<br>            3310                        3315                        3320 | 9987 |
| AGC GGA CTC GGC GAC CGC ATC GCC CGG ACC GGG GTC GCC GCG CTG CCG<br>Ser Gly Leu Gly Asp Arg Ile Ala Arg Thr Gly Val Ala Ala Leu Pro<br>        3325                        3330                        3335 | 10035 |
| ACC GAG CGG GCG CTC GCA CTG TTC GAC AGC GCC CTG CGC CGC GGC GGT<br>Thr Glu Arg Ala Leu Ala Leu Phe Asp Ser Ala Leu Arg Arg Gly Gly<br>3340                        3345                        3350                    3355 | 10083 |
| GAG GTC GTG TTC CCG CTG TCC ATC AAC CGT TCC GCG CTG CGC AGG GCC<br>Glu Val Val Phe Pro Leu Ser Ile Asn Arg Ser Ala Leu Arg Arg Ala<br>                    3360                        3365                    3370 | 10131 |

| | |
|---|---|
| GAG TTC GTG CCG GAG GTC CTG CGC GGC ATG GTC AGG GCG AAG CTG CGC<br>Glu Phe Val Pro Glu Val Leu Arg Gly Met Val Arg Ala Lys Leu Arg<br>              3375                            3380                          3385 | 10179 |
| GCC GCC GGG CAG GCC GAG GCG GCA GGG CCG AAC GTG GTC GAC CGG CTC<br>Ala Ala Gly Gln Ala Glu Ala Ala Gly Pro Asn Val Val Asp Arg Leu<br>3390                        3395                      3400 | 10227 |
| GCC GGT CGG TCC GAG TCC GAC CAG GTC GCC GGG CTG GCC GAA CTG GTG<br>Ala Gly Arg Ser Glu Ser Asp Gln Val Ala Gly Leu Ala Glu Leu Val<br>3405                        3410                      3415 | 10275 |
| CGT TCA CAC GCG GCG GCG GTC TCC GGG TAC GGC TCG GCC GAC CAG CTC<br>Arg Ser His Ala Ala Ala Val Ser Gly Tyr Gly Ser Ala Asp Gln Leu<br>3420                        3425                      3430                      3435 | 10323 |
| CCC GAG CGC AAG GCG TTC AAG GAC CTC GGT TTC GAC TCG CTG GCC GCG<br>Pro Glu Arg Lys Ala Phe Lys Asp Leu Gly Phe Asp Ser Leu Ala Ala<br>              3440                            3445                          3450 | 10371 |
| GTG GAG CTG CGC AAC CGC CTC GGT ACC GCG ACC GGC GTG CGG CTG CCC<br>Val Glu Leu Arg Asn Arg Leu Gly Thr Ala Thr Gly Val Arg Leu Pro<br>              3455                            3460                          3465 | 10419 |
| AGC ACG TTG GTG TTC GAC CAC CCG ACT CCG CTG GCG GTG GCC GAA CAC<br>Ser Thr Leu Val Phe Asp His Pro Thr Pro Leu Ala Val Ala Glu His<br>              3470                            3475                          3480 | 10467 |
| CTG CGG GAC AGG CTG TTC GCG GCC TCA CCG GCG GTG GAC ATC GGC GAC<br>Leu Arg Asp Arg Leu Phe Ala Ala Ser Pro Ala Val Asp Ile Gly Asp<br>              3485                            3490                          3495 | 10515 |
| CGG CTG GAC GAG CTG GAG AAG GCG CTC GAA GCC CTG TCC GCC GAG GAC<br>Arg Leu Asp Glu Leu Glu Lys Ala Leu Glu Ala Leu Ser Ala Glu Asp<br>3500                        3505                      3510                      3515 | 10563 |
| GGG CAC GAC GAC GTG GGC CAG CGC CTG GAG TCG CTG CTG CGC CGG TGG<br>Gly His Asp Asp Val Gly Gln Arg Leu Glu Ser Leu Leu Arg Arg Trp<br>              3520                            3525                          3530 | 10611 |
| AAC AGC AGG CGG GCG GAC GCC CCG AGC ACG TCC GCG ATC AGC GAG GAC<br>Asn Ser Arg Arg Ala Asp Ala Pro Ser Thr Ser Ala Ile Ser Glu Asp<br>              3535                            3540                          3545 | 10659 |
| GCC AGT GAC GAC GAG CTG TTC TCG ATG CTC GAC CAG CGG TTC GGC GGG<br>Ala Ser Asp Asp Glu Leu Phe Ser Met Leu Asp Gln Arg Phe Gly Gly<br>              3550                            3555                          3560 | 10707 |
| GGA GAG GAC CTG TAGATG AGC GGT GAC AAC GGC ATG ACC GAG GAA AAG<br>Gly Glu Asp Leu     Met Ser Gly Asp Asn Gly Met Thr Glu Glu Lys<br>              3565                  1                              5                          10 | 10755 |
| CTC CGG CGC TAC CTC AAG CGC ACC GTC ACC GAG CTC GAC TCG GTG ACC<br>Leu Arg Arg Tyr Leu Lys Arg Thr Val Thr Glu Leu Asp Ser Val Thr<br>              15                            20                            25 | 10803 |
| GCG CGC CTG CGT GAA GTC GAG CAC CGG GCC GGT GAG CCG ATC GCG ATC<br>Ala Arg Leu Arg Glu Val Glu His Arg Ala Gly Glu Pro Ile Ala Ile<br>              30                            35                            40 | 10851 |
| GTC GGC ATG GCG TGC CGG TTC CCC GGC GAC GTG GAC TCG CCG GAG TCG<br>Val Gly Met Ala Cys Arg Phe Pro Gly Asp Val Asp Ser Pro Glu Ser<br>              45                            50                            55 | 10899 |
| TTC TGG GAG TTC GTG TCC GGC GGC GGG GAC GCC ATC GCG GAG GCC CCC<br>Phe Trp Glu Phe Val Ser Gly Gly Gly Asp Ala Ile Ala Glu Ala Pro<br>60                          65                            70                          75 | 10947 |
| GCC GAC CGC GGC TGG GAG CCG GAC CCC GAC GCG CGG CTG GGC GGG ATG<br>Ala Asp Arg Gly Trp Glu Pro Asp Pro Asp Ala Arg Leu Gly Gly Met<br>                    80                            85                            90 | 10995 |
| CTC GCG GCC GCG GGC GAC TTC GAC GCG GGC TTC TTC GGG ATC TCG CCG<br>Leu Ala Ala Ala Gly Asp Phe Asp Ala Gly Phe Phe Gly Ile Ser Pro<br>              95                            100                          105 | 11043 |
| CGC GAG GCG CTG GCG ATG GAC CCG CAG CAG CGG ATC ATG CTG GAG ATC<br>Arg Glu Ala Leu Ala Met Asp Pro Gln Gln Arg Ile Met Leu Glu Ile<br>              110                            115                        120 | 11091 |

```
TCG TGG GAG GCG CTG GAG CGC GCC GGC CAC GAT CCG GTG TCC CTG CGC    11139
Ser Trp Glu Ala Leu Glu Arg Ala Gly His Asp Pro Val Ser Leu Arg
    125                 130                 135

GGC AGC GCG ACC GGG GTG TTC ACC GGT GTC GGC ACC GTG GAC TAC GGC    11187
Gly Ser Ala Thr Gly Val Phe Thr Gly Val Gly Thr Val Asp Tyr Gly
140                 145                 150                 155

CCG CGA CCC GAC GAG GCC CCG GAC GAG GTC CTG GGC TAC GTC GGC ACC    11235
Pro Arg Pro Asp Glu Ala Pro Asp Glu Val Leu Gly Tyr Val Gly Thr
                160                 165                 170

GGC ACC GCC TCC AGC GTC GCC TCC GGC CGG GTC GCC TAC TGC CTG GGC    11283
Gly Thr Ala Ser Ser Val Ala Ser Gly Arg Val Ala Tyr Cys Leu Gly
                175                 180                 185

CTG GAA GGC CCG GCG ATG ACC GTC GAC ACC GCC TGT TCC TCC GGG CTC    11331
Leu Glu Gly Pro Ala Met Thr Val Asp Thr Ala Cys Ser Ser Gly Leu
            190                 195                 200

ACC GCC CTG CAC CTG GCG ATG GAG TCG CTG CGC CGG GAC GAG TGC GGC    11379
Thr Ala Leu His Leu Ala Met Glu Ser Leu Arg Arg Asp Glu Cys Gly
205                 210                 215

CTG GCG CTG GCC GGC GGC GTG ACG GTG ATG AGC AGT CCC GGG GCG TTC    11427
Leu Ala Leu Ala Gly Gly Val Thr Val Met Ser Ser Pro Gly Ala Phe
220                 225                 230                 235

ACC GAG TTC CGC AGC CAG GGC GGG CTC GCC GCC GAC GGC CGC TGC AAG    11475
Thr Glu Phe Arg Ser Gln Gly Gly Leu Ala Ala Asp Gly Arg Cys Lys
                240                 245                 250

CCG TTC TCG AAG GCC GCC GAC GGG TTC GGC CTG GCC GAG GGT GCC GGG    11523
Pro Phe Ser Lys Ala Ala Asp Gly Phe Gly Leu Ala Glu Gly Ala Gly
                255                 260                 265

GTC CTG GTG CTG CAA CGG CTG TCG GCC GCG CGG CGG GAG GGC AGA CCG    11571
Val Leu Val Leu Gln Arg Leu Ser Ala Ala Arg Arg Glu Gly Arg Pro
                270                 275                 280

GTG CTG GCC GTG CTG CGG GGC TCG GCG GTC AAC CAG GAC GGC GCC AGC    11619
Val Leu Ala Val Leu Arg Gly Ser Ala Val Asn Gln Asp Gly Ala Ser
285                 290                 295

AAC GGG CTG ACC GCG CCG AGC GGA CCC GCG CAG CAG CGG GTC ATC CGC    11667
Asn Gly Leu Thr Ala Pro Ser Gly Pro Ala Gln Gln Arg Val Ile Arg
300                 305                 310                 315

CGG GCG CTG GAG AAC GCC GGT GTC CGG GCG GGC GAC GTC GAC TAC GTG    11715
Arg Ala Leu Glu Asn Ala Gly Val Arg Ala Gly Asp Val Asp Tyr Val
                320                 325                 330

GAG GCC CAC GGC ACC GGC ACC AGG CTG GGC GAC CCC ATC GAG GTG CAC    11763
Glu Ala His Gly Thr Gly Thr Arg Leu Gly Asp Pro Ile Glu Val His
                335                 340                 345

GCG CTG CTC TCG ACC TAC GGC GCG GAA CGC GAC CCG GAC GAT CCA CTG    11811
Ala Leu Leu Ser Thr Tyr Gly Ala Glu Arg Asp Pro Asp Asp Pro Leu
            350                 355                 360

TGG ATC GGT TCG GTC AAG TCC AAC ATT GGC CAC ACC CAG GCC GCC GCC    11859
Trp Ile Gly Ser Val Lys Ser Asn Ile Gly His Thr Gln Ala Ala Ala
    365                 370                 375

GGC GTC GCC GGG GTG ATG AAG GCG GTG CTG GCG CTG CGG CAC GGC GAG    11907
Gly Val Ala Gly Val Met Lys Ala Val Leu Ala Leu Arg His Gly Glu
380                 385                 390                 395

ATG CCG CGC ACG CTG CAC TTC GAC GAG CCC TCG CCG CAG ATC GAG TGG    11955
Met Pro Arg Thr Leu His Phe Asp Glu Pro Ser Pro Gln Ile Glu Trp
                400                 405                 410

GAC CTG GGC GCG GTG TCG GTG GTG TCG CAG GCG CGG TCG TGG CCC GCC    12003
Asp Leu Gly Ala Val Ser Val Val Ser Gln Ala Arg Ser Trp Pro Ala
                415                 420                 425

GGC GAG AGG CCC CGC AGG GCG GGC GTC TCC TCG TTC GGC ATC AGC GGC    12051
Gly Glu Arg Pro Arg Arg Ala Gly Val Ser Ser Phe Gly Ile Ser Gly
                430                 435                 440
```

| | |
|---|---|
| ACC AAC GCG CAC GTC ATC GTC GAA GAG GCG CCC GAG GCC GAC GAG CCC<br>Thr Asn Ala His Val Ile Val Glu Glu Ala Pro Glu Ala Asp Glu Pro<br>445 450 455 | 12099 |
| GAG CCG GCA CCC GAC TCG GGT CCG GTC CCG CTG GTG TTG TCC GGC CGC<br>Glu Pro Ala Pro Asp Ser Gly Pro Val Pro Leu Val Leu Ser Gly Arg<br>460 465 470 475 | 12147 |
| GAC GAG CAG GCG ATG CGG GCG CAG GCG GGA CGG CTG GCA GAC CAC CTC<br>Asp Glu Gln Ala Met Arg Ala Gln Ala Gly Arg Leu Ala Asp His Leu<br>480 485 490 | 12195 |
| GCC CGC GAG CCG CGG AAC TCG TTG CGC GAC ACC GGT TTC ACG CTG GCC<br>Ala Arg Glu Pro Arg Asn Ser Leu Arg Asp Thr Gly Phe Thr Leu Ala<br>495 500 505 | 12243 |
| ACC CGC CGC AGC GCG TGG GAG CAC CGC GCG GTG GTG GTC GGC GAC CGC<br>Thr Arg Arg Ser Ala Trp Glu His Arg Ala Val Val Val Gly Asp Arg<br>510 515 520 | 12291 |
| GAC GAC GCC CTC GCC GGG CTG CGC GCG GTG GCC GAC GGC CGC ATC GCC<br>Asp Asp Ala Leu Ala Gly Leu Arg Ala Val Ala Asp Gly Arg Ile Ala<br>525 530 535 | 12339 |
| GAC CGG ACG GCC ACC GGG CAG GCC CGA ACT CGC CGC GGC GTC GCG ATG<br>Asp Arg Thr Ala Thr Gly Gln Ala Arg Thr Arg Arg Gly Val Ala Met<br>540 545 550 555 | 12387 |
| GTG TTC CCC GGC CAG GGC GCG CAG TGG CAG GGG ATG GCC CGC GAC CTG<br>Val Phe Pro Gly Gln Gly Ala Gln Trp Gln Gly Met Ala Arg Asp Leu<br>560 565 570 | 12435 |
| CTG CGG GAG TCG CAG GTA TTC GCC GAC TCG ATC CGC GAC TGC GAG CGG<br>Leu Arg Glu Ser Gln Val Phe Ala Asp Ser Ile Arg Asp Cys Glu Arg<br>575 580 585 | 12483 |
| GCG CTG GCC CCG CAC GTC GAC TGG TCG CTG ACC GAC CTG CTC AGC GGC<br>Ala Leu Ala Pro His Val Asp Trp Ser Leu Thr Asp Leu Leu Ser Gly<br>590 595 600 | 12531 |
| GCG CGA CCG CTG GAC CGG GTC GAC GTC GTC CAG CCC GCG CTC TTC GCC<br>Ala Arg Pro Leu Asp Arg Val Asp Val Val Gln Pro Ala Leu Phe Ala<br>605 610 615 | 12579 |
| GTC ATG GTG TCG CTG GCG GCG CTG TGG CGC TCC CAC GGC GTC GAG CCC<br>Val Met Val Ser Leu Ala Ala Leu Trp Arg Ser His Gly Val Glu Pro<br>620 625 630 635 | 12627 |
| GCC GCG GTC GTC GGC CAC TCG CAG GGC GAG ATC GCC GCC GCG CAC GTC<br>Ala Ala Val Val Gly His Ser Gln Gly Glu Ile Ala Ala Ala His Val<br>640 645 650 | 12675 |
| GCC GGC GCG CTC ACC CTG GAG GAC GCC GCC AAG CTC GTC GCG GTC CGG<br>Ala Gly Ala Leu Thr Leu Glu Asp Ala Ala Lys Leu Val Ala Val Arg<br>655 660 665 | 12723 |
| AGC CGG GTC CTG GCC CGG CTC GGC GGC CAG GGC GGC ATG GCG TCG TTC<br>Ser Arg Val Leu Ala Arg Leu Gly Gly Gln Gly Gly Met Ala Ser Phe<br>670 675 680 | 12771 |
| GGG CTG GGC ACC GAG CAG GCG GCC GAA CGG ATC GGG CGC TTC GCG GGC<br>Gly Leu Gly Thr Glu Gln Ala Ala Glu Arg Ile Gly Arg Phe Ala Gly<br>685 690 695 | 12819 |
| GCG CTC TCC ATC GCC TCG GTC AAC GGC CCC CGG TCG GTC GTC GTC GCG<br>Ala Leu Ser Ile Ala Ser Val Asn Gly Pro Arg Ser Val Val Val Ala<br>700 705 710 715 | 12867 |
| GGG GAG AGC GGG CCG CTG GAC GAG CTG ATC GCC GAG TGC GAG GCC GAA<br>Gly Glu Ser Gly Pro Leu Asp Glu Leu Ile Ala Glu Cys Glu Ala Glu<br>720 725 730 | 12915 |
| GGC ATA ACG GCG CGC CGC ATC CCC GTC GAC TAC GCC TCC CAC TCA CCG<br>Gly Ile Thr Ala Arg Arg Ile Pro Val Asp Tyr Ala Ser His Ser Pro<br>735 740 745 | 12963 |
| CAG GTG GAG TCG CTG CGC GAG GAG CTG CTG ACC GAG CTG GCG GGC ATC<br>Gln Val Glu Ser Leu Arg Glu Glu Leu Leu Thr Glu Leu Ala Gly Ile<br>750 755 760 | 13011 |

```
TCC CCG GTG TCG GCG GAC GTG GCG CTC TAC TCG ACC ACG ACC GGG CAG    13059
Ser Pro Val Ser Ala Asp Val Ala Leu Tyr Ser Thr Thr Thr Gly Gln
765                 770                 775

CCC ATC GAC ACC GCC ACG ATG GAC ACC GCC TAC TGG TAC GCG AAC CTG    13107
Pro Ile Asp Thr Ala Thr Met Asp Thr Ala Tyr Trp Tyr Ala Asn Leu
780                 785                 790                 795

CGC GAG CAG GTC CGC TTC CAG GAC GCG ACG CGG CAG CTC GCC GAG GCG    13155
Arg Glu Gln Val Arg Phe Gln Asp Ala Thr Arg Gln Leu Ala Glu Ala
                800                 805                 810

GGG TTC GAC GCG TTC GTC GAG GTC AGC CCG CAT CCG GTG CTG ACC GTC    13203
Gly Phe Asp Ala Phe Val Glu Val Ser Pro His Pro Val Leu Thr Val
            815                 820                 825

GGC ATC GAG GCC ACG CTG GAC TCC GCG CTC CCG GCC GAC GCC GGC GCC    13251
Gly Ile Glu Ala Thr Leu Asp Ser Ala Leu Pro Ala Asp Ala Gly Ala
        830                 835                 840

TGC GTC GTG GGC ACC CTG CGG CGG GAC CGC GGC GGC CTG GCC GAC TTC    13299
Cys Val Val Gly Thr Leu Arg Arg Asp Arg Gly Gly Leu Ala Asp Phe
845                 850                 855

CAC ACC GCG CTC GGC GAG GCG TAC GCG CAG GGC GTG GAG GTC GAC TGG    13347
His Thr Ala Leu Gly Glu Ala Tyr Ala Gln Gly Val Glu Val Asp Trp
860                 865                 870                 875

AGC CCC GCC TTC GCC GAC GCG CGG CCG GTC GAG CTG CCC GTC TAC CCG    13395
Ser Pro Ala Phe Ala Asp Ala Arg Pro Val Glu Leu Pro Val Tyr Pro
                880                 885                 890

TTC CAG CGG CAG CGG TAC TGG CTG CCC ATC CCC ACC GGC GGG CGC GCA    13443
Phe Gln Arg Gln Arg Tyr Trp Leu Pro Ile Pro Thr Gly Gly Arg Ala
            895                 900                 905

CGG GAC GAG GAC GAC GAC TGG CGC TAC CAG GTC GTA TGG CGG GAA GCC    13491
Arg Asp Glu Asp Asp Asp Trp Arg Tyr Gln Val Val Trp Arg Glu Ala
        910                 915                 920

GAG TGG GAG AGC GCT TCG CTG GCC GGA CGC GTG CTG CTG GTG ACC GGA    13539
Glu Trp Glu Ser Ala Ser Leu Ala Gly Arg Val Leu Leu Val Thr Gly
925                 930                 935

CCG GGC GTG CCG TCC GAG TTG TCG GAC GCC ATC CGA AGT GGA CTG GAG    13587
Pro Gly Val Pro Ser Glu Leu Ser Asp Ala Ile Arg Ser Gly Leu Glu
940                 945                 950                 955

CAG AGC GGT GCG ACG GTC CTG ACC TGC GAC GTG GAA TCC CGT TCG ACC    13635
Gln Ser Gly Ala Thr Val Leu Thr Cys Asp Val Glu Ser Arg Ser Thr
                960                 965                 970

ATC GGC ACC GCA CTG GAG GCC GCC GAC ACC GAC GCT CTG TCC ACT GTG    13683
Ile Gly Thr Ala Leu Glu Ala Ala Asp Thr Asp Ala Leu Ser Thr Val
            975                 980                 985

GTG TCG CTG CTG TCC CGC GAC GGC GAG GCC GTC GAT CCG TCG CTG GAC    13731
Val Ser Leu Leu Ser Arg Asp Gly Glu Ala Val Asp Pro Ser Leu Asp
        990                 995                 1000

GCG CTC GCC CTG GTC CAG GCC CTC GGA GCG GCC GGG GTC GAA GCA CCG    13779
Ala Leu Ala Leu Val Gln Ala Leu Gly Ala Ala Gly Val Glu Ala Pro
1005                1010                1015

CTG TGG GTG CTG ACC CGC AAC GCC GTG CAG GTG GCC GAC GGC GAA CTG    13827
Leu Trp Val Leu Thr Arg Asn Ala Val Gln Val Ala Asp Gly Glu Leu
1020                1025                1030                1035

GTC GAT CCG GCG CAG GCC ATG GTG GGC GGT CTC GGC CGC GTG GTC GGC    13875
Val Asp Pro Ala Gln Ala Met Val Gly Gly Leu Gly Arg Val Val Gly
                1040                1045                1050

ATC GAG CAG CCG GGG CGC TGG GGC GGT CTG GTG GAC CTG GTC GAC GCC    13923
Ile Glu Gln Pro Gly Arg Trp Gly Gly Leu Val Asp Leu Val Asp Ala
            1055                1060                1065

GAT GCC GCG TCG ATC CGG TCG CTG GCC GCG GTG CTG GCG GAC CCG CGC    13971
Asp Ala Ala Ser Ile Arg Ser Leu Ala Ala Val Leu Ala Asp Pro Arg
        1070                1075                1080
```

```
GGC GAG GAG CAG GTC GCG ATC CGG GCG GAC GGG ATC AAG GTG GCG AGG    14019
Gly Glu Glu Gln Val Ala Ile Arg Ala Asp Gly Ile Lys Val Ala Arg
        1085                1090                1095

CTC GTG CCC GCC CCC GCC CGC GCC GCA CGC ACC CGC TGG AGC CCT CGC    14067
Leu Val Pro Ala Pro Ala Arg Ala Ala Arg Thr Arg Trp Ser Pro Arg
1100                1105                1110                1115

GGC ACC GTG CTG GTC ACC GGC GGC ACC GGA GGG ATC GGC GCG CAC GTC    14115
Gly Thr Val Leu Val Thr Gly Gly Thr Gly Gly Ile Gly Ala His Val
            1120                1125                1130

GCC CGC TGG CTG GCC CGC TCG GGC GCC GAG CAC CTG GTG CTG CTG GGC    14163
Ala Arg Trp Leu Ala Arg Ser Gly Ala Glu His Leu Val Leu Leu Gly
                1135                1140                1145

AGG CGC GGT GCC GAC GCA CCC GGC GCG TCC GAG CTG AGG GAG GAG CTG    14211
Arg Arg Gly Ala Asp Ala Pro Gly Ala Ser Glu Leu Arg Glu Glu Leu
                    1150                1155                1160

ACC GCG CTC GGC ACG GGC GTG ACC ATC GCC GCC TGC GAC GTC GCC GAC    14259
Thr Ala Leu Gly Thr Gly Val Thr Ile Ala Ala Cys Asp Val Ala Asp
1165                1170                1175

CGG GCG CGG CTC GAA GCG GTG CTC GCC GCG GAG CGC GCC GAG GGA CGC    14307
Arg Ala Arg Leu Glu Ala Val Leu Ala Ala Glu Arg Ala Glu Gly Arg
    1180                1185                1190                1195

ACG GTC AGC GCC GTG ATG CAC GCG GCG GGG GTT TCC ACG TCC ACG CCC    14355
Thr Val Ser Ala Val Met His Ala Ala Gly Val Ser Thr Ser Thr Pro
        1200                1205                1210

CTC GAC GAC CTC ACC GAA GCC GAG TTC ACC GAG ATC GCC GAC GTG AAG    14403
Leu Asp Asp Leu Thr Glu Ala Glu Phe Thr Glu Ile Ala Asp Val Lys
            1215                1220                1225

GTG CGC GGC ACC GTC AAC CTG GAC GAG CTC TGC CCG GAC CTC GAC GCG    14451
Val Arg Gly Thr Val Asn Leu Asp Glu Leu Cys Pro Asp Leu Asp Ala
                1230                1235                1240

TTC GTG TTG TTC TCC TCC AAC GCG GGC GTG TGG GGC AGT CCG GGG CTC    14499
Phe Val Leu Phe Ser Ser Asn Ala Gly Val Trp Gly Ser Pro Gly Leu
                    1245                1250                1255

GCC TCC TAC GCG GCG GCC AAC GCC TTC CTC GAC GGC TTC GCG CGG CGG    14547
Ala Ser Tyr Ala Ala Ala Asn Ala Phe Leu Asp Gly Phe Ala Arg Arg
1260                1265                1270                1275

CGC CGG AGC GAG GGC GCG CCG GTG ACG TCC ATC GCC TGG GGG CTC TGG    14595
Arg Arg Ser Glu Gly Ala Pro Val Thr Ser Ile Ala Trp Gly Leu Trp
    1280                1285                1290

GCC GGG CAG AAC ATG GCC GGG GAC GAG GGC GGC GAG TAC CTG CGC AGC    14643
Ala Gly Gln Asn Met Ala Gly Asp Glu Gly Gly Glu Tyr Leu Arg Ser
        1295                1300                1305

CAG GGC CTG CGG GCC ATG GAC CCG GAT CGG GCC GTC GAG GAA CTG CAC    14691
Gln Gly Leu Arg Ala Met Asp Pro Asp Arg Ala Val Glu Glu Leu His
            1310                1315                1320

ATC ACC CTC GAC CAC GGT CAG ACG TCC GTG TCG GTC GTG GAC ATG GAT    14739
Ile Thr Leu Asp His Gly Gln Thr Ser Val Ser Val Val Asp Met Asp
                1325                1330                1335

CGC AGG CGG TTC GTC GAG CTG TTC ACC GCG GCC CGG CAC CGG CCG CTG    14787
Arg Arg Arg Phe Val Glu Leu Phe Thr Ala Ala Arg His Arg Pro Leu
                    1340                1345                1350                1355

TTC GAC GAG ATC GCC GGT GCC CGG GCG GAA GCC CGG CAG AGC GAG GAG    14835
Phe Asp Glu Ile Ala Gly Ala Arg Ala Glu Ala Arg Gln Ser Glu Glu
                1360                1365                1370

GGC CCG GCG CTC GCC CAG CGG CTC GCG GCG CTG TCG ACG GCC GAG AGG    14883
Gly Pro Ala Leu Ala Gln Arg Leu Ala Ala Leu Ser Thr Ala Glu Arg
            1375                1380                1385

CGC GAG CAC CTC GCC CAC CTG ATC CGC GCC GAG GTC GCC GCG GTG CTC    14931
Arg Glu His Leu Ala His Leu Ile Arg Ala Glu Val Ala Ala Val Leu
        1390                1395                1400
```

| | | |
|---|---|---|
| GGC CAC GGC GAC GAC GCG GCG ATC GAC CGC GAC CGC GCC TTC CGC GAC<br>Gly His Gly Asp Asp Ala Ala Ile Asp Arg Asp Arg Ala Phe Arg Asp<br>1405                      1410                     1415 | | 14979 |
| CTC GGC TTC GAC TCC ATG ACC GCC GTC GAC CTG CGG AAC CGG CTC GCC<br>Leu Gly Phe Asp Ser Met Thr Ala Val Asp Leu Arg Asn Arg Leu Ala<br>1420                      1425                    1430                    1435 | | 15027 |
| GCG GTG ACC GGG GTG CGG GAA GCC GCG ACG GTG GTC TTC GAC CAC CCG<br>Ala Val Thr Gly Val Arg Glu Ala Ala Thr Val Val Phe Asp His Pro<br>            1440                    1445                    1450 | | 15075 |
| ACC ATC ACC CGG CTC GCC GAC CAC TAC CTG GAG CGG CTC GTC GGC GCA<br>Thr Ile Thr Arg Leu Ala Asp His Tyr Leu Glu Arg Leu Val Gly Ala<br>1455                     1460                    1465 | | 15123 |
| GCA GAG GCG GAG CAA GCC CCG GCG CTC GTG CGC GAG GTG CCG AAG GAT<br>Ala Glu Ala Glu Gln Ala Pro Ala Leu Val Arg Glu Val Pro Lys Asp<br>1470                     1475                    1480 | | 15171 |
| GCC GAC GAC CCG ATC GCG ATC GTC GGC ATG GCC TGC CGC TTC CCC GGC<br>Ala Asp Asp Pro Ile Ala Ile Val Gly Met Ala Cys Arg Phe Pro Gly<br>1485                     1490                    1495 | | 15219 |
| GGC GTG CAC AAC CCC GGT GAG CTG TGG GAG TTC ATC GTC GGC CGC GGA<br>Gly Val His Asn Pro Gly Glu Leu Trp Glu Phe Ile Val Gly Arg Gly<br>1500                     1505                    1510                    1515 | | 15267 |
| GAC GCC GTG ACG GAG ATG CCC ACC GAC CGC GGC TGG GAC CTC GAC GCG<br>Asp Ala Val Thr Glu Met Pro Thr Asp Arg Gly Trp Asp Leu Asp Ala<br>            1520                    1525                    1530 | | 15315 |
| CTG TTC GAC CCC GAC CCG CAG CGC CAC GGA ACC AGC TAC TCG CGA CAC<br>Leu Phe Asp Pro Asp Pro Gln Arg His Gly Thr Ser Tyr Ser Arg His<br>            1535                    1540                    1545 | | 15363 |
| GGC GCG TTC CTC GAC GGG GCC GCC GAC TTC GAC GCG GCG TTC TTC GGG<br>Gly Ala Phe Leu Asp Gly Ala Ala Asp Phe Asp Ala Ala Phe Phe Gly<br>            1550                    1555                    1560 | | 15411 |
| ATC TCG CCG CGC GAG GCG CTG GCG ATG GAC CCG CAG CAG CGC CAG GTC<br>Ile Ser Pro Arg Glu Ala Leu Ala Met Asp Pro Gln Gln Arg Gln Val<br>1565                     1570                    1575 | | 15459 |
| CTG GAA ACG ACG TGG GAG CTG TTC GAG AAC GCC GGC ATC GAC CCG CAC<br>Leu Glu Thr Thr Trp Glu Leu Phe Glu Asn Ala Gly Ile Asp Pro His<br>1580                     1585                    1590                    1595 | | 15507 |
| TCG CTG CGG GGC AGC GAC ACC GGC GTC TTC CTC GGC GCC GCG TAC CAG<br>Ser Leu Arg Gly Ser Asp Thr Gly Val Phe Leu Gly Ala Ala Tyr Gln<br>            1600                    1605                    1610 | | 15555 |
| GGC TAC GGC CAG GAC GCG GTG GTG CCC GAG GAC AGC GAG GGC TAC CTG<br>Gly Tyr Gly Gln Asp Ala Val Val Pro Glu Asp Ser Glu Gly Tyr Leu<br>            1615                    1620                    1625 | | 15603 |
| CTC ACC GGC AAC TCC TCC GCC GTG GTG TCC GGC CGG GTC GCC TAC GTG<br>Leu Thr Gly Asn Ser Ser Ala Val Val Ser Gly Arg Val Ala Tyr Val<br>            1630                    1635                    1640 | | 15651 |
| CTG GGG CTG GAA GGC CCC GCG GTC ACG GTG GAC ACG GCG TGT TCG TCG<br>Leu Gly Leu Glu Gly Pro Ala Val Thr Val Asp Thr Ala Cys Ser Ser<br>1645                     1650                    1655 | | 15699 |
| TCG TTG GTG GCC TTG CAT TCG GCG TGT GGG TCG TTG CGT GAC GGT GAC<br>Ser Leu Val Ala Leu His Ser Ala Cys Gly Ser Leu Arg Asp Gly Asp<br>1660                     1665                    1670                    1675 | | 15747 |
| TGC GGT CTT GCG GTG GCC GGT GGT GTG TCG GTG ATG GCG GGC CCG GAG<br>Cys Gly Leu Ala Val Ala Gly Gly Val Ser Val Met Ala Gly Pro Glu<br>            1680                    1685                    1690 | | 15795 |
| GTG TTC ACC GAG TTC TCC CGC CAG GGC GGC TTG GCC GTG GAC GGG CGC<br>Val Phe Thr Glu Phe Ser Arg Gln Gly Gly Leu Ala Val Asp Gly Arg<br>            1695                    1700                    1705 | | 15843 |
| TGC AAG GCG TTC TCC GCG GAG GCC GAC GGC TTC GGT TTC GCC GAG GGC<br>Cys Lys Ala Phe Ser Ala Glu Ala Asp Gly Phe Gly Phe Ala Glu Gly<br>1710                     1715                    1720 | | 15891 |

-continued

| | |
|---|---|
| GTC GCG GTG GTC CTG CTC CAG CGG TTG TCC GAC GCC CGC AGG GCG GGT<br>Val Ala Val Val Leu Leu Gln Arg Leu Ser Asp Ala Arg Arg Ala Gly<br>1725               1730               1735 | 15939 |
| CGC CAG GTG CTC GGC GTG GTC GCG GGC TCG GCG ATC AAC CAG GAC GGC<br>Arg Gln Val Leu Gly Val Val Ala Gly Ser Ala Ile Asn Gln Asp Gly<br>1740               1745               1750               1755 | 15987 |
| GCG AGC AAC GGT CTC GCG GCG CCG AGC GGC GTC GCC CAG CAG CGC GTG<br>Ala Ser Asn Gly Leu Ala Ala Pro Ser Gly Val Ala Gln Gln Arg Val<br>               1760               1765               1770 | 16035 |
| ATC CGC AAG GCG TGG GCG CGT GCG GGG ATC ACC GGC GCG GAT GTG GCC<br>Ile Arg Lys Ala Trp Ala Arg Ala Gly Ile Thr Gly Ala Asp Val Ala<br>               1775               1780               1785 | 16083 |
| GTG GTG GAG GCG CAT GGG ACC GGT ACG CGG CTG GGC GAT CCG GTG GAG<br>Val Val Glu Ala His Gly Thr Gly Thr Arg Leu Gly Asp Pro Val Glu<br>1790               1795                          1800 | 16131 |
| GCG TCG GCG TTG CTG GCT ACT TAC GGC AAG TCG CGC GGG TCG TCG GGC<br>Ala Ser Ala Leu Leu Ala Thr Tyr Gly Lys Ser Arg Gly Ser Ser Gly<br>1805               1810               1815 | 16179 |
| CCG GTG CTG CTG GGT TCG GTG AAG TCG AAC ATC GGT CAC GCG CAG GCG<br>Pro Val Leu Leu Gly Ser Val Lys Ser Asn Ile Gly His Ala Gln Ala<br>1820               1825               1830               1835 | 16227 |
| GCC GCG GGT GTC GCG GGC GTG ATC AAG GTG GTC CTG GGG TTG AAC CGC<br>Ala Ala Gly Val Ala Gly Val Ile Lys Val Val Leu Gly Leu Asn Arg<br>               1840               1845               1850 | 16275 |
| GGC CTG GTG CCG CCG ATG CTC TGC CGC GGC GAG CGG TCG CCG CTG ATC<br>Gly Leu Val Pro Pro Met Leu Cys Arg Gly Glu Arg Ser Pro Leu Ile<br>               1855               1860               1865 | 16323 |
| GAA TGG TCC TCG GGT GGT GTG GAA CTT GCC GAG GCC GTG AGC CCG TGG<br>Glu Trp Ser Ser Gly Gly Val Glu Leu Ala Glu Ala Val Ser Pro Trp<br>               1870               1875               1880 | 16371 |
| CCT CCG GCC GCG GAC GGG GTG CGC CGG GCC GGT GTG TCG GCG TTC GGG<br>Pro Pro Ala Ala Asp Gly Val Arg Arg Ala Gly Val Ser Ala Phe Gly<br>1885               1890               1895 | 16419 |
| GTG AGC GGG ACG AAC GCG CAC GTG ATC ATC GCC GAG CCC CCG GAG CCC<br>Val Ser Gly Thr Asn Ala His Val Ile Ile Ala Glu Pro Pro Glu Pro<br>1900               1905               1910               1915 | 16467 |
| GAG CCG CTG CCG GAA CCC GGA CCG GTG GGC GTG CTG GCC GCT GCG AAC<br>Glu Pro Leu Pro Glu Pro Gly Pro Val Gly Val Leu Ala Ala Ala Asn<br>               1920               1925               1930 | 16515 |
| TCG GTG CCC GTA CTG CTG TCG GCC AGG ACC GAG ACC GCG TTG GCA GCG<br>Ser Val Pro Val Leu Leu Ser Ala Arg Thr Glu Thr Ala Leu Ala Ala<br>               1935               1940               1945 | 16563 |
| CAG GCG CGG CTC CTG GAG TCC GCA GTG GAC GAC TCG GTT CCG TTG ACG<br>Gln Ala Arg Leu Leu Glu Ser Ala Val Asp Asp Ser Val Pro Leu Thr<br>1950               1955               1960 | 16611 |
| GCA TTG GCT TCC GCG CTG GCC ACC GGA CGC GCC CAC CTG CCG CGT CGT<br>Ala Leu Ala Ser Ala Leu Ala Thr Gly Arg Ala His Leu Pro Arg Arg<br>1965               1970               1975 | 16659 |
| GCG GCG TTG CTG GCA GGC GAC CAC GAA CAG CTC CGC GGG CAG TTG CGA<br>Ala Ala Leu Leu Ala Gly Asp His Glu Gln Leu Arg Gly Gln Leu Arg<br>1980               1985               1990               1995 | 16707 |
| GCG GTC GCC GAG GGC GTT GCG GCT CCC GGT GCC ACC ACC GGA ACC GCC<br>Ala Val Ala Glu Gly Val Ala Ala Pro Gly Ala Thr Thr Gly Thr Ala<br>               2000               2005               2010 | 16755 |
| TCC GCC GGC GGC GTG GTT TTC GTC TTC CCA GGT CAG GGT GCT CAG TGG<br>Ser Ala Gly Gly Val Val Phe Val Phe Pro Gly Gln Gly Ala Gln Trp<br>2015               2020               2025 | 16803 |
| GAG GGC ATG GCC CGG GGC TTG CTC TCG GTC CCC GTC TTC GCC GAG TCG<br>Glu Gly Met Ala Arg Gly Leu Leu Ser Val Pro Val Phe Ala Glu Ser<br>               2030               2035               2040 | 16851 |

-continued

| | |
|---|---|
| ATC GCC GAG TGC GAT GCG GTG TTG TCG GAG GTG GCC GGG TTC TCG GCC<br>Ile Ala Glu Cys Asp Ala Val Leu Ser Glu Val Ala Gly Phe Ser Ala<br>2045                     2050                     2055 | 16899 |
| TCC GAA GTG CTG GAG CAG CGT CCG GAC GCG CCG TCG CTG GAG CGG GTC<br>Ser Glu Val Leu Glu Gln Arg Pro Asp Ala Pro Ser Leu Glu Arg Val<br>2060                     2065                     2070                     2075 | 16947 |
| GAC GTC GTA CAG CCG GTG TTG TTC TCC GTG ATG GTG TCG CTG GCG CGG<br>Asp Val Val Gln Pro Val Leu Phe Ser Val Met Val Ser Leu Ala Arg<br>                  2080                     2085                     2090 | 16995 |
| CTG TGG GGC GCT TGC GGA GTC AGC CCC TCG GCC GTC ATC GGC CAT TCG<br>Leu Trp Gly Ala Cys Gly Val Ser Pro Ser Ala Val Ile Gly His Ser<br>                  2095                     2100                     2105 | 17043 |
| CAG GGC GAG ATC GCC GCC GCG GTG GTG GCC GGG GTG TTG TCG CTG GAG<br>Gln Gly Glu Ile Ala Ala Ala Val Val Ala Gly Val Leu Ser Leu Glu<br>2110                     2115                     2120 | 17091 |
| GAC GGC GTG CGC GTC GTG GCC CTG CGC GCG AAG GCG TTG CGT GCG CTG<br>Asp Gly Val Arg Val Val Ala Leu Arg Ala Lys Ala Leu Arg Ala Leu<br>2125                     2130                     2135 | 17139 |
| GCG GGC AAG GGC GGC ATG GTC TCG TTG GCG GCT CCC GGT GAA CGC GCC<br>Ala Gly Lys Gly Gly Met Val Ser Leu Ala Ala Pro Gly Glu Arg Ala<br>2140                     2145                     2150                     2155 | 17187 |
| CGC GCG CTG ATC GCA CCG TGG GAG GAC CGG ATC TCC GTC GCG GCG GTC<br>Arg Ala Leu Ile Ala Pro Trp Glu Asp Arg Ile Ser Val Ala Ala Val<br>                  2160                     2165                     2170 | 17235 |
| AAC TCC CCG TCC TCG GTC GTG GTC TCC GGC GAT CCG GAG GCG CTG GCC<br>Asn Ser Pro Ser Ser Val Val Val Ser Gly Asp Pro Glu Ala Leu Ala<br>                  2175                     2180                     2185 | 17283 |
| GAA CTC GTC GCA CGT TGC GAG GAC GAG GGC GTG CGC GCC AAG ACG CTC<br>Glu Leu Val Ala Arg Cys Glu Asp Glu Gly Val Arg Ala Lys Thr Leu<br>                  2190                     2195                     2200 | 17331 |
| CCG GTG GAC TAC GCC TCG CAC TCC CGC CAC GTC GAG GAG ATC CGC GAG<br>Pro Val Asp Tyr Ala Ser His Ser Arg His Val Glu Glu Ile Arg Glu<br>2205                     2210                     2215 | 17379 |
| ACG ATC CTC GCC GAC CTC GAC GGC ATC TCC GCG CGG CGT GCC GCC ATC<br>Thr Ile Leu Ala Asp Leu Asp Gly Ile Ser Ala Arg Arg Ala Ala Ile<br>2220                     2225                     2230                     2235 | 17427 |
| CCG CTC TAC TCC ACG CTG CAC GGC GAA CGG CGC GAC GGC GCC GAC ATG<br>Pro Leu Tyr Ser Thr Leu His Gly Glu Arg Arg Asp Gly Ala Asp Met<br>                  2240                     2245                     2250 | 17475 |
| GGT CCG CGG TAC TGG TAC GAC AAC CTG CGC TCC CAG GTG CGC TTC GAC<br>Gly Pro Arg Tyr Trp Tyr Asp Asn Leu Arg Ser Gln Val Arg Phe Asp<br>2255                     2260                     2265 | 17523 |
| GAG GCG GTC TCG GCC GCC GTC GCC GAC GGT CAC GCC ACC TTC GTC GAG<br>Glu Ala Val Ser Ala Ala Val Ala Asp Gly His Ala Thr Phe Val Glu<br>                  2270                     2275                     2280 | 17571 |
| ATG AGC CCG CAC CCG GTG CTC ACC GCG GCG GTG CAG GAG ATC GCC GCG<br>Met Ser Pro His Pro Val Leu Thr Ala Ala Val Gln Glu Ile Ala Ala<br>2285                     2290                     2295 | 17619 |
| GAC GCC GTG GCC ATC GGG TCG CTG CAC CGC GAC ACC GCG GAG GAG CAC<br>Asp Ala Val Ala Ile Gly Ser Leu His Arg Asp Thr Ala Glu Glu His<br>2300                     2305                     2310                     2315 | 17667 |
| CTG ATC GCC GAG CTC GCC CGG GCG CAC GTG CAC GGC GTG GCC GTG GAC<br>Leu Ile Ala Glu Leu Ala Arg Ala His Val His Gly Val Ala Val Asp<br>                  2320                     2325                     2330 | 17715 |
| TGG CGG AAC GTC TTC CCG GCG GCA CCT CCG GTG GCG CTG CCC AAC TAC<br>Trp Arg Asn Val Phe Pro Ala Ala Pro Pro Val Ala Leu Pro Asn Tyr<br>                  2335                     2340                     2345 | 17763 |
| CCG TTC GAG CCC CAG CGG TAC TGG CTC GCG CCG GAG GTG TCC GAC CAG<br>Pro Phe Glu Pro Gln Arg Tyr Trp Leu Ala Pro Glu Val Ser Asp Gln<br>                  2350                     2355                     2360 | 17811 |

| | |
|---|---|
| CTC GCC GAC AGC CGC TAC CGC GTC GAC TGG CGA CCG CTG GCC ACC ACG<br>Leu Ala Asp Ser Arg Tyr Arg Val Asp Trp Arg Pro Leu Ala Thr Thr<br>                2365                             2370                         2375 | 17859 |
| CCG GTG GAC CTG GAA GGC GGC TTC CTG GTC CAC GGG TCC GCA CCG GAG<br>Pro Val Asp Leu Glu Gly Gly Phe Leu Val His Gly Ser Ala Pro Glu<br>2380                       2385                          2390                       2395 | 17907 |
| TCG CTG ACC AGC GCA GTC GAG AAG GCC GGA GGC CGC GTC GTG CCG GTC<br>Ser Leu Thr Ser Ala Val Glu Lys Ala Gly Gly Arg Val Val Pro Val<br>                2400                             2405                       2410 | 17955 |
| GCC TCG GCC GAC CGC GAA GCC TCG GCG GCC CTG CGG GAG GTG CCG GGC<br>Ala Ser Ala Asp Arg Glu Ala Ser Ala Ala Leu Arg Glu Val Pro Gly<br>                2415                             2420                       2425 | 18003 |
| GAG GTC GCC GGC GTG CTC TCG GTC CAC ACC GGC GCC GCA ACG CAC CTC<br>Glu Val Ala Gly Val Leu Ser Val His Thr Gly Ala Ala Thr His Leu<br>                2430                             2435                       2440 | 18051 |
| GCC CTG CAC CAG TCG CTG GGT GAG GCC GGC GTG CGG GCC CCG CTC TGG<br>Ala Leu His Gln Ser Leu Gly Glu Ala Gly Val Arg Ala Pro Leu Trp<br>                2445                             2450                       2455 | 18099 |
| CTG GTC ACC AGC CGA GCG GTC GCG CTC GGG GAG TCC GAG CCG GTC GAT<br>Leu Val Thr Ser Arg Ala Val Ala Leu Gly Glu Ser Glu Pro Val Asp<br>2460                       2465                          2470                       2475 | 18147 |
| CCC GAG CAG GCG ATG GTG TGG GGT CTC GGG CGC GTC ATG GGC CTG GAG<br>Pro Glu Gln Ala Met Val Trp Gly Leu Gly Arg Val Met Gly Leu Glu<br>                2480                             2485                       2490 | 18195 |
| ACC CCG GAA CGG TGG GGC GGT CTG GTG GAC CTG CCC GCC GAA CCC GCG<br>Thr Pro Glu Arg Trp Gly Gly Leu Val Asp Leu Pro Ala Glu Pro Ala<br>                2495                             2500                       2505 | 18243 |
| CCG GGG GAC GGC GAG GCG TTC GTC GCC TGC CTC GGC GCG GAC GGC CAC<br>Pro Gly Asp Gly Glu Ala Phe Val Ala Cys Leu Gly Ala Asp Gly His<br>                2510                             2515                       2520 | 18291 |
| GAG GAC CAG GTC GCG ATC CGT GAC CAC GCC CGC TAC GGC CGC CGC CTC<br>Glu Asp Gln Val Ala Ile Arg Asp His Ala Arg Tyr Gly Arg Arg Leu<br>                2525                             2530                       2535 | 18339 |
| GTC CGC GCC CCG CTG GGC ACC CGC GAG TCG AGC TGG GAG CCG GCG GGC<br>Val Arg Ala Pro Leu Gly Thr Arg Glu Ser Ser Trp Glu Pro Ala Gly<br>2540                       2545                          2550                       2555 | 18387 |
| ACG GCG CTG GTC ACC GGC GGC ACC GGT GCG CTC GGC GGC CAC GTC GCC<br>Thr Ala Leu Val Thr Gly Gly Thr Gly Ala Leu Gly Gly His Val Ala<br>                2560                             2565                       2570 | 18435 |
| CGC CAC CTC GCC AGG TGC GGG GTG GAG GAC CTG GTG CTG GTC AGC AGG<br>Arg His Leu Ala Arg Cys Gly Val Glu Asp Leu Val Leu Val Ser Arg<br>                2575                             2580                       2585 | 18483 |
| CGC GGC GTC GAC GCT CCC GGC GCG GCC GAG CTG GAA GCC GAA CTG GTC<br>Arg Gly Val Asp Ala Pro Gly Ala Ala Glu Leu Glu Ala Glu Leu Val<br>                2590                             2595                       2600 | 18531 |
| GCC CTC GGC GCG AAG ACG ACC ATC ACC GCC TGC GAC GTG GCC GAC CGC<br>Ala Leu Gly Ala Lys Thr Thr Ile Thr Ala Cys Asp Val Ala Asp Arg<br>2605                       2610                          2615 | 18579 |
| GAG CAG CTC TCC AAG CTG CTG GAA GAA CTG CGC GGG CAG GGA CGT CCG<br>Glu Gln Leu Ser Lys Leu Leu Glu Glu Leu Arg Gly Gln Gly Arg Pro<br>2620                       2625                          2630                       2635 | 18627 |
| GTG CGG ACC GTC GTG CAC ACC GCC GGG GTG CCC GAA TCG AGG CCG CTG<br>Val Arg Thr Val Val His Thr Ala Gly Val Pro Glu Ser Arg Pro Leu<br>                2640                             2645                       2650 | 18675 |
| CAC GAG ATC GGC GAG CTG GAG TCG GTC TGC GCG GCG AAG GTG ACC GGG<br>His Glu Ile Gly Glu Leu Glu Ser Val Cys Ala Ala Lys Val Thr Gly<br>                2655                             2660                       2665 | 18723 |
| GCC CGG CTG CTC GAC GAG CTG TGC CCG GAC GCC GAG ACC TTC GTC CTG<br>Ala Arg Leu Leu Asp Glu Leu Cys Pro Asp Ala Glu Thr Phe Val Leu<br>                2670                             2675                       2680 | 18771 |

```
TTC TCG TCC GGA GCG GGG GTG TGG GGC AGT GCG AAC CTC GGC GCC TAC    18819
Phe Ser Ser Gly Ala Gly Val Trp Gly Ser Ala Asn Leu Gly Ala Tyr
    2685            2690            2695

TCC GCG GCC AAC GCC TAC CTC GAC GCG CTG GCC CAC CGC CGC CGT GCG    18867
Ser Ala Ala Asn Ala Tyr Leu Asp Ala Leu Ala His Arg Arg Arg Ala
2700            2705            2710            2715

GAA GGC CGT GCG GCG ACG TCC GTC GCG TGG GGC GCC TGG GCG GGC GAG    18915
Glu Gly Arg Ala Ala Thr Ser Val Ala Trp Gly Ala Trp Ala Gly Glu
        2720            2725            2730

GGC ATG GCC ACC GGC GAC CTC GAG GGG CTC ACC CGG CGC GGC CTG CGC    18963
Gly Met Ala Thr Gly Asp Leu Glu Gly Leu Thr Arg Arg Gly Leu Arg
            2735            2740            2745

CCG ATG GCG CCC GAG CGC GCG ATC CGC GCG CTG CAC CAG GCG CTG GAC    19011
Pro Met Ala Pro Glu Arg Ala Ile Arg Ala Leu His Gln Ala Leu Asp
        2750            2755            2760

AAC GGC GAC ACG TGC GTT TCG ATC GCC GAC GTC GAC TGG GAG GCC TTC    19059
Asn Gly Asp Thr Cys Val Ser Ile Ala Asp Val Asp Trp Glu Ala Phe
    2765            2770            2775

GCG GTC GGC TTC ACC GCC GCC CGG CCG CGT CCG CTG CTG GAC GAG CTC    19107
Ala Val Gly Phe Thr Ala Ala Arg Pro Arg Pro Leu Leu Asp Glu Leu
2780            2785            2790            2795

GTC ACG CCG GCG GTG GGG GCC GTC CCC GCG GTG CAG GCG GCC CCG GCG    19155
Val Thr Pro Ala Val Gly Ala Val Pro Ala Val Gln Ala Ala Pro Ala
        2800            2805            2810

CGG GAG ATG ACG TCG CAG GAG TTG CTG GAG TTC ACG CAC TCG CAC GTC    19203
Arg Glu Met Thr Ser Gln Glu Leu Leu Glu Phe Thr His Ser His Val
            2815            2820            2825

GCG GCG ATC CTC GGG CAT TCC AGC CCG GAC GCG GTC GGG CAG GAC CAG    19251
Ala Ala Ile Leu Gly His Ser Ser Pro Asp Ala Val Gly Gln Asp Gln
        2830            2835            2840

CCG TTC ACC GAG CTC GGC TTC GAC TCG CTG ACC GCG GTC GGG CTG CGC    19299
Pro Phe Thr Glu Leu Gly Phe Asp Ser Leu Thr Ala Val Gly Leu Arg
    2845            2850            2855

AAC CAG CTC CAG CAG GCC ACC GGG CTC GCG CTG CCC GCG ACC CTG GTG    19347
Asn Gln Leu Gln Gln Ala Thr Gly Leu Ala Leu Pro Ala Thr Leu Val
2860            2865            2870            2875

TTC GAG CAC CCC ACG GTC CGC AGG TTG GCC GAC CAC ATA GGA CAG CAG    19395
Phe Glu His Pro Thr Val Arg Arg Leu Ala Asp His Ile Gly Gln Gln
        2880            2885            2890

CTC GAC AGC GGG ACT CCC GCC CGG GAA GCG AGC AGC GCT CTT CGC GAC    19443
Leu Asp Ser Gly Thr Pro Ala Arg Glu Ala Ser Ser Ala Leu Arg Asp
            2895            2900            2905

GGC TAC CGG CAG GCG GGC GTG TCG GGC AGG GTC CGG TCC TAC CTC GAC    19491
Gly Tyr Arg Gln Ala Gly Val Ser Gly Arg Val Arg Ser Tyr Leu Asp
        2910            2915            2920

CTG CTG GCG GGG CTG TCG GAC TTC CGC GAG CAC TTC GAC GGC TCC GAC    19539
Leu Leu Ala Gly Leu Ser Asp Phe Arg Glu His Phe Asp Gly Ser Asp
    2925            2930            2935

GGG TTC TCC CTC GAT CTC GTG GAC ATG GCC GAC GGT CCC GGA GAG GTC    19587
Gly Phe Ser Leu Asp Leu Val Asp Met Ala Asp Gly Pro Gly Glu Val
2940            2945            2950            2955

ACG GTG ATC TGC TGC GCG GGA ACG GCG GCG ATC TCC GGT CCG CAC GAG    19635
Thr Val Ile Cys Cys Ala Gly Thr Ala Ala Ile Ser Gly Pro His Glu
            2960            2965            2970

TTC ACC CGG CTC GCC GGG GCG CTG CGC GGA ATC GCT CCG GTT CGG GCC    19683
Phe Thr Arg Leu Ala Gly Ala Leu Arg Gly Ile Ala Pro Val Arg Ala
        2975            2980            2985

GTG CCC CAG CCC GGC TAC GAG GAG GGC GAA CCT CTG CCG TCG TCG ATG    19731
Val Pro Gln Pro Gly Tyr Glu Glu Gly Glu Pro Leu Pro Ser Ser Met
    2990            2995            3000
```

-continued

```
GCG GCG GTG GCG GCG GTG CAG GCC GAT GCG GTC ATC AGG ACA CAG GGG    19779
Ala Ala Val Ala Ala Val Gln Ala Asp Ala Val Ile Arg Thr Gln Gly
3005                3010                3015

GAC AAG CCG TTC GTG GTG GCC GGT CAC TCC GCG GGG GCA CTG ATG GCC    19827
Asp Lys Pro Phe Val Val Ala Gly His Ser Ala Gly Ala Leu Met Ala
3020                3025                3030                3035

TAC GCG CTG GCG ACC GAA CTG CTC GAT CGC GGG CAC CCG CCA CGC GGT    19875
Tyr Ala Leu Ala Thr Glu Leu Leu Asp Arg Gly His Pro Pro Arg Gly
                3040                3045                3050

GTC GTC CTG ATC GAC GTC TAC CCG CCC GGT CAC CAG GAC GCG ATG AAC    19923
Val Val Leu Ile Asp Val Tyr Pro Pro Gly His Gln Asp Ala Met Asn
3055                3060                3065

GCC TGG CTG GAG GAG CTG ACC GCC ACG CTG TTC GAC CGC GAG ACG GTG    19971
Ala Trp Leu Glu Glu Leu Thr Ala Thr Leu Phe Asp Arg Glu Thr Val
3070                3075                3080

CGG ATG GAC GAC ACC AGG CTC ACC GCC CTG GGC GCC TAC GAC CGC CTC    20019
Arg Met Asp Asp Thr Arg Leu Thr Ala Leu Gly Ala Tyr Asp Arg Leu
3085                3090                3095

ACC GGT CAG TGG CGA CCC CGG GAA ACC GGG CTG CCG ACG CTG CTG GTC    20067
Thr Gly Gln Trp Arg Pro Arg Glu Thr Gly Leu Pro Thr Leu Leu Val
3100                3105                3110                3115

AGC GCC GGC GAG CCG ATG GGT CCG TGG CCC GAC GAC AGC TGG AAG CCG    20115
Ser Ala Gly Glu Pro Met Gly Pro Trp Pro Asp Asp Ser Trp Lys Pro
                3120                3125                3130

ACG TGG CCC TTC GAG CAC GAC ACC GTC GCC GTC CCC GGC GAC CAC TTC    20163
Thr Trp Pro Phe Glu His Asp Thr Val Ala Val Pro Gly Asp His Phe
3135                3140                3145

ACG ATG GTG CAG GAA CAC GCC GAC GCG ATC GCG CGG CAC ATC GAC GCC    20211
Thr Met Val Gln Glu His Ala Asp Ala Ile Ala Arg His Ile Asp Ala
                3150                3155                3160

TGG CTG GGC GGA GGG AAT TCA TGA                                    20235
Trp Leu Gly Gly Gly Asn Ser
3165            3170
```

(2) INFORMATION FOR SEQ ID NO:4:

(i) SEQUENCE CHARACTERISTICS:
        (A) LENGTH: 3567 amino acids
        (B) TYPE: amino acid
        (D) TOPOLOGY: linear (ii) MOLECULE TYPE: protein (xi) SEQUENCE DESCRIPTION: SEQ ID NO:4:

```
Val Thr Asp Ser Glu Lys Val Ala Glu Tyr Leu Arg Arg Ala Thr Leu
1               5                   10                  15

Asp Leu Arg Ala Ala Arg Gln Arg Ile Arg Glu Leu Glu Ser Asp Pro
            20                  25                  30

Ile Ala Ile Val Ser Met Ala Cys Arg Leu Pro Gly Gly Val Asn Thr
        35                  40                  45

Pro Gln Arg Leu Trp Glu Leu Leu Arg Glu Gly Gly Glu Thr Leu Ser
    50                  55                  60

Gly Phe Pro Thr Asp Arg Gly Trp Asp Leu Ala Arg Leu His His Pro
65                  70                  75                  80

Asp Pro Asp Asn Pro Gly Thr Ser Tyr Val Asp Lys Gly Gly Phe Leu
                85                  90                  95

Asp Asp Ala Ala Gly Phe Asp Ala Glu Phe Phe Gly Val Ser Pro Arg
            100                 105                 110

Glu Ala Ala Ala Met Asp Pro Gln Arg Leu Leu Leu Glu Thr Ser
        115                 120                 125
```

-continued

Trp Glu Leu Val Glu Asn Ala Gly Ile Asp Pro His Ser Leu Arg Gly
130                 135                 140

Thr Ala Thr Gly Val Phe Leu Gly Val Ala Lys Phe Gly Tyr Gly Glu
145                 150                 155                 160

Asp Thr Ala Ala Ala Glu Asp Val Glu Gly Tyr Ser Val Thr Gly Val
                165                 170                 175

Ala Pro Ala Val Ala Ser Gly Arg Ile Ser Tyr Thr Met Gly Leu Glu
            180                 185                 190

Gly Pro Ser Ile Ser Val Asp Thr Ala Cys Ser Ser Leu Val Ala
        195                 200                 205

Leu His Leu Ala Val Glu Ser Leu Arg Lys Gly Glu Ser Ser Met Ala
210                 215                 220

Val Val Gly Gly Ala Ala Val Met Ala Thr Pro Gly Val Phe Val Asp
225                 230                 235                 240

Phe Ser Arg Gln Arg Ala Leu Ala Ala Asp Gly Arg Ser Lys Ala Phe
                245                 250                 255

Gly Ala Gly Ala Asp Gly Phe Gly Phe Ser Glu Gly Val Thr Leu Val
            260                 265                 270

Leu Leu Glu Arg Leu Ser Glu Ala Arg Arg Asn Gly His Glu Val Leu
        275                 280                 285

Ala Val Val Arg Gly Ser Ala Leu Asn Gln Asp Gly Ala Ser Asn Gly
290                 295                 300

Leu Ser Ala Pro Ser Gly Pro Ala Gln Arg Val Ile Arg Gln Ala
305                 310                 315                 320

Leu Glu Ser Cys Gly Leu Glu Pro Gly Asp Val Asp Ala Val Glu Ala
                325                 330                 335

His Gly Thr Gly Thr Ala Leu Gly Asp Pro Ile Glu Ala Asn Ala Leu
            340                 345                 350

Leu Asp Thr Tyr Gly Arg Asp Arg Asp Ala Asp Arg Pro Leu Trp Leu
        355                 360                 365

Gly Ser Val Lys Ser Asn Ile Gly His Thr Gln Ala Ala Gly Val
370                 375                 380

Thr Gly Leu Leu Lys Val Val Leu Ala Leu Arg Asn Gly Glu Leu Pro
385                 390                 395                 400

Ala Thr Leu His Val Glu Glu Pro Thr Pro His Val Asp Trp Ser Ser
                405                 410                 415

Gly Gly Val Ala Leu Leu Ala Gly Asn Gln Pro Trp Arg Arg Gly Glu
            420                 425                 430

Arg Thr Arg Arg Ala Arg Val Ser Ala Phe Gly Ile Ser Gly Thr Asn
        435                 440                 445

Ala His Val Ile Val Glu Glu Ala Pro Glu Arg Glu His Arg Glu Thr
450                 455                 460

Thr Ala His Asp Gly Arg Pro Val Pro Leu Val Val Ser Ala Arg Thr
465                 470                 475                 480

Thr Ala Ala Leu Arg Ala Gln Ala Ala Gln Ile Ala Glu Leu Leu Glu
                485                 490                 495

Arg Pro Asp Ala Asp Leu Ala Gly Val Gly Leu Gly Leu Ala Thr Thr
            500                 505                 510

Arg Ala Arg His Glu His Arg Ala Ala Val Val Ala Ser Thr Arg Glu
        515                 520                 525

Glu Ala Val Arg Gly Leu Arg Glu Ile Ala Ala Gly Ala Ala Thr Ala
530                 535                 540

Asp Ala Val Val Glu Gly Val Thr Glu Val Asp Gly Arg Asn Val Val
545                 550                 555                 560

-continued

Phe Leu Phe Pro Gly Gln Gly Ser Gln Trp Ala Gly Met Gly Ala Glu
                565                 570                 575

Leu Leu Ser Ser Ser Pro Val Phe Ala Gly Lys Ile Arg Ala Cys Asp
            580                 585                 590

Glu Ser Met Ala Pro Met Gln Asp Trp Lys Val Ser Asp Val Leu Arg
        595                 600                 605

Gln Ala Pro Gly Ala Pro Gly Leu Asp Arg Val Asp Val Val Gln Pro
    610                 615                 620

Val Leu Phe Ala Val Met Val Ser Leu Ala Glu Leu Trp Arg Ser Tyr
625                 630                 635                 640

Gly Val Glu Pro Ala Ala Val Val Gly His Ser Gln Gly Glu Ile Ala
                645                 650                 655

Ala Ala His Val Ala Gly Ala Leu Thr Leu Glu Asp Ala Ala Lys Leu
                660                 665                 670

Val Val Gly Arg Ser Arg Leu Met Arg Ser Leu Ser Gly Glu Gly Gly
                675                 680                 685

Met Ala Ala Val Ala Leu Gly Glu Ala Ala Val Arg Glu Arg Leu Arg
        690                 695                 700

Pro Trp Gln Asp Arg Leu Ser Val Ala Ala Val Asn Gly Pro Arg Ser
705                 710                 715                 720

Val Val Val Ser Gly Glu Pro Gly Ala Leu Arg Ala Phe Ser Glu Asp
                725                 730                 735

Cys Ala Ala Glu Gly Ile Arg Val Arg Asp Ile Asp Val Asp Tyr Ala
                740                 745                 750

Ser His Ser Pro Gln Ile Glu Arg Val Arg Glu Glu Leu Leu Glu Thr
            755                 760                 765

Thr Gly Asp Ile Ala Pro Arg Pro Ala Arg Val Thr Phe His Ser Thr
        770                 775                 780

Val Glu Ser Arg Ser Met Asp Gly Thr Glu Leu Asp Ala Arg Tyr Trp
785                 790                 795                 800

Tyr Arg Asn Leu Arg Glu Thr Val Arg Phe Ala Asp Ala Val Thr Arg
                805                 810                 815

Leu Ala Glu Ser Gly Tyr Asp Ala Phe Ile Glu Val Ser Pro His Pro
            820                 825                 830

Val Val Val Gln Ala Val Glu Glu Ala Val Glu Glu Ala Asp Gly Ala
            835                 840                 845

Glu Asp Ala Val Val Gly Ser Leu His Arg Asp Gly Gly Asp Leu
        850                 855                 860

Ser Ala Phe Leu Arg Ser Met Ala Thr Ala His Val Ser Gly Val Asp
865                 870                 875                 880

Ile Arg Trp Asp Val Ala Leu Pro Gly Ala Ala Pro Phe Ala Leu Pro
                885                 890                 895

Thr Tyr Pro Phe Gln Arg Lys Tyr Trp Leu Gln Pro Ala Ala Pro
        900                 905                 910

Ala Ala Ala Ser Asp Glu Leu Ala Tyr Arg Val Ser Trp Thr Pro Ile
            915                 920                 925

Glu Lys Pro Glu Ser Gly Asn Leu Asp Gly Asp Trp Leu Val Val Thr
        930                 935                 940

Pro Leu Ile Ser Pro Glu Trp Thr Glu Met Leu Cys Glu Ala Ile Asn
945                 950                 955                 960

Ala Asn Gly Gly Arg Ala Leu Arg Cys Glu Val Asp Thr Ser Ala Ser
                965                 970                 975

Arg Thr Glu Met Ala Gln Ala Val Ala Gln Ala Gly Thr Gly Phe Arg

-continued

```
                980             985             990
Gly Val Leu Ser Leu Leu Ser Ser Asp Glu Ser Ala Cys Arg Pro Gly
                    995             1000            1005

Val Pro Ala Gly Ala Val Gly Leu Leu Thr Leu Val Gln Ala Leu Gly
1010            1015            1020

Asp Ala Gly Val Asp Ala Pro Val Trp Cys Leu Thr Gln Gly Ala Val
1025            1030            1035            1040

Arg Thr Pro Ala Asp Asp Leu Ala Arg Pro Ala Gln Thr Thr Ala
            1045            1050            1055

His Gly Phe Ala Gln Val Ala Gly Leu Glu Leu Pro Arg Trp Gly
        1060            1065            1070

Gly Val Val Asp Leu Pro Glu Ser Val Asp Asp Ala Ala Leu Arg Leu
        1075            1080            1085

Leu Val Ala Val Leu Arg Gly Gly Arg Ala Glu Asp His Leu Ala
        1090            1095            1100

Val Arg Asp Gly Arg Leu His Gly Arg Arg Val Val Arg Ala Ser Leu
1105            1110            1115            1120

Pro Gln Ser Gly Ser Arg Ser Trp Thr Pro His Gly Thr Val Leu Val
            1125            1130            1135

Thr Gly Ala Ala Ser Pro Val Gly Asp Gln Leu Val Arg Trp Leu Ala
            1140            1145            1150

Asp Arg Gly Ala Glu Arg Leu Val Leu Ala Gly Ala Cys Pro Gly Asp
        1155            1160            1165

Asp Leu Leu Ala Ala Val Glu Glu Ala Gly Ala Ser Ala Val Val Cys
        1170            1175            1180

Ala Gln Asp Ala Ala Ala Leu Arg Glu Ala Leu Gly Asp Glu Pro Val
1185            1190            1195            1200

Thr Ala Leu Val His Ala Gly Thr Leu Thr Asn Phe Gly Ser Ile Ser
            1205            1210            1215

Glu Val Ala Pro Glu Glu Phe Ala Glu Thr Ile Ala Ala Lys Thr Ala
            1220            1225            1230

Leu Leu Ala Val Leu Asp Glu Val Leu Gly Asp Arg Ala Val Glu Arg
            1235            1240            1245

Glu Val Tyr Cys Ser Ser Val Ala Gly Ile Trp Gly Gly Ala Gly Met
            1250            1255            1260

Ala Ala Tyr Ala Ala Gly Ser Ala Tyr Leu Asp Ala Leu Ala Glu His
1265            1270            1275            1280

His Arg Ala Arg Gly Arg Ser Cys Thr Ser Val Ala Trp Thr Pro Trp
            1285            1290            1295

Ala Leu Pro Gly Gly Ala Val Asp Asp Gly Tyr Leu Arg Glu Arg Gly
            1300            1305            1310

Leu Arg Ser Leu Ser Ala Asp Arg Ala Met Arg Thr Trp Glu Arg Val
            1315            1320            1325

Leu Ala Ala Gly Pro Val Ser Val Ala Val Ala Asp Val Asp Trp Pro
            1330            1335            1340

Val Leu Ser Glu Gly Phe Ala Thr Arg Pro Thr Ala Leu Phe Ala
1345            1350            1355            1360

Glu Leu Ala Gly Arg Gly Gly Gln Ala Glu Ala Glu Pro Asp Ser Gly
            1365            1370            1375

Pro Thr Gly Glu Pro Ala Gln Arg Leu Ala Gly Leu Ser Pro Asp Glu
            1380            1385            1390

Gln Gln Glu Asn Leu Leu Glu Leu Val Ala Asn Ala Val Ala Glu Val
            1395            1400            1405
```

-continued

```
Leu Gly His Glu Ser Ala Ala Glu Ile Asn Val Arg Arg Ala Phe Ser
    1410                1415                1420

Glu Leu Gly Leu Asp Ser Leu Asn Ala Met Ala Leu Arg Lys Arg Leu
1425                1430                1435                1440

Ser Ala Ser Thr Gly Leu Arg Leu Pro Ala Ser Leu Val Phe Asp His
                1445                1450                1455

Pro Thr Val Thr Ala Leu Ala Gln His Leu Arg Ala Arg Leu Val Gly
            1460                1465                1470

Asp Ala Asp Gln Ala Ala Val Arg Val Gly Ala Ala Asp Glu Ser
        1475                1480                1485

Glu Pro Ile Ala Ile Val Gly Ile Gly Cys Arg Phe Pro Gly Gly Ile
    1490                1495                1500

Gly Ser Pro Glu Gln Leu Trp Arg Val Leu Ala Glu Gly Ala Asn Leu
1505                1510                1515                1520

Thr Thr Gly Phe Pro Ala Asp Arg Gly Trp Asp Ile Gly Arg Leu Tyr
                1525                1530                1535

His Pro Asp Pro Asp Asn Pro Gly Thr Ser Tyr Val Asp Lys Gly Gly
            1540                1545                1550

Phe Leu Thr Asp Ala Ala Asp Phe Asp Pro Gly Phe Gly Ile Thr
        1555                1560                1565

Pro Arg Glu Ala Leu Ala Met Asp Pro Gln Gln Arg Leu Met Leu Glu
    1570                1575                1580

Thr Ala Trp Glu Ala Val Glu Arg Ala Gly Ile Asp Pro Asp Ala Leu
1585                1590                1595                1600

Arg Gly Thr Asp Thr Gly Val Phe Val Gly Met Asn Gly Gln Ser Tyr
                1605                1610                1615

Met Gln Leu Leu Ala Gly Glu Ala Glu Arg Val Asp Gly Tyr Gln Gly
        1620                1625                1630

Leu Gly Asn Ser Ala Ser Val Leu Ser Gly Arg Ile Ala Tyr Thr Phe
    1635                1640                1645

Gly Trp Glu Gly Pro Ala Leu Thr Val Asp Thr Ala Cys Ser Ser Ser
1650                1655                1660

Leu Val Gly Ile His Leu Ala Met Gln Ala Leu Arg Arg Gly Glu Cys
1665                1670                1675                1680

Ser Leu Ala Leu Ala Gly Gly Val Thr Val Met Ser Asp Pro Tyr Thr
                1685                1690                1695

Phe Val Asp Phe Ser Thr Gln Arg Gly Leu Ala Ser Asp Gly Arg Cys
        1700                1705                1710

Lys Ala Phe Ser Ala Arg Ala Asp Gly Phe Ala Leu Ser Glu Gly Val
    1715                1720                1725

Ala Ala Leu Val Leu Glu Pro Leu Ser Arg Ala Arg Ala Asn Gly His
    1730                1735                1740

Gln Val Leu Ala Val Leu Arg Gly Ser Ala Val Asn Gln Asp Gly Ala
1745                1750                1755                1760

Ser Asn Gly Leu Ala Ala Pro Asn Gly Pro Ser Gln Glu Arg Val Ile
                1765                1770                1775

Arg Gln Ala Leu Ala Ala Ser Gly Val Pro Ala Ala Asp Val Asp Val
            1780                1785                1790

Val Glu Ala His Gly Thr Gly Thr Glu Leu Gly Asp Pro Ile Glu Ala
        1795                1800                1805

Gly Ala Leu Ile Ala Thr Tyr Gly Gln Asp Arg Asp Arg Pro Leu Arg
    1810                1815                1820

Leu Gly Ser Val Lys Thr Asn Ile Gly His Thr Gln Ala Ala Ala Gly
1825                1830                1835                1840
```

```
Ala Ala Gly Val Ile Lys Val Val Leu Ala Met Arg His Gly Met Leu
            1845                1850                1855

Pro Arg Ser Leu His Ala Asp Glu Leu Ser Pro His Ile Asp Trp Glu
            1860                1865                1870

Ser Gly Ala Val Glu Val Leu Arg Glu Val Pro Trp Pro Ala Gly
            1875                1880            1885

Glu Arg Pro Arg Arg Ala Gly Val Ser Ser Phe Gly Val Ser Gly Thr
            1890                1895                1900

Asn Ala His Val Ile Val Glu Glu Ala Pro Ala Glu Gln Glu Ala Ala
1905                1910                1915                1920

Arg Thr Glu Arg Gly Pro Leu Pro Phe Val Leu Ser Gly Arg Ser Glu
            1925                1930                1935

Ala Val Val Ala Ala Gln Ala Arg Ala Leu Ala Glu His Leu Arg Asp
            1940                1945                1950

Thr Pro Glu Leu Gly Leu Thr Asp Ala Ala Trp Thr Leu Ala Thr Gly
            1955                1960                1965

Arg Ala Arg Phe Asp Val Arg Ala Ala Val Leu Gly Asp Asp Arg Ala
            1970                1975                1980

Gly Val Cys Ala Glu Leu Asp Ala Leu Ala Glu Gly Arg Pro Ser Ala
1985                1990                1995                2000

Asp Ala Val Ala Pro Val Thr Ser Ala Pro Arg Lys Pro Val Leu Val
            2005                2010                2015

Phe Pro Gly Gln Gly Ala Gln Trp Val Gly Met Ala Arg Asp Leu Leu
            2020                2025                2030

Glu Ser Ser Glu Val Phe Ala Glu Ser Met Ser Arg Cys Ala Glu Ala
            2035                2040                2045

Leu Ser Pro His Thr Asp Trp Lys Leu Leu Asp Val Val Arg Gly Asp
            2050                2055                2060

Gly Gly Pro Asp Pro His Glu Arg Val Asp Val Leu Gln Pro Val Leu
2065                2070                2075                2080

Phe Ser Ile Met Val Ser Leu Ala Glu Leu Trp Arg Ala His Gly Val
            2085                2090                2095

Thr Pro Ala Ala Val Val Gly His Ser Gln Gly Glu Ile Ala Ala Ala
            2100                2105                2110

His Val Ala Gly Ala Leu Ser Leu Glu Ala Ala Ala Lys Val Val Ala
            2115                2120                2125

Leu Arg Ser Gln Val Leu Arg Glu Leu Asp Asp Gln Gly Gly Met Val
            2130                2135                2140

Ser Val Gly Ala Ser Arg Asp Glu Leu Glu Thr Val Leu Ala Arg Trp
2145                2150                2155                2160

Asp Gly Arg Val Ala Val Ala Ala Val Asn Gly Pro Gly Thr Ser Val
            2165                2170                2175

Val Ala Gly Pro Thr Ala Glu Leu Asp Glu Phe Phe Ala Glu Ala Glu
            2180                2185                2190

Ala Arg Glu Met Lys Pro Arg Arg Ile Ala Val Arg Tyr Ala Ser His
            2195                2200                2205

Ser Pro Glu Val Ala Arg Ile Glu Asp Arg Leu Ala Ala Glu Leu Gly
            2210                2215                2220

Thr Ile Thr Ala Val Arg Gly Ser Val Pro Leu His Ser Thr Val Thr
2225                2230                2235                2240

Gly Glu Val Ile Asp Thr Ser Ala Met Asp Ala Ser Tyr Trp Tyr Arg
            2245                2250                2255

Asn Leu Arg Arg Pro Val Leu Phe Glu Gln Ala Val Arg Gly Leu Val
```

-continued

```
          2260                2265                2270
Glu Gln Gly Phe Asp Thr Phe Val Glu Val Ser Pro His Pro Val Leu
        2275                2280                2285
Leu Met Ala Val Glu Thr Ala Glu His Ala Gly Ala Glu Val Thr
    2290                2295                2300
Cys Val Pro Thr Leu Arg Arg Glu Gln Ser Gly Pro His Glu Phe Leu
2305                2310                2315                2320
Arg Asn Leu Leu Arg Ala His Val His Gly Val Gly Ala Asp Leu Arg
                2325                2330                2335
Pro Ala Val Ala Gly Gly Arg Pro Ala Glu Leu Pro Thr Tyr Pro Phe
            2340                2345                2350
Glu His Gln Arg Phe Trp Pro Arg Pro His Arg Pro Ala Asp Val Ser
        2355                2360                2365
Ala Leu Gly Val Arg Gly Ala Glu His Pro Leu Leu Leu Ala Ala Val
    2370                2375                2380
Asp Val Pro Gly His Gly Gly Ala Val Phe Thr Gly Arg Leu Ser Thr
2385                2390                2395                2400
Asp Glu Gln Pro Trp Leu Ala Glu His Val Val Gly Gly Arg Thr Leu
                2405                2410                2415
Val Pro Gly Ser Val Leu Val Asp Leu Ala Leu Ala Ala Gly Glu Asp
            2420                2425                2430
Val Gly Leu Pro Val Leu Glu Glu Leu Val Leu Gln Arg Pro Leu Val
        2435                2440                2445
Leu Ala Gly Ala Gly Ala Leu Leu Arg Met Ser Val Gly Ala Pro Asp
    2450                2455                2460
Glu Ser Gly Arg Arg Thr Ile Asp Val His Ala Ala Glu Asp Val Ala
2465                2470                2475                2480
Asp Leu Ala Asp Ala Gln Trp Ser Gly His Ala Thr Gly Thr Leu Ala
                2485                2490                2495
Gln Gly Val Ala Ala Gly Pro Arg Asp Thr Glu Gln Trp Pro Pro Glu
            2500                2505                2510
Asp Ala Val Arg Ile Pro Leu Asp Asp His Tyr Asp Gly Leu Ala Glu
        2515                2520                2525
Gln Gly Tyr Glu Tyr Gly Pro Ser Phe Gln Ala Leu Arg Ala Ala Trp
    2530                2535                2540
Arg Lys Asp Asp Ser Val Tyr Ala Glu Val Ser Ile Ala Ala Asp Glu
2545                2550                2555                2560
Glu Gly Tyr Ala Phe His Pro Val Leu Leu Asp Ala Val Ala Gln Thr
            2565                2570                2575
Leu Ser Leu Gly Ala Leu Gly Glu Pro Gly Gly Gly Lys Leu Pro Phe
        2580                2585                2590
Ala Trp Asn Thr Val Thr Leu His Ala Ser Gly Ala Thr Ser Val Arg
    2595                2600                2605
Val Val Ala Thr Pro Ala Gly Ala Asp Ala Met Ala Leu Arg Val Thr
    2610                2615                2620
Asp Pro Ala Gly His Leu Val Ala Thr Val Asp Ser Leu Val Val Arg
2625                2630                2635                2640
Ser Thr Gly Glu Lys Trp Glu Gln Pro Glu Pro Arg Gly Gly Glu Gly
            2645                2650                2655
Glu Leu His Ala Leu Asp Trp Gly Arg Leu Ala Glu Pro Gly Ser Thr
        2660                2665                2670
Gly Arg Val Val Ala Ala Asp Ala Ser Asp Leu Asp Ala Val Leu Arg
    2675                2680                2685
```

```
Ser Gly Glu Pro Glu Pro Asp Ala Val Leu Val Arg Tyr Glu Pro Glu
    2690            2695                2700

Gly Asp Asp Pro Arg Ala Ala Arg His Gly Val Leu Trp Ala Ala
2705            2710            2715                2720

Ala Leu Val Arg Arg Trp Leu Glu Gln Glu Leu Pro Gly Ala Thr
            2725            2730            2735

Leu Val Ile Ala Thr Ser Gly Ala Val Thr Val Ser Asp Asp Ser
            2740            2745            2750

Val Pro Glu Pro Gly Ala Ala Met Trp Gly Val Ile Arg Cys Ala
            2755            2760            2765

Gln Ala Glu Ser Pro Asp Arg Phe Val Leu Leu Asp Thr Asp Ala Glu
    2770            2775            2780

Pro Gly Met Leu Pro Ala Val Pro Asp Asn Pro Gln Leu Ala Leu Arg
2785            2790            2795            2800

Gly Asp Asp Val Phe Val Pro Arg Leu Ser Pro Leu Ala Pro Ser Ala
                2805            2810            2815

Leu Thr Leu Pro Ala Gly Thr Gln Arg Leu Val Pro Gly Asp Gly Ala
            2820            2825            2830

Ile Asp Ser Val Ala Phe Glu Pro Ala Pro Asp Val Glu Gln Pro Leu
    2835            2840            2845

Arg Ala Gly Glu Val Arg Val Asp Val Arg Ala Thr Gly Val Asn Phe
    2850            2855            2860

Arg Asp Val Leu Leu Ala Leu Gly Met Tyr Pro Gln Lys Ala Asp Met
2865            2870            2875            2880

Gly Thr Glu Ala Ala Gly Val Val Thr Ala Val Gly Pro Asp Val Asp
                2885            2890            2895

Ala Phe Ala Pro Gly Asp Arg Val Leu Gly Leu Phe Gln Gly Ala Phe
            2900            2905            2910

Ala Pro Ile Ala Val Thr Asp His Arg Leu Leu Ala Arg Val Pro Asp
            2915            2920            2925

Gly Trp Ser Asp Ala Asp Ala Ala Val Pro Ile Ala Tyr Thr Thr
    2930            2935            2940

Ala His Tyr Ala Leu His Asp Leu Ala Gly Leu Arg Ala Gly Gln Ser
2945            2950            2955            2960

Val Leu Ile His Ala Ala Ala Gly Gly Val Gly Met Ala Ala Val Ala
                2965            2970            2975

Leu Ala Arg Arg Ala Gly Ala Glu Val Leu Ala Thr Ala Gly Pro Ala
            2980            2985            2990

Lys His Gly Thr Leu Arg Ala Leu Gly Leu Asp Asp Glu His Ile Ala
            2995            3000            3005

Ser Ser Arg Glu Thr Gly Phe Ala Arg Lys Phe Arg Glu Arg Thr Gly
    3010            3015            3020

Gly Arg Gly Val Asp Val Val Leu Asn Ser Leu Thr Gly Glu Leu Leu
3025            3030            3035            3040

Asp Glu Ser Ala Asp Leu Leu Ala Glu Asp Gly Val Phe Val Glu Met
                3045            3050            3055

Gly Lys Thr Asp Leu Arg Asp Ala Gly Asp Phe Arg Gly Arg Tyr Ala
            3060            3065            3070

Pro Phe Asp Leu Gly Glu Ala Gly Asp Asp Arg Leu Gly Glu Ile Leu
            3075            3080            3085

Arg Glu Val Val Gly Leu Leu Gly Ala Gly Glu Leu Asp Arg Leu Pro
    3090            3095            3100

Val Ser Ala Trp Glu Leu Gly Ser Ala Pro Ala Ala Leu Gln His Met
3105            3110            3115            3120
```

-continued

```
Ser Arg Gly Arg His Val Gly Lys Leu Val Leu Thr Gln Pro Ala Pro
            3125                3130                3135

Val Asp Pro Asp Gly Thr Val Leu Ile Thr Gly Gly Thr Gly Thr Leu
            3140                3145                3150

Gly Arg Leu Leu Ala Arg His Leu Val Thr Glu His Gly Val Arg His
            3155                3160                3165

Leu Leu Leu Val Ser Arg Arg Gly Ala Asp Ala Pro Gly Ser Asp Glu
            3170                3175                3180

Leu Arg Ala Glu Ile Glu Asp Leu Gly Ala Ser Ala Glu Ile Ala Ala
3185                3190                3195                3200

Cys Asp Thr Ala Asp Arg Asp Ala Leu Ser Ala Leu Leu Asp Gly Leu
            3205                3210                3215

Pro Arg Pro Leu Thr Gly Val Val His Ala Ala Gly Val Leu Ala Asp
            3220                3225                3230

Gly Leu Val Thr Ser Ile Asp Glu Pro Ala Val Glu Gln Val Leu Arg
            3235                3240                3245

Ala Lys Val Asp Ala Ala Trp Asn Leu His Glu Leu Thr Ala Asn Thr
            3250                3255                3260

Gly Leu Ser Phe Phe Val Leu Phe Ser Ser Ala Ala Ser Val Leu Ala
3265                3270                3275                3280

Gly Pro Gly Gln Gly Val Tyr Ala Ala Ala Asn Glu Ser Leu Asn Ala
            3285                3290                3295

Leu Ala Ala Leu Arg Arg Thr Arg Gly Leu Pro Ala Lys Ala Leu Gly
            3300                3305                3310

Trp Gly Leu Trp Ala Gln Ala Ser Glu Met Thr Ser Gly Leu Gly Asp
            3315                3320                3325

Arg Ile Ala Arg Thr Gly Val Ala Ala Leu Pro Thr Glu Arg Ala Leu
            3330                3335                3340

Ala Leu Phe Asp Ser Ala Leu Arg Arg Gly Gly Glu Val Val Phe Pro
3345                3350                3355                3360

Leu Ser Ile Asn Arg Ser Ala Leu Arg Arg Ala Glu Phe Val Pro Glu
            3365                3370                3375

Val Leu Arg Gly Met Val Arg Ala Lys Leu Arg Ala Ala Gly Gln Ala
            3380                3385                3390

Glu Ala Ala Gly Pro Asn Val Val Asp Arg Leu Ala Gly Arg Ser Glu
            3395                3400                3405

Ser Asp Gln Val Ala Gly Leu Ala Glu Leu Val Arg Ser His Ala Ala
            3410                3415                3420

Ala Val Ser Gly Tyr Gly Ser Ala Asp Gln Leu Pro Glu Arg Lys Ala
3425                3430                3435                3440

Phe Lys Asp Leu Gly Phe Asp Ser Leu Ala Ala Val Glu Leu Arg Asn
            3445                3450                3455

Arg Leu Gly Thr Ala Thr Gly Val Arg Leu Pro Ser Thr Leu Val Phe
            3460                3465                3470

Asp His Pro Thr Pro Leu Ala Val Ala Glu His Leu Arg Asp Arg Leu
            3475                3480                3485

Phe Ala Ala Ser Pro Ala Val Asp Ile Gly Asp Arg Leu Asp Glu Leu
            3490                3495                3500

Glu Lys Ala Leu Glu Ala Leu Ser Ala Glu Asp Gly His Asp Asp Val
3505                3510                3515                3520

Gly Gln Arg Leu Glu Ser Leu Leu Arg Arg Trp Asn Ser Arg Arg Ala
            3525                3530                3535

Asp Ala Pro Ser Thr Ser Ala Ile Ser Glu Asp Ala Ser Asp Asp Glu
```

```
                3540                3545                3550
Leu Phe Ser Met Leu Asp Gln Arg Phe Gly Gly Glu Asp Leu
        3555                3560                3565
```

(2) INFORMATION FOR SEQ ID NO:5:

(i) SEQUENCE CHARACTERISTICS:
        (A) LENGTH: 3170 amino acids
        (B) TYPE: amino acid
        (D) TOPOLOGY: linear (ii) MOLECULE TYPE: protein (xi) SEQUENCE DESCRIPTION: SEQ ID NO:5:

```
Met Ser Gly Asp Asn Gly Met Thr Glu Glu Lys Leu Arg Arg Tyr Leu
 1               5                  10                  15
Lys Arg Thr Val Thr Glu Leu Asp Ser Val Thr Ala Arg Leu Arg Glu
             20                  25                  30
Val Glu His Arg Ala Gly Glu Pro Ile Ala Ile Val Gly Met Ala Cys
         35                  40                  45
Arg Phe Pro Gly Asp Val Asp Ser Pro Glu Ser Phe Trp Glu Phe Val
     50                  55                  60
Ser Gly Gly Asp Ala Ile Ala Glu Ala Pro Ala Asp Arg Gly Trp
 65                  70                  75                  80
Glu Pro Asp Pro Asp Ala Arg Leu Gly Gly Met Leu Ala Ala Gly
                 85                  90                  95
Asp Phe Asp Ala Gly Phe Phe Gly Ile Ser Pro Arg Glu Ala Leu Ala
                100                 105                 110
Met Asp Pro Gln Gln Arg Ile Met Leu Glu Ile Ser Trp Glu Ala Leu
            115                 120                 125
Glu Arg Ala Gly His Asp Pro Val Ser Leu Arg Gly Ser Ala Thr Gly
        130                 135                 140
Val Phe Thr Gly Val Gly Thr Val Asp Tyr Gly Pro Arg Pro Asp Glu
145                 150                 155                 160
Ala Pro Asp Glu Val Leu Gly Tyr Val Gly Thr Gly Thr Ala Ser Ser
                165                 170                 175
Val Ala Ser Gly Arg Val Ala Tyr Cys Leu Gly Leu Glu Gly Pro Ala
            180                 185                 190
Met Thr Val Asp Thr Ala Cys Ser Ser Gly Leu Thr Ala Leu His Leu
        195                 200                 205
Ala Met Glu Ser Leu Arg Arg Asp Glu Cys Gly Leu Ala Leu Ala Gly
    210                 215                 220
Gly Val Thr Val Met Ser Ser Pro Gly Ala Phe Thr Glu Phe Arg Ser
225                 230                 235                 240
Gln Gly Gly Leu Ala Ala Asp Gly Arg Cys Lys Pro Phe Ser Lys Ala
                245                 250                 255
Ala Asp Gly Phe Gly Leu Ala Glu Gly Ala Gly Val Leu Val Leu Gln
            260                 265                 270
Arg Leu Ser Ala Ala Arg Arg Glu Gly Arg Pro Val Leu Ala Val Leu
        275                 280                 285
Arg Gly Ser Ala Val Asn Gln Asp Gly Ala Ser Asn Gly Leu Thr Ala
    290                 295                 300
Pro Ser Gly Pro Ala Gln Gln Arg Val Ile Arg Arg Ala Leu Glu Asn
305                 310                 315                 320
Ala Gly Val Arg Ala Gly Asp Val Asp Tyr Val Glu Ala His Gly Thr
                325                 330                 335
```

-continued

```
Gly Thr Arg Leu Gly Asp Pro Ile Glu Val His Ala Leu Leu Ser Thr
            340                 345                 350

Tyr Gly Ala Glu Arg Asp Pro Asp Pro Leu Trp Ile Gly Ser Val
        355                 360                 365

Lys Ser Asn Ile Gly His Thr Gln Ala Ala Gly Val Ala Gly Val
370                 375                 380

Met Lys Ala Val Leu Ala Leu Arg His Gly Glu Met Pro Arg Thr Leu
385                 390                 395                 400

His Phe Asp Glu Pro Ser Pro Gln Ile Glu Trp Asp Leu Gly Ala Val
                405                 410                 415

Ser Val Val Ser Gln Ala Arg Ser Trp Pro Ala Gly Glu Arg Pro Arg
                420                 425                 430

Arg Ala Gly Val Ser Ser Phe Gly Ile Ser Gly Thr Asn Ala His Val
            435                 440                 445

Ile Val Glu Glu Ala Pro Glu Ala Asp Glu Pro Glu Pro Ala Pro Asp
450                 455                 460

Ser Gly Pro Val Pro Leu Val Leu Ser Gly Arg Asp Glu Gln Ala Met
465                 470                 475                 480

Arg Ala Gln Ala Gly Arg Leu Ala Asp His Leu Ala Arg Glu Pro Arg
                485                 490                 495

Asn Ser Leu Arg Asp Thr Gly Phe Thr Leu Ala Thr Arg Ser Ala
            500                 505                 510

Trp Glu His Arg Ala Val Val Gly Asp Arg Asp Ala Leu Ala
        515                 520                 525

Gly Leu Arg Ala Val Ala Asp Gly Arg Ile Ala Asp Arg Thr Ala Thr
        530                 535                 540

Gly Gln Ala Arg Thr Arg Arg Gly Val Ala Met Val Phe Pro Gly Gln
545                 550                 555                 560

Gly Ala Gln Trp Gln Gly Met Ala Arg Asp Leu Leu Arg Glu Ser Gln
                565                 570                 575

Val Phe Ala Asp Ser Ile Arg Asp Cys Glu Arg Ala Leu Ala Pro His
                580                 585                 590

Val Asp Trp Ser Leu Thr Asp Leu Leu Ser Gly Ala Arg Pro Leu Asp
                595                 600                 605

Arg Val Asp Val Val Gln Pro Ala Leu Phe Ala Val Met Val Ser Leu
            610                 615                 620

Ala Ala Leu Trp Arg Ser His Gly Val Glu Pro Ala Val Val Gly
625                 630                 635                 640

His Ser Gln Gly Glu Ile Ala Ala His Val Ala Gly Ala Leu Thr
                645                 650                 655

Leu Glu Asp Ala Ala Lys Leu Val Ala Val Arg Ser Arg Val Leu Ala
            660                 665                 670

Arg Leu Gly Gly Gln Gly Gly Met Ala Ser Phe Gly Leu Gly Thr Glu
        675                 680                 685

Gln Ala Ala Glu Arg Ile Gly Arg Phe Ala Gly Ala Leu Ser Ile Ala
        690                 695                 700

Ser Val Asn Gly Pro Arg Ser Val Val Ala Gly Glu Ser Gly Pro
705                 710                 715                 720

Leu Asp Glu Leu Ile Ala Glu Cys Glu Ala Glu Gly Ile Thr Ala Arg
                725                 730                 735

Arg Ile Pro Val Asp Tyr Ala Ser His Ser Pro Gln Val Glu Ser Leu
            740                 745                 750

Arg Glu Glu Leu Leu Thr Glu Leu Ala Gly Ile Ser Pro Val Ser Ala
        755                 760                 765
```

-continued

```
Asp Val Ala Leu Tyr Ser Thr Thr Thr Gly Gln Pro Ile Asp Thr Ala
        770                 775                 780

Thr Met Asp Thr Ala Tyr Trp Tyr Ala Asn Leu Arg Glu Gln Val Arg
785                 790                 795                 800

Phe Gln Asp Ala Thr Arg Gln Leu Ala Glu Ala Gly Phe Asp Ala Phe
                805                 810                 815

Val Glu Val Ser Pro His Pro Val Leu Thr Val Gly Ile Glu Ala Thr
                820                 825                 830

Leu Asp Ser Ala Leu Pro Ala Asp Ala Gly Ala Cys Val Val Gly Thr
        835                 840                 845

Leu Arg Arg Asp Arg Gly Gly Leu Ala Asp Phe His Thr Ala Leu Gly
        850                 855                 860

Glu Ala Tyr Ala Gln Gly Val Glu Val Asp Trp Ser Pro Ala Phe Ala
865                 870                 875                 880

Asp Ala Arg Pro Val Glu Leu Pro Val Tyr Pro Phe Gln Arg Gln Arg
                885                 890                 895

Tyr Trp Leu Pro Ile Pro Thr Gly Gly Arg Ala Arg Asp Glu Asp Asp
                900                 905                 910

Asp Trp Arg Tyr Gln Val Val Trp Arg Glu Ala Glu Trp Glu Ser Ala
        915                 920                 925

Ser Leu Ala Gly Arg Val Leu Val Thr Gly Pro Gly Val Pro Ser
        930                 935                 940

Glu Leu Ser Asp Ala Ile Arg Ser Gly Leu Glu Gln Ser Gly Ala Thr
945                 950                 955                 960

Val Leu Thr Cys Asp Val Glu Ser Arg Ser Thr Ile Gly Thr Ala Leu
                965                 970                 975

Glu Ala Ala Asp Thr Asp Ala Leu Ser Thr Val Val Ser Leu Leu Ser
                980                 985                 990

Arg Asp Gly Glu Ala Val Asp Pro Ser Leu Asp Ala Leu Ala Leu Val
        995                 1000                1005

Gln Ala Leu Gly Ala Ala Gly Val Glu Ala Pro Leu Trp Val Leu Thr
        1010                1015                1020

Arg Asn Ala Val Gln Val Ala Asp Gly Glu Leu Val Asp Pro Ala Gln
1025                1030                1035                1040

Ala Met Val Gly Gly Leu Gly Arg Val Val Gly Ile Glu Gln Pro Gly
                1045                1050                1055

Arg Trp Gly Gly Leu Val Asp Leu Val Asp Ala Asp Ala Ala Ser Ile
                1060                1065                1070

Arg Ser Leu Ala Ala Val Leu Ala Asp Pro Arg Gly Glu Glu Gln Val
        1075                1080                1085

Ala Ile Arg Ala Asp Gly Ile Lys Val Ala Arg Leu Val Pro Ala Pro
        1090                1095                1100

Ala Arg Ala Ala Arg Thr Arg Trp Ser Pro Arg Gly Thr Val Leu Val
1105                1110                1115                1120

Thr Gly Gly Thr Gly Gly Ile Gly Ala His Val Ala Arg Trp Leu Ala
                1125                1130                1135

Arg Ser Gly Ala Glu His Leu Val Leu Leu Gly Arg Arg Gly Ala Asp
                1140                1145                1150

Ala Pro Gly Ala Ser Glu Leu Arg Glu Glu Leu Thr Ala Leu Gly Thr
        1155                1160                1165

Gly Val Thr Ile Ala Ala Cys Asp Val Ala Asp Arg Ala Arg Leu Glu
        1170                1175                1180

Ala Val Leu Ala Ala Glu Arg Ala Glu Gly Arg Thr Val Ser Ala Val
```

-continued

```
            1185                1190                1195                1200
Met His Ala Ala Gly Val Ser Thr Ser Thr Pro Leu Asp Asp Leu Thr
                    1205                1210                1215

Glu Ala Glu Phe Thr Glu Ile Ala Asp Val Lys Val Arg Gly Thr Val
            1220                1225                1230

Asn Leu Asp Glu Leu Cys Pro Asp Leu Asp Ala Phe Val Leu Phe Ser
            1235                1240                1245

Ser Asn Ala Gly Val Trp Gly Ser Pro Gly Leu Ala Ser Tyr Ala Ala
            1250                1255                1260

Ala Asn Ala Phe Leu Asp Gly Phe Ala Arg Arg Arg Ser Glu Gly
1265                1270                1275                1280

Ala Pro Val Thr Ser Ile Ala Trp Gly Leu Trp Ala Gly Gln Asn Met
            1285                1290                1295

Ala Gly Asp Glu Gly Gly Glu Tyr Leu Arg Ser Gln Gly Leu Arg Ala
            1300                1305                1310

Met Asp Pro Asp Arg Ala Val Glu Glu Leu His Ile Thr Leu Asp His
            1315                1320                1325

Gly Gln Thr Ser Val Ser Val Val Asp Met Asp Arg Arg Arg Phe Val
            1330                1335                1340

Glu Leu Phe Thr Ala Ala Arg His Arg Pro Leu Phe Asp Glu Ile Ala
1345                1350                1355                1360

Gly Ala Arg Ala Glu Ala Arg Gln Ser Glu Glu Gly Pro Ala Leu Ala
            1365                1370                1375

Gln Arg Leu Ala Ala Leu Ser Thr Ala Glu Arg Arg Glu His Leu Ala
            1380                1385                1390

His Leu Ile Arg Ala Glu Val Ala Ala Leu Gly His Gly Asp Asp
            1395                1400                1405

Ala Ala Ile Asp Arg Asp Arg Ala Phe Arg Asp Leu Gly Phe Asp Ser
            1410                1415                1420

Met Thr Ala Val Asp Leu Arg Asn Arg Leu Ala Ala Val Thr Gly Val
1425                1430                1435                1440

Arg Glu Ala Ala Thr Val Val Phe Asp His Pro Thr Ile Thr Arg Leu
            1445                1450                1455

Ala Asp His Tyr Leu Glu Arg Leu Val Gly Ala Ala Glu Ala Glu Gln
            1460                1465                1470

Ala Pro Ala Leu Val Arg Glu Val Pro Lys Asp Ala Asp Pro Ile
            1475                1480                1485

Ala Ile Val Gly Met Ala Cys Arg Phe Pro Gly Gly Val His Asn Pro
            1490                1495                1500

Gly Glu Leu Trp Glu Phe Ile Val Gly Arg Gly Asp Ala Val Thr Glu
1505                1510                1515                1520

Met Pro Thr Asp Arg Gly Trp Asp Leu Asp Ala Leu Phe Asp Pro Asp
            1525                1530                1535

Pro Gln Arg His Gly Thr Ser Tyr Ser Arg His Gly Ala Phe Leu Asp
            1540                1545                1550

Gly Ala Ala Asp Phe Asp Ala Ala Phe Phe Gly Ile Ser Pro Arg Glu
            1555                1560                1565

Ala Leu Ala Met Asp Pro Gln Gln Arg Gln Val Leu Glu Thr Thr Trp
1570                1575                1580

Glu Leu Phe Glu Asn Ala Gly Ile Asp Pro His Ser Leu Arg Gly Ser
1585                1590                1595                1600

Asp Thr Gly Val Phe Leu Gly Ala Ala Tyr Gln Gly Tyr Gly Gln Asp
            1605                1610                1615
```

```
Ala Val Val Pro Glu Asp Ser Glu Gly Tyr Leu Leu Thr Gly Asn Ser
             1620                1625                1630

Ser Ala Val Val Ser Gly Arg Val Ala Tyr Val Leu Gly Leu Glu Gly
         1635                1640                1645

Pro Ala Val Thr Val Asp Thr Ala Cys Ser Ser Leu Val Ala Leu
     1650                1655                1660

His Ser Ala Cys Gly Ser Leu Arg Asp Gly Asp Cys Gly Leu Ala Val
1665                1670                1675                1680

Ala Gly Gly Val Ser Val Met Ala Gly Pro Glu Val Phe Thr Glu Phe
             1685                1690                1695

Ser Arg Gln Gly Gly Leu Ala Val Asp Gly Arg Cys Lys Ala Phe Ser
         1700                1705                1710

Ala Glu Ala Asp Gly Phe Gly Phe Ala Glu Gly Val Ala Val Val Leu
     1715                1720                1725

Leu Gln Arg Leu Ser Asp Ala Arg Arg Ala Gly Arg Gln Val Leu Gly
     1730                1735                1740

Val Val Ala Gly Ser Ala Ile Asn Gln Asp Gly Ala Ser Asn Gly Leu
1745                1750                1755                1760

Ala Ala Pro Ser Gly Val Ala Gln Gln Arg Val Ile Arg Lys Ala Trp
             1765                1770                1775

Ala Arg Ala Gly Ile Thr Gly Ala Asp Val Ala Val Val Glu Ala His
         1780                1785                1790

Gly Thr Gly Thr Arg Leu Gly Asp Pro Val Glu Ala Ser Ala Leu Leu
     1795                1800                1805

Ala Thr Tyr Gly Lys Ser Arg Gly Ser Ser Gly Pro Val Leu Leu Gly
     1810                1815                1820

Ser Val Lys Ser Asn Ile Gly His Ala Gln Ala Ala Gly Val Ala
1825                1830                1835                1840

Gly Val Ile Lys Val Val Leu Gly Leu Asn Arg Gly Leu Val Pro Pro
             1845                1850                1855

Met Leu Cys Arg Gly Glu Arg Ser Pro Leu Ile Glu Trp Ser Ser Gly
         1860                1865                1870

Gly Val Glu Leu Ala Glu Ala Val Ser Pro Trp Pro Ala Ala Asp
     1875                1880                1885

Gly Val Arg Arg Ala Gly Val Ser Ala Phe Gly Val Ser Gly Thr Asn
     1890                1895                1900

Ala His Val Ile Ile Ala Glu Pro Pro Glu Pro Glu Pro Leu Pro Glu
1905                1910                1915                1920

Pro Gly Pro Val Gly Val Leu Ala Ala Ala Asn Ser Val Pro Val Leu
             1925                1930                1935

Leu Ser Ala Arg Thr Glu Thr Ala Leu Ala Ala Gln Ala Arg Leu Leu
         1940                1945                1950

Glu Ser Ala Val Asp Asp Ser Val Pro Leu Thr Ala Leu Ala Ser Ala
     1955                1960                1965

Leu Ala Thr Gly Arg Ala His Leu Pro Arg Arg Ala Ala Leu Leu Ala
     1970                1975                1980

Gly Asp His Glu Gln Leu Arg Gly Gln Leu Arg Ala Val Ala Glu Gly
1985                1990                1995                2000

Val Ala Ala Pro Gly Ala Thr Thr Gly Thr Ala Ser Ala Gly Gly Val
             2005                2010                2015

Val Phe Val Phe Pro Gly Gln Gly Ala Gln Trp Glu Gly Met Ala Arg
         2020                2025                2030

Gly Leu Leu Ser Val Pro Val Phe Ala Glu Ser Ile Ala Glu Cys Asp
     2035                2040                2045
```

```
Ala Val Leu Ser Glu Val Ala Gly Phe Ser Ala Ser Glu Val Leu Glu
    2050                2055                2060
Gln Arg Pro Asp Ala Pro Ser Leu Glu Arg Val Asp Val Val Gln Pro
2065                2070                2075                2080
Val Leu Phe Ser Val Met Val Ser Leu Ala Arg Leu Trp Gly Ala Cys
            2085                2090                2095
Gly Val Ser Pro Ser Ala Val Ile Gly His Ser Gln Gly Glu Ile Ala
        2100                2105                2110
Ala Ala Val Val Ala Gly Val Leu Ser Leu Glu Asp Gly Val Arg Val
        2115                2120                2125
Val Ala Leu Arg Ala Lys Ala Leu Arg Ala Leu Ala Gly Lys Gly Gly
        2130                2135                2140
Met Val Ser Leu Ala Ala Pro Gly Glu Arg Ala Arg Ala Leu Ile Ala
2145                2150                2155                2160
Pro Trp Glu Asp Arg Ile Ser Val Ala Ala Val Asn Ser Pro Ser Ser
            2165                2170                2175
Val Val Val Ser Gly Asp Pro Glu Ala Leu Ala Glu Leu Val Ala Arg
        2180                2185                2190
Cys Glu Asp Glu Gly Val Arg Ala Lys Thr Leu Pro Val Asp Tyr Ala
        2195                2200                2205
Ser His Ser Arg His Val Glu Ile Arg Glu Thr Ile Leu Ala Asp
        2210                2215                2220
Leu Asp Gly Ile Ser Ala Arg Arg Ala Ala Ile Pro Leu Tyr Ser Thr
2225                2230                2235                2240
Leu His Gly Glu Arg Arg Asp Gly Ala Asp Met Gly Pro Arg Tyr Trp
            2245                2250                2255
Tyr Asp Asn Leu Arg Ser Gln Val Arg Phe Asp Glu Ala Val Ser Ala
            2260                2265                2270
Ala Val Ala Asp Gly His Ala Thr Phe Val Glu Met Ser Pro His Pro
        2275                2280                2285
Val Leu Thr Ala Ala Val Gln Glu Ile Ala Ala Asp Ala Val Ala Ile
        2290                2295                2300
Gly Ser Leu His Arg Asp Thr Ala Glu Glu His Leu Ile Ala Glu Leu
2305                2310                2315                2320
Ala Arg Ala His Val His Gly Val Ala Val Asp Trp Arg Asn Val Phe
            2325                2330                2335
Pro Ala Ala Pro Pro Val Ala Leu Pro Asn Tyr Pro Phe Glu Pro Gln
            2340                2345                2350
Arg Tyr Trp Leu Ala Pro Glu Val Ser Asp Gln Leu Ala Asp Ser Arg
            2355                2360                2365
Tyr Arg Val Asp Trp Arg Pro Leu Ala Thr Thr Pro Val Asp Leu Glu
        2370                2375                2380
Gly Gly Phe Leu Val His Gly Ser Ala Pro Glu Ser Leu Thr Ser Ala
2385                2390                2395                2400
Val Glu Lys Ala Gly Gly Arg Val Val Pro Val Ser Ala Asp Arg
            2405                2410                2415
Glu Ala Ser Ala Ala Leu Arg Glu Val Pro Gly Glu Val Ala Gly Val
        2420                2425                2430
Leu Ser Val His Thr Gly Ala Ala Thr His Leu Ala Leu His Gln Ser
        2435                2440                2445
Leu Gly Glu Ala Gly Val Arg Ala Pro Leu Trp Leu Val Thr Ser Arg
        2450                2455                2460
Ala Val Ala Leu Gly Glu Ser Glu Pro Val Asp Pro Glu Gln Ala Met
```

-continued

```
         2465                2470                2475                2480
Val Trp Gly Leu Gly Arg Val Met Gly Leu Glu Thr Pro Glu Arg Trp
                 2485                2490                2495
Gly Gly Leu Val Asp Leu Pro Ala Glu Pro Ala Pro Gly Asp Gly Glu
         2500                2505                2510
Ala Phe Val Ala Cys Leu Gly Ala Asp Gly His Glu Asp Gln Val Ala
         2515                2520                2525
Ile Arg Asp His Ala Arg Tyr Gly Arg Arg Leu Val Arg Ala Pro Leu
         2530                2535                2540
Gly Thr Arg Glu Ser Ser Trp Glu Pro Ala Gly Thr Ala Leu Val Thr
2545                2550                2555                2560
Gly Gly Thr Gly Ala Leu Gly Gly His Val Ala Arg His Leu Ala Arg
                 2565                2570                2575
Cys Gly Val Glu Asp Leu Val Leu Val Ser Arg Arg Gly Val Asp Ala
                 2580                2585                2590
Pro Gly Ala Ala Glu Leu Glu Ala Glu Leu Val Ala Leu Gly Ala Lys
                 2595                2600                2605
Thr Thr Ile Thr Ala Cys Asp Val Ala Asp Arg Glu Gln Leu Ser Lys
         2610                2615                2620
Leu Leu Glu Glu Leu Arg Gly Gln Gly Arg Pro Val Arg Thr Val Val
2625                2630                2635                2640
His Thr Ala Gly Val Pro Glu Ser Arg Pro Leu His Glu Ile Gly Glu
                 2645                2650                2655
Leu Glu Ser Val Cys Ala Ala Lys Val Thr Gly Ala Arg Leu Leu Asp
                 2660                2665                2670
Glu Leu Cys Pro Asp Ala Glu Thr Phe Val Leu Phe Ser Ser Gly Ala
         2675                2680                2685
Gly Val Trp Gly Ser Ala Asn Leu Gly Ala Tyr Ser Ala Ala Asn Ala
         2690                2695                2700
Tyr Leu Asp Ala Leu Ala His Arg Arg Ala Glu Gly Arg Ala Ala
2705                2710                2715                2720
Thr Ser Val Ala Trp Gly Ala Trp Ala Gly Glu Gly Met Ala Thr Gly
                 2725                2730                2735
Asp Leu Glu Gly Leu Thr Arg Arg Gly Leu Arg Pro Met Ala Pro Glu
         2740                2745                2750
Arg Ala Ile Arg Ala Leu His Gln Ala Leu Asp Asn Gly Asp Thr Cys
         2755                2760                2765
Val Ser Ile Ala Asp Val Asp Trp Glu Ala Phe Ala Val Gly Phe Thr
         2770                2775                2780
Ala Ala Arg Pro Arg Pro Leu Leu Asp Glu Leu Val Thr Pro Ala Val
2785                2790                2795                2800
Gly Ala Val Pro Ala Val Gln Ala Ala Pro Ala Arg Glu Met Thr Ser
                 2805                2810                2815
Gln Glu Leu Leu Glu Phe Thr His Ser His Val Ala Ala Ile Leu Gly
                 2820                2825                2830
His Ser Ser Pro Asp Ala Val Gly Gln Asp Gln Pro Phe Thr Glu Leu
                 2835                2840                2845
Gly Phe Asp Ser Leu Thr Ala Val Gly Leu Arg Asn Gln Leu Gln Gln
         2850                2855                2860
Ala Thr Gly Leu Ala Leu Pro Ala Thr Leu Val Phe Glu His Pro Thr
2865                2870                2875                2880
Val Arg Arg Leu Ala Asp His Ile Gly Gln Gln Leu Asp Ser Gly Thr
                 2885                2890                2895
```

```
Pro Ala Arg Glu Ala Ser Ser Ala Leu Arg Asp Gly Tyr Arg Gln Ala
        2900                2905                2910

Gly Val Ser Gly Arg Val Arg Ser Tyr Leu Asp Leu Leu Ala Gly Leu
        2915                2920                2925

Ser Asp Phe Arg Glu His Phe Asp Gly Ser Asp Gly Phe Ser Leu Asp
        2930                2935                2940

Leu Val Asp Met Ala Asp Gly Pro Gly Glu Val Thr Val Ile Cys Cys
2945                2950                2955                2960

Ala Gly Thr Ala Ala Ile Ser Gly Pro His Glu Phe Thr Arg Leu Ala
        2965                2970                2975

Gly Ala Leu Arg Gly Ile Ala Pro Val Arg Ala Val Pro Gln Pro Gly
        2980                2985                2990

Tyr Glu Glu Gly Glu Pro Leu Pro Ser Ser Met Ala Ala Val Ala Ala
        2995                3000                3005

Val Gln Ala Asp Ala Val Ile Arg Thr Gln Gly Asp Lys Pro Phe Val
3010                3015                3020

Val Ala Gly His Ser Ala Gly Ala Leu Met Ala Tyr Ala Leu Ala Thr
3025                3030                3035                3040

Glu Leu Leu Asp Arg Gly His Pro Pro Arg Gly Val Val Leu Ile Asp
        3045                3050                3055

Val Tyr Pro Pro Gly His Gln Asp Ala Met Asn Ala Trp Leu Glu Glu
        3060                3065                3070

Leu Thr Ala Thr Leu Phe Asp Arg Glu Thr Val Arg Met Asp Asp Thr
        3075                3080                3085

Arg Leu Thr Ala Leu Gly Ala Tyr Asp Arg Leu Thr Gly Gln Trp Arg
        3090                3095                3100

Pro Arg Glu Thr Gly Leu Pro Thr Leu Leu Val Ser Ala Gly Glu Pro
3105                3110                3115                3120

Met Gly Pro Trp Pro Asp Asp Ser Trp Lys Pro Thr Trp Pro Phe Glu
        3125                3130                3135

His Asp Thr Val Ala Val Pro Gly Asp His Phe Thr Met Val Gln Glu
        3140                3145                3150

His Ala Asp Ala Ile Ala Arg His Ile Asp Ala Trp Leu Gly Gly Gly
        3155                3160                3165

Asn Ser
    3170

(2) INFORMATION FOR SEQ ID NO:6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 1a (xi) SEQUENCE DESCRIPTION: SEQ ID NO:6:

GGGAGCATGC TCTCGGTGCG CGGCGGCCGC                                    30

(2) INFORMATION FOR SEQ ID NO:7:

(i) SEQUENCE CHARACTERISTICS:
        (A) LENGTH: 30 base pairs
        (B) TYPE: nucleic acid
        (C) STRANDEDNESS: single
        (D) TOPOLOGY: linear
```

(iii) HYPOTHETICAL: NO (ix) FEATURE:
            (A) NAME/KEY: PCR primer 1b (xi) SEQUENCE DESCRIPTION: SEQ ID NO:7:

GCCCTGCAGC GCGTACTCCG AGGTGGCGGT                                              30

(2) INFORMATION FOR SEQ ID NO:8:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (iii) HYPOTHETICAL: NO (ix) FEATURE:
            (A) NAME/KEY: PCR primer 2a (xi) SEQUENCE DESCRIPTION: SEQ ID NO:8:

TGGTCTGCAG GCGAGGCCGG ACACCGAGG                                               29

(2) INFORMATION FOR SEQ ID NO:9:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (ix) FEATURE:
            (A) NAME/KEY: PCR primer 2b (xi) SEQUENCE DESCRIPTION: SEQ ID NO:9:

GGAAGAAGTC AAAGTTCCTC GGTCCCTTCT                                              30

(2) INFORMATION FOR SEQ ID NO:10:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (ix) FEATURE:
            (A) NAME/KEY: PCR primer 3a (xi) SEQUENCE DESCRIPTION: SEQ ID NO:10:

GCGCGAGCTC GACGACCAGG GCGGCATGGT                                              30

(2) INFORMATION FOR SEQ ID NO:11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (iii) HYPOTHETICAL: NO (ix) FEATURE:
            (A) NAME/KEY: PCR primer 3b (xi) SEQUENCE DESCRIPTION: SEQ ID NO:11:

```
GGTGGCATGC TGCGACCACT GCGCGTCGGC                                       30
```

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 4a (xi) SEQUENCE DESCRIPTION: SEQ ID NO:12:

```
AGCTGCATGC TCTGGACTGG GGACGGCTAG                                       30
```

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 4b (xi) SEQUENCE DESCRIPTION: SEQ ID NO:13:

```
CGCGGGATCC CAGCTCCCAC GCCGATACCG                                       30
```

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 5a (xi) SEQUENCE DESCRIPTION: SEQ ID NO:14:

```
TGCAGAATTC GCTGGCCGCG CTCTGGCGCT                                       30
```

(2) INFORMATION FOR SEQ ID NO:15:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 5b (xi) SEQUENCE DESCRIPTION: SEQ ID NO:15:

```
GAGAGCTGCA GCATGAGCCG CTGCTGCGGG                                       30
```

(2) INFORMATION FOR SEQ ID NO:16:

(i) SEQUENCE CHARACTERISTICS:
        (A) LENGTH: 30 base pairs
        (B) TYPE: nucleic acid (C) STRANDEDNESS: single
        (D) TOPOLOGY: linear (iii) HYPOTHETICAL: NO (ix) FEATURE:
        (A) NAME/KEY: PCR primer 6a (xi) SEQUENCE DESCRIPTION: SEQ ID NO:16:

CATGCTGCAG GACTTCAGCC GGATGAACTC                30

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 6b (xi) SEQUENCE DESCRIPTION: SEQ ID NO:17:

GAGGAAGCTT CCAGCCGGTC CAGTTCGTCC                30

(2) INFORMATION FOR SEQ ID NO:18:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 7a (xi) SEQUENCE DESCRIPTION: SEQ ID NO:18:

CGCCCGAATT CGAGGCGCTG GGCGCCCGGA C              31

(2) INFORMATION FOR SEQ ID NO:19:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 7b (xi) SEQUENCE DESCRIPTION: SEQ ID NO:19:

CCACCTGCAG CGCGGGACCT TCCAGCCCC                 29

(2) INFORMATION FOR SEQ ID NO:20:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 8a (xi) SEQUENCE DESCRIPTION: SEQ ID NO:20:

GTGGGTCGCT GCAGACGGTG ACTGCGG 27

(2) INFORMATION FOR SEQ ID NO:21:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 8b (xi) SEQUENCE DESCRIPTION: SEQ ID NO:21:

GGTCAAGCTT CGTCGGCGAG CAGCTTCTC 29

(2) INFORMATION FOR SEQ ID NO:22:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 9a (xi) SEQUENCE DESCRIPTION: SEQ ID NO:22:

GCGCCGAATT CTCGAGACGG CGTGGGAGGC A 31

(2) INFORMATION FOR SEQ ID NO:23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 9b (xi) SEQUENCE DESCRIPTION: SEQ ID NO:23:

TTGCGGTACC AGTAGGAGGC GTCCATCGCG 30

(2) INFORMATION FOR SEQ ID NO:24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (ix) FEATURE:
        (A) NAME/KEY: PCR primer 10a (xi) SEQUENCE DESCRIPTION: SEQ ID NO:24:

GCTGGGATCC CGCGGCGCGG GTTGCAGCAC 30

(2) INFORMATION FOR SEQ ID NO:25:

(i) SEQUENCE CHARACTERISTICS:

(A) LENGTH: 30 base pairs
                (B) TYPE: nucleic acid
                (C) STRANDEDNESS: single
                (D) TOPOLOGY: linear (iii) HYPOTHETICAL: NO (ix) FEATURE:
                (A) NAME/KEY: PCR primer 10b (xi) SEQUENCE DESCRIPTION: SEQ ID NO:25:

CGGAACTCGG TGAGCATGCC GGGACTGCTC                                                30

(2) INFORMATION FOR SEQ ID NO:26:

(i) SEQUENCE CHARACTERISTICS:
                (A) LENGTH: 29 base pairs
                (B) TYPE: nucleic acid
                (C) STRANDEDNESS: single
                (D) TOPOLOGY: linear (iii) HYPOTHETICAL: NO (ix) FEATURE:
                (A) NAME/KEY: PCR primer 11a (xi) SEQUENCE DESCRIPTION: SEQ ID NO:26:

ATGCTCGAGA TCTCGTGGGA GGCGCTGGA                                                 29

(2) INFORMATION FOR SEQ ID NO:27:

(i) SEQUENCE CHARACTERISTICS:
                (A) LENGTH: 30 base pairs
                (B) TYPE: nucleic acid
                (C) STRANDEDNESS: single
                (D) TOPOLOGY: linear (iii) HYPOTHETICAL: NO (ix) FEATURE:
                (A) NAME/KEY: PCR primer 11b (xi) SEQUENCE DESCRIPTION: SEQ ID NO:27:

AGAACTCGGT GAGCATGCCC GGGCCCGCCA                                                30